(12) United States Patent
Ishikawa et al.

(10) Patent No.: US 8,314,094 B2
(45) Date of Patent: Nov. 20, 2012

(54) BENZOXAZINONE DERIVATIVE

(75) Inventors: Shiho Ishikawa, Susono (JP); Takashi Mizutani, Moriya (JP); Tsuyoshi Nagase, Tokushima (JP); Nagaaki Sato, Saitama (JP); Hidekazu Takahashi, Tsukuba (JP)

(73) Assignee: MSD K.K, Tokyo (JP)

( * ) Notice: Subject to any disclaimer, the term of this patent is extended or adjusted under 35 U.S.C. 154(b) by 425 days.

(21) Appl. No.: 12/678,785

(22) PCT Filed: Oct. 2, 2008

(86) PCT No.: PCT/JP2008/067883
§ 371 (c)(1),
(2), (4) Date: Apr. 1, 2010

(87) PCT Pub. No.: WO2009/044788
PCT Pub. Date: Apr. 9, 2009

(65) Prior Publication Data
US 2010/0210636 A1    Aug. 19, 2010

(30) Foreign Application Priority Data

Oct. 5, 2007 (JP) .................. 2007-261629

(51) Int. Cl.
| A61K 31/536 | (2006.01) |
| A61K 31/5365 | (2006.01) |
| C07D 265/14 | (2006.01) |
| C07D 413/02 | (2006.01) |
| C07D 498/04 | (2006.01) |

(52) U.S. Cl. .................. 514/230.5; 544/92; 544/91
(58) Field of Classification Search ............... 514/230.5; 544/92, 91
See application file for complete search history.

(56) References Cited

U.S. PATENT DOCUMENTS

| 6,509,334 B1 | 1/2003 | Zhang et al. |
| 2002/0049204 A1 | 4/2002 | Zhang et al. |
| 2010/0056597 A1 | 3/2010 | Takahashi et al. |

FOREIGN PATENT DOCUMENTS

| EP | 0 204 534 B1 | 1/1991 |
| JP | 2002-543193 A | 12/2002 |
| WO | 2009/038021 A1 | 3/2009 |
| WO | 2009/044788 A1 | 4/2009 |
| WO | 2009/081789 A1 | 7/2009 |
| WO | 2009/099086 A1 | 8/2009 |
| WO | 2009/131065 A1 | 10/2009 |

OTHER PUBLICATIONS

Cancer [online], [retrieved on Jul. 6, 2007] Retrieved from the Internet, URL: http://www.nlm.nih.gov/medlineplus/cancer.html.*

Lala et al., Role of nitric oxide in tumor progression: Lessons from experimental tumors, Cancer and Metastasis Reviews (1998), 17, 91-106.*

Golub et al., Molecular Classification of Cancer: Class Discovery and Class Prediction by Gene Expression Monitoring, Science (1999), vol. 286, 531-537.*

Moon, Y. et al., "Identification of a Mammalian Long Chain Fatty Acyl Elongase Regulated by Sterol Regulatory Element-binding Protein", The Journal of Biological Chemistry, 2001, pp. 45358-45366, vol. 27, No. 48.

* cited by examiner

Primary Examiner — Kristin Bianchi
(74) Attorney, Agent, or Firm — Janet E. Fair; John C. Todaro

(57) ABSTRACT

[PROBLEMS]
To provide a compound useful as an agent for the treatment of circulatory diseases, nervous system diseases, metabolic diseases, reproductive system diseases, and digestive tract diseases.
[MEANS FOR SOLVING PROBLEMS]
The compound, which is for use as an active ingredient, is represented by the formula (I):

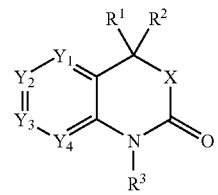

[wherein $R^1$ represents optionally halogenated $C_{1-6}$ alkyl, etc.; $R^2$ represents, e.g., a group represented by the formula (II-1) or (II-4)

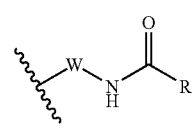

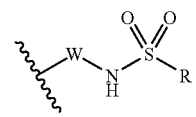

(wherein W represents $C_{1-6}$ alkylene, etc. and R represents $C_{1-6}$ alkyl, etc.); $R^3$ represents hydrogen, $C_{1-6}$ alkyl, etc.; X represents —O—, —NH—, etc.; and $Y_1, Y_2, Y_3$, and $Y_4$ each independently represents —CH—, —N—, etc.].

17 Claims, No Drawings

BENZOXAZINONE DERIVATIVE

CROSS-REFERENCE TO RELATED APPLICATIONS

This application is a U.S. National Phase application under 35 U.S.C. §371 of PCT Application No. PCT/JP2008/067883, filed Oct. 2, 2008, which published as WO 2009/044788 A1 on Apr. 9, 2009, and claims priority under 35 U.S.C. §365(b) from Japanese patent application No. JP2007-261629, filed Oct. 5, 2007.

TECHNICAL FIELD

The benzoxazinone derivatives of the present invention are useful as an inhibitor of a long-chain fatty acyl elongase (hereinafter sometimes abbreviated as LCE) and as a treatment agent for various cardiovascular diseases, nervous system diseases, metabolic diseases, reproductive system diseases and gastrointestinal system diseases.

BACKGROUND ART

The biosynthesis of fatty acids is carried out by an acetyl CoA carboxylase and a fatty acid synthase. LCE is one of the fatty acid synthases, and it is known that in a fatty acid synthesis pathway in which the synthesis is started using acetyl CoA as a substrate, LCE elongates a carbon chain of mainly a fatty acid having 12 or more carbon atoms, for example, lauric acid to myristic acid, myristic acid to palmitic acid, palmitic acid to stearic acid, palmitoleic acid to vaccenic acid, and so on [J. Biol. Chem., 276 (48), 45358-45366, (2001)] (Non-patent document 1). Further, it is known that excess long-chain fatty acids in the body cause an increase in neutral fat, phospholipid, cholesteryl ester, and the like, and moreover causes accumulation of fat.

Further, it is known that excessively accumulated fat causes, for example, insulin resistance, diabetes, hypertension, hyperlipidemia, obesity and the like, and when several these factors are combined, risk of onset of atherosclerosis is significantly increased, and such symptoms are called metabolic syndrome. It is also known that high neutral fat or obesity increases risk of, for example, pancreatitis, hepatic dysfunction, cancer such as breast cancer, uterine cancer, ovarian cancer, colon cancer or prostate cancer, menstrual abnormality, arthritis, gout, cholecystitis, gastroesophageal reflux, obesity hypoventilation syndrome (Pickwickian syndrome), sleep apnea syndrome and the like. It is widely known that diabetes often leads to, onset of, for example, angina pectoris, heart failure, stroke, claudication, retinopathy, failing vision, renal failure, neuropathy, skin ulcer, infection and so on [see The Merck Manual of Medical Information], second home edition, Merck & Co., 2003].

Accordingly, an LCE inhibitor is useful as a preventive and/or remedy for these diseases.

As conventionally known benzoxazinone derivatives, for example, those described in JP-T-2002-543193 can be exemplified. These compounds have a benzoxazinone backbone, however, the $R^2$ moiety in the present invention is limited to C1-6 alkyl or C2-6 alkenyl, and therefore, they are different from those of the present invention. Further, this reference example relates to a progesterone receptor modulator, and there is no disclosure of an LCE inhibitory effect.

Further, compounds having an LCE inhibitory activity have been completely unknown until now.

Non-patent document 1: J. Biol. Chem., 276 (48), 45358-45366, (2001)

Patent document 1: JP-T-2002-543193

DISCLOSURE OF THE INVENTION

Problems that the Invention is to Solve

An object of the invention is to provide a compound having an LCE inhibitory effect.

Means for Solving the Problems

As a result of intensive studies, the present inventors have found that compounds represented by the general formula (I) have an excellent LCE inhibitory effect, and have completed the present invention.

That is, the invention provides (1) a compound represented by the formula (I) or a pharmaceutically acceptable salt thereof.

[Chemical Formula 1]

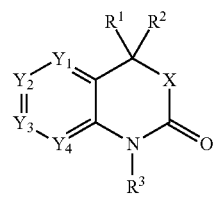

(I)

[In the formula, $R^1$ represents optionally halogenated $C_{1-6}$ alkyl or optionally halogenated $C_{3-8}$ cycloalkyl;

$R^2$ represents a substituent selected from a group consisting of the following groups:

[Chemical Formula 2]

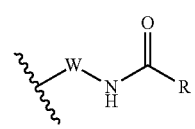

(II-1)

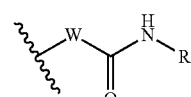

(II-2)

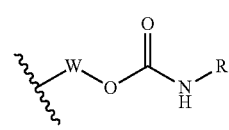

(II-3)

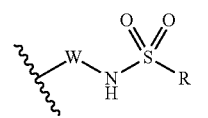

(II-4)

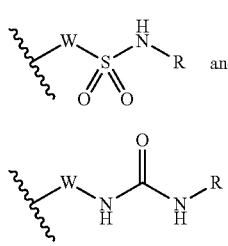

wherein W represents $C_{1-6}$ alkylene, $C_{2-6}$ alkenylene, $C_{2-6}$ alkynylene or $C_{3-6}$ cycloalkylene, wherein the alkylene, alkenylene, alkynylene or cycloalkylene may be substituted by optionally halogenated $C_{1-3}$ alkyl, optionally halogenated $C_{1-3}$ alkyloxy, hydroxyl or halogen; and R represents $C_{1-6}$ alkyl, $C_{3-8}$ cycloalkyl, aryl or heteroaryl, wherein the $C_{1-6}$ alkyl, $C_{3-8}$ cycloalkyl, aryl or heteroaryl may be substituted by halogen, optionally halogenated $C_{1-6}$ alkyl, optionally halogenated $C_{1-6}$ alkyloxy, $C_{1-6}$ alkylsulfonyl, cyano, phenyl, $C_{1-6}$ alkylthio, hydroxyl, amino, $C_{1-6}$ alkylamino, di-$C_{1-6}$ alkylamino, hydroxy-$C_{1-6}$ alkyl, amino-$C_{1-6}$ alkyl, $C_{1-6}$ alkylamino-$C_{1-6}$ alkyl, di-$C_{1-6}$ alkylaminoalkyl, $C_{1-6}$ alkoxy-$C_{1-6}$ alkyl, $C_{1-6}$ alkylcarbonyl, $C_{1-6}$ alkylcarbonylamino, $C_{1-6}$ alkylcarbamoyl, $C_{3-8}$ cycloalkylcarbamoyl, $C_{1-6}$ alkylsulfonylamino or $C_{1-6}$ alkylaminosulfonyl;

$R^3$ represents a hydrogen atom, $C_{1-6}$ alkyl, aryl or heteroaryl;

X represents —O—, —C($R^{4a}$)($R^{4b}$)— or —N$R^5$—;

$R^{4a}$, $R^{4b}$ and $R^5$ each independently represent hydrogen, $C_{1-6}$ alkyl, $C_{3-8}$ cycloalkyl, aryl or heteroaryl, wherein the $C_{1-6}$ alkyl, $C_{3-8}$ cycloalkyl, aryl or heteroaryl may be substituted by halogen, optionally halogenated $C_{1-6}$ alkyl, optionally halogenated $C_{1-6}$ alkyloxy, $C_{1-6}$ alkylsulfonyl, cyano, aryl or heteroaryl;

$Y_1$ represents —C$R^6$— or —N—;
$Y_2$ represents —C$R^7$— or —N—;
$Y_3$ represents —C$R^8$— or —N—;
$Y_4$ represents —C$R^9$— or —N—;

$R^6$, $R^7$, $R^8$ and $R^9$ each independently represent a hydrogen atom, halogen, cyano, $C_{1-6}$ alkyl, $C_{3-8}$ cycloalkyl, $C_{1-6}$ alkoxy, hydroxyl, hydroxy-$C_{1-6}$ alkyl, amino, $C_{1-6}$ alkylamino, di-$C_{1-6}$ alkylamino, amino-$C_{1-6}$ alkyl, $C_{1-6}$ alkylamino-$C_{1-6}$ alkyl, di-$C_{1-6}$ alkylamino-($C_{(C1-6)}$)alkyl, $C_{1-6}$ alkoxy-$C_{1-6}$ alkyl, heterocyclyl, aryl, heteroaryl, $C_{1-6}$ alkylsulfonyl, $C_{1-6}$ alkylsulfinyl, $C_{1-6}$ alkylthio, arylsulfonyl, heteroarylsulfonyl, arylsulfinyl, heteroarylsulfinyl, arylthio, heteroarylthio, $C_{1-6}$ alkylcarbonyl, arylcarbonyl, heteroarylcarbonyl, $C_{1-6}$ alkylcarbonylamino, arylcarbonylamino, heteroarylcarbonylamino, $C_{1-6}$ alkylcarbamoyl, $C_{3-8}$ cycloalkylcarbamoyl, heterocyclylcarbamoyl, arylcarbamoyl, heteroarylcarbamoyl, $C_{1-6}$ alkylsulfonylamino, arylsulfonylamino, heteroarylsulfonylamino, $C_{1-6}$ alkylsulfamoyl, arylsulfamoyl or heteroarylsulfamoyl, wherein the alkyl, cycloalkyl, heterocyclyl, aryl or heteroaryl may be substituted by a group selected from the group consisting of halogen, optionally halogenated $C_{1-6}$ alkyl, optionally halogenated $C_{1-6}$ alkyloxy, $C_{1-6}$ alkylsulfonyl, carboxyl and cyano.

Further, the invention provides:

(2) an inhibitor of a long-chain fatty acyl elongase (LCE) comprising the compound represented by the formula (I) or a pharmaceutically acceptable salt thereof as an active ingredient;

(3) a pharmaceutical composition comprising the compound represented by the formula (I) or a pharmaceutically acceptable salt thereof and a pharmaceutically acceptable additive; and (4) a treatment agent for metabolic syndrome, fatty liver, hyperlipidemia, dyslipidemia, non-alcoholic fatty liver, obesity, diabetes, bulimia, a malignant neoplasm or an infectious disease, comprising the compound represented by the formula (I) or a pharmaceutically acceptable salt thereof as an active ingredient.

Hereinafter, the meanings of the terms to be used in this description will be described to illustrate the invention in more detail.

Examples of the "aryl" include phenyl and naphthyl.

The "heteroaryl" means 5- or 6-membered monocyclic heteroaryl having one or more, preferably one to three heteroatoms which are the same or different and are selected from the group consisting of an oxygen atom, a nitrogen atom and a sulfur atom, or condensed cyclic heteroaryl formed by condensation of the monocyclic heteroaryl with the above-mentioned aryl, or condensation of the monocyclic heteroaryl groups which are the same or different. Examples thereof include pyrrolyl, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzimidazolyl, benzoxazolyl, benzisoxazolyl, benzothiazolyl, benzisothiazolyl, indazolyl, purinyl, quinolyl, isoquinolyl, phthalazinyl, naphthyridinyl, quinoxalinyl, quinazolinyl, cinnolinyl, pteridinyl and pyrido[3,2-b]pyridyl.

The "heterocyclyl" means a monocyclic or bicyclic ring which is saturated, partially saturated or unsaturated and contains 4 to 10 atoms including 1, 2, or 3 heteroatoms selected from nitrogen, oxygen and sulfur, and, for example, pyrrolidinyl, oxazolidinyl, thiazolidinyl, piperidinyl, morpholinyl, piperazinyl, pyrrolidonyl, pyridonyl, dioxolanyl, tetrahydrofuranyl and tetrahydropyranyl are exemplified.

The "$C_{3-8}$ cycloalkyl" means cycloalkyl having 3 to 8 carbon atoms, and examples thereof include cyclopropyl, cyclobutyl, cyclopentyl and cyclohexyl.

The "halogen" means a fluorine atom, a chlorine atom, a bromine atom or an iodine atom.

The "$C_{1-6}$ alkyl" means linear or branched alkyl having 1 to 6 carbon atoms, and examples thereof include methyl, ethyl, n-propyl, isopropyl, n-butyl, isobutyl, sec-butyl, tert-butyl, n-pentyl, isopentyl, n-hexyl and isohexyl.

The "$C_{1-6}$ alkylene" includes linear alkylene having 1 to 6 carbon atoms and branched alkylene having 3 to 6 carbon atoms, and specific examples thereof include methylene, ethylene, propylene, butylene, pentylene and hexylene.

The "$C_{2-6}$ alkenylene" includes linear alkenylene having 2 to 6 carbon atoms including one carbon-carbon double bond in the chain and branched alkenylene having 3 to 6 carbon atoms including one carbon-carbon double bond in the chain, and specific examples thereof include vinylene, 1-propenylene, 2-propenylene, 1-butenylene, 2-butenylene, 3-butenylene, 2-pentenylene, 3-pentenylene, 4-pentenylene and 1-hexenylene.

The "$C_{2-6}$ alkynylene" includes linear alkynylene having 2 to 6 carbon atoms and branched alkynylene having 3 to 6 carbon atoms, and specifically, for example, the following groups are exemplified.

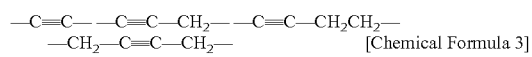

[Chemical Formula 3]

The "$C_{3-6}$ cycloalkylene" includes cycloalkylene having 3 to 6 carbon atoms, and specific examples thereof include 1,1-cyclopropylene, 1,2-cyclopropylene, 1,1-cyclobutanylene, 1,2-cyclobutanylene, 1,3-cyclobutanylene, 1,1-cyclopentenylene, 1,2-cyclohexenylene, 1,3-cyclohexenylene and 1,4-cyclohexenylene.

The "optionally halogenated $C_{1-6}$ alkyl" means $C_{1-6}$ alkyl which may be substituted by one or more, preferably one to three of the above-mentioned halogens which are the same or different at any substitutable positions, and examples thereof include, in addition to unsubstituted $C_{1-6}$ alkyl, halogenated $C_{1-6}$ alkyl such as fluoromethyl, difluoromethyl, trifluoromethyl, 2-fluoroethyl, 1,2-difluoroethyl, chloromethyl, 2-chloroethyl, 1,2-dichloroethyl, bromomethyl and iodomethyl. Similarly, the optionally halogenated $C_{1-3}$ alkyl means $C_{1-3}$ alkyl which may be substituted by one or more, preferably one to three of the above-mentioned halogens which are the same or different at any substitutable positions.

The "$C_{1-6}$ alkoxy" means linear or branched alkoxy having 1 to 6 carbon atoms, and is also referred to as "$C_{1-6}$ alkyloxy", and examples thereof include methoxy, ethoxy, propoxy, isopropoxy, butoxy, tert-butoxy and pentyloxy.

The "optionally halogenated $C_{1-6}$ alkoxy" means linear or branched alkoxy having 1 to 6 carbon atoms which may be substituted by one or more, preferably one to three of the above-mentioned halogens which are the same or different at any substitutable positions, and examples thereof include, in addition to unsubstituted $C_{1-6}$ alkoxy, chloromethoxy, fluoromethoxy, trifluoromethoxy, chloroethoxy, fluoroethoxy, dichloroethoxy and difluoroethoxy. Similarly, the "optionally halogenated $C_{1-3}$ alkoxy" means linear or branched alkoxy having 1 to 3 carbon atoms which may be substituted by one or more, preferably one to three of the above-mentioned halogens which are the same or different at any substitutable positions.

The "$C_{1-6}$ alkylsulfonyl" means a group in which $C_{1-6}$ alkyl is bound to sulfonyl, and specific examples thereof include methylsulfonyl, ethylsulfonyl, n-propylsulfonyl, isopropylsulfonyl and n-butylsulfonyl.

The "$C_{1-6}$ alkylsulfinyl" means a group in which $C_{1-6}$ alkyl is bound to sulfinyl, and specific examples thereof include methylsulfinyl, ethylsulfinyl, n-propylsulfinyl, isopropylsulfinyl and n-butylsulfinyl.

The "$C_{1-6}$ alkylthio" means a group in which $C_{1-6}$ alkyl is bound to a sulfur atom, and specific examples thereof include methylthio, ethylthio, n-propylthio, isopropylthio and n-butylthio.

The "$C_{1-6}$ alkylamino" means amino mono-substituted by the above-mentioned $C_{1-6}$ alkyl, and examples thereof include methylamino, ethylamino, propylamino, isopropylamino and butylamino.

The "di-$C_{1-6}$ alkylamino" means amino di-substituted by the above-mentioned $C_{1-6}$ alkyl groups which are the same or different, and examples thereof include dimethylamino, diethylamino, dipropylamino, methylpropylamino and diisopropylamino.

The "$C_{1-6}$ alkylamino-$C_{1-6}$ alkyl" means $C_{1-6}$ alkyl mono-substituted by the above-mentioned $C_{1-6}$ alkylamino, and examples thereof include methylaminomethyl, ethylaminomethyl, propylaminomethyl and isopropylaminomethyl.

The "di-$C_{1-6}$ alkylamino-$C_{1-6}$ alkyl" means $C_{1-6}$ alkyl mono-substituted by the above-mentioned di-$C_{1-6}$ alkylamino, and examples thereof include dimethylaminomethyl, diethylaminomethyl and ethylmethylaminomethyl.

The "amino-$C_{1-6}$ alkyl" means the above-mentioned alkyl in which one of the hydrogen atoms is replaced by an amino group, and examples thereof include aminomethyl, aminoethyl and aminopropyl.

The "$C_{1-6}$ alkyloxy-$C_{1-6}$ alkyl" means $C_{1-6}$ alkyl substituted by a $C_{1-6}$ alkyloxy group, and specific examples thereof include methoxymethyl, ethoxymethyl, n-propyloxymethyl, isopropyloxymethyl and 1-methoxyethyl.

The "$C_{1-6}$ alkyloxycarbonyl" means a group in which $C_{1-6}$ alkyloxy is bound to a carbonyl group (—CO—) and includes an alkyloxycarbonyl group having 1 to 6 carbon atoms, and specific examples thereof include methoxycarbonyl, ethoxycarbonyl, n-propyloxycarbonyl, isopropyloxycarbonyl, n-butoxycarbonyl and tert-butoxycarbonyl.

The "$C_{1-6}$ alkyloxycarbonylamino" means a group in which $C_{1-6}$ alkyloxycarbonyl is bound to an amino group (—NH$_2$—) and includes alkyloxycarbonylamino having 1 to 6 carbon atoms, and specific examples thereof include methoxycarbonylamino, ethoxycarbonylamino, n-propyloxycarbonylamino, isopropyloxycarbonylamino and n-butoxycarbonylamino.

The "$C_{1-6}$ alkyloxycarbonyl($C_{1-6}$ alkyl)amino" means a group in which lower alkyloxycarbonyl is bound to the nitrogen atom of mono-$C_{1-6}$ alkylamino instead of a hydrogen atom, and specific examples thereof include methoxycarbonyl(methyl)amino, ethoxycarbonyl(methyl)amino and n-propyloxycarbonyl(methyl)amino.

The "$C_{1-6}$ alkylcarbonyl" means a group in which $C_{1-6}$ alkyl is bound to carbonyl and includes alkylcarbonyl having 1 to 6 carbon atoms, and specific examples thereof include acetyl, propionyl, butyryl, isobutyryl and valeryl.

The "$C_{1-6}$ alkylcarbonyloxy" means a group in which $C_{1-6}$ alkylcarbonyl is bound to an oxygen atom, and specific examples thereof include acetoxy, propionyloxy, valeryloxy, isovaleryloxy and pivaloyloxy.

The "$C_{1-6}$ alkylcarbonylamino" means a group in which one of the hydrogen atoms of an amino group is replaced by $C_{1-6}$ alkylcarbonyl, and specific examples thereof include acetamide, propionylamino, isobutyrylamino and valerylamino.

The "$C_{1-6}$ alkylcarbonyl($C_{1-6}$ alkyl)amino" means a group in which a hydrogen atom attached to the nitrogen atom of mono-$C_{1-6}$ alkylamino is replaced by lower alkylcarbonyl, and examples thereof include methylcarbonyl(methyl)amino, ethylcarbonyl(methyl)amino and n-propylcarbonyl(methyl)amino.

The "mono-$C_{1-6}$ alkylcarbamoyl" means a group in which one of the hydrogen atoms of a carbamoyl group (—CONH$_2$) is replaced by $C_{1-6}$ alkyl, and specific examples thereof include methylcarbamoyl, ethylcarbamoyl, n-propylcarbamoyl, isopropylcarbamoyl and n-butylcarbamoyl.

The "di-$C_{1-6}$ alkylcarbamoyl" means a group in which two hydrogen atoms of a carbamoyl group are replaced by $C_{1-6}$ alkyl, and specific examples thereof include dimethylcarbamoyl, diethylcarbamoyl, ethylmethylcarbamoyl, di(n-propyl)carbamoyl, methyl(n-propyl)carbamoyl and diisopropylcarbamoyl. Further, the di-$C_{1-6}$ alkylcarbamoyl also include a group forming nitrogen-containing heterocyclyl by combining two alkyl groups together with the nitrogen atom.

The "$C_{3-8}$ cycloalkylcarbamoyl" means a group in which one of the hydrogen atoms of carbamoyl is replaced by $C_{3-8}$ cycloalkyl, and specific examples thereof include cyclopropylcarbamoyl, cyclobutylcarbamoyl and cyclopentylcarbamoyl.

The "mono-$C_{1-6}$ alkylcarbamoylamino" means a group in which one of the hydrogen atoms of an amino group is replaced by mono-$C_{1-6}$ alkylcarbamoyl, and specific examples thereof include methylcarbamoylamino, ethylcarbamoylamino, n-propylcarbamoylamino and isopropylcarbamoylamino.

The "di-$C_{1-6}$ alkylcarbamoylamino" means a group in which one of the hydrogen atoms of an amino group is replaced by di-$C_{1-6}$ alkylcarbamoyl, and specific examples thereof include dimethylcarbamoylamino, diethylcarbamoylamino, di(n-propyl)carbamoylamino and diisopropylcarbamoylamino.

The "mono-$C_{1-6}$ alkylcarbamoyl($C_{1-6}$ alkyl)amino" means a group in which a hydrogen atom attached to the nitrogen atom of mono-lower alkylamino is replaced by mono-lower alkylcarbamoyl, and specific examples thereof include monomethylcarbamoyl(methyl)amino, monoethylcarbamoyl(methyl)amino and [mono(n-propyl)carbamoyl](methyl)amino.

The "di-$C_{1-6}$ alkylcarbamoyl($C_{1-6}$ alkyl)amino" means a group in which a hydrogen atom attached to the nitrogen atom of mono-$C_{1-6}$ alkylamino is replaced by a di-$C_{1-6}$ alkylcarbamoyl group, and specific examples thereof include dimethylcarbamoyl(methyl)amino, diethylcarbamoyl(methyl)amino and [di(n-propyl)carbamoyl](methyl)amino.

The "mono-$C_{1-6}$ alkylcarbamoyloxy" means a group in which mono-$C_{1-6}$ alkylcarbamoyl is bound to an oxygen atom, and specific examples thereof include methylcarbamoyloxy, ethylcarbamoyloxy, n-propylcarbamoyloxy and isopropylcarbamoyloxy.

The "di-$C_{1-6}$ alkylcarbamoyloxy" means a group in which di-$C_{1-6}$ alkylcarbamoyl is bound to an oxygen atom, and specific examples thereof include dimethylcarbamoyloxy, diethylcarbamoyloxy, ethylmethylcarbamoyloxy, di(n-propyl)carbamoyloxy and methyl(n-propyl)carbamoyloxy.

The "$C_{1-6}$ alkylsulfonylamino" means a group in which one of the hydrogen atoms of an amino group is replaced by $C_{1-6}$ alkylsulfonyl, and specific examples thereof include methylsulfonylamino, ethylsulfonylamino, n-propylsulfonylamino and isopropylsulfonylamino.

The "$C_{1-6}$ alkylsulfonyl($C_{1-6}$ alkyl)amino group" means a group in which a hydrogen atom attached to the nitrogen atom of mono-$C_{1-6}$ alkylamino is replaced by $C_{1-6}$ alkylsulfonyl, and specific examples thereof include methanesulfonylmethylamino, ethanesulfonylmethylamino and n-propanesulfonylmethylamino.

The "mono-$C_{1-6}$ alkylsulfamoyl" means a group in which one of the hydrogen atoms of a sulfamoyl group (—$SO_2NH_2$) is replaced by $C_{1-6}$ alkyl, and specific examples thereof include monomethylsulfamoyl, monoethylsulfamoyl and mono(n-propyl)sulfamoyl.

The "di-$C_{1-6}$ alkylsulfamoyl" means a group in which two hydrogen atoms of a sulfamoyl group are each replaced by $C_{1-6}$ alkyl, and specific examples thereof include dimethylsulfamoyl, diethylsulfamoyl and di(n-propyl)sulfamoyl.

The "mono-$C_{1-6}$ alkylsulfamoylamino" means a group in which one of the hydrogen atoms of an amino group is replaced by mono-$C_{1-6}$ alkylsulfamoyl, and specific examples thereof include (monomethylsulfamoyl)amino, (monoethylsulfamoyl)amino and [mono(n-propyl)sulfamoyl]amino.

The "(di-$C_{1-6}$ alkylsulfamoyl)amino" means a group in which one of the hydrogen atoms of an amino group is replaced by di-$C_{1-6}$ alkylsulfamoyl, and specific examples thereof include (dimethylsulfamoyl)amino, (diethylsulfamoyl)amino and (ethylmethylsulfamoyl)amino.

The "mono-$C_{1-6}$ alkylsulfamoyl($C_{1-6}$ alkyl)amino" means a group in which a hydrogen atom attached to the nitrogen atom of mono-$C_{1-6}$ alkylamino is replaced by mono-$C_{1-6}$ alkylsulfamoyl, and specific examples thereof include monomethylsulfamoyl(methyl)amino, monoethylsulfamoyl(methyl)amino and [mono(n-propyl)sulfamoyl](methyl)amino.

The "di-$C_{1-6}$ alkylsulfamoyl($C_{1-6}$ alkyl)amino" means a group in which a hydrogen atom attached to the nitrogen atom of mono-$C_{1-6}$ alkylamino is replaced by di-$C_{1-6}$ alkylsulfamoyl, and specific examples thereof include dimethylsulfamoyl(methyl)amino, diethylsulfamoyl(methyl)amino and [di(n-propyl)sulfamoyl](methyl)amino.

The "arylthio" means a group in which the above-mentioned aryl is bound to a sulfur atom.

The "heteroarylthio" means a group in which the above-mentioned heteroaryl is bound to a sulfur atom.

The "arylsulfonyl" means a group in which the above-mentioned aryl is bound to sulfonyl.

The "heteroarylsulfonyl" means a group in which the above-mentioned heteroaryl is bound to sulfonyl.

The "arylsulfonylamino" means a group in which one of the hydrogen atoms of an amino group is replaced by arylsulfonyl.

The "heteroarylsulfonylamino" means a group in which one of the hydrogen atoms of an amino group is replaced by heteroarylsulfonyl.

The "arylsulfinyl" means a group in which the above-mentioned aryl is bound to sulfinyl.

The "heteroarylsulfinyl" means a group in which the above-mentioned heteroaryl is bound to sulfinyl.

The "arylcarbonyl" means a group in which the above-mentioned aryl is bound to carbonyl.

The "heteroarylcarbonyl" means a group in which the above-mentioned heteroaryl is bound to carbonyl.

The "arylcarbonylamino" means a group in which one of the hydrogen atoms of an amino group is replaced by the above-mentioned arylcarbonyl.

The "heteroarylcarbonylamino" means a group in which one of the hydrogen atoms of an amino group is replaced by the above-mentioned heteroarylcarbonyl.

The "heterocyclylcarbamoyl" means a group in which one of the hydrogen atoms of carbamoyl is replaced by the above-mentioned heterocyclyl.

The "arylcarbamoyl" means a group in which one of the hydrogen atoms of carbamoyl is replaced by the above-mentioned aryl.

The "heteroarylcarbamoyl" means a group in which one of the hydrogen atoms of carbamoyl is replaced by the above-mentioned heteroaryl.

The "arylsulfamoyl" means a group in which one of the hydrogen atoms of sulfamoyl is replaced by aryl.

The "heteroarylsulfamoyl" means a group in which one of the hydrogen atoms of sulfamoyl is replaced by heteroaryl.

The "salt" of the compound according to the invention means a commonly used pharmaceutically acceptable salt, and an acid addition salt at the basic functional group can be exemplified in the case where the compound has a basic functional group.

Examples of the acid addition salt include inorganic acid salts such as hydrochlorides, sulfates, nitrates, phosphates and perchlorates; organic acid salts such as maleates, fumarates, tartrates, citrates, ascorbates and trifluoroacetates; and sulfonates such as methanesulfonates, isethionates, benzenesulfonates and p-toluenesulfonates.

The "treatment agent" means an agent to be given for the purpose of treating and/or preventing various diseases.

For illustrating the compounds according to the invention more specifically, the respective symbols to be used in the formula (I) and the like will be described in more detail with reference to preferred specific examples thereof.

$R^1$ represents optionally halogenated $C_{1-6}$ alkyl or optionally halogenated $C_{3-8}$ cycloalkyl.

As specific $R^1$, $C_{1-6}$ alkyl such as methyl, ethyl, n-propyl, isopropyl, n-butyl, isobutyl, t-butyl, fluoromethyl, difluoromethyl, trifluoromethyl, trichloromethyl, 2,2-chloroethyl, 2,2-difluoroethyl, trichloroethyl and trifluoroethyl; $C_{3-8}$ cycloalkyl such as cyclopropyl, cyclobutyl, cyclopentyl, cyclohexyl, fluorocyclopropyl, fluorocyclobutyl and fluorocyclopentyl are exemplified, and preferably, methyl, ethyl trichloromethyl, trifluoromethyl or the like is recommended, and particularly trifluoromethyl is recommended.

$R^2$ represents a group selected from the group consisting of the following groups.

[Chemical Formula 4]

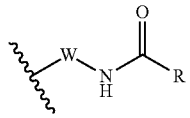
(II-1)

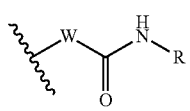
(II-2)

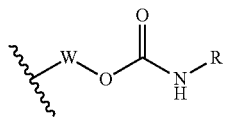
(II-3)

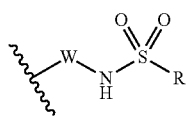
(II-4)

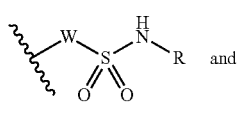
(II-5) and

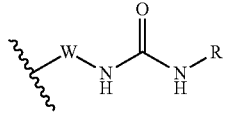
(II-6)

In the formulae, W represents $C_{1-6}$ alkylene, $C_{2-6}$ alkenylene, $C_{2-6}$ alkynylene or $C_{3-6}$ cycloalkylene, wherein the alkylene, alkenylene, alkynylene or cycloalkylene may be substituted by optionally halogenated $C_{1-3}$ alkyl, optionally halogenated $C_{1-3}$ alkyloxy, hydroxyl or halogen; and R represents $C_{1-6}$ alkyl, $C_{3-8}$ cycloalkyl, aryl or heteroaryl, wherein the $C_{1-6}$ alkyl, $C_{3-8}$ cycloalkyl, aryl or heteroaryl may be substituted by halogen, optionally halogenated $C_{1-6}$ alkyl, optionally halogenated $C_{1-6}$ alkyloxy, $C_{1-6}$ alkylsulfonyl, cyano, phenyl, $C_{1-6}$ alkylthio, hydroxyl, amino, $C_{1-6}$ alkylamino, di-$C_{1-6}$ alkylamino, hydroxy-$C_{1-6}$ alkyl, amino-$C_{1-6}$ alkyl, $C_{1-6}$ alkylamino($C_{1-6}$)alkyl, di-$C_{1-6}$ alkylamino($C_{1-6}$) alkyl, $C_{1-6}$ alkoxy-$C_{1-6}$ alkyl, $C_{1-6}$ alkylcarbonyl, $C_{1-6}$ alkylcarbonylamino, $C_{1-6}$ alkylcarbamoyl, $C_{3-8}$ cycloalkylcarbamoyl, $C_{1-6}$ alkylsulfonylamino or $C_{1-6}$ alkylaminosulfonyl.

As W, specifically, the following groups:

[Chemical Formula 5]

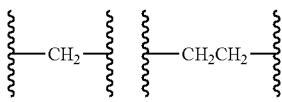

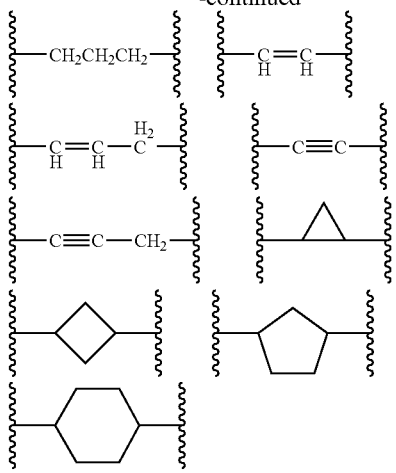

and the like are exemplified, and preferably, —$CH_2$—, —$CH_2CH_2$— or —$CH_2CH_2CH_2$— is recommended.

As R, specifically, methyl, ethyl, n-propyl, isopropyl, n-butyl, isobutyl, t-butyl, cyclopropyl, cyclobutyl, cyclopentyl, cyclohexyl, phenyl, fluorophenyl, chlorophenyl, difluorophenyl, methanesulfonylphenyl, methylphenyl, isopropylphenyl, methoxyphenyl, trifluoromethylphenyl, cyanophenyl, naphthyl, pyridinyl, fluoropyridinyl, methylpyridinyl, trifluoromethylpyridinyl, methoxypyridinyl, pyrazinyl, pyridazinyl, imidazolyl, methylimidazolyl, benzimidazolyl, oxazolyl, ethyloxazolyl, oxadiazolyl, thiazolyl, methylthiazolyl, thiadiazolyl, pyrrolidinyl, piperidinyl, morpholinyl and the like are exemplified.

As R in the formula (II-1), preferably, phenyl or heteroaryl (particularly pyridyl) is exemplified, and the phenyl or heteroaryl may be substituted by a substituent selected from the group consisting of halogen, cyano, optionally halogenated $C_{1-6}$ alkyl, optionally halogenated $C_{1-6}$ alkyloxy, $C_{1-6}$ alkylsulfonyl, $C_{1-6}$ alkylthio, hydroxyl, amino, $C_{1-6}$ alkylamino, di-$C_{1-6}$ alkylamino, hydroxy-$C_{1-6}$ alkyl, amino-$C_{1-6}$ alkyl, $C_{1-6}$ alkylamino-$C_{1-6}$ alkyl, di-$C_{1-6}$ alkylamino-$C_{1-6}$ alkyl, $C_{1-6}$ alkoxy-$C_{1-6}$ alkyl, $C_{1-6}$ alkylcarbonyl, $C_{1-6}$ alkylcarbonylamino, $C_{1-6}$ alkylcarbamoyl, $C_{3-8}$ cycloalkylcarbamoyl, $C_{1-6}$ alkylsulfonylamino and $C_{1-6}$ alkylaminosulfonyl.

As R in the formula (II-1), more preferably, phenyl, fluorophenyl, chlorophenyl, tolyl, isopropylphenyl, methoxyphenyl, trifluoromethylphenyl, methanesulfonylphenyl, pyridyl, fluoropyridyl, methylpyridyl, trifluoromethylpyridyl, methoxypyridyl or the like is recommended.

Further, as W in the formula (II-1), preferably, —$CH_2$—, —$CH_2CH_2$— or —$CH_2CH_2CH_2$— is exemplified.

As R and W in the formula (II-2), preferably, the same groups as those illustrated for the formula (II-1) are exemplified.

As R and W in the formula (II-3), preferably, the same groups as those illustrated for the formula (II-1) are exemplified.

As R and W in the formula (II-4), preferably, the same groups as those illustrated for the formula (II-1) are exemplified.

As R and W in the formula (II-5), preferably, the same groups as those illustrated for the formula (II-1) are exemplified.

As R and W in the formula (II-6), preferably, the same groups as those illustrated for the formula (II-1) are exemplified.

Among these, as $R^2$, preferably, the group represented by the formula (II-1), (II-4) or (II-6) is exemplified.

$R^3$ represents a hydrogen atom, $C_{1-6}$ alkyl, aryl or heteroaryl.

As specific $R^3$, a hydrogen atom, $C_{1-6}$ alkyl such as methyl, ethyl, n-propyl, isopropyl, n-butyl, isobutyl and t-butyl; aryl such as phenyl and naphthyl; heteroaryl such as pyridinyl, pyrimidinyl, pyridazinyl, pyrazyl, pyrazolyl, pyrrolyl, imidazolyl, triazolyl, oxazolyl, isoxazolyl, oxadiazolyl, thiazolyl, isothiazolyl, thiadiazolyl, tetrazolyl, pyridazinyl, pyrazinyl, furyl, thienyl, indolyl, benzofuranyl, benzothienyl, benzimidazolyl, benzoxazolyl, benzisoxazolyl, benzothiazolyl, benzisothiazolyl, indazolyl, purinyl, quinolyl, isoquinolyl, phthalazinyl, naphthyridinyl, quinoxalinyl, quinazolinyl, cinnolinyl, pteridinyl and pyrido[3,2-b]pyridyl are exemplified, and preferably, a hydrogen atom is recommended.

X represents —O—, —C($R^{4a}$)($R^{4b}$)— or —$NR^5$—, and $R^{4a}$, $R^{4b}$ and $R^5$ each independently represent hydrogen, $C_{1-6}$ alkyl, $C_{3-8}$ cycloalkyl, aryl or heteroaryl, wherein the $C_{1-6}$ alkyl, $C_{3-8}$ cycloalkyl, aryl or heteroaryl may be substituted by halogen, optionally halogenated $C_{1-6}$ alkyl, optionally halogenated $C_{1-6}$ alkyloxy, $C_{1-6}$ alkylsulfonyl, cyano, aryl or heteroaryl.

As X, preferably, —O— or —$NR^5$— is exemplified, and as $R^5$, a hydrogen atom, $C_{1-6}$ alkyl, $C_{3-6}$ cycloalkyl or the like is exemplified, and particularly, —O—, —NH— or the like is recommended.

$Y_1$ represents —$CR^6$— or —N—;
$Y_2$ represents —$CR^7$— or —N—;
$Y_3$ represents —$CR^8$— or —N—; and
$Y_4$ represents —$CR^9$— or —N—.

$R^6$, $R^7$, $R^8$ and $R^9$ each independently represent a hydrogen atom, halogen, cyano, $C_{1-6}$ alkyl, $C_{3-8}$ cycloalkyl, $C_{1-6}$ alkoxy, hydroxyl, hydroxy-$C_{1-6}$ alkyl, amino, $C_{1-6}$ alkylamino, di-$C_{1-6}$ alkylamino, amino-$C_{1-6}$ alkyl, $C_{1-6}$ alkylamino-$C_{1-6}$ alkyl, di-$C_{1-6}$ alkylamino-($C_{1-6}$)alkyl, $C_{1-6}$ alkoxy-$C_{1-6}$ alkyl, heterocyclyl, aryl, heteroaryl, $C_{1-6}$ alkylsulfonyl, $C_{1-6}$ alkylsulfinyl, $C_{1-6}$ alkylthio, arylsulfonyl, heteroarylsulfonyl, arylsulfinyl, heteroarylsulfinyl, arylthio, heteroarylthio, $C_{1-6}$ alkylcarbonyl, arylcarbonyl, heteroarylcarbonyl, $C_{1-6}$ alkylcarbonylamino, arylcarbonylamino, heteroarylcarbonylamino, $C_{1-6}$ alkylcarbamoyl, $C_{3-8}$ cycloalkylcarbamoyl, heterocyclylcarbamoyl, arylcarbamoyl, heteroarylcarbamoyl, $C_{1-6}$ alkylsulfonylamino, arylsulfonylamino, heteroarylsulfonylamino, $C_{1-6}$ alkylsulfamoyl, arylsulfamoyl or heteroarylsulfamoyl, wherein the alkyl, cycloalkyl, heterocyclyl, aryl or heteroaryl may be substituted by a group selected from the group consisting of halogen, optionally halogenated $C_{1-6}$ alkyl, optionally halogenated $C_{1-6}$ alkyloxy, $C_{1-6}$ alkylsulfonyl, carboxyl and cyano.

As a combination of $Y_1$, $Y_2$, $Y_3$ and $Y_4$, specifically, combinations of:
—$CR^6$—, —$CR^7$—, —$CR^8$— and —$CR^9$—;
—N—, —$CR^7$—, —$CR^8$— and —$CR^9$—;
—$CR^6$—, —N—, —$CR^8$— and —$CR^9$—;
—$CR^6$—, —$CR^7$—, —N— and —$CR^9$—; and
—$CR^6$—, —$CR^7$—, —$CR^8$— and —N— are exemplified, and more preferably, a combination of:
—$CR^6$—, —$CR^7$—, —$CR^8$— and —$CR^9$—; or
—$CR^6$—, —$CR^7$—, —N— and —$CR^9$— is recommended.

As specific $R^6$, $R^7$, $R^8$ and $R^9$, each independently, a hydrogen atom, a fluorine atom, a chlorine atom, a bromine atom, cyano, methyl, ethyl, methoxy, phenyl, carboxyphenyl, p-tolyl, pyridyl, methylpyridyl, methoxypyridyl, oxazol, pyrrolyl, imidazolyl, pyrazolyl, triazolyl, tetrazolyl, N-methylpyrazolyl, thienyl, furyl, methylcarbonylamino, ethylcarbonylamino, methylcarbamoyl, difluoroethylcarbamoyl, trifluoroethylcarbamoyl, cyclopentylcarbamoyl, tetrahydrofuranylcarbamoyl, pyrrolidone, pyridone and the like are exemplified.

In the case where $R^6$, $R^7$, $R^8$ and $R^9$ are present with respect to $Y_1$, $Y_2$, $Y_3$ and $Y_4$, that is, in the case where $Y_1$, $Y_2$, $Y_3$ and $Y_4$ are —$CR^6$—, —$CR^7$—, —$CR^8$— and —$CR^9$—, respectively, as $R^6$, $R^7$, $R^8$ and $R^9$, it is recommended that preferably, at least one of $R^6$, $R^7$, $R^8$ and $R^9$ is a group selected from the group consisting of halogen, cyano, $C_{1-6}$ alkyl, $C_{3-8}$ cycloalkyl, $C_{1-6}$ alkoxy, hydroxyl, hydroxy-$C_{1-6}$ alkyl, amino, $C_{1-6}$ alkylamino, di-$C_{1-6}$ alkylamino, amino-$C_{1-6}$ alkyl, $C_{1-6}$ alkylamino-$C_{1-6}$ alkyl, di-$C_{1-6}$ alkylaminoalkyl, $C_{1-6}$ alkoxy-$C_{1-6}$ alkyl, heterocyclyl, aryl, heteroaryl, $C_{1-6}$ alkylsulfonyl, $C_{1-6}$ alkylsulfinyl, $C_{1-6}$ alkylthio, arylsulfonyl, heteroarylsulfonyl, arylsulfinyl, heteroarylsulfinyl, arylthio, heteroarylthio, $C_{1-6}$ alkylcarbonyl, arylcarbonyl, heteroarylcarbonyl, $C_{1-6}$ alkylcarbonylamino, arylcarbonylamino, heteroarylcarbonylamino, $C_{1-6}$ alkylcarbamoyl, $C_{3-8}$ cycloalkylcarbamoyl, heterocyclylcarbamoyl, arylcarbamoyl, heteroarylcarbamoyl, $C_{1-6}$ alkylsulfonylamino, arylsulfonylamino, heteroarylsulfonylamino, $C_{1-6}$ alkylsulfamoyl, arylsulfamoyl and heteroarylsulfamoyl, wherein the aryl or heteroaryl may be substituted by a group selected from the group consisting of halogen, optionally halogenated $C_{1-6}$ alkyl, optionally halogenated $C_{1-6}$ alkyloxy, $C_{1-6}$ alkylsulfonyl, carboxyl and cyano, and the rest are each a hydrogen atom.

As a preferred embodiment of the compound represented by the formula (I), compounds represented by the formula (I-1) are exemplified. In the formula, $R^1$, $R^2$, $R^3$, $Y_1$, $Y_2$, $Y_3$ and $Y_4$ have the same meanings as described above.

[Chemical Formula 6]

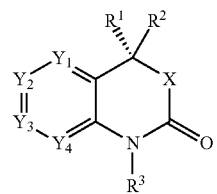

(I-1)

As the compound represented by the formula (I), specifically, the following compounds and the like are exemplified:
[6-chloro-2-oxo-4-(trifluoromethyl)-1,4-dihydro-2H-3,1-benzoxazin-4-yl]methyl(pyridin-3-yl)carbamate;
[6-chloro-2-oxo-4-(trifluoromethyl)-1,4-dihydro-2H-3,1-benzoxazin-4-yl]methyl(cyclopentyl)carbamate;
N-{[6-chloro-2-oxo-4-(trifluoromethyl)-1,4-dihydro-2H-3,1-benzoxazin-4-yl]methyl}-4-fluorobenzamide;
N-{[(4S*)-6-chloro-2-oxo-4-(trifluoromethyl)-1,4-dihydro-2H-3,1-benzoxazin-4-yl]methyl}-4-fluorobenzamide;
N-{2-[6-chloro-2-oxo-4-(trifluoromethyl)-1,4-dihydro-2H-3,1-benzoxazin-4-yl]ethyl}-4-fluorobenzamide;
N-{2-[(4R*)-6-chloro-2-oxo-4-(trifluoromethyl)-1,4-dihydro-2H-3,1-benzoxazin-4-yl]ethyl}-4-fluorobenzamide;
N-{3-[6-chloro-2-oxo-4-(trifluoromethyl)-1,4-dihydro-2H-3,1-benzoxazin-4-yl]propyl}-4-fluorobenzamide;
N-{3-[(4R*)-6-chloro-2-oxo-4-(trifluoromethyl)-1,4-dihydro-2H-3,1-benzoxazin-4-yl]propyl}-4-fluorobenzamide;
N-{[6-chloro-2-oxo-4-(trifluoromethyl)-1,4-dihydro-2H-3,1-benzoxazin-4-yl]methyl}-4-methylbenzamide;
N-{[6-chloro-2-oxo-4-(trifluoromethyl)-1,4-dihydro-2H-3,1-benzoxazin-4-yl]methyl}-5-cyclopropylisoxazole-3-carboxamide;

3-[6-chloro-2-oxo-4-(trifluoromethyl)-1,4-dihydro-2H-3,1-benzoxazin-4-yl]-N-pyridin-3-ylpropanamide;

N-{[6-chloro-2-oxo-4-(trifluoromethyl)-1,4-dihydro-2H-3,1-benzoxazin-4-yl]methyl}pyridine-2-sulfonamide;

N-{[6-chloro-2-oxo-4-(trifluoromethyl)-1,4-dihydro-2H-3,1-benzoxazin-4-yl]methyl}benzenesulfonamide;

N-{2-[6-chloro-2-oxo-4-(trifluoromethyl)-1,4-dihydro-2H-3,1-benzoxazin-4-yl]ethyl}benzenesulfonamide;

N-{3-[6-chloro-2-oxo-4-(trifluoromethyl)-1,4-dihydro-2H-3,1-benzoxazin-4-yl]propyl}pyridine-2-sulfonamide;

N-{3-[(4R*)-6-chloro-2-oxo-4-(trifluoromethyl)-1,4-dihydro-2H-3,1-benzoxazin-4-yl]propyl}pyridine-2-sulfonamide;

N-{2-[6-chloro-2-oxo-4-(trifluoromethyl)-1,4-dihydro-2H-3,1-benzoxazin-4-yl]ethyl}pyridine-2-sulfonamide;

N-{2-[(4R*)-6-chloro-2-oxo-4-(trifluoromethyl)-1,4-dihydro-2H-3,1-benzoxazin-4-yl]ethyl}pyridine-2-sulfonamide;

N-{[6-chloro-2-oxo-4-(trifluoromethyl)-1,4-dihydro-2H-3,1-benzoxazin-4-yl]methyl}-N'-(4-fluorophenyl)urea;

N-{[(4S*)-6-chloro-2-oxo-4-(trifluoromethyl)-1,4-dihydro-2H-3,1-benzoxazin-4-yl]methyl}-N'-(4-fluorophenyl)urea;

N-{[6-chloro-2-oxo-4-(trifluoromethyl)-1,4-dihydro-2H-3,1-benzoxazin-4-yl]methyl}-N'-pyridin-4-ylurea;

4-fluoro-N-{[2-oxo-6-(1H-pyrazol-5-yl)-4-(trifluoromethyl)-1,4-dihydro-2H-3,1-benzoxazin-4-yl]methyl}benzamide;

(4S*)-4-fluoro-N-{[2-oxo-6-(1H-pyrazol-5-yl)-4-(trifluoromethyl)-1,4-dihydro-2H-3,1-benzoxazin-4-yl]methyl}benzamide;

4-fluoro-N-{[6-isoxazol-4-yl-2-oxo-4-(trifluoromethyl)-1,4-dihydro-2H-3,1-benzoxazin-4-yl]methyl}benzamide;

4-fluoro-N-{[2-oxo-6-(1H-pyrazol-4-yl)-4-(trifluoromethyl)-1,4-dihydro-2H-3,1-benzoxazin-4-yl]methyl}benzamide;

(4S*)-4-fluoro-N-{[2-oxo-6-(1H-pyrazol-4-yl)-4-(trifluoromethyl)-1,4-dihydro-2H-3,1-benzoxazin-4-yl]methyl}benzamide;

4-fluoro-N-{[6-(1-methyl-1H-pyrazol-4-yl)-2-oxo-4-(trifluoromethyl)-1,4-dihydro-2H-3,1-benzoxazin-4-yl]methyl}benzamide;

(4S*)-4-fluoro-N-{[6-(1-methyl-1H-pyrazol-4-yl)-2-oxo-4-(trifluoromethyl)-1,4-dihydro-2H-3,1-benzoxazin-4-yl]methyl}benzamide;

4-fluoro-N-{[6-(3-methyl-1H-pyrazol-5-yl)-2-oxo-4-(trifluoromethyl)-1,4-dihydro-2H-3,1-benzoxazin-4-yl]methyl}benzamide;

4-fluoro-N-{[6-(4-methyl-1H-pyrazol-5-yl)-2-oxo-4-(trifluoromethyl)-1,4-dihydro-2H-3,1-benzoxazin-4-yl]methyl}benzamide;

4-fluoro-N-{[2-oxo-6-(1H-pyrrol-2-yl)-4-(trifluoromethyl)-1,4-dihydro-2H-3,1-benzoxazin-4-yl]methyl}benzamide;

4-fluoro-N-{[6-(2-furyl)-2-oxo-4-(trifluoromethyl)-1,4-dihydro-2H-3,1-benzoxazin-4-yl]methyl}benzamide;

4-fluoro-N-{[6-(2-thienyl)-2-oxo-4-(trifluoromethyl)-1,4-dihydro-2H-3,1-benzoxazin-4-yl]methyl}benzamide;

4-fluoro-N-{[2-oxo-6-(1H-pyrazol-3-yl)-4-(trifluoromethyl)-1,4-dihydro-2H-3,1-benzoxazin-4-yl]methyl}benzenesulfonamide;

4-fluoro-N-{[(4S*)-2-oxo-6-(1H-pyrazol-3-yl)-4-(trifluoromethyl)-1,4-dihydro-2H-3,1-benzoxazin-4-yl]methyl}benzenesulfonamide;

N-{[2-oxo-6-(1H-pyrazol-3-yl)-4-(trifluoromethyl)-1,4-dihydro-2H-3,1-benzoxazin-4-yl]methyl}pyridine-2-sulfonamide;

N-{[(4S*)-2-oxo-6-(1H-pyrazol-3-yl)-4-(trifluoromethyl)-1,4-dihydro-2H-3,1-benzoxazin-4-yl]methyl}pyridine-2-sulfonamide;

4-fluoro-N-({2-oxo-4-(trifluoromethyl)-6-[3-(trifluoromethyl)-1H-pyrazol-5-yl]-1,4-dihydro-2H-3,1-benzoxazin-4-yl}methyl)benzamide;

4-fluoro-N-{[2-oxo-6-(2-oxopyrrolidin-1-yl)-4-(trifluoromethyl)-1,4-dihydro-2H-3,1-benzoxazin-4-yl]methyl}benzamide;

(4S*)-4-fluoro-N-{[2-oxo-6-(2-oxopyrrolidin-1-yl)-4-(trifluoromethyl)-1,4-dihydro-2H-3,1-benzoxazin-4-yl]methyl}benzamide;

4-fluoro-N-{[2-oxo-6-(propionylamino)-4-(trifluoromethyl)-1,4-dihydro-2H-3,1-benzoxazin-4-yl]methyl}benzamide;

4-fluoro-N-{[2-oxo-6-(1H-1,2,4-triazol-5-yl)-4-(trifluoromethyl)-1,4-dihydro-2H-3,1-benzoxazin-4-yl]methyl}benzamide;

N-{[6-(benzoylamino)-2-oxo-4-(trifluoromethyl)-1,4-dihydro-2H-3,1-benzoxazin-4-yl]methyl}-4-fluorobenzamide;

4-fluoro-N-{[2-oxo-6-(2-oxo-1,3-oxazolidin-3-yl)-4-(trifluoromethyl)-1,4-dihydro-2H-3,1-benzoxazin-4-yl]methyl}benzamide;

4-fluoro-N-{[(4S*)-2-oxo-6-(2-oxo-1,3-oxazolidin-3-yl)-4-(trifluoromethyl)-1,4-dihydro-2H-3,1-benzoxazin-4-yl]methyl}benzamide;

4-fluoro-N-{[6-(3-methyl-2-oxazolidin-1-yl)-2-oxo-4-(trifluoromethyl)-1,4-dihydro-2H-3,1-benzoxazin-4-yl]methyl}benzamide;

4-fluoro-N-{[2-oxo-6-(2-oxopyridin-1(2H)-yl)-4-(trifluoromethyl)-1,4-dihydro-2H-3,1-benzoxazin-4-yl]methyl}benzamide;

4-fluoro-N-{[2-oxo-6-(1H-pyrazol-1-yl)-4-(trifluoromethyl)-1,4-dihydro-2H-3,1-benzoxazin-4-yl]methyl}benzamide;

4-fluoro-N-{[(4S*)-2-oxo-6-(1H-pyrazol-1-yl)-4-(trifluoromethyl)-1,4-dihydro-2H-3,1-benzoxazin-4-yl]methyl}benzamide;

4-fluoro-N-{[6-(4-methyl-1H-pyrazol-1-yl)-2-oxo-4-(trifluoromethyl)-1,4-dihydro-2H-3,1-benzoxazin-4-yl]methyl}benzamide;

4-fluoro-N-{[6-(3-methyl-1H-pyrazol-1-yl)-2-oxo-4-(trifluoromethyl)-1,4-dihydro-2H-3,1-benzoxazin-4-yl]methyl}benzamide;

N-{[6-(3-amino-1H-pyrazol-1-yl)-2-oxo-4-(trifluoromethyl)-1,4-dihydro-2H-3,1-benzoxazin-4-yl]methyl}-4-fluorobenzamide;

4-fluoro-N-{[2-oxo-4-(trifluoromethyl)-6-[3-(trifluoromethyl)-1H-pyrazol-1-yl]-1,4-dihydro-2H-3,1-benzoxazin-4-yl]methyl}benzamide;

4-fluoro-N-{[6-[(3S)-3-hydroxy-2-oxopyrrolidin-1-yl]-2-oxo-4-(trifluoromethyl)-1,4-dihydro-2H-3,1-benzoxazin-4-yl]methyl}benzamide;

4-fluoro-N-{[2-oxo-6-(1H-pyrazol-5-yl)-4-(trifluoromethyl)-1,2,3,4-tetrahydroquinazolin-4-yl]methyl}benzamide;

4-fluoro-N-{[(4S*)-2-oxo-6-(1H-pyrazol-5-yl)-4-(trifluoromethyl)-1,2,3,4-tetrahydroquinazolin-4-yl]methyl}benzamide;

N-{[6-chloro-2-oxo-4-(trifluoromethyl)-1,2,3,4-tetrahydroquinazolin-4-yl]methyl}4-fluorobenzamide;

N-{[(4S*)-6-chloro-2-oxo-4-(trifluoromethyl)-1,2,3,4-tetrahydroquinazolin-4-yl]methyl}4-fluorobenzamide;

4-fluoro-N-{[2-oxo-6-(1H-pyrazol-4-yl)-4-(trifluoromethyl)-1,2,3,4-tetrahydroquinazolin-4-yl]methyl}benzamide;

N-{[2-oxo-4-(trifluoromethyl)-1,4-dihydro-2H-3,1-benzoxazin-4-yl]methyl}benzamide;
4-fluoro-N-{[2-oxo-4-(trifluoromethyl)-1,4-dihydro-2H-3,1-benzoxazin-4-yl]methyl}benzamide;
4-fluoro-N-{[6-methyl-2-oxo-4-(trifluoromethyl)-1,4-dihydro-2H-3,1-benzoxazin-4-yl]methyl}benzamide;
N-{[2-oxo-6-(1H-pyrazol-4-yl)-4-(trifluoromethyl)-1,4-dihydro-2H-3,1-benzoxazin-4-yl]methyl}pyridine-2-sulfonamide;
N-bicyclo[2.2.1]heptan-2-yl-4-{[(4-fluorobenzoyl)amino]methyl}-2-oxo-4-(trifluoromethyl)-1,4-dihydro-2H-3,1-benzoxazine-6-carboxamide; and
4-fluoro-N-{[2-oxo-6-(3-phenyl-1H-pyrazol-5-yl)-4-(trifluoromethyl)-1,4-dihydro-2H-3,1-benzoxazin-4-yl]methyl}benzamide.

Method for Producing Compound Represented by Formula (I)

The compound represented by the formula (I) can be prepared by the following method.

Production Method 1

Production Method 1 is a method for producing a compound represented by the formula (I-Ia).

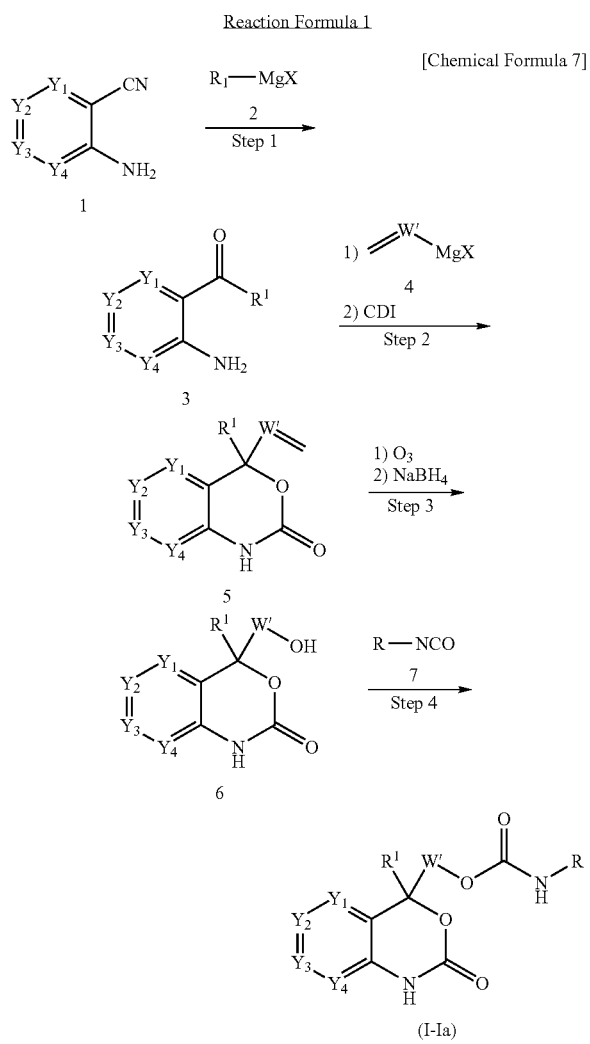

[In the formula, W' represents W or protected W and is particularly preferably $C_{1-6}$ alkylene, and other symbols have the same meanings as described above.]

Step 1

Compound 1 and Compound 2 are subjected to a Grignard reaction in a reaction solvent, whereby Compound 3 is obtained. As the used amount of the Compound 2, an amount of from 1 to 10 moles per mole of the Compound 1 is exemplified, and preferably, an amount of from 1 to 2 moles per mole of the Compound 1 is recommended.

As the reaction solvent, diethyl ether, tetrahydrofuran (hereinafter referred to as "THF"), 1,4-dioxane (hereinafter referred to as "dioxane"), N,N-dimethylformamide (hereinafter referred to as "DMF") and the like are exemplified.

As the reaction temperature, a temperature of from 0 to 100° C. is exemplified, and generally, the reaction is completed in 1 to 24 hours. After the reaction, an acid is added to the reaction solution to stop the reaction, and Compound 3 is obtained.

The Compound 3 can be isolated and purified by a known separation and purification method such as concentration, concentration in vacuo, crystallization, solvent extraction, reprecipitation or chromatography (the same shall apply to the following reactions).

As the Compound 2, for example, methyl magnesium bromide and the like are exemplified. Further, as the Compound 1, for example, 2-amino-5-chloro-benzonitrile and the like are exemplified.

Step 2

The Compound 3 and Compound 4 are subjected to a Grignard reaction to obtain a product, and the obtained compound is reacted with carbonyldiimidazole (hereinafter referred to as "CDI"), whereby Compound 5 is obtained.

As the Compound 4, vinyl magnesium bromide and the like are exemplified.

The Grignard reaction can be carried out according to Step 1.

In the reaction of the obtained compound with CDI, as the used amount of CDI, an amount of from 1 to 5 moles per mole of the Compound 3 is exemplified, and preferably, an amount of from 1 to 3 moles per mole of the Compound 3 is recommended.

As the reaction solvent, methylene chloride, chloroform, diethyl ether, THF, dioxane and the like are exemplified.

As the reaction temperature, a temperature of from 0 to 80° C. is exemplified, and generally, the reaction is completed in 1 to 24 hours.

Incidentally, instead of CDI, for example, triphosgene or the like can also be used.

Step 3

The Compound 5 is subjected to ozonolysis, and the resulting product is reduced, whereby Compound 6 is obtained. The ozonolysis of the Compound 5 is carried out by passing ozone through a solution of the Compound 5 in dichloromethane, chloroform, methanol, ethanol, or the like or a mixed solvent thereof.

As the reaction temperature, a temperature of from −78 to 0° C. is exemplified, and generally, the reaction is completed in 1 to 24 hours. After ozone is removed from the resulting reaction solution by nitrogen replacement or the like, sodium borohydride is added to the reaction system to effect reduction, whereby Compound 6 is obtained.

As the used amount of sodium borohydride, an amount of from 1 to 10 moles per mole of the Compound 5 is exemplified, and preferably, an amount of from 1 to 3 moles per mole of the Compound 5 is recommended.

As the reaction temperature, a temperature of from 0 to 20° C. is exemplified, and generally, the reaction is completed in 0.1 to 1 hour.

Step 4

The Compound 6 and Compound 7 are condensed, whereby a compound represented by the formula (I-1a) is obtained. As the used amount of the Compound 7, an amount of from 1 to 3 moles per mole of the Compound 6 is exemplified, and preferably, an amount of from 1 to 2 moles per mole of the Compound 6 is recommended.

As the reaction solvent, methylene chloride, chloroform, diethyl ether, THF, dioxane, DMF and the like are exemplified.

As the reaction temperature, a temperature of from 0 to 80° C. is exemplified, and generally, the reaction is completed in 1 to 24 hours.

Incidentally, as the Compound 7, for example, 4-fluorophenylisocyanate and the like are exemplified.

The thus obtained compound represented by the formula (I-1a) can be isolated and purified by a known separation and purification method such as concentration, concentration in vacuo, crystallization, solvent extraction, reprecipitation or chromatography (the same shall apply to the following reactions).

Production Method 2

Production Method 2 is an alternative synthetic method of the Compound 3 using Compound 8 as a raw material.

Further, Production Method 2 can also be carried out according to a known method (J. Org. Chem. 1998, 63, 8536) or the like.

Reaction Formula 2

[Chemical Formula 8]

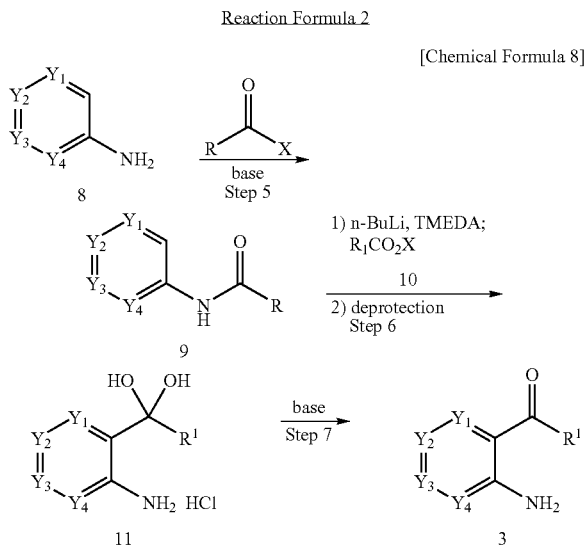

[In the formula, each symbol has the same meaning as described above.]

Step 5

In a reaction solvent, Compound 8 is reacted with an acid halide or an acid anhydride in the presence of a base, whereby Compound 9 is obtained. As the acid halide or acid anhydride, pivaloyl chloride, di-t-butyl dicarbonate and the like are exemplified, and as the used amount of the acid halide or acid anhydride, an amount of from 1 to 5 moles per mole of the Compound 8 is exemplified, and preferably, an amount of from 1 to 2 moles per mole of the Compound 8 is recommended.

As the base, sodium hydroxide, potassium hydroxide, sodium carbonate, potassium carbonate, sodium methoxide, sodium ethoxide and the like are exemplified, and as the used amount of the base, an amount of from 1 to 3 moles per mole of the Compound 8 is exemplified, and preferably, an amount of from 1 to 2 moles per mole of the Compound 8 is recommended.

As the reaction solvent, THF, dioxane, t-butyl methyl ether or a mixed solvent thereof is exemplified.

As the reaction temperature, a temperature of from 0 to 50° C. is exemplified, and generally, the reaction is completed in 1 to 24 hours.

As the Compound 8, 4-chloroaniline and the like are exemplified.

Step 6

The Compound 9 is treated with a base in a reaction solvent, and thereafter, the resulting product is reacted with Compound 10, followed by deprotection, whereby Compound 11 is obtained.

That is, to a THF solution of the Compound 9, n-butyl lithium and tetramethylethylenediamine (hereinafter referred to as "TMEDA") is added, and a reaction is allowed to proceed at −20 to 0° C. for about 30 minutes. Then, the Compound 10 is added thereto, and a reaction is allowed to proceed at −78 to 0° C. for 1 to 10 hours. To the resulting product, an acid is added, and the mixture is stirred at 0 to 50° C. for 0.1 to 2 hours to effect deprotection, whereby Compound 11 is obtained.

As the Compound 10, ethyl trifluoroacetate and the like are exemplified.

As the acid, sulfuric acid, nitric acid, acetic acid or a mixture thereof is exemplified, and as the used amount thereof, an amount of from 5 to 100 moles per mole of the Compound 9 is exemplified.

Step 7

The Compound 11 is treated with a base in a reaction solvent, whereby the Compound 3 is obtained.

As the base, sodium hydroxide, sodium acetate, sodium carbonate, potassium carbonate, sodium methoxide, sodium ethoxide and the like are exemplified, and as the used amount of the base, an amount of from 1 to 10 moles per mole of the Compound 11 is exemplified, and preferably, an amount of from 1 to 3 moles per mole of the Compound 11 is recommended.

As the reaction solvent, an ether solvent such as THF, dioxane, t-butyl methyl ether or water, or a mixed solvent thereof is exemplified.

As the reaction temperature, a temperature of from 0 to 50° C. is exemplified, preferably, a temperature of from 0 to 30° C. is recommended, and generally, the reaction is completed in 0.1 to 1 hour.

The thus obtained Compound 3 can be isolated and purified by a known separation and purification method such as concentration, concentration in vacuo, crystallization, solvent extraction, reprecipitation or chromatography.

Production Method 3

Production Method 3 is a method for producing a compound represented by the formula (I-1b).

Reaction Formula 3

[Chemical Formula 9]

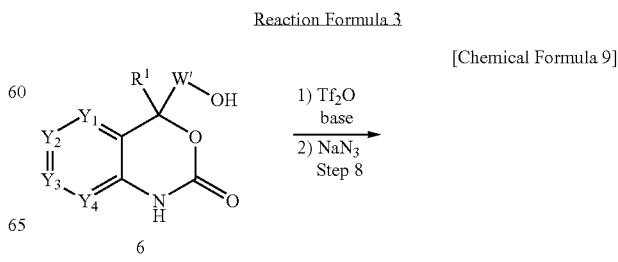

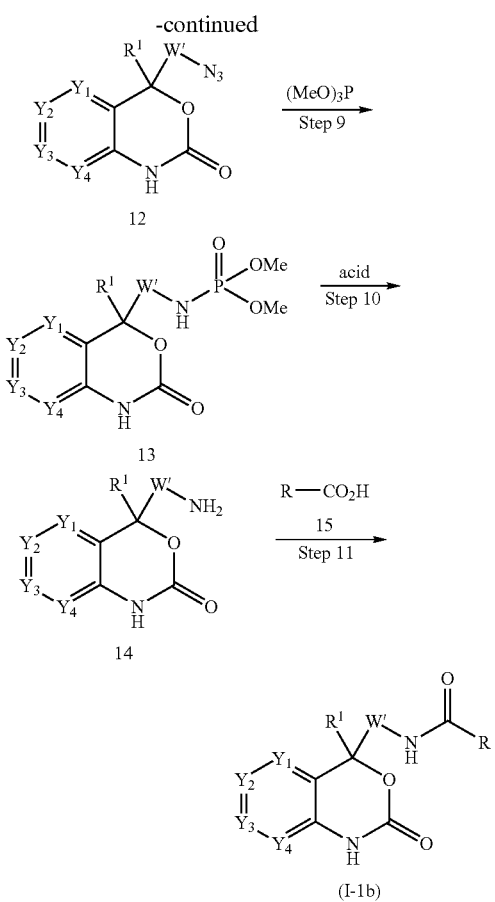

[In the formula, each symbol has the same meaning as described above.]

Step 8

In a reaction solvent, the Compound 6 is reacted with trifluoromethanesulfonic anhydride in the presence of a base, and thereafter, the resulting product is reacted with sodium azide, whereby Compound 12 is obtained.

As the used amount of trifluoromethanesulfonic anhydride, an amount of from 1 to 5 moles per mole of the Compound 6 is exemplified, and preferably, an amount of from 1 to 3 moles per mole of the Compound 6 is recommended.

As the base, triethylamine, diisopropylethylamine, 2,6-lutidine, pyridine and the like are exemplified, and as the used amount of the base, an amount of from 1 to 10 moles, preferably from 1 to 5 moles per mole of the Compound 6 is exemplified.

As the reaction solvent, methylene chloride, chloroform, diethyl ether, THF, DMF and the like are exemplified.

As the reaction temperature, a temperature of from 0 to 60° C. is exemplified, preferably, a temperature of from 0 to 30° C. is recommended, and generally, the reaction is completed in 1 to 3 hours.

The resulting intermediate can be used in the subsequent reaction as such, however, the subsequent reaction may be carried out after the intermediate is isolated and purified.

That is, the resulting intermediate is reacted with sodium azide in a reaction solvent, whereby Compound 12 is obtained. As the used amount of sodium azide, an amount of from 1 to 10 moles per mole of the Compound 6 is exemplified, and preferably, an amount of from 1 to 5 moles per mole of the Compound 6 is recommended.

As the reaction solvent, methylene chloride, chloroform, diethyl ether, THF, DMF and the like are exemplified.

As the reaction temperature, a temperature of from 0 to 100° C. is exemplified, preferably, a temperature of from 0 to 80° C. is recommended, and generally, the reaction is completed in 6 to 24 hours.

Step 9

The Compound 12 is reacted with trimethyl phosphite in a reaction solvent, whereby Compound 13 is obtained.

As the used amount of trimethyl phosphite, an amount of from 1 to 3 moles per mole of the Compound 12 is exemplified, and preferably, an amount of from 1 to 1.5 moles per mole of the Compound 12 is recommended.

As the reaction solvent, THF, dioxane, a THF-water mixed solvent and the like are exemplified.

As the reaction temperature, a temperature of from 0 to 100° C. is exemplified, preferably, a temperature of from 0 to 80° C. is recommended, and generally, the reaction is completed in 1 to 24 hours.

Step 10

The Compound 13 is treated with an acid, whereby Compound 14 is obtained. As the acid, a 4 N hydrochloric acid/dioxane and the like are exemplified.

As the used amount of the acid, an amount of from 10 to 100 moles per mole of the Compound 13 is exemplified.

As the reaction temperature, a temperature of from 0 to 100° C. is exemplified, preferably, a temperature of from 25 to 80° C. is recommended, and generally, the reaction is completed in 6 to 24 hours.

Step 11

The Compound 14 and Compound 15 are condensed, whereby a compound represented by the formula (I-1b) is obtained.

The condensation can be carried out by a conventionally known method, and a method in which the Compound 14 is reacted with the Compound 15 in the presence of a condensing agent, a method in which the carboxylic acid moiety of the Compound 15 is activated by a conventionally known method to form a reactive derivative and then, the derivative and the Compound 14 are amidated and the like are exemplified (see "Pepuchido Gosei no Kiso to Jikken", Nobuo Izumiya, et al., Maruzen Co., Ltd., 1983).

As the reaction using a condensing agent, for example, the following method is exemplified.

That is, the Compound 15 and the Compound 14 are condensed using a condensing agent in a reaction solvent, whereby a compound represented by the formula (I-1b) is obtained.

As the used amount of the Compound 15, an amount of from 1 to 3 moles per mole of the Compound 14 is exemplified.

As the condensing agent, dicyclohexylcarbodiimide, 1-ethyl-3-(3-dimethylaminopropyl)-carbodiimide and the like are exemplified, and as the used amount of the condensing agent, an amount of from 1 to 3 moles per mole of the Compound 14 is exemplified.

Further, for the purpose of accelerating the reaction, hydroxybenzotriazole (hereinafter referred to as "HOBT") or the like may be added to the reaction system. As the used amount of HOBT, an amount of from 1 to 3 moles per mole of the Compound 14 is exemplified.

As the reaction solvent, THF, dioxane, DMF, DMSO, dichloromethane or a mixed solvent thereof is exemplified.

As the reaction temperature, a temperature of from 20 to 100° C. is exemplified, preferably, a temperature of from 20 to 50° C. is recommended, and generally, the reaction is completed in 1 to 24 hours.

As the Compound 15, 4-fluorobenzoic acid and the like are exemplified.

The thus obtained compound represented by the formula (I-1b) can be isolated and purified by a known separation and purification method such as concentration, concentration in vacuo, crystallization, solvent extraction, reprecipitation or chromatography.

Production Method 4

Production Method 4 is a method for producing a compound represented by the formula (I-1c).

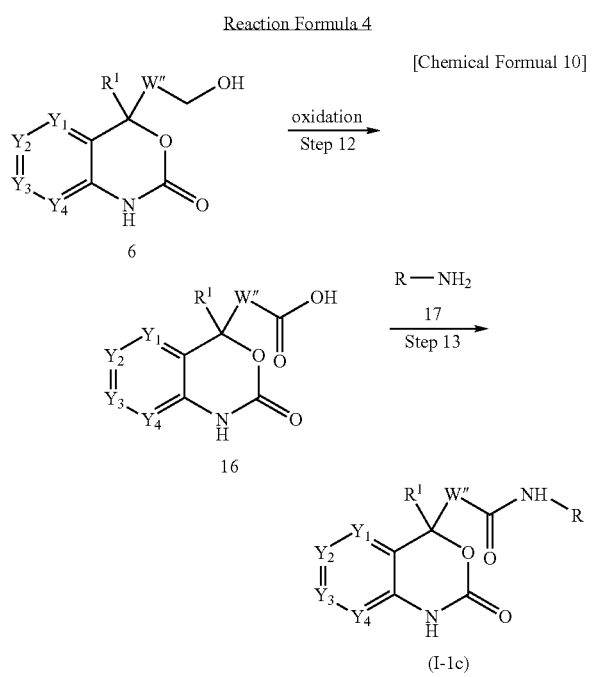

[In the formula, W" has the same meaning as W' and is particularly preferably C$_{1-5}$ alkylene, and other symbols have the same meanings as described above.]

Step 12

The Compound 6 is oxidized in a reaction solvent, whereby Compound 16 is obtained. The oxidation method is not particularly limited, however, for example, the oxidation can be carried out using chromic acid/concentrated sulfuric acid.

As the used amount of chromic acid, an amount of from 1 to 3 moles per mole of the Compound 6 is exemplified, and as the used amount of concentrated sulfuric acid, an amount of from 1 to 20 moles per mole of the Compound 6 is exemplified.

As the reaction solvent, an acetone-water mixed solvent is exemplified.

As the reaction temperature, a temperature of from 0 to 50° C. is exemplified, preferably, a temperature of from 0 to 30° C. is recommended, and generally, the reaction is completed in 1 to 24 hours.

Step 13

The Compound 16 and Compound 17 are condensed, whereby a compound represented by the formula (I-1c) is obtained. The condensation method is not particularly limited, however, for example, the condensation can be carried out according to Step 11.

The thus obtained compound represented by the formula (I-1c) can be isolated and purified by a known separation and purification method such as concentration, concentration in vacuo, crystallization, solvent extraction, reprecipitation or chromatography.

Production Method 5

Production Method 5 is a method for producing a compound represented by the formula (I-1d) or (I-1e).

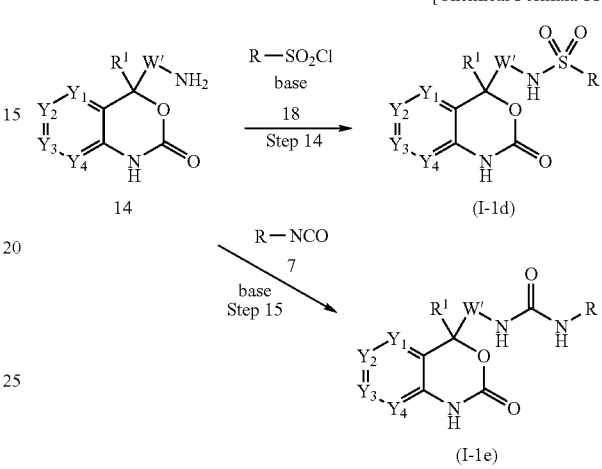

[In the formula, each symbol has the same meaning as described above.]

Step 14

The Compound 14 is reacted with Compound 18 in a reaction solvent in the presence of a base, whereby a compound represented by the formula (I-1d) is obtained.

As the used amount of the Compound 18, an amount of from 1 to 5 moles per mole of the Compound 14 is exemplified, and preferably, an amount of from 1 to 3 moles per mole of the Compound 14 is recommended.

As the base, triethylamine, diisopropylethylamine, 2,6-lutidine, pyridine and the like are exemplified, and as the used amount of the base, an amount of from 1 to 10 moles, preferably from 1 to 5 moles per mole of the Compound 14 is exemplified.

As the reaction solvent, THF, dioxane, DMF, DMSO, dichloromethane, or a mixed solvent thereof is exemplified.

As the reaction temperature, a temperature of from 0 to 60° C. is exemplified, preferably, a temperature of from 0 to 30° C. is recommended, and generally, the reaction is completed in 1 to 24 hours.

Step 15

The Compound 14 is reacted with the Compound 7 in a reaction solvent in the presence of a base, whereby a compound represented by the formula (I-1e) is obtained.

As the used amount of the Compound 7, an amount of from 1 to 5 moles per mole of the Compound 14 is exemplified, and preferably, 1 to 3 moles per mole of the Compound 14 is recommended.

As the base, triethylamine, diisopropylethylamine, 2,6-lutidine, pyridine and the like are exemplified, and as the used amount of the base, an amount of from 1 to 10 moles, preferably from 1 to 5 moles per mole of the Compound 14 is exemplified.

As the reaction solvent, THF, dioxane, DMF, DMSO, dichloromethane, or a mixed solvent thereof is exemplified.

As the reaction temperature, a temperature of from 0 to 50° C. is exemplified, preferably, a temperature of from 0 to 30° C. is recommended, and generally, the reaction is completed in 1 to 24 hours.

As the Compound 18, benzenesulfonyl chloride and the like are exemplified.

The thus obtained compound represented by the formula (I-1d) or (I-1e) can be isolated and purified by a known separation and purification method such as concentration, concentration in vacuo, crystallization, solvent extraction, reprecipitation or chromatography.

Production Method 6

Production Method 6 is a method for producing a compound having any of substituents $R^6$ to $R^9$ in the formula (I).

Reaction Formula 6

[Chemical Formula 12]

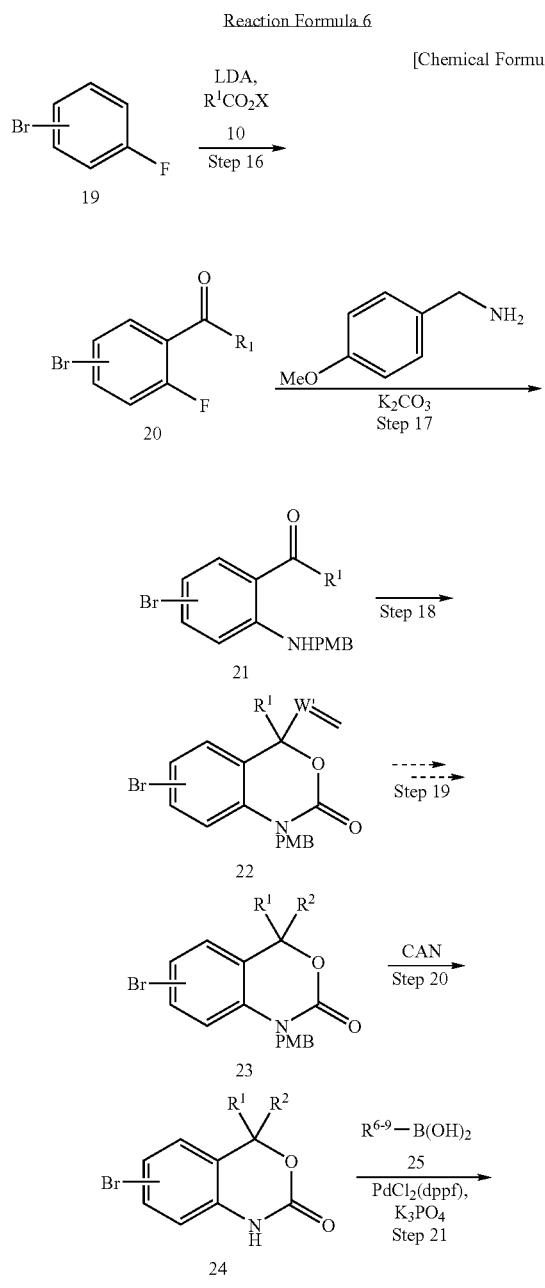

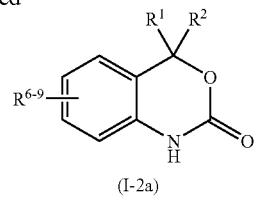

(I-2a)

[In the formula, $R^{6-9}$ means any of $R^6$ to $R^9$, and other symbols have the same meanings as described above.]

Step 16

Compound 19 is reacted with the Compound 10 in a reaction solvent in the presence of a base, whereby Compound 20 is obtained. As the used amount of the Compound 10, an amount of from 1 to 5 moles per mole of the Compound 19 is exemplified, and preferably, an amount of from 1 to 3 moles per mole of the Compound 19 is recommended.

Further, as the base, lithium diisopropylamide and the like are exemplified, and as the used amount of the base, an amount of from 1 to 5 moles is exemplified, and preferably, an amount of from 1 to 2 moles per mole of the Compound 19 is recommended.

As the reaction solvent, THF, diethyl ether, DMF and the like are exemplified.

As the reaction temperature, a temperature of from −78 to 100° C. is exemplified, preferably, a temperature of from −78 to 0° C. is recommended, and generally, the reaction is completed in 1 to 24 hours.

Step 17

The Compound 20 is reacted with 4-methoxybenzylamine in a reaction solvent in the presence of a base, whereby Compound 21 is obtained.

As the used amount of 4-methoxybenzylamine, an amount of from 1 to 10 moles per mole of the Compound 20 is exemplified, and preferably, an amount of from 1 to 5 moles per mole of the Compound 20 is recommended.

Further, as the base, potassium carbonate, triethylamine and the like are exemplified, and as the used amount of the base, an amount of from 1 to 10 moles is exemplified, and preferably, an amount of from 1 to 5 moles per mole of the Compound 20 is recommended.

As the reaction solvent, toluene, xylene and the like are exemplified.

As the reaction temperature, a temperature of from 0 to 100° C. is exemplified, preferably, a temperature of from 50 to 100° C. is recommended, and generally, the reaction is completed in 1 to 24 hours.

Step 18

The Compound 21 is subjected to a reaction according to Step 2, whereby Compound 22 is obtained. The reaction condition is according to Step 2.

Step 19

According to the Production Method 1 or by combining thereof using the Compound 22, Compound 23 is obtained.

Step 20

The Compound 23 is reacted with cerium ammonium nitrate (CAN) in a reaction solvent, whereby Compound 24 is obtained.

As the used amount of CAN, an amount of from 1 to 10 moles is exemplified, and preferably, an amount of from 1 to 5 moles per mole of the Compound 23 is recommended.

As the reaction solvent, an acetonitrile-water mixed solvent is exemplified.

As the reaction temperature, a temperature of from 0 to 100° C. is exemplified, preferably, a temperature of from 0 to 50° C. is recommended, and generally, the reaction is completed in 1 to 24 hours.

Step 21

The Compound 24 is reacted with Compound 25 in the presence of a palladium chloride-1,1-bis(diphenylphosphino)ferrocene complex and a base, whereby a compound represented by the formula (I-2a) is obtained.

As the used amount of the Compound 25, an amount of from 1 to 5 moles is exemplified, and preferably, an amount of from 2 to 4 moles per mole of the Compound 24 is recommended.

As the used amount of the palladium chloride-1,1-bis (diphenylphosphino)ferrocene complex, an amount of from 0.1 to 1.0 moles is exemplified, and preferably, an amount of from 0.1 to 0.3 moles per mole of the Compound 24 is recommended.

As the base, potassium phosphate, potassium carbonate, sodium hydrogen carbonate and the like are exemplified, and as the used amount of the base in this case, an amount of from 1 to 5 moles per mole of the Compound 24 is exemplified.

Further, the reaction is preferably carried out under microwave irradiation.

As the reaction solvent, a DMF-water mixed solvent is exemplified.

As the reaction temperature, a temperature of from 20 to 150° C. is exemplified, preferably, a temperature of from 80 to 120° C. is recommended, and generally, the reaction is completed in 1 to 24 hours.

Incidentally, as the Compound 25, for example, 3-pyrazole boronic acid and the like are exemplified.

The thus obtained compound represented by the formula (I-2a) can be isolated and purified by a known separation and purification method such as concentration, concentration in vacuo, crystallization, solvent extraction, reprecipitation or chromatography.

Production Method 7

Production Method 7 is an alternative production method of a compound having any of various substituents as $R^6$ to $R^9$ in the formula (I).

Reaction Formula 7

[Chemical Formula 13]

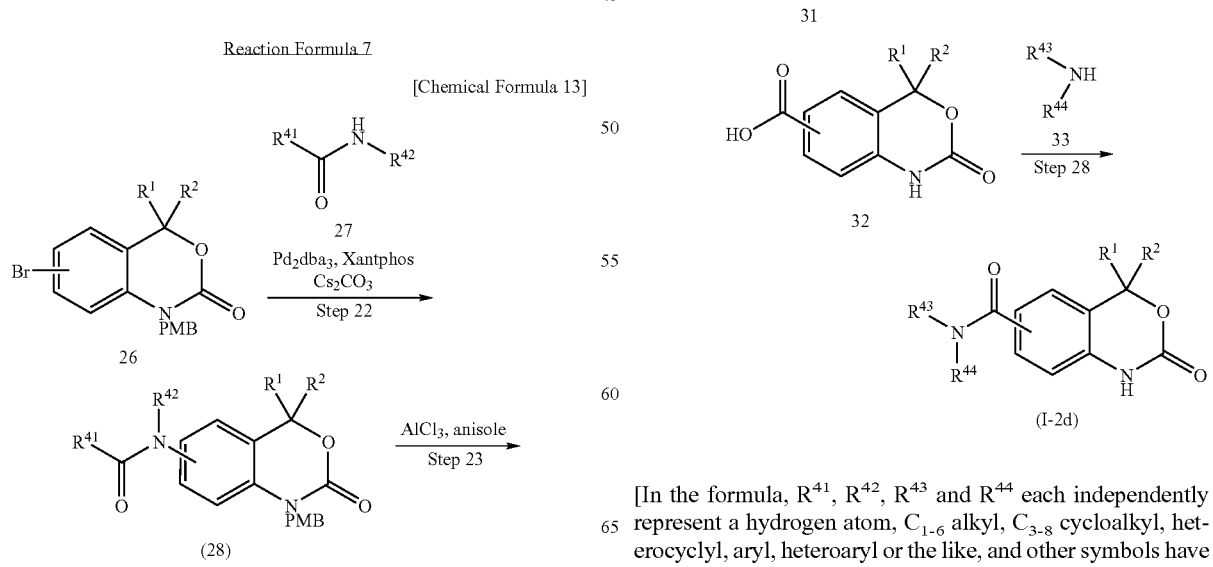

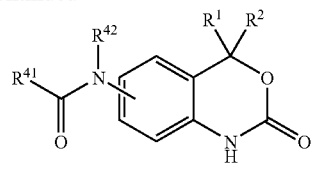

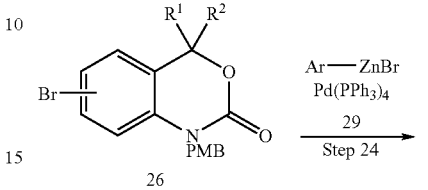

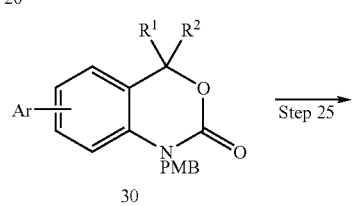

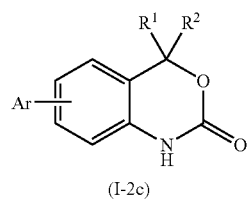

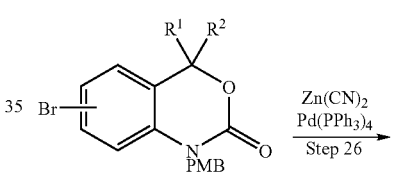

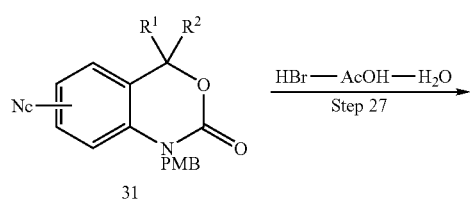

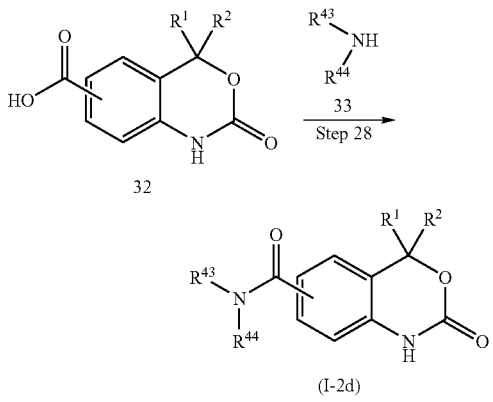

[In the formula, $R^{41}$, $R^{42}$, $R^{43}$ and $R^{44}$ each independently represent a hydrogen atom, $C_{1-6}$ alkyl, $C_{3-8}$ cycloalkyl, heterocyclyl, aryl, heteroaryl or the like, and other symbols have the same meanings as described above.]

Step 22

Compound 26 is reacted with Compound 27 in the presence of cesium carbonate, xantphos and tris(dibenzylideneacetone)dipalladium, whereby Compound 28 is obtained.

As the used amount of the Compound 27, an amount of from 1 to 10 moles is exemplified, and preferably, an amount of from 1 to 5 moles per mole of the Compound 26 is recommended.

As the used amount of xantphos and as the used amount of tris(dibenzylideneacetone)dipalladium, an amount of from 0.01 to 1 mole per mole of the Compound 26 is exemplified respectively.

Further, as the used amount of cesium carbonate, an amount of from 1 to 10 moles is exemplified, and preferably, an amount of from 1 to 3 moles per mole of the Compound 26 is recommended.

As the reaction solvent, DMF, THF, dioxane and the like are exemplified. As the reaction temperature, a temperature of from 30 to 150° C. is exemplified, preferably, a temperature of from 60 to 120° C. is recommended, and generally, the reaction is completed in 1 to 24 hours.

As the Compound 27, 2-pyrrolidinone and the like are exemplified.

Step 23

The p-methoxybenzyl group of the Compound 28 is deprotected, whereby a compound represented by the formula (I-2b) is obtained. The deprotection is carried out by treating the Compound 28 with aluminum chloride in a reaction solvent in the presence of anisole.

As the used amount of aluminum chloride, an amount of from 1 to 20 moles is exemplified, and preferably, an amount of from 5 to 15 moles per mole of the Compound 28 is recommended.

Further, as the used amount of anisole, an amount of from 5 to 50 moles is exemplified, and preferably, an amount of from 10 to 20 moles per mole of the Compound 28 is recommended.

In this reaction, anisole can also be used as the reaction solvent, however, a solvent such as dichloroethane may be used.

As the reaction temperature, a temperature of from 20 to 150° C. is exemplified, preferably, a temperature of from 60 to 120° C. is recommended, and generally, the reaction is completed in 1 to 24 hours.

Step 24

The Compound 26 is reacted with Compound 29 in a reaction solvent in the presence of tetrakis(triphenylphosphine)palladium, whereby Compound 30 is obtained.

As the used amount of tetrakis(triphenylphosphine)palladium, an amount of from 0.01 to 1 mole is exemplified, and preferably, an amount of from 0.01 to 0.2 moles per mole of the Compound 26 is recommended.

Further, as the used amount of the Compound 29, an amount of from 1 to 10 moles is exemplified, and preferably, an amount of from 1 to 5 moles per mole of the Compound 26 is recommended.

As the reaction solvent, DMF, THF, dioxane and the like are exemplified.

As the reaction temperature, a temperature of from 20 to 150° C. is exemplified, preferably, a temperature of from 50 to 100° C. is recommended, and generally, the reaction is completed in 1 to 24 hours.

As the Compound 29, (1H-imidazol-2-yl)zinc bromide and the like are exemplified.

Step 25

The p-methoxybenzyl group of the Compound 30 is deprotected by the method described in Protective Groups in Organic Synthesis mentioned below, whereby a compound represented by the formula (I-2c) is obtained.

Step 26

The Compound 26 is reacted with zinc cyanide in a reaction solvent such as DMF in the presence of tetrakis(triphenylphosphine)palladium, whereby Compound 31 is obtained. The reaction condition is according to Step 17.

Step 27

The cyano group of the Compound 31 is hydrolyzed by hydrogen bromide, whereby Compound 32 is obtained.

As the used amount of hydrogen bromide, an amount of from 1 to 20 moles per mole of the Compound 31 is exemplified. As the reaction temperature, a temperature of from 50 to 150° C. is exemplified, preferably, a temperature of from 50 to 100° C. is recommended, and generally, the reaction is completed in 1 to 24 hours.

Step 28

The Compound 32 and Compound 33 are amidated according to Step 13, whereby a compound represented by the formula (I-2d) is obtained. The amidation method can be carried out according to Step 11.

As the Compound 33, 4-fluoroaniline and the like are exemplified.

The thus obtained compounds represented by the formulae (I-2b), (I-2c) and (I-2d) can be isolated and purified by a known separation and purification method such as concentration, concentration in vacuo, crystallization, solvent extraction, reprecipitation or chromatography.

Production Method 8

Production Method 8 is an alternative production method of a compound having any of various nitrogen-containing substituent as $R^6$ to $R^9$ in the formula (I).

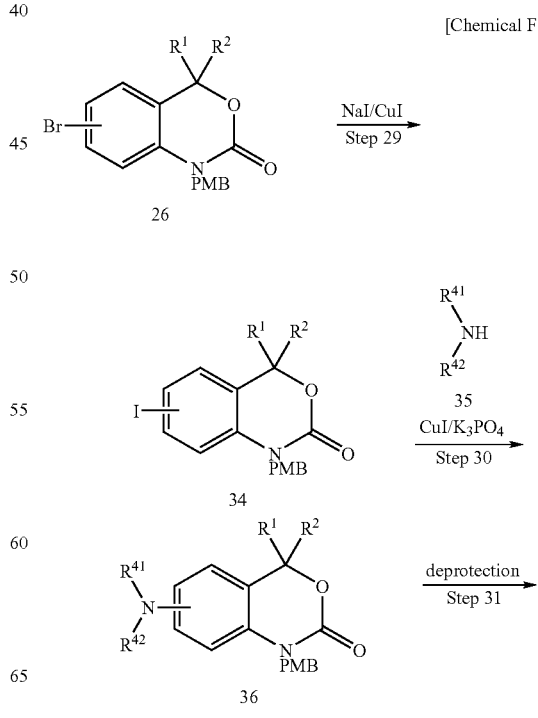

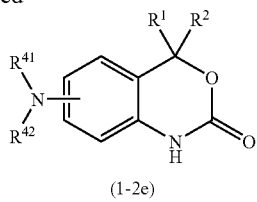

(1-2e)

[In the formula, each symbol has the same meaning as described above.]

Step 29

In a reaction solvent, the Compound 26 is reacted with sodium iodide and copper iodide in the presence of a ligand, whereby Compound 34 is obtained.

As the used amount of sodium iodide, an amount of from 1 to 20 moles, preferably from 1 to 5 moles per mole of the Compound 26 is exemplified, and as the used amount of copper iodide, an amount of from 0.1 to 2 moles, preferably from 0.2 to 1 mole per mole of the Compound 26 is exemplified.

As the ligand, N,N-dimethylenediamine and the like are exemplified, and as the used amount thereof, an amount of from 0.1 to 3 moles is exemplified, and preferably, an amount of from 0.2 to 2 moles per mole of the Compound 26 is recommended.

As the reaction solvent, diethyl ether, THF, dioxane and the like are exemplified.

As the reaction temperature, a temperature of from 20 to 150° C. is exemplified, preferably, a temperature of from 50 to 120° C. is recommended, and generally, the reaction is completed in 1 to 48 hours.

Step 30

In a reaction solvent, the Compound 34 is reacted with a nitrogen-containing compound (Compound 35) in the presence of a ligand, copper iodide and potassium phosphate, whereby Compound 36 is obtained.

As the used amount of copper iodide, an amount of from 0.1 to 2 moles, preferably from 0.1 to 1 mole per mole of the Compound 34 is exemplified, and as the used amount of potassium phosphate, an amount of from 1 to 10 moles, preferably from 1 to 3 moles per mole of the Compound 34 is exemplified.

As the Compound 35, imidazole, triazole, tetrazole, pyrrolidone and the like are exemplified, and as the used amount thereof, an amount of from 1 to 10 moles, preferably from 1 to 5 moles per mole of the Compound 34 is exemplified.

As the ligand, N,N-dimethylenediamine and the like are exemplified, and as the used amount thereof, an amount of from 0.1 to 3 moles is exemplified, and preferably, an amount of from 0.2 to 2 moles per mole of the Compound 26 is recommended.

As the reaction solvent, diethyl ether, THF, dioxane and the like are exemplified.

As the reaction temperature, a temperature of from 20 to 150° C. is exemplified, preferably, a temperature of from 50 to 120° C. is recommended, and generally, the reaction is completed in 1 to 24 hours.

Step 31

The protective group of the Compound 36 is removed according to Step 23, whereby a compound represented by the formula (I-2e) is obtained.

The thus obtained compound represented by the formula (I-2e) can be isolated and purified by a known separation and purification method such as concentration, concentration in vacuo, crystallization, solvent extraction, reprecipitation or chromatography.

Production Method 9

Production Method 9 is a method for producing a compound in which X is —NR$^5$— in the formula (I).

Reaction Formula 9

[Chemical Formula 15]

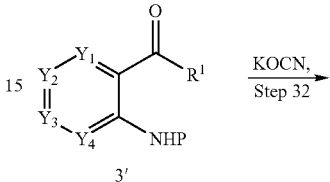

3'

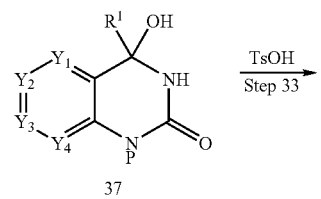

37

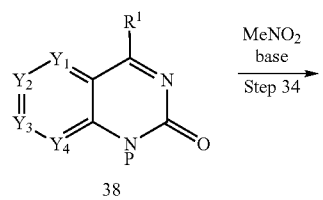

38

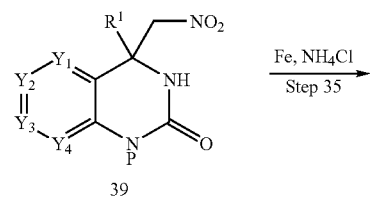

39

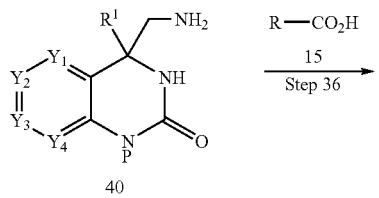

40

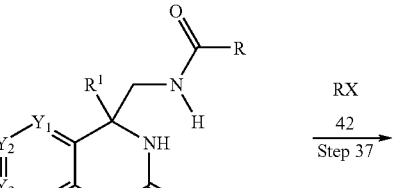

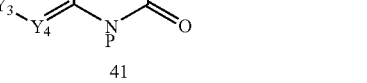

41

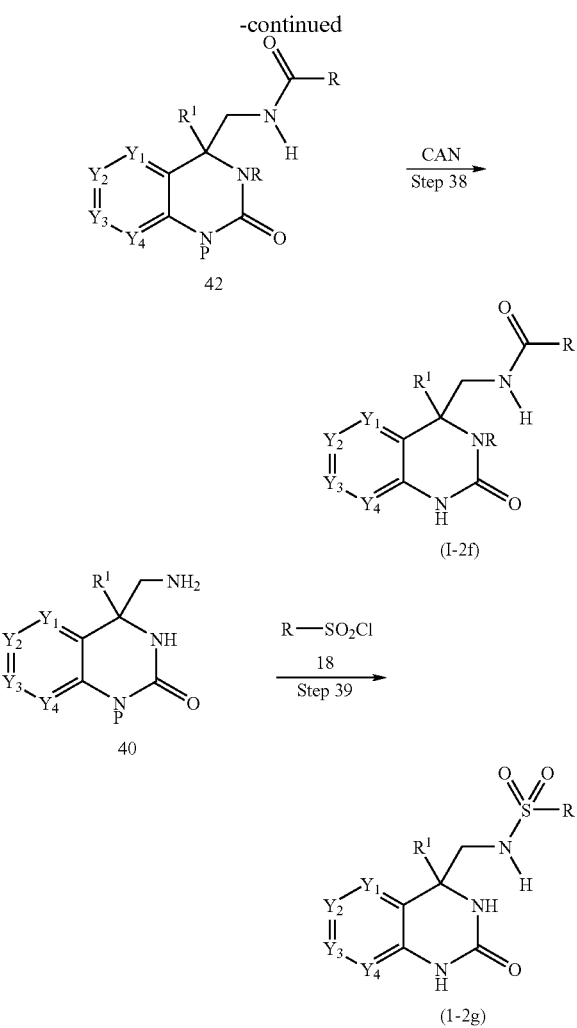

[In the formula, P represents a protective group such as a 4-methoxybenzyl group or represents hydrogen, and other symbols have the same meanings as described above.]

Step 32

Compound 3' is reacted with KOCN in a reaction solvent, whereby Compound 37 is obtained. As the used amount of KOCN, an amount of from 1 to 10 moles is exemplified, and preferably, an amount of from 1 to 5 moles per mole of the Compound 3' is recommended. Incidentally, the Compound 3' is a compound which is identical to the Compound 3 or whose amino group is protected.

As the reaction temperature, a temperature of from 30 to 100° C. is exemplified, preferably, a temperature of from 50 to 80° C. is recommended, and generally, the reaction is completed in 1 to 24 hours.

As the reaction solvent, for example, an acetic acid-water mixed solvent is exemplified.

Step 33

Compound 37 is reacted in a reaction solvent in the presence of p-toluenesulfonic acid, whereby Compound 38 is obtained.

As the used amount of p-toluenesulfonic acid, an amount of from 0.01 to 1 mole is exemplified, and preferably, an amount of from 0.01 to 0.1 moles per mole of the Compound 37 is recommended.

As the reaction solvent, benzene, toluene, xylene and the like are exemplified.

As the reaction temperature, a temperature of from 50° C. to the boiling point of the solvent is exemplified, and generally, the reaction is completed in 1 to 12 hours.

Step 34

Compound 38 is reacted with nitromethane in the presence of a base, whereby Compound 39 is obtained.

As the used amount of nitromethane, an amount of from 1 to 100 moles is exemplified, and preferably, an amount of from 1 to 20 moles per mole of the Compound 38 is recommended. Further, nitromethane may be used as a solvent.

As the base, diisopropylethylamine, triethylamine and the like are exemplified, and as the used amount thereof, an amount of from 1 to 20 moles is exemplified, and preferably, an amount of from 1 to 10 moles per mole of the Compound 38 is recommended.

As the reaction solvent, benzene, toluene, xylene and the like are exemplified.

As the reaction temperature, a temperature of from 30 to 100° C. is exemplified, and generally, the reaction is completed in 1 to 12 hours.

Step 35

The nitro group of the Compound 39 is reduced using iron/ammonium chloride, whereby Compound 40 is obtained.

With regard to the used amount of iron/ammonium chloride, as the used amount of iron, an amount of from 1 to 10 moles per mole of the Compound 39 is exemplified, and preferably, an amount of from 1 to 5 moles is recommended. Meanwhile, as the used amount of ammonium chloride, an amount of from 1 to 10 moles is exemplified, and preferably, an amount of from 1 to 5 moles per mole of the Compound 39 is recommended.

As the reaction temperature, a temperature of from 30 to 120° C. is exemplified, and generally, the reaction is completed in 1 to 24 hours.

As the reaction solvent, a methanol-water mixed solvent is exemplified.

Step 36

The Compound 40 is condensed with the Compound 15 according to Step 11, whereby Compound 41 is obtained.

Step 37

The Compound 41 is reacted with Compound 42 in the presence of a base, whereby Compound 43 is obtained. As the used amount of the base, an amount of from 1 to 20 moles is exemplified, and preferably, an amount of from 1 to 5 moles per mole of the Compound 41 is recommended.

As the base, potassium carbonate, sodium hydride or the like is used.

As the used amount of the Compound 42, an amount of from 1 to 20 moles is exemplified, and preferably, an amount of from 1 to 5 moles per mole of the Compound 41 is recommended.

As the Compound 42, methyl iodide, ethyl iodide, benzyl bromide or the like is used.

Step 38

By using Compound 43, deprotection is carried out by the method according to Step 20, whereby a compound represented by the formula (I-2f) is obtained. Further, the deprotection may be carried out by a reaction according to the method described in Protective Groups in Organic Synthesis.

Step 39

The Compound 40 is reacted with the Compound 18 according to Step 14, whereby a compound represented by the formula (I-2g) is obtained.

The thus obtained compound represented by the formula (I-2f) or (I-2g) can be isolated and purified by a known separation and purification method such as concentration, concentration in vacuo, crystallization, solvent extraction, reprecipitation or chromatography.

In the above-mentioned production methods, in the case where an amino group, an imino group, a hydroxyl group, a carboxyl group, an oxo group, a carbonyl group or the like which is not involved in the reaction is present in the reaction materials, after the amino group, hydroxyl group, carboxyl group, oxo group or carbonyl group is properly protected by a protective group for an amino group, a protective group for a hydroxyl group, a protective group for a carboxyl group or a protective group for an oxo group or a carbonyl group, each reaction of the above-mentioned production methods is carried out, and the protective group can be removed after the reaction.

The method for introducing and removing the protective group varies depending on the type of the protective group, the stability of the objective compound or the like, however, it can be carried out by the method described in the document [see Protective Groups in Organic Synthesis, T. W. Greene, John Wiley & Sons, (1981)] or a modified method thereof, for example, by solvolysis using an acid or a base, i.e., by a method of treating the compound with, for example, 0.01 moles to a large excess amount of an acid, preferably trifluoroacetic acid, formic acid, hydrochloric acid or the like, or with an equimolar amount to a large excess amount of a base, preferably potassium hydroxide, calcium hydroxide or the like; by chemical reduction using a metal hydride complex or the like; or by catalytic reduction using a palladium-carbon catalyst, a Raney nickel catalyst or the like.

The protective group for an amino group is not particularly limited as long as it has its function, and examples thereof include aralkyl groups such as a benzyl group, a p-methoxybenzyl group and a 3,4-dimethoxybenzyl group; $C_{1-6}$ alkanoyl groups such as an acetyl group and a pivaloyl group; a benzoyl group; arylalkanoyl groups such as a phenylacetyl group; $C_{1-6}$ alkoxycarbonyl groups such as an ethoxycarbonyl group and a t-butoxycarbonyl group; alkyloxycarbonyl groups such as a benzyloxycarbonyl group; $C_{1-6}$ alkylsilyl groups such as a trimethylsilyl group and a t-butyldimethylsilyl group; a tetrahydropyranyl group; a trimethylsilylethoxymethyl group; and arylsulfonyl groups such as a toluenesulfonyl group, and particularly preferred is an acetyl group, a benzoyl group, a t-butoxycarbonyl group, a trimethylsilylethoxymethyl group, a methylsulfonyl group or the like.

The protective group for a hydroxyl group is not particularly limited as long as it has its function, and examples thereof include $C_{1-6}$ alkyl groups such as a methyl group, an ethyl group and a propyl group; $C_{1-6}$ alkylsilyl groups such as a trimethylsilyl group and a t-butyldimethylsilyl group; $C_{1-6}$ alkoxymethyl groups such as a methoxymethyl group and a 2-methoxyethoxymethyl group; a tetrahydropyranyl group; a trimethylsilylethoxymethyl group; aralkyl groups such as a benzyl group and a p-methoxybenzyl group; and acyl groups such as an acetyl group, and particularly preferred is a methyl group, a methoxymethyl group, a tetrahydropyranyl group, a trimethylsilylethoxymethyl group, a t-butyldimethylsilyl group, an acetyl group or the like.

The protective group for a carboxyl group is not particularly limited as long as it has its function, and examples thereof include $C_{1-6}$ alkyl groups such as a methyl group and an ethyl group; halo-$C_{1-6}$ alkyl groups such as a 2,2,2-trichloroethyl group; and aralkyl groups such as a benzyl group and a p-methoxybenzyl group, and particularly preferred is a methyl group, an ethyl group, a t-butyl group, a 2-propenyl group, a benzyl group, a p-methoxybenzyl group or the like.

The protective group for an oxo group and a carbonyl group is not particularly limited as long as it has its function, and examples thereof include acetals and ketals such as ethylene ketal, dimethyl ketal and S,S'-dimethyl ketal.

The thus obtained compounds of the invention can be isolated and purified by a known separation and purification method such as concentration, concentration in vacuo, crystallization, solvent extraction, reprecipitation or chromatography.

These compounds can be converted into pharmaceutically acceptable salts thereof according to a common procedure, and conversely, such salts can also be converted into the corresponding free compounds according to a common procedure.

Depending on the type of the substituent thereof, the compounds of the invention may have stereoisomers or tautomers such as optical isomers, diastereomers or geometrical isomers, and the compounds of the invention include all these stereoisomers and tautomers and mixtures thereof.

The usefulness of the compounds according to the invention as a pharmaceutical will be demonstrated in, for example, the following pharmacological test example.

Pharmacological Test Example 1

LCE Enzymatic Activity Inhibition Test

A test compound was dissolved in dimethylsulfoxide (DMSO) at 10 mM, and then, the resulting solution was further diluted with DMSO to prepare a 1000-fold stock solution having a concentration 1000 times higher than the concentration to be evaluated. An LCE enzymatic activity inhibition test was carried out by a modified method of Moon (J. Biol. Chem., Vol. 276, pp. 45358-45366, (2001)) et al. That is, the diluted test compound was added to a 96-well assay plate (Corning, 96-Well Assay Block) in an amount of 1.0 µL per well, and thereafter, 50 µL of a phosphate buffer solution (a 100 mM potassium phosphate buffer solution (pH 6.5)), 25 µL of a substrate solution (a 100 mM potassium phosphate buffer solution (pH 6.5), 4.0 µM rotenone, 80 µM fatty acid-free bovine serum albumin, 160 µM palmitoyl-CoA, 80 µM malonyl-CoA, 3.5 µM [$^{14}$C]-malonyl-CoA (1.92 GBq/mmol, manufactured by Amersham, Inc.)) was added to each well, and further, 25 µL of an enzyme solution (a 100 mM potassium phosphate buffer solution (pH 6.5), 100 µg/mL human LCE) was added thereto. Then, the upper part of the plate was hermetically closed with a seal member, and the plate was incubated at 37° C. for 90 minutes while gently shaking and stirring. Thereafter, to each well, 100 µL of 5 N HCl was added and the assay plate was stirred at room temperature for 5 minutes, whereby the enzymatic reaction was stopped and also acyl-CoA was hydrolyzed. Thereafter, the enzymatic reaction solution in each well was adsorbed to each well of a 96-well GF/C filter plate (PerkinElmer, Unifilter 96GF/C) through which water had been passed in advance, and then, each well was washed with water to remove unadsorbed malonyl-CoA and the GF/C filter plate was dried at 50° C. for 60 minutes. Thereafter, to each well, 30 µL of a scintillator (PerkinElmer, Microscinti 0) was added and the upper part of the plate was sealed, and the radioactivity of the fixed [$^{14}$C] was measured using a microplate scintillation counter (PerkinElmer, Top Count) from which the enzymatic activity was determined The human LCE enzyme inhibitory activity of the test compound was calculated using the radioactivity obtained from a well to which DMSO containing no test compound is added as a control. When the activities of the compounds of the invention were examined using this assay, these compounds inhibited the activity of human LCE. The results are shown in Table 1.

TABLE 1

| Example No. | Name | IC$_{50}$ (nM) |
| --- | --- | --- |
| 27 | N-{[(4S*)-6-chloro-2-oxo-4-(trifluoromethyl)-1,4-dihydro-2H-3,1-benzoxazin-4-yl]methyl}4-fluorobenzamide | 13 |
| 32 | N-{2-[(4R*)-6-chloro-2-oxo-4-(trifluoromethyl)-1,4-dihydro-2H-3,1-benzoxazin-4-yl]ethyl}-4-fluorobenzamide | 22 |
| 33 | N-{3-[(4R*)-6-chloro-2-oxo-4-(trifluoromethyl)-1,4-dihydro-2H-3,1-benzoxazin-4-yl]propyl}-4-fluorobenzamide | 17 |
| 119 | N-{3-[(4R*)-6-chloro-2-oxo-4-(trifluoromethyl)-1,4-dihydro-2H-3,1-benzoxazin-4-yl]propyl}pyridine-2-sulfonamide | 128 |
| 120 | N-{2-[(4R*)-6-chloro-2-oxo-4-(trifluoromethyl)-1,4-dihydro-2H-3,1-benzoxazin-4-yl]ethyl}pyridine-2-sulfonamide | 5.4 |
| 123 | N-{[(4S*)-6-chloro-2-oxo-4-(trifluoromethyl)-1,4-dihydro-2H-3,1-benzoxazin-4-yl]methyl}-N'-(4-fluorophenyl)urea | 18 |
| 125 | (4S*)-4-fluoro-N-{[2-oxo-6-(1H-pyrazol-5-yl)-4-(trifluoromethyl)-1,4-dihydro-2H-3,1-benzoxazin-4-yl]methyl}benzamide | 2.7 |
| 132 | (4S*)-4-fluoro-N-{[2-oxo-6-(1H-pyrazol-4-yl)-4-(trifluoromethyl)-1,4-dihydro-2H-3,1-benzoxazin-4-yl]methyl}benzamide | 9.6 |
| 133 | (4S*)-4-fluoro-N-{[6-(1-methyl-1H-pyrazol-4-yl)-2-oxo-4-(trifluoromethyl)-1,4-dihydro-2H-3,1-benzoxazin-4-yl]methyl}benzamide | 119 |
| 146 | 4-fluoro-N-{[6-(2-furyl)-2-oxo-4-(trifluoromethyl)-1,4-dihydro-2H-3,1-benzoxazin-4-yl]methyl}benzamide | 14 |
| 147 | 4-fluoro-N-{[2-oxo-6-(2-thienyl)-4-(trifluoromethyl)-1,4-dihydro-2H-3,1-benzoxazin-4-yl]methyl}benzamide | 13 |
| 150 | 4-fluoro-N-{[(4S*)-2-oxo-6-(1H-pyrazol-3-yl)-4-(trifluoromethyl)-1,4-dihydro-2H-3,1-benzoxazin-4-yl]methyl}benzenesulfonamide | 17 |
| 151 | N-{[(4S*)-2-oxo-6-(1H-pyrazol-3-yl)-4-(trifluoromethyl)-1,4-dihydro-2H-3,1-benzoxazin-4-yl]methyl}pyridine-2-sulfonamide | 16 |
| 154 | (4S*)-4-fluoro-N-{[2-oxo-6-(2-oxopyrrolidin-1-yl)-4-(trifluoromethyl)-1,4-dihydro-2H-3,1-benzoxazin-4-yl]methyl}benzamide | 15 |
| 173 | 4-fluoro-N-{[(4S*)-2-oxo-6-(2-oxo-1,3-oxazolidin-3-yl)-4-(trifluoromethyl)-1,4-dihydro-2H-3,1-benzoxazin-4-yl]methyl}benzamide | 108 |
| 174 | 4-fluoro-N-{[6-(3-methyl-2-oxazolidin-1-yl)-2-oxo-4-(trifluoromethyl)-1,4-dihydro-2H-3,1-benzoxazin-4-yl]methyl}benzamide | 5.3 |
| 176 | 4-fluoro-N-{[(4S*)-2-oxo-6-(1H-pyrazol-1 yl)-4-(trifluoromethyl)-1,4-dihydro-2H-3,1-benzoxazin-4-yl]methyl}benzamide | 19 |
| 178 | 4-fluoro-N-{[6-(3-methyl-1H-pyrazol-1-yl)-2-oxo-4-(trifluoromethyl)-1,4-dihydro-2H-3,1-benzoxazin-4-yl]methyl}benzamide | 7.3 |
| 182 | 4-fluoro-N-{[(4S*)-2-oxo-6-(1H-pyrazol-5-yl)-4-(trifluoromethyl)-1,2,3,4-tetrahydroquinazolin-4-yl]methyl}benzamide | 6.6 |
| 187 | N-{[(4S*)-6-chloro-2-oxo-4-(trifluoromethyl)-1,2,3,4-tetrahydroquinazolin-4-yl]methyl}4-fluorobenzamide | 45 |

The compound represented by the general formula (I) can be administered orally or parenterally, and by formulating the compound into a preparation suitable for such an administration route, the compound can be used as a treatment agent for cardiovascular diseases such as hypertension, angina pectoris, heart failure, myocardial infarction, stroke, claudication, diabetic nephropathy, diabetic retinopathy, reduced vision, electrolyte abnormality and atherosclerosis; central nervous system diseases such as bulimia and diabetic neuropathy; metabolic diseases such as metabolic syndrome, obesity, diabetes, insulin resistance, hyperlipidemia, hypercholesterolemia, hypertriglyceridemia, dyslipidemia, non-alcoholic fatty liver, hormone secretion abnormality, gout and fatty liver; reproductive system diseases such as menstrual disorder and sexual dysfunction; gastrointestinal system diseases such as hepatic dysfunction, pancreatitis, cholecystitis and gastroesophageal reflux; respiratory system diseases such as obesity hypoventilation syndrome (Pickwickian syndrome) and sleep apnea syndrome; infectious diseases caused by bacteria, fungi or paracites; malignant neoplasms; inflammatory diseases such as arthritis and skin ulcer; and the like.

One aspect of the invention is to provide a method for treating or preventing a disease, illness or condition caused by the modulation of LCE including administering a therapeutically or prophylactically effective amount of the compound (I) or a pharmaceutically acceptable salt thereof according to the invention to a subject in need thereof.

Another aspect of the invention is to provide a method for treating or preventing metabolic syndrome, fatty liver, hyperlipidemia, dyslipidemia, non-alcoholic fatty liver, obesity, diabetes, bulimia, a malignant neoplasm or an infectious disease including administering a therapeutically or prophylactically effective amount of the compound (I) or a pharmaceutically acceptable salt thereof according to the invention to a subject in need thereof.

Still another aspect of the invention is to provide a method for treating metabolic syndrome, fatty liver, hyperlipidemia, obesity, diabetes, bulimia, a malignant neoplasm or an infectious disease including administering a therapeutically effective amount of the compound (I) or a pharmaceutically acceptable salt thereof according to the invention to a subject in need thereof.

Still another aspect of the invention is to provide a method for treating or preventing diabetes including administering a therapeutically or prophylactically effective amount of the compound (I) or a pharmaceutically acceptable salt thereof according to the invention to a subject in need thereof.

Still another aspect of the invention is to provide a method for treating or preventing obesity including administering a therapeutically or prophylactically effective amount of the compound (I) or a pharmaceutically acceptable salt thereof according to the invention to a subject in need thereof.

Still another aspect of the invention is to provide a method for treating or preventing an obesity-related disease selected from the group consisting of overconsumption, bulimia, hypertension, increase in plasma insulin concentration, insulin resistance, hyperlipidemia, endometrial cancer, breast cancer, prostate cancer, colon cancer, renal cancer, osteoarthritis, obstructive sleep apnea, heart diseases, abnormal heart rhythms, arrhythmia, myocardial infarction, congestive heart failure, coronary heart diseases, sudden death, stroke, polycystic ovary, craniopharyngioma, metabolic syndrome, insulin resistance syndrome, sexual dysfunction, hypogonadism, infertility, hypogonadism, hirsutism, obesity-related gastroesophageal reflux, obesity hypoventilation syndrome (Pickwickian syndrome), inflammation, systemic vasculitis, atherosclerosis, hypercholesterolemia, hyperuricemia, low back pain, inflammation, systemic vasculitis, atherosclerosis, hypercholesterolemia, hyperuricemia, low back pain, gallbladder diseases, gout, constipation, irritable bowel syndrome, inflammatory bowel syndrome, heart hypertrophy and left ventricular hypertrophy including administering a therapeutically or prophylactically effective amount of the compound (I) or a pharmaceutically acceptable salt thereof according to the invention to a subject in need thereof.

Still another aspect of the invention is to provide a method for treating or preventing hyperlipidemia or dyslipidemia including administering a therapeutically or prophylactically effective amount of the compound (I) or a pharmaceutically acceptable salt thereof according to the invention to a subject in need thereof.

Still another aspect of the invention is to provide a method for calorie intake including administering a therapeutically or prophylactically effective amount of the compound (I) or a pharmaceutically acceptable salt thereof according to the invention to a subject in need thereof.

Still another aspect of the invention is to provide a method for reducing food intake including administering a therapeutically or prophylactically effective amount of the compound (I) or a pharmaceutically acceptable salt thereof according to the invention to a subject in need thereof.

Still another aspect of the invention is to provide a method for increasing satiety including administering a therapeutically or prophylactically effective amount of the compound (I) or a pharmaceutically acceptable salt thereof according to the invention to a subject in need thereof.

Still another aspect of the invention is to provide a method for reducing appetite including administering a therapeutically or prophylactically effective amount of the compound (I) or a pharmaceutically acceptable salt thereof according to the invention to a subject in need thereof.

Further, the invention relates to a method for treating or preventing obesity including administering the compound (I) or a pharmaceutically acceptable salt thereof according to the invention in combination with a therapeutically or prophylactically effective amount of another agent which is known to be useful for treating or preventing a condition thereof.

Further, the invention relates to a method for treating or preventing diabetes including administering the compound (I) or a pharmaceutically acceptable salt thereof according to the invention in combination with a therapeutically or prophylactically effective amount of another agent which is known to be useful for treating or preventing a condition thereof. Further, the invention relates to a method for treating or preventing hyperlipidemia or dyslipidemia including administering the compound (I) or a pharmaceutically acceptable salt thereof according to the invention in combination with a therapeutically or prophylactically effective amount of another agent which is known to be useful for treating or preventing a condition thereof.

Another aspect of the invention is to provide a pharmaceutical composition containing the compound (I) or a pharmaceutically acceptable salt thereof according to the invention and a pharmaceutically acceptable carrier.

Still another aspect of the invention relates to the compound (I) or a pharmaceutically acceptable salt thereof according to the invention for use as a medicine.

Still another aspect of the invention relates to use of the compound (I) or a pharmaceutically acceptable salt thereof according to the invention for producing a medicine which is useful for treating, preventing or suppressing a disease caused by LCE of a subject in need thereof.

Still another aspect of the invention relates to use of the compound (I) or a pharmaceutically acceptable salt thereof according to the invention for producing a medicine which is useful for treating or preventing metabolic syndrome, hyperlipidemia, dyslipidemia, non-alcoholic fatty liver, obesity, diabetes, bulimia, a malignant neoplasm or an infectious disease of a subject in need thereof.

Still another aspect of the invention relates to use of the compound (I) or a pharmaceutically acceptable salt thereof according to the invention for producing a medicine which is useful for treating or preventing obesity of a subject in need thereof. Still another aspect of the invention relates to use of the compound (I) or a pharmaceutically acceptable salt thereof according to the invention for producing a medicine which is useful for treating or preventing diabetes of a subject in need thereof. Still another aspect of the invention relates to use of the compound (I) or a pharmaceutically acceptable salt thereof according to the invention for producing a medicine which is useful for treating or preventing hyperlipidemia, dyslipidemia of a subject in need thereof.

Still another aspect of the invention relates to use of a therapeutically effective amount of the compound (I) or a pharmaceutically acceptable salt thereof according to the invention and a therapeutically effective amount of an agent selected from the group consisting of insulin resistance improving agents, insulin-mimetics, sulfonylureas, α-glucosidase inhibitors, dipeptidyl peptidase-4 (DPP-4 or DP-IV) inhibitors, glucagon-like peptide-1 (GLP-1) agonists, HMG-CoA reductase inhibitors, serotonin-like substances, β3-adrenaline receptor agonists, neuropeptide Y1 antagonists, neuropeptide Y2 agonists, neuropeptide Y5 antagonists, pancreatic lipase inhibitors, cannabinoid CB1 receptor antagonists or inverse agonists, melanin-concentrating hormone receptor agonists, melanocortin-4 receptor agonists, bombesin receptor subtype-3 agonists, ghrelin antagonists, PYY, $PYY_{3-36}$ and NK-1 antagonists or a pharmaceutically acceptable salt thereof, wherein the use is for producing a medicine which is useful for treating, controlling or preventing obesity, diabetes, a diabetes-related disease or an obesity-related disease of a subject in need thereof.

Still another aspect of the invention relates to use of a therapeutically effective amount of the compound (I) or a pharmaceutically acceptable salt thereof according to the invention and a therapeutically effective amount of an agent selected from the group consisting of insulin resistance improving agents, insulin-mimetics, sulfonylureas, α-glucosidase inhibitors, dipeptidyl peptidase-4 (DPP-4 or DP-IV) inhibitors, glucagon-like peptide-1 (GLP-1) agonists, HMG-CoA reductase inhibitors, serotonin-like substances, β3-adrenaline receptor agonists, neuropeptide Y1 antagonists, neuropeptide Y2 agonists, neuropeptide Y5 antagonists, pancreatic lipase inhibitors, cannabinoid CB1 receptor antagonists or inverse agonists, melanin-concentrating hormone receptor agonists, melanocortin-4 receptor agonists, bombesin receptor subtype-3 agonists, ghrelin antagonists, PYY, PYY$_{3-36}$ and NK-1 antagonists or a pharmaceutically acceptable salt thereof for producing a medicine to be used for treating or preventing obesity, diabetes, a diabetes-related disease or an obesity-related disease, wherein the effective amount of the compound (I) or a pharmaceutically acceptable salt thereof according to the invention and the effective amount of the above-mentioned agent are used simultaneously or separately.

Still another aspect of the invention relates to a product containing a therapeutically effective amount of the compound (I) or a pharmaceutically acceptable salt thereof according to the invention and a therapeutically effective amount of an agent selected from the group consisting of insulin resistance improving agents, insulin-mimetics, sulfonylureas, α-glucosidase inhibitors, dipeptidyl peptidase-4 (DPP-4 or DP-IV) inhibitors, glucagon-like peptide-1 (GLP-1) agonists, HMG-CoA reductase inhibitors, serotonin-like substances, β3-adrenaline receptor agonists, neuropeptide Y1 antagonists, neuropeptide Y2 agonists, neuropeptide Y5 antagonists, pancreatic lipase inhibitors, cannabinoid CB1 receptor antagonists or inverse agonists, melanin-concentrating hormone receptor agonists, melanocortin-4 receptor agonists, bombesin receptor subtype-3 agonists, ghrelin antagonists, PYY, PYY$_{3-36}$ and NK-1 antagonists or a pharmaceutically acceptable salt thereof as a drug combination for simultaneous, separate or successive use for obesity, diabetes, a diabetes-related disease or an obesity-related disease.

Still another aspect of the invention relates to use of a therapeutically effective amount of the compound (I) or a pharmaceutically acceptable salt thereof according to the invention and a therapeutically effective amount of an agent selected from the group consisting of simvastatin, mevastatin, ezetimibe, atorvastatin, sitagliptin, metformin, sibutramine, orlistat, Qnexa (trade name) and phentermine or a pharmaceutically acceptable salt thereof, wherein the use is for producing a medicine which is useful for treating, controlling or preventing obesity, diabetes, a diabetes-related disease or an obesity-related disease of a subject in need thereof.

When the compound according to the invention is clinically used, it is also possible to formulate it into any of various preparations by adding a pharmaceutically acceptable additive in accordance with the dosage form thereof and then administer the resulting preparation. As the additive at this time, any of various additives commonly used in the pharmaceutical field can be used, and examples thereof include gelatin, lactose, sucrose, titanium oxide, starch, crystalline cellulose, methylated cellulose, hydroxypropyl methyl cellulose, carboxymethyl cellulose, cornstarch, microcrystalline wax, white petrolatum, magnesium aluminometasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, palmitoleic acid, light silicic acid anhydride, talc, a vegetable oil, benzyl alcohol, gum Arabic, propylene glycol, polyalkylene glycol, cyclodextrin and hydroxypropyl cyclodextrin.

Examples of the dosage form of the preparation as a mixture of the compound with such an additive include solid preparations such as tablets, capsules, granules, powders and suppositories; and liquid preparations such as syrups, elixirs and injections, and these preparations can be prepared according to a common procedure in the pharmaceutical field. Incidentally, the liquid preparation may be also in the form that the ingredients are dissolved or suspended in water or another suitable vehicle before use. Further, particularly in the case of an injection, the ingredients may be dissolved or suspended in physiological saline or a glucose solution as needed, and further, a buffer or a preservative may be added thereto.

The compound according to the invention is effective in animals and plants including humans and mammals other than humans in need of treatment with the compound. As the mammals, preferred are humans, it does not matter whether the humans are male or female. As the mammals other than humans, for example, companion animals such as dogs and cats are exemplified. The compound according to the invention is effective in obesity or an obesity-related disease of such dogs and cats. Whether or not the treatment with the compound is needed can be easily determined by an ordinary physician, veterinarian or clinician.

In the case where the compound according to the invention is used in, for example, a clinical field, the dose and frequency thereof vary depending on the sex, age, body weight, and severity of symptoms of a patient and the type and range of intended treatment effect. However, generally, in the case of oral administration, the administration is preferably performed at a daily dose from 0.01 to 100 mg/kg, preferably from 0.03 to 1 mg/kg per adult once or in divided doses. Further, in the case of parenteral administration, the administration is preferably performed at a daily dose of from 0.001 to 10 mg/kg, preferably from 0.001 to 0.1 mg/kg, more preferably from 0.01 to 0.1 mg/kg per adult once or in divided doses.

For oral administration, tablets containing an active ingredient in an amount of from 1.0 to 1000 mg, particularly, in an amount of 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 and 1000.0 mg are preferred for adjusting the dosage in accordance with the symptoms of a patient to be treated. The compound can be administered by the prescription once to four times per day, preferably once or twice per day.

In the case where the compound according to the invention is applied to the treatment or prevention of obesity and/or diabetes and/or hyperlipidemia and/or dyslipidemia and/or non-alcoholic fatty liver or other diseases, when the daily dosage of the compound according to the invention is about 0.1 mg to about 100 mg per kg of body weight of animal, more preferably, when the application is performed by a single administration or a divided administration of two to six times per day, or it is performed with a sustained-release preparation, a sufficient result can be generally obtained. For most large mammals, the total daily dosage is from about 1.0 mg to about 1000 mg, preferably from about 1 mg to about 50 mg. In the case of an adult having a body weight of 70 kg, generally, the total daily dosage is presumably from about 7 mg to about 350 mg. The prescription of this dosage can be adjusted for obtaining a maximum therapeutic effect.

A normal physician, veterinarian or clinician can easily determine an effective dosage necessary for treating, preventing, inhibiting, suppressing or arresting the progress of disease and perform treatment.

These preparations can contain the compound according to the invention in an amount of from 1.0 to 100% by weight, preferably from 1.0 to 60% by weight of the total preparation. These preparations may further contain another therapeutically effective compound.

The compound according to the invention can be used in combination with any other agent useful for the treatment of a disease, for example, a cardiovascular disease such as hypertension, angina pectoris, heart failure, myocardial infarction, stroke, claudication, diabetic nephropathy, diabetic retinopathy, reduced vision, electrolyte abnormality or atherosclerosis; a central nervous system disease such as bulimia or diabetic neuropathy; a metabolic disease such as metabolic syndrome, obesity, diabetes, insulin resistance, hyperlipidemia, hypercholesterolemia, hypertriglyceridemia, dyslipidemia, non-alcoholic fatty liver, hormone secretion abnormality, gout or fatty liver; a reproductive system disease such as menstrual disorder or sexual dysfunction; a gastrointestinal system disease such as hepatic dysfunction, pancreatitis, cholecystitis or gastroesophageal reflux; a respiratory system disease such as obesity hypoventilation syndrome (Pickwickian syndrome) or sleep apnea syndrome; an infectious disease caused by a bacterum, a fungus or a paracite; a malignant neoplasm; an inflammatory disease such as arthritis or skin ulcer; or the like. The individual ingredients in the case of such a combination can be administered at different times or at the same time as divided preparations or a single preparation during the period of treatment. Accordingly, the invention should be so interpreted that it includes all modes of administration at the same time or at different times, and the administration in the invention should be interpreted so. The scope of the combination of the compound according to the invention with any other agent useful for the treatment of the above-mentioned disease should include, in principle, any combination thereof with every pharmaceutical preparation useful for the treatment of the above-mentioned disease.

The above-mentioned combination includes a combination of the composition of the invention not only with one other active substance but also with two or more other active substances. There are a lot of examples of the combination of the composition of the invention with one or more active substances selected from the remedies for the above-mentioned diseases. For example, in the case where metabolic syndrome is intended to be treated, controlled or prevented, a combination of the composition of the invention with one or more active substances selected from a remedy for hyperlipidemia, a lipid reducing agent and an antidiabetic agent is favorable. In particular, a composition containing an anti-obesity agent and an antihypertensive agent in addition to an antidiabetic agent and/or a remedy for hyperlipidemia or a lipid reducing agent exhibits a synergistic effect on the treatment, control or prevention of metabolic syndrome.

As the agent to be combined with the present agent, for example, ACAT inhibitors, α-blockers, aldose reductase inhibitors, α-amylase inhibitors, angiotensin-converting enzyme inhibitors, angiotensin receptor antagonists, anion exchange resins, appetite suppressants, antioxidants, antiplatelet agents, β-blockers, biguanide agents, calcium antagonists, CB1 receptor inverse agonists/antagonists, CETP inhibitors, cholesterol absorption inhibitors, DGAT inhibitors, DP-IV inhibitors, diuretic agents, eicosapentaenoic acid, endothelin antagonists, FLAP inhibitors, FXR modulators, ghrelin antagonists, GLP-1 agonists, GLP-1 secretory agents, glucagon antagonists, glucokinase activators, glucocorticoid receptor ligands, α-glucosidase inhibitors, GPAT inhibitors, histamine H3 receptor ligands, HMG-CoA reductase inhibitors, HSD inhibitors, insulin and insulin-like drugs, kinase inhibitors such as VEGF inhibitors and PDGF inhibitors, leptin, lipase inhibitors, 5-LO inhibitors, LXR ligands, melanocortin agonists, MCH antagonists, MTTP inhibitors, orexin antagonists, opioid antagonists, neuropeptide Y antagonists, nicotinic agonists, PPAR ligands, PTP-1B inhibitors, SCD-1 inhibitors, serotonin transporter inhibitors, SGLT inhibitors, SUR ligands, thyroid hormone agonists, UCP activators, VPAC receptor agonists and the like can be exemplified.

Advantage of the Invention

The compounds according to the invention have an excellent LCE inhibitory effect and are useful as a treatment agent for various diseases related to LCE such as cardiovascular diseases, nervous system diseases, metabolic diseases, reproductive system diseases and gastrointestinal system diseases.

BEST MODE FOR CARRYING OUT THE INVENTION

Hereinafter, the invention will be more specifically described with reference to Examples and Production Examples, however, the invention is by no means limited to these.

EXAMPLES

In thin-layer chromatography in Examples and Production Examples, Silica gel$_{60}$ F$_{254}$ (Merck) was used as a plate, and a UV detector was used as a detection unit. Wakogel™ C-300 or C-200 (Wako Pure Chemical Industries, Ltd.), FLASH+ Cartridge (Biotage) or Chromatorex (FUJI SILYSIA CHEMICAL) was used as a column silica gel. MS spectra were measured using ZQ 2000 (Waters). NMR spectra were measured using dimethyl sulfoxide as an internal standard in the case of performing the measurement in a deuteriated dimethyl sulfoxide solution with a JNM-AL 400 (JEOL), Mercury 400 (400 MHz; Varian) or Inova 400 (400 MHz; Varian) spectrometer, and all δ values are indicated in ppm.

The meanings of the abbreviations in NMR measurement will be shown below.
s: singlet
d: doublet
dd: double doublet
t: triplet
dt: double triplet
q: quartet
m: multiplet
br: broad
J: coupling constant
Hz: hertz
DMSO-d$_6$: deuteriated dimethyl sulfoxide Example 1

(6-chloro-4-cyclopropyl-2-oxo-1,4-dihydro-2H-3,1-benzoxazin-4-yl)methyl(4-fluorophenyl)carbamate 1) Synthesis of
(2-amino-5-chlorophenyl)cyclopropyl)methanone 2-Amino-5-chlorobenzonitrile (500 mg, 3.28 mmol) was dissolved in THF (10 mL), and while stirring the reaction solution at 0° C., cyclopropyl magnesium bromide (0.5 M THF solution, 26.4 mL) was added dropwise thereto. The reaction solution was stirred overnight under heating at 80° C., followed by ice-cooling, and 2 N hydrochloric acid was added thereto under ice-cooling. After the reaction solution was stirred at room temperature for 2 hours, the solution was diluted with ethyl acetate and then neutralized with a saturated aqueous sodium hydrogen carbonate solution. The organic layer was separated and washed with saturated brine and then dried over magnesium sulfate. After the drying agent was removed by filtration, the solvent was evaporated under reduced pressure. The resulting residue was purified by silica gel column chromatography (ethyl acetate/hexane=3/1), whereby (2-amino-5-chlorophenyl)(cyclopropyl)methanone (453 mg, 83%) was obtained as a yellow solid.

$^1$H-NMR (400 MHz, CDCl$_3$) δ: 0.98-1.03 (2H, m), 1.16-1.20 (2H, m), 2.54-2.60 (1H, m), 6.61 (1H, d, J=8.8 Hz), 7.21 (1H, dd, J=8.8, 2.4 Hz), 7.92 (1H, d, J=2.4 Hz)

2) Synthesis of 6-chloro-4-cyclopropyl-4-vinyl-1,4-dihydro-2H-3,1-benzoxazin-2-one (2-Amino-5-chlorophenyl)(cyclopropyl)methanone (450 mg, 2.30 mmol) was dissolved in THF (5 mL), and while stirring the reaction solution at 0° C., vinyl magnesium bromide (1.0 M THF solution, 5.7 mL) was added dropwise thereto. The reaction solution was stirred overnight at room temperature, and then, a saturated aqueous ammonium chloride solution was added to the solution. After the solution was diluted with ethyl acetate, the organic layer was separated and washed with saturated brine and then dried over magnesium sulfate. After the drying agent was removed by filtration, the solvent was evaporated under reduced pressure. The resulting residue was dissolved in THF (5 mL), and 1,1-carbonyldiimidazole (CDI) (745 mg) was added thereto at room temperature. The reaction solution was stirred at room temperature for 2 hours, followed by ice-cooling, and water was added to the reaction solution. The solution was diluted with ethyl acetate and a saturated aqueous ammonium chloride solution was added thereto. The organic layer was separated and washed with saturated brine and then dried over magnesium sulfate. After the drying agent was removed by filtration, the solvent was evaporated under reduced pressure. The resulting residue was purified by silica gel column chromatography (ethyl acetate/hexane=1/2), whereby 6-chloro-4-cyclopropyl-4-vinyl-1,4-dihydro-2H-3,1-benzoxazin-2-one (610 mg) was quantitatively obtained as a pale white solid.

$^1$H-NMR (400 MHz, DMSO-d$_6$) δ: 0.30-0.36 (1H, m), 0.44-0.58 (2H, m), 0.65-0.72 (1H, m), 1.50-1.57 (1H, m), 5.10 (1H, dd, J=17.1, 1.0 Hz), 5.27 (1H, dd, J=10.7, 1.0 Hz), 5.90 (1H, dd, J=17.1, 10.7 Hz), 6.90 (1H, d, J=8.3 Hz), 7.36 (1H, dd, J=8.5, 2.2 Hz), 7.42 (1H, d, J=2.0 Hz), 10.40 (1H, s)

3) Synthesis of 6-chloro-4-cyclopropyl-4-(hydroxymethyl)-1,4-dihydro-2H-3,1-benzoxazin-2-one 6-Chloro-4-cyclopropyl-4-vinyl-1,4-dihydro-2H-3,1-benzoxazin-2-one (590 mg, 2.36 mmol) was dissolved in dichloromethane (2.5 mL) and methanol (2.5 mL), and the resulting solution was stirred at −78° C. in an ozone atmospher. After it was confirmed by thin-layer chromatography that the raw materials disappeared, the ozone atmospher was replaced by a nitrogen atmospher, and the solution was stirred for 5 minutes. The temperature of the reaction solution was raised to 0° C., and sodium borohydride (26.8 mg, 7.1 mmol) was added thereto. The reaction solution was stirred at 0° C. for 30 minutes, and then, acetone was added thereto to stop the reaction. After the solvent was evaporated under reduced pressure, water (50 mL) and 1 N hydrochloric acid were added to the residue and the pH thereof was adjusted to about 4, and then, the solution was stirred at room temperature. The resulting white solid was collected by filtration, washed with water and then dried under reduced pressure, whereby the objective compound (487 mg, 81%) was obtained.

$^1$H-NMR (400 MHz, DMSO-d$_6$) δ: 0.09-0.15 (1H, m), 0.29-0.35 (1H, m), 0.37-0.49 (2H, m), 1.33-1.40 (1H, m), 3.69 (1H, d, J=11.7 Hz), 3.85 (1H, d, J=11.7 Hz), 6.82 (1H, d, J=8.3 Hz), 7.28 (1H, dd, J=8.3, 2.4 Hz), 7.37 (1H, d, J=2.4 Hz)

4) Synthesis of (6-chloro-4-cyclopropyl-2-oxo-1,4-dihydro-2H-3,1-benzoxazin-4-yl)methyl(4-fluorophenyl)carbamate To a solution of THF (0.5 mL) of 6-chloro-4-cyclopropyl-4-(hydroxymethyl)-1,4-dihydro-2H-3,1-benzoxazin-2-one (30 mg, 0.124 mmol) and TEA (20.7 μL, 0.15 mmol), 1-fluorophenyl-4-isocyanate (17 μL, 0.15 mmol) was added dropwise at room temperature. After the reaction solution was stirred overnight at room temperature, the solvent was evaporated under reduced pressure, and the residue was separated by filtration and washed with chloroform. After the mother liquid was concentrated, the residue was purified by thin-layer silica gel column chromatography (ethyl acetate/hexane=1/1) and crystallized with ethyl acetate/heptane, whereby the objective compound (9.5 mg, 20%) was obtained as a white solid.

$^1$H-NMR (400 MHz, DMSO-d$_6$) δ: 0.12-0.18 (1H, m), 0.23-0.29 (1H, m), 0.44-0.55 (2H, m), 1.39-1.46 (1H, m), 4.51 (1H, d, J=12.2 Hz), 4.76 (1H, d, J=12.2 Hz), 6.88 (1H, d, J=8.3 Hz), 7.10 (2H, t, J=8.3 Hz), 7.34 (1H, dd, J=8.3, 2.4 Hz), 7.38-7.48 (2H, br m), 7.51 (1H, d, J=2.4 Hz)

Example 2

(4-methyl-2-oxo-1,4-dihydro-2H-3,1-benzoxazin-4-yl)methyl(4-fluorophenyl)carbamate The title compound was obtained by a method according to Example 1 using 2-aminobenzonitrile, methyl magnesium bromide and 1-fluorophenyl-4-isocyanate as raw materials.

$^1$H-NMR (400 MHz, DMSO-d$_6$) δ: 1.64 (3H, s), 4.31 (1H, d, J=12.2 Hz), 4.55 (1H, d, J=12.2 Hz), 6.89 (1H, d, J=8.8 Hz), 7.04 (1H, d, J=8.8 Hz), 7.05-7.15 (2H, m), 7.27 (1H, t, J=8.8 Hz), 7.32 (1H, d, J=8.8 Hz), 7.44 (2H, br s)

Example 3

[6-chloro-2-oxo-4-phenyl-1,4-dihydro-2H-3,1-benzoxazin-4-yl]methyl(4-fluorophenyl)carbamate The title compound was obtained by a method according to Example 1 using 2-amino-5-chlorobenzonitrile, phenyl magnesium bromide and 1-fluorophenyl-4-isocyanate as raw materials.

$^1$H-NMR (400 MHz, DMSO-d$_6$) δ: 4.70 (1H, d, J=12.2 Hz), 4.94 (1H, d, J=12.2 Hz), 6.94 (1H, d, J=8.8 Hz), 7.09-7.13 (2H, m), 7.32-7.34 (2H, m), 7.38-7.46 (6H, m), 7.76 (1H, d, J=2.4 Hz)

Example 4

[6-chloro-2-oxo-4-phenyl-1,4-dihydro-2H-3,1-benzoxazin-4-yl]methyl(pyridin-3-yl)carbamate The title compound was obtained by a method according to Example 1 using 2-amino-5-chlorobenzonitrile, phenyl magnesium bromide and pyridine-3-isocyanate as raw materials.

$^1$H-NMR (400 MHz, DMSO-d$_6$) δ: 4.74 (1H, d, J=12.7 Hz), 4.97 (1H, d, J=12.7 Hz), 6.94 (1H, d, J=8.3 Hz), 7.29-7.34 (3H, m), 7.37-7.46 (4H, m), 7.78 (1H, d, J=2.0 Hz), 7.87 (1H, br s), 8.21 (1H, dd, J=4.4, 1.5 Hz), 8.61 (1H, br s)

Example 5

[6-chloro-4-methyl-2-oxo-1,4-dihydro-2H-3,1-benzoxazin-4-yl]methyl(4-fluorophenyl)carbamate The title compound was obtained by a method according to Example 1 using 2-amino-5-chlorobenzonitrile, methyl magnesium bromide and 1-fluorophenyl-4-isocyanate as raw materials.

¹H-NMR (400 MHz, DMSO-d₆) δ: 1.64 (3H, s), 4.33 (1H, d, J=12.2 Hz), 4.57 (1H, d, J=12.2 Hz), 6.90 (1H, d, J=8.8 Hz), 7.11 (2H, t, J=8.8 Hz), 7.33 (1H, dd, J=8.8, 2.4 Hz), 7.42 (2H, br s), 7.46 (1H, d, J=2.4 Hz), 9.73 (1H, br s)

Example 6

[6-chloro-4-isopropyl-2-oxo-1,4-dihydro-2H-3,1-benzoxazin-4-yl]methyl(4-fluorophenyl)carbamate The title compound was obtained by a method according to Example 1 using 2-amino-5-chlorobenzonitrile, isopropyl magnesium bromide and 1-fluorophenyl-4-isocyanate as raw materials.
¹H-NMR (400 MHz, DMSO-d₆) δ: 0.80 (3H, d, J=6.8 Hz), 0.97 (3H, d, J=6.8 Hz), 2.28 (1H, q, J=6.8 Hz), 4.51 (1H, d, J=12.2 Hz), 4.69 (1H, d, J=12.2 Hz), 6.86 (1H, d, J=8.3 Hz), 7.05-7.12 (2H, br m), 7.31 (1H, dd, J=8.3, 2.0 Hz), 7.36-7.43 (2H, br m), 7.44 (1H, d, J=2.0 Hz)

Example 7

[6-chloro-4-ethyl-2-oxo-1,4-dihydro-2H-3,1-benzoxazin-4-yl]methyl(4-fluorophenyl)carbamate The title compound was obtained by a method according to Example 1 using 2-amino-5-chlorobenzonitrile, ethyl magnesium bromide and 1-fluorophenyl-4-isocyanate as raw materials.
¹H-NMR (400 MHz, DMSO-d₆) δ: 0.79 (3H, t, J=7.3 Hz), 1.91-2.08 (2H, m), 4.35 (1H, d J=12.2 Hz), 4.58 (1H, d, J=12.2 Hz), 6.88 (1H, d, J=8.8 Hz), 7.10 (2H, t, J=8.8 Hz), 7.32 (1H, dd, J=8.8, 2.4 Hz), 7.36-7.46 (2H, br m), 7.44 (1H, d, J=2.4 Hz)

Example 8

[6-chloro-2-oxo-4-(trifluoromethyl)-1,4-dihydro-2H-3,1-benzoxazin-4-yl]methyl-pyrrolidine-1-carboxylate The title compound was obtained by a method according to Example 1 using 6-chloro-4-(hydroxymethyl)-4-(trifluoromethyl)-1,4-dihydro-2H-3,1-benzoxazin-2-one and pyrrolidine-1-carbonyl chloride as raw materials.
¹H-NMR (400 MHz, CDCl₃) δ: 1.64-1.85 (4H, m), 3.03-3.09 (1H, m), 3.18-3.24 (1H, m), 3.33-3.37 (2H, m), 4.59 (1H, d, J=12.2 Hz), 4.81 (1H, d, J=12.2 Hz), 6.89 (1H, d, J=8.8 Hz), 7.34 (1H, br s), 7.36 (1H, dd, J=8.8, 2.4 Hz), 9.36 (1H, br s)

Example 9

[6-chloro-2-oxo-4-(trifluoromethyl)-1,4-dihydro-2H-3,1-benzoxazin-4-yl]methyl(4-methoxyphenyl)carbamate The title compound was obtained by a method according to Example 1 using 6-chloro-4-(hydroxymethyl)-4-(trifluoromethyl)-1,4-dihydro-2H-3,1-benzoxazin-2-one and 4-methoxyphenyl isocyanate as raw materials.
¹H-NMR (400 MHz, DMSO-d₆) δ: 3.71 (3H, s), 4.79 (1H, d, J=12.7 Hz), 5.04 (1H, d J=12.7 Hz), 6.84-6.86 (2H, br m), 7.00 (1H, dd, J=8.8, 1.0 Hz), 7.32 (2H, s), 7.52-7.54 (1H, m), 7.75 (1H, s), 9.60-9.63 (1H, br m)

Example 10

[6-chloro-2-oxo-4-(trifluoromethyl)-1,4-dihydro-2H-3,1-benzoxazin-4-yl]methyl(4-phenoxyphenyl)carbamate The title compound was obtained by a method according to Example 1 using 6-chloro-4-(hydroxymethyl)-4-(trifluoromethyl)-1,4-dihydro-2H-3,1-benzoxazin-2-one and 4-phenoxyphenyl isocyanate as raw materials.
¹H-NMR (400 MHz, DMSO-d₆) δ: 4.83 (1H, d, J=12.2 Hz), 5.07 (1H, d, J=12.2 Hz), 6.93-7.02 (5H, m), 7.09 (1H, dd, J=7.3, 7.3 Hz), 7.35 (2H, dd, J=8.8, 7.3 Hz), 7.44 (2J, br s), 7.53 (1H, dd, J=8.8, 2.2 Hz), 7.76 (1H, br s)

Example 11

[6-chloro-2-oxo-4-(trifluoromethyl)-1,4-dihydro-2H-3,1-benzoxazin-4-yl]methyl[4-(benzyloxy)phenyl]carbamate The title compound was obtained by a method according to Example 1 using 6-chloro-4-(hydroxymethyl)-4-(trifluoromethyl)-1,4-dihydro-2H-3,1-benzoxazin-2-one and 4-(benzyloxy)phenyl isocyanate as raw materials.
¹H-NMR (400 MHz, DMSO-d₆) δ: 4.79 (1H, d, J=12.2 Hz), 5.04 (2H, s), 5.04 (1H, dd, J=12.2 Hz), 6.92-6.95 (2H, br m), 7.00 (1H, d, J=8.8 Hz), 7.30-7.44 (7H, m), 7.52 (1H, dd, J=8.8, 2.2 Hz), 7.73-7.75 (1H, br m)

Example 12

[6-chloro-2-oxo-4-(trifluoromethyl)-1,4-dihydro-2H-3,1-benzoxazin-4-yl]methyl(4-fluorophenyl)caramate The title compound was obtained by a method according to Example 1 using 6-chloro-4-(hydroxymethyl)-4-(trifluoromethyl)-1,4-dihydro-2H-3,1-benzoxazin-2-one and (4-fluorophenyl)isocyanate as raw materials.
¹H-NMR (400 MHz, DMSO-d₆) δ: 4.82 (1H, d, J=12.2 Hz), 5.07 (1H, d, J=12.2 Hz), 7.00 (1H, d, J=8.8 Hz), 7.10-7.15 (2H, br m), 7.44 (2H, br s), 7.53 (1H, dd, J=8.8, 2.4 Hz), 7.76 (1H, br s)

Example 13

[6-chloro-2-oxo-4-(trifluoromethyl)-1,4-dihydro-2H-3,1-benzoxazin-4-yl]methyl(4-chlorophenyl)carbamate The title compound was obtained by a method according to Example 1 using 6-chloro-4-(hydroxymethyl)-4-(trifluoromethyl)-1,4-dihydro-2H-3,1-benzoxazin-2-one and (4-chlorophenyl)isocyanate as raw materials.
¹H-NMR (400 MHz, CD₃OD) δ: 4.77 (1H, d, J=12.3 Hz), 5.04 (1H, d, J=12.3 Hz), 6.94 (1H, d, J=8.6 Hz), 7.23 (2H, d, J=8.2 Hz), 7.37 (2H, br s), 7.44 (1H, dd, J=8.6, 2.2 Hz), 7.56 (1H, br s)

Example 14

[6-chloro-2-oxo-4-(trifluoromethyl)-1,4-dihydro-2H-3,1-benzoxazin-4-yl]methyl(2,4-difluorophenyl)carbamate The title compound was obtained by a method according to Example 1 using 6-chloro-4-(hydroxymethyl)-4-(trifluoromethyl)-1,4-dihydro-2H-3,1-benzoxazin-2-one and (2,4-difluorophenyl)isocyanate as raw materials.
$^1$H-NMR (400 MHz, CDCl$_3$) δ: 4.74 (1H, d, J=12.7 Hz), 4.92 (1H, d, J=12.7 Hz), 6.72-6.89 (2H, m), 6.85 (1H, d, J=8.8 Hz), 7.32 (1H, br s), 7.39 (1H, dd, J=8.8, 2.0 Hz), 7.95 (1H, br s), 8.31 (1H, s)

Example 15

[6-chloro-2-oxo-4-(trifluoromethyl)-1,4-dihydro-2H-3,1-benzoxazin-4-yl]methyl(3-fluorophenyl)carbamate The title compound was obtained by a method according to Example 1 using 6-chloro-4-(hydroxymethyl)-4-(trifluoromethyl)-1,4-dihydro-2H-3,1-benzoxazin-2-one and (3-fluorophenyl)isocyanate as raw materials.
$^1$H-NMR (400 MHz, DMSO-d$_6$) δ: 4.85 (1H, d, J=12.2 Hz), 5.09 (1H, d, J=12.2 Hz), 6.84 (1H, td, J=8.8, 2.0 Hz), 7.01 (1H, d, J=8.3 Hz), 7.19-7.23 (1H, br m), 7.31 (2H, dd, J=15.6, 8.3 Hz), 7.54 (1H, dd, J=8.8, 2.0 Hz), 7.77 (1H, s)

Example 16

[6-chloro-2-oxo-4-(trifluoromethyl)-1,4-dihydro-2H-pyrido[2,3-d][1,3]oxazin-4-yl]methyl(4-fluorophenyl)carbamate 1) Synthesis of 1-(2-amino-5-chloropyridin-3-yl)-2,2,2-trifluoroethanone N-(5-chloro-2-pyridinyl)-2,2-dimethylpropanamide (20.0 g, 94.0 mmol) and TMEDA (12.0 g, 103 mmol) were dissolved in t-butyl methyl ether (150 mL), and while stirring the reaction solution at −20° C., n-butyl lithium (2.66 M hexane solution, 88.3 mL) was added dropwise thereto. After stirring the reaction solution at 0° C. for 2 hours, the solution was cooled to −78° C. and ethyl trifluoroacetate (16.8 mL, 140 mmol) was added thereto. The temperature of the reaction solution was raised to 0° C. and the solution was stirred for 3 hours. Then, water and 2 N hydrochloric acid were sequentially added, and the pH of the reaction solution was adjusted to about 9. After the solution was diluted with ethyl acetate, the organic layer was separated and the solvent was evaporated under reduced pressure. To the residue, acetic acid (60 mL), concentrated hydrochloric acid (20 mL) and water (40 mL) were added, and the solution was stirred for 10 hours under heating at 100° C. After the solution was cooled to room temperature, the resulting solid was collected by filtration and washed with ethyl acetate. The obtained solid and sodium acetate (7.64 g) were mixed in water (15 mL) and t-butyl methyl ether (70 mL), and the solution was stirred at room temperature for 30 minutes. The solution was diluted with ethyl acetate, which was then washed with water and saturated brine, and dried over magnesium sulfate. After the drying agent was removed by filtration, the solvent was evaporated under reduced pressure, whereby the objective compound (10.1 g, 47.8%) was obtained as a yellow solid.
$^1$H-NMR (400 MHz, CDCl$_3$) δ: 6.32 (2H, br s), 7.54 (1H, br s), 8.15 (1H, br s)

2) Synthesis of [6-chloro-2-oxo-4-(trifluoromethyl)-1,4-dihydro-2H-pyrido[2,3-d][1,3]oxazin-4-yl]methyl(4-fluorophenyl)carbamate The title compound was obtained by a method according to Example 1 using 1-(2-amino-5-chloropyridin-3-yl)-2,2,2-trifluoroethanone and (4-fluorophenyl)isocyanate as raw materials.
$^1$H-NMR (400 MHz, DMSO-d$_6$) δ: 4.86 (1H, d, J=12.2 Hz), 5.05 (1H, d, J=12.2 Hz), 7.12-7.14 (2H, br m), 7.42-7.44 (2H, br m), 8.37 (1H, d, J=2.4 Hz), 8.50 (1H, d, J=2.4 Hz)

Example 17

[6-chloro-2-oxo-4-(trifluoromethyl)-1,4-dihydro-2H-pyrido[2,3-d][1,3]oxazin-4-yl]ethyl(4-fluorophenyl)carbamate The title compound was obtained by a method according to Example 1 and Example 16 using 2-amino-5-chloropyridine, ethyl trifluoroacetate, allyl magnesium bromide and (4-fluorophenyl)isocyanate as raw materials.
$^1$H-NMR (400 MHz, DMSO-d$_6$) δ: 2.97-3.04 (1H, m), 3.27-3.38 (1H, m), 4.18-4.30 (2H, m), 7.09 (2H, dd, J=8.8, 8.8 Hz), 7.33 (2H, br s), 8.23 (1H, br s), 8.34 (1H, d, J=2.0 Hz)

Example 18

[6-chloro-2-oxo-4-(trifluoromethyl)-1,4-dihydro-2H-3,1-benzoxazin-4-yl]methyl[4-(methylsulfonyl)phenyl]carbamate The title compound was obtained by a method according to Example 1 using 6-chloro-4-(hydroxymethyl)-4-(trifluoromethyl)-1,4-dihydro-2H-3,1-benzoxazin-2-one and 4-(methylsulfonyl)phenyl isocyanate as raw materials.
$^1$H-NMR (400 MHz, DMSO-d$_6$) δ: 3.15 (3H, s), 4.87 (1H, d, J=12.2 Hz), 5.11 (1H, d, J=12.2 Hz), 7.00 (1H, d, J=8.8 Hz), 7.53 (1H, dd, J=8.8, 2.4 Hz), 7.66 (2H, d, J=8.8 Hz), 7.76 (1H, s), 7.83 (2H, d, J=8.8 Hz)

Example 19

[6-chloro-2-oxo-4-(trifluoromethyl)-1,4-dihydro-2H-3,1-benzoxazin-4-yl]methyl(pyridin-3-yl)carbamate The title compound was obtained by a method according to Example 1 using 6-chloro-4-(hydroxymethyl)-4-(trifluoromethyl)-1,4-dihydro-2H-3,1-benzoxazin-2-one and pyridine-3-isocyanate as raw materials.
$^1$H-NMR (400 MHz, DMSO-d$_6$) δ: 4.84 (1H, d, J=12.2 Hz), 5.08 (1H, d, J=12.2 Hz), 6.99 (1H, d, J=8.8 Hz), 7.32 (1H, br s), 7.51 (1H, dd, J=8.8, 2.2 Hz), 7.75 (1H, s), 7.87 (1H, br s), 8.23 (1H, dd, J=4.9, 1.5 Hz), 8.59 (1H, br s)

Example 20

2-[({[6-chloro-2-oxo-4-(trifluoromethyl)-1,4-dihydro-2H-3,1-benzoxazin-4-yl]methoxy}carbonyl)amino]pyridinium trifluoroacetate The title compound was obtained by a method according to Example 1 using 6-chloro-4-(hydroxymethyl)-4-(trifluoromethyl)-1,4-dihydro-2H-3,1-benzoxazin-2-one and pyridine-2-isocyanate as raw materials.
$^1$H-NMR (400 MHz, DMSO-d$_6$) δ: 4.80 (1H, d, J=12.2 Hz), 5.08 (1H, d, J=12.2 Hz), 7.00 (1H, d, J=8.3 Hz), 7.05-7.08 (1H, m), 7.53 (1H, dd, J=8.3, 2.4 Hz), 7.69-7.72 (1H, m), 7.74-7.78 (2H, m), 8.24-8.26 (1H, m)

Example 21

[6-chloro-2-oxo-4-(trifluoromethyl)-1,4-dihydro-2H-3,1-benzoxazin-4-yl]methyl(cyclopentyl)carbamate The title compound was obtained by a method according to Example 1 using 6-chloro-4-(hydroxymethyl)-4-(trifluoromethyl)-1,4-dihydro-2H-3,1-benzoxazin-2-one and cyclopentyl isocyanate as raw materials.

$^1$H-NMR (400 MHz, DMSO-d$_6$) δ: 1.28-1.57 (6H, m), 1.68-1.76 (2H, m), 3.70-3.75 (1H, m), 4.62 (1H, d, J=12.2 Hz), 4.92 (1H, d, J=12.2 Hz), 6.97 (1H, d, J=8.8 Hz), 7.38 (1H, d, J=6.8 Hz), 7.50 (1H, d, J=8.8 Hz), 7.63 (1H, s)

Example 22

[8-methoxy-2-oxo-4-(trifluoromethyl)-1,4-dihydro-2H-3,1-benzoxazin-4-yl]methyl(4-fluorophenyl) carbamate The title compound was obtained by a method according to Example 1 and Example 16 using 2-methoxyaniline, ethyl trifluoroacetate and (4-fluorophenyl)isocyanate as raw materials.

$^1$H-NMR (400 MHz, DMSO-d$_6$) δ: 3.84 (3H, s), 4.75 (1H, d, J=12.2 Hz), 5.01 (1H, d, J=12.2 Hz), 7.10-7.14 (5H, m), 7.41-7.46 (2H, br m)

Example 23

[6-chloro-1-methyl-2-oxo-4-(trifluoromethyl)-1,4-dihydro-2H-3,1-benzoxazin-4-yl]methyl(4-fluorophenyl)carbamate 1) Synthesis of 6-chloro-4-(trifluoromethyl)-4-vinyl-1,4-dihydro-2H-3,1-benzoxazin-2-one The title compound was obtained by a method according to Example 1 and Example 16 using 4-chloroaniline, ethyl trifluoroacetate and vinyl magnesium bromide as raw materials.

$^1$H-NMR (400 MHz, DMSO-d$_6$) δ: 5.66 (1H, d, J=16.8 Hz), 5.69 (1H, d, J=11.0 Hz), 6.64 (1H, dd, J=16.8, 11.0 Hz), 7.00 (1H, d, J=8.8 Hz), 7.51 (1H, dd, J=8.8, 2.4 Hz), 7.61 (1H, d, J=2.4 Hz), 10.99 (1H, s)

2) Synthesis of 6-chloro-1-methyl-4-(trifluoromethyl)-4-vinyl-1,4-dihydro-2H-3,1-benzoxazin-2-one To a stirred solution of 6-chloro-4-(trifluoromethyl)-4-vinyl-1,4-dihydro-2H-3,1-benzoxazin-2-one (100 mg, 0.36 mmol) in DMF (1 mL), sodium hydride (60%, 29 mg, 0.72 mmol) were added at 0° C. After the mixture was stirred at 0° C. for 30 minutes, methyl iodide (44.8 μL, 0.72 mmol) was added dropwise thereto. After the reaction solution was stirred overnight at room temperature, water was added thereto. The solution was diluted with ethyl acetate and a saturated aqueous ammonium chloride solution was added thereto. The organic layer was separated and washed with saturated brine and then dried over magnesium sulfate. After the drying agent was removed by filtration, the solvent was evaporated under reduced pressure, whereby the objective compound (107 mg, quant.) was obtained as a pale brown solid.

$^1$H-NMR (400 MHz, CDCl$_3$) δ: 3.41 (3H, s), 5.66 (1H, d, J=10.7 Hz), 5.67 (1H, d, J=17.1 Hz), 6.18 (1H, dd, J=17.1, 10.7 Hz), 6.94 (1H, d, J=8.8 Hz), 7.34 (1H, d, J=2.4 Hz), 7.42 (1H, dd, J=8.8, 2.4 Hz)

3) [6-chloro-1-methyl-2-oxo-4-(trifluoromethyl)-1,4-dihydro-2H-3,1-benzoxazin-4-yl]methyl(4-fluorophenyl)carbamate The title compound was obtained by a method according to Example 1 using 6-chloro-1-methyl-4-(trifluoromethyl)-4-vinyl-1,4-dihydro-2H-3,1-benzoxazin-2-one and (4-fluorophenyl)isocyanate as raw materials.

$^1$H-NMR (400 MHz, DMSO-d$_6$) δ: 3.36 (3H, s), 4.85 (1H, d, J=12.2 Hz), 5.10 (1H, d, J=12.2 Hz), 7.09-7.15 (2H, m), 7.29 (1H, d, J=8.8 Hz), 7.41-7.46 (2H, br m), 7.66 (1H, dd, J=8.8, 2.4 Hz), 7.82 (1H, d, J=2.4 Hz)

Example 24

[5-methoxy-2-oxo-4-(trifluoromethyl)-1,4-dihydro-2H-3,1-benzoxazin-4-yl]methyl(4-fluorophenyl) carbamate The title compound was obtained by a method according to Example 1 and Example 16 using 3-methoxyaniline, ethyl trifluoroacetate and (4-fluorophenyl)isocyanate as raw materials.

$^1$H-NMR (400 MHz, DMSO-d$_6$) δ: 3.84 (3H, s), 4.75 (1H, d, J=12.2 Hz), 5.01 (1H, d, J=12.2 Hz), 7.08-7.15 (5H, m), 7.44 (2H, br s)

Example 25

[6-fluoro-2-oxo-4-(trifluoromethyl)-1,4-dihydro-2H-3,1-benzoxazin-4-yl]methyl(4-fluorophenyl)carbamate The title compound was obtained by a method according to Example 1 and Example 16 using 4-fluoroaniline, ethyl trifluoroacetate and (4-fluorophenyl)isocyanate as raw materials.

$^1$H-NMR (400 MHz, DMSO-d$_6$) δ: 4.80 (1H, d, J=12.2 Hz), 5.03 (1H, d, J=12.2 Hz), 7.01 (1H, dd, J=8.8, 4.9 Hz), 7.05-7.18 (2H, br m), 7.33-7.38 (1H, m), 7.44 (2H, br s), 7.59 (1H, dd, J=8.8, 2.4 Hz), 9.85 (1H, br s)

Example 26

[6-fluoro-2-oxo-4-(trifluoromethyl)-1,4-dihydro-2H-3,1-benzoxazin-4-yl]methyl(pyridin-3-yl)carbamate The title compound was obtained by a method according to Example 1 and Example 16 using 4-fluoroaniline, ethyl trifluoroacetate and pyridine-3-isocyanate as raw materials.

$^1$H-NMR (400 MHz, DMSO-d$_6$) δ: 4.82 (1H, d, J=12.2 Hz), 5.05 (1H, d, J=12.2 Hz), 7.00 (1H, dd, J=9.0, 4.6 Hz), 7.24-7.39 (2H, m), 7.60 (1H, dd, J=9.0, 2.7 Hz), 7.85 (1H, br s), 8.21 (1H, dd, J=4.6, 1.2 Hz), 8.57 (1H, br s), 10.03 (1H, br s)

Example 27

N-{[6-chloro-2-oxo-4-(trifluoromethyl)-1,4-dihydro-2H-3,1-benzoxazin-4-yl]methyl}-4-fluorobenzamide 1) Synthesis of 6-chloro-4-(hydroxymethyl)-4-(trifluoromethyl)-1,4-dihydro-2H-3,1-benzoxazin-2-one According to Example 1, the objective compound was synthesized from a known compound (J. Org. Chem., 1998, 63, 8536) 1-(2-amino-5-chlorophenyl)-2,2,2-trifluoroethanone.

$^1$H-NMR (400 MHz, DMSO-d$_6$) δ: 3.93 (1H, d, J=12.2 Hz), 4.23 (1H, d, J=12.2 Hz), 6.91 (1H, d, J=8.3 Hz), 7.43 (1H, dd, J=8.3, 2.2 Hz), 7.52 (1H, br s)

2) Synthesis of 4-(azidomethyl)-6-chloro-4-(trifluoromethyl)-1,4-dihydro-2H-3,1-benzoxazin-2-one 6-Chloro-4-(hydroxymethyl)-4-(trifluoromethyl)-1,4-dihydro-2H-3,1-benzoxazin-2-one (4.0 g, 14.2 mmol) was dissolved in chloroform (30 mL) and THF (15 mL), and while stirring the mixture at 0° C., 2,6-dimethylpyridine (13.2 mL, 113 mmol) and trifluoromethanesulfonic anhydride (9.6 mL, 56.8 mmol) were sequentially added thereto. After the reaction solution was stirred for 3 hours under ice-cooling, a saturated aqueous sodium hydrogen carbonate solution was added thereto under ice-cooling. Then, the solution was diluted with ethyl acetate and the organic layer was separated. The organic layer was washed sequentially with a 10% aqueous citric acid solution and saturated brine and then dried over magnesium sulfate. After the drying agent was removed by filtration, the solvent was evaporated under reduced pressure. The resulting residue was dissolved in DMF (50 mL), and sodium azide (1.53 g, 23.5 mmol) was added thereto. After the reaction solution was stirred overnight at 80° C., the temperature of the solution was brought to room temperature and water was added thereto. The solution was diluted with ethyl acetate and the organic layer was separated. The organic layer was washed with saturated brine and then dried over magnesium sulfate. After the drying agent was removed by filtration, the solvent was evaporated under reduced pressure. The residue was purified by silica gel column chromatography (ethyl acetate/hexane=1/2), whereby the objective compound (3.47 g, 80%) was obtained as a white solid.

$^1$H-NMR (400 MHz, DMSO-d$_6$) δ: 4.25 (1H, d, J=14.1 Hz), 4.55 (1H, d, J=14.1 Hz), 7.00 (1H, d, J=8.8 Hz), 7.54 (1H, dd, J=8.8, 2.2 Hz), 7.73 (1H, d, J=2.2 Hz), 11.03 (1H, br s)

3) Synthesis of [6-chloro-2-oxo-4-(trifluoromethyl)-1,4-dihydro-2H-3,1-benzoxazin-4-yl]methylamine hydrochloride To a mixed solution of THF (20 mL) and water (10 mL) containing 4-(azidomethyl)-6-chloro-4-(trifluoromethyl)-1,4-dihydro-2H-3,1-benzoxazin-2-one (2.59 g, 8.44 mmol), trimethyl phosphite (2 mL, 16.9 mmol) was added at room temperature, and the reaction solution was stirred at 60° C. for 5 hours. After the reaction solution was left to cool, water was added thereto, and the resulting solution was diluted with ethyl acetate and the organic layer was separated. The organic layer was washed with saturated brine and then dried over magnesium sulfate. After the drying agent was removed by filtration, the solvent was evaporated under reduced pressure. To the residue, a 4 N hydrochloric acid-dioxane solution (30 mL) was added, and the mixture was stirred at 40° C. for 24 hours. After the mixture was left to cool, the resulting solid was collected by filtration and washed with ethyl acetate and then dried under reduced pressure, whereby the objective compound (2.31 g, 86%) was obtained as a white solid.

$^1$H-NMR (400 MHz, DMSO-d$_6$) δ: 3.57 (1H, d, J=14.1 Hz), 4.27 (1H, d, J=14.1 Hz), 7.01 (1H, d, J=8.8 Hz), 7.56 (1H, dd, J=8.8, 2.2 Hz), 7.77 (1H, d, J=2.2 Hz), 8.44 (2H, s), 11.10 (1H, s)

4) Synthesis of N-{[6-chloro-2-oxo-4-(trifluoromethyl)-1,4-dihydro-2H-3,1-benzoxazin-4-yl]methyl}-4-fluorobenzamide While stirring a solution of DMF (20 mL) containing [6-chloro-2-oxo-4-(trifluoromethyl)-1,4-dihydro-2H-3,1-benzoxazin-4-yl]methylamine hydrochloride (2.0 g, 6.3 mmol), 4-fluorobenzoic acid (972 mg, 6.94 mmol), hydroxybenzotriazole hydrochloride (852 mg, 6.3 mmol) and triethylamine (2.1 mL, 15.8 mmol) at 0° C., 1-ethyl-3-(3-dimethylaminopropyl)carbodiimide hydrochloride (1.45 g, 7.57 mmol) was added little by little thereto. After the reaction solution was stirred at room temperature for 5 hours, water was added thereto. Then, the resulting solution was diluted with ethyl acetate and the organic layer was separated. The organic layer was washed with saturated brine and then dried over magnesium sulfate. After the drying agent was removed by filtration, the solvent was evaporated under reduced pressure. The residue was purified by silica gel column chromatography (ethyl acetate/hexane=1/1), whereby the objective compound (2.1 g, 82%) was obtained as a white solid.

$^1$H-NMR (400 MHz, DMSO-d$_6$) δ: 3.87 (1H, dd, J=14.4, 4.4 Hz), 4.58 (1H, dd, J=14.4, 7.6 Hz), 6.92 (1H, d, J=8.3 Hz), 7.25 (2H, t, J=9.3 Hz), 7.43-7.50 (2H, m), 7.71-7.78 (2H, m), 8.81 (1H, dd, J=7.6, 4.4 Hz), 10.19 (1H, s)

Synthesis of N-{[(4S*)-6-chloro-2-oxo-4-(trifluoromethyl)-1,4-dihydro-2H-3,1-benzoxazin-4-yl]methyl}-4-fluorobenzamide N-{[6-chloro-2-oxo-4-(trifluoromethyl)-1,4-dihydro-2H-3,1-benzoxazin-4-yl]methyl}-4-fluorobenzamide was subjected to optical resolution by HPLC (Chiralpack AD-H, n-hexane:2-propanol=4:1), and a fraction eluted at a later time was concentrated, whereby the objective compound was obtained.

Example 28

N-{[6-chloro-2-oxo-4-(trifluoromethyl)-1,4-dihydro-2H-pyrido[3,4-d][1,3]oxazin-4-yl]methyl}-4-fluorobenzamide The title compound was obtained by a method according to Example 27 using 3-amino-6-chloropyridine, ethyl trifluoroacetate and 4-fluorobenzoic acid as raw materials.

$^1$H-NMR (400 MHz, DMSO-d$_6$) δ: 4.07 (1H, d, J=10.7 Hz), 4.23 (1H, d, J=10.7 Hz), 7.36 (2H, t, J=8.8 Hz), 7.64 (1H, s), 8.01 (2H, dd, J=8.8, 5.4 Hz), 8.51 (1H, s), 8.65 (1H, s)

Example 29

N-{[2-oxo-4-(trifluoromethyl)-1,4-dihydro-2H-3,1-benzoxazin-4-yl]methyl}benzamide The title compound was obtained by a method according to Example 27 using aniline, ethyl trifluoroacetate and benzoic acid as raw materials.

$^1$H-NMR (400 MHz, DMSO-d$_6$) δ: 3.82 (1H, d, J=14.5 Hz), 4.62 (1H, d, J=14.5 Hz), 6.91 (1H, d, J=8.2 Hz), 7.05 (1H, t, J=7.8 Hz), 7.34-7.41 (4H, m), 7.46-7.50 (1H, m), 7.64 (2H, d, J=7.8 Hz)

Example 30

N-{[2-oxo-4-(trifluoromethyl)-1,4-dihydro-2H-3,1-benzoxazin-4-yl]methyl}pyridine-2-carboxamide The title compound was obtained by a method according to Example 27 using aniline, ethyl trifluoroacetate and pyridine-2-carboxylic acid as raw materials.

$^1$H-NMR (400 MHz, DMSO-d$_6$) δ: 4.14 (1H, d, J=14.5 Hz), 4.39 (1H, d, J=14.5 Hz), 6.89 (1H, d, J=8.0 Hz), 7.08

(1H, t, J=7.8 Hz), 7.36 (1H, t, J=7.5 Hz), 7.50 (1H, d, J=7.8 Hz), 7.55-7.58 (1H, m), 7.93-7.98 (2H, m), 8.56 (1H, d, J=4.5 Hz)

Example 31

4-fluoro-N-{[2-oxo-4-(trifluoromethyl)-1,4-dihydro-2H-3,1-benzoxazin-4-yl]methyl}benzamide The title compound was obtained by a method according to Example 27 using aniline, ethyl trifluoroacetate and 4-fluorobenzoic acid as raw materials.
$^1$H-NMR (400 MHz, DMSO-d$_6$) δ: 3.78 (1H, d, J=14.7 Hz), 4.57 (1H, d, J=14.7 Hz), 6.87 (1H, d, J=8.2 Hz), 7.01 (1H, t, J=8.0 Hz), 7.20 (2H, t, J=9.0 Hz), 7.32 (2H, t, J=8.2 Hz), 7.67-7.71 (2H, m)

Example 32

N-{2-[6-chloro-2-oxo-4-(trifluoromethyl)-1,4-dihydro-2H-3,1-benzoxazin-4-yl]ethyl}-4-fluorobenzamide The title compound was obtained by a method according to Example 27 using 1-(2-amino-5-chlorphenyl)-2,2,2-trifluoroethanone, allyl magnesium bromide and 4-fluorobenzoic acid as raw materials.
$^1$H-NMR (400 MHz, DMSO-d$_6$) δ: 2.29-2.40 (1H, m), 2.70-2.80 (1H, m), 3.31 (2H, dd, J=13.2, 6.8 Hz), 6.93 (1H, d, J=8.8 Hz), 7.21-7.28 (2H, m), 7.40 (1H, dd, J=8.8, 2.4 Hz), 7.51-7.53 (1H, m), 7.72-7.79 (2H, m), 8.48 (1H, t, J=5.6 Hz), 10.83 (1H, s)

N-{2-[(4R*)-6-chloro-2-oxo-4-(trifluoromethyl)-1,4-dihydro-2H-3,1-benzoxazin-4-yl]ethyl}-4-fluorobenzamide N-{2-[6-chloro-2-oxo-4-(trifluoromethyl)-1,4-dihydro-2H-3,1-benzoxazin-4-yl]ethyl}-4-fluorobenzamide was subjected to optical resolution by HPLC (Chiralpack AD-H, n-hexane:2-propanol=3:1), and a fraction eluted at a later time was concentrated, whereby the objective compound was obtained.

Example 33

N-{3-[6-chloro-2-oxo-4-(trifluoromethyl)-1,4-dihydro-2H-3,1-benzoxazin-4-yl]propyl}-4-fluorobenzamide The title compound was obtained by a method according to Example 27 using 1-(2-amino-5-chlorphenyl)-2,2,2-trifluoroethanone, 3-butenyl magnesium bromide and 4-fluorobenzoic acid as raw materials.
$^1$H-NMR (400 MHz, DMSO-d$_6$) δ: 1.25-1.40 (1H, m), 1.47-1.64 (1H, m), 2.03-2.17 (1H, m), 2.54-2.64 (1H, m), 3.19-3.37 (2H, m), 6.95 (1H, d, J=8.5 Hz), 7.24-7.29 (2H, m), 7.48 (1H, dd, J=8.5, 2.2 Hz), 7.60 (1H, s), 7.84-7.91 (2H, m), 8.51 (1H, t, J=5.6 Hz), 10.85 (1H, s)

N-{3-[(4R*)-6-chloro-2-oxo-4-(trifluoromethyl)-1,4-dihydro-2H-3,1-benzoxazin-4-yl]propyl}-4-fluorobenzamide N-{3-[6-chloro-2-oxo-4-(trifluoromethyl)-1,4-dihydro-2H-3,1-benzoxazin-4-yl]propyl}-4-fluorobenzamide was subjected to optical resolution by HPLC (Chiralpack AD-H, n-hexane:2-propanol=3:1), and a fraction eluted at a later time was concentrated, whereby the objective compound was obtained.

Example 34

N-{[6-chloro-2-oxo-4-(trifluoromethyl)-1,4-dihydro-2H-3,1-benzoxazin-4-yl]methyl}-3-fluorobenzamide The title compound was obtained by a method according to Example 27 using [6-chloro-2-oxo-4-(trifluoromethyl)-1,4-dihydro-2H-3,1-benzoxazin-4-yl]methylamine hydrochloride and 3-fluorobenzoic acid as raw materials.
$^1$H-NMR (400 MHz, DMSO-d$_6$) δ: 3.87 (1H, dd, J=14.6, 4.4 Hz), 4.57 (1H, dd, J=14.6, 7.8 Hz), 6.91 (1H, d, J=8.8 Hz), 7.32-7.39 (1H, m), 7.42-7.53 (6H, m), 8.88 (1H, dd, J=7.8, 4.4 Hz), 10.87 (1H, s)

Example 35

N-{[6-chloro-2-oxo-4-(trifluoromethyl)-1,4-dihydro-2H-3,1-benzoxazin-4-yl]methyl}-2-fluorobenzamide The title compound was obtained by a method according to Example 27 using [6-chloro-2-oxo-4-(trifluoromethyl)-1,4-dihydro-2H-3,1-benzoxazin-4-yl]methylamine hydrochloride and 2-fluorobenzoic acid as raw materials.
$^1$H-NMR (400 MHz, DMSO-d$_6$) δ: 3.86 (1H, dd, J=14.4, 4.4 Hz), 4.55 (1H, dd, J=14.4, 7.6 Hz), 6.93 (1H, d, J=8.8 Hz), 7.16-7.23 (2H, m), 7.29 (1H, td, J=7.4, 1.8 Hz), 7.42-7.50 (3H, m), 8.78 (1H, dd, J=7.6, 4.4 Hz), 10.85 (1H, s)

Example 36

N-{[6-chloro-2-oxo-4-(trifluoromethyl)-1,4-dihydro-2H-3,1-benzoxazin-4-yl]methyl}-4-methylbenzamide The title compound was obtained by a method according to Example 27 using [6-chloro-2-oxo-4-(trifluoromethyl)-1,4-dihydro-2H-3,1-benzoxazin-4-yl]methylamine hydrochloride and 4-methylbenzoic acid as raw materials.
$^1$H-NMR (400 MHz, DMSO-d$_6$) δ: 2.30 (3H, s), 3.82 (1H, dd, J=14.6, 4.4 Hz), 4.58 (1H, dd, J=14.6, 7.8 Hz), 6.90 (1H, d, J=8.3 Hz), 7.20 (2H, d, J=8.3 Hz), 7.40-7.48 (2H, m), 7.57 (2H, d, J=8.3 Hz), 8.69 (1H, dd, J=7.8, 4.4 Hz), 10.84 (1H, s)

Example 37

N-{[6-chloro-2-oxo-4-(trifluoromethyl)-1,4-dihydro-2H-3,1-benzoxazin-4-yl]methyl}-2-methylbenzamide The title compound was obtained by a method according to Example 27 using [6-chloro-2-oxo-4-(trifluoromethyl)-1,4-dihydro-2H-3,1-benzoxazin-4-yl]methylamine hydrochloride and 2-methylbenzoic acid as raw materials.
$^1$H-NMR (400 MHz, DMSO-d$_6$) δ: 2.01 (3H, s), 3.76 (1H, dd, J=14.6, 4.4 Hz), 4.62 (1H, dd, J=14.6, 7.8 Hz), 6.93 (1H, d, J=8.8 Hz), 7.04-7.06 (1H, m), 7.13-7.16 (2H, m), 7.23-7.29 (1H, m), 7.47-7.50 (2H, m), 8.75 (1H, dd, J=7.8, 4.4 Hz), 10.85 (1H, s)

Example 38

N-{[6-chloro-2-oxo-4-(trifluoromethyl)-1,4-dihydro-2H-3,1-benzoxazin-4-yl]methyl}-3-methylbenzamide The title compound was obtained by a method according to Example 27 using [6-chloro-2-oxo-4-(trifluoromethyl)-1,4-dihydro-2H-3,1-benzoxazin-4-yl]methylamine hydrochloride and 3-methylbenzoic acid as raw materials.
$^1$H-NMR (400 MHz, DMSO-$d_6$) δ: 2.29 (3H, s), 3.83 (1H, dd, J=14.6, 4.4 Hz), 4.58 (1H, dd, J=14.6, 7.8 Hz), 6.91 (1H, d, J=8.3 Hz), 7.25-7.31 (2H, m), 7.41-7.49 (5H, m), 8.73 (1H, dd, J=7.8, 4.4 Hz), 10.86 (1H, s)

Example 39

N-{[6-chloro-2-oxo-4-(trifluoromethyl)-1,4-dihydro-2H-3,1-benzoxazin-4-yl]methyl}biphenyl-4-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 4-phenylbenzoic acid as raw materials.
$^1$H-NMR (400 MHz, DMSO-$d_6$) δ: 3.87 (1H, dd, J=14.6, 4.4 Hz), 4.62 (1H, dd, J=14.6, 7.8 Hz), 6.92 (1H, d, J=8.3 Hz), 7.37-7.49 (5H, m), 7.64-7.79 (6H, m), 8.84 (1H, dd, J=7.8, 4.4 Hz), 10.86 (1H, s)

Example 40

N-{[6-chloro-2-oxo-4-(trifluoromethyl)-1,4-dihydro-2H-3,1-benzoxazin-4-yl]methyl}biphenyl-2-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 2-phenylbenzoic acid as raw materials.
$^1$H-NMR (400 MHz, DMSO-$d_6$) δ: 3.70 (1H, dd, J=14.4, 4.6 Hz), 4.37 (1H, dd, J=14.4, 7.3 Hz), 6.95 (1H, d, J=8.8 Hz), 7.00 (1H, dd, J=7.6, 1.2 Hz), 7.21-7.25 (2H, m), 7.27-7.36 (5H, m), 7.41-7.51 (3H, m), 8.65 (1H, dd, J=7.3, 4.6 Hz), 10.83 (1H, s)

Example 41

N-{[6-chloro-2-oxo-4-(trifluoromethyl)-1,4-dihydro-2H-3,1-benzoxazin-4-yl]methyl}isonicotinamide The title compound was obtained by a method according to Example 27 using [6-chloro-2-oxo-4-(trifluoromethyl)-1,4-dihydro-2H-3,1-benzoxazin-4-yl]methylamine hydrochloride and isonicotinic acid as raw materials.
$^1$H-NMR (400 MHz, DMSO-$d_6$) δ: 3.90 (1H, dd, J=14.6, 4.4 Hz), 4.57 (1H, dd, J=14.6, 7.6 Hz), 6.92 (1H, d, J=8.5 Hz), 7.43-7.49 (2H, m), 7.53 (2H, dd, J=4.4, 1.5 Hz), 8.66 (2H, dd, J=4.4, 1.5 Hz), 9.08 (1H, dd, J=7.6, 4.4 Hz), 10.87 (1H, s)

Example 42

N-{[6-chloro-2-oxo-4-(trifluoromethyl)-1,4-dihydro-2H-3,1-benzoxazin-4-yl]methyl}nicotinamide The title compound was obtained by a method according to Example 27 using [6-chloro-2-oxo-4-(trifluoromethyl)-1,4-dihydro-2H-3,1-benzoxazin-4-yl]methylamine hydrochloride and nicotinic acid as raw materials.
$^1$H-NMR (400 MHz, DMSO-$d_6$) δ: 3.89 (1H, dd, J=14.6, 4.4 Hz), 4.58 (1H, dd, J=14.6, 7.8 Hz), 6.92 (1H, d, J=8.3 Hz), 7.41-7.52 (3H, m), 7.98 (1H, dt, J=7.8, 2.0 Hz), 8.66 (1H, dd, J=4.9, 2.0 Hz), 8.75 (1H, d, J=2.0 Hz), 8.99 (1H, dd, J=7.8, 4.4 Hz), 10.87 (1H, s)

Example 43

N-{[6-chloro-2-oxo-4-(trifluoromethyl)-1,4-dihydro-2H-3,1-benzoxazin-4-yl]methyl}pyridine-2-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and pyridine-2-carboxylic acid as raw materials.
$^1$H-NMR (400 MHz, DMSO-$d_6$) δ: 4.16 (1H, dd, J=14.6, 5.9 Hz), 4.42 (1H, dd, J=14.6, 7.3 Hz), 6.91 (1H, d, J=8.8 Hz), 7.46 (1H, dd, J=8.8, 2.2 Hz), 7.57-7.62 (1H, m), 7.63-7.65 (1H, br m), 7.94-8.02 (2H, m), 8.57-8.62 (1H, m), 8.73 (1H, t, J=6.6 Hz), 10.88 (1H, s)

Example 44

N-{[6-chloro-2-oxo-4-(trifluoromethyl)-1,4-dihydro-2H-3,1-benzoxazin-4-yl]methyl}-4-methoxybenzamide The title compound was obtained by a method according to Example 27 using [6-chloro-2-oxo-4-(trifluoromethyl)-1,4-dihydro-2H-3,1-benzoxazin-4-yl]methylamine hydrochloride and 4-methoxybenzoic acid as raw materials.
$^1$H-NMR (400 MHz, DMSO-$d_6$) δ: 3.76 (3H, s), 3.81 (1H, dd, J=14.4, 4.4 Hz), 4.57 (1H, dd, J=14.4, 7.8 Hz), 6.88-6.95 (3H, m), 7.41-7.45 (2H, m), 7.64-7.68 (2H, m), 8.61 (1H, dd, J=7.8, 4.4 Hz), 10.84 (1H, s)

Example 45

N-{[6-chloro-2-oxo-4-(trifluoromethyl)-1,4-dihydro-2H-3,1-benzoxazin-4-yl]methyl}-4-(trifluoromethyl)benzamide The title compound was obtained by a method according to Example 27 using [6-chloro-2-oxo-4-(trifluoromethyl)-1,4-dihydro-2H-3,1-benzoxazin-4-yl]methylamine hydrochloride and 4-trifluoromethylbenzoic acid as raw materials.
$^1$H-NMR (400 MHz, DMSO-$d_6$) δ: 3.89 (1H, dd, J=14.6, 4.4 Hz), 4.59 (1H, dd, J=14.6, 7.8 Hz), 6.91 (1H, d, J=8.5 Hz), 7.45 (1H, dd, J=8.5, 2.2 Hz), 7.48 (1H, s), 7.78-7.84 (4H, m), 9.03 (1H, dd, J=7.8, 4.4 Hz), 10.86 (1H, s)

Example 46

N-{[6-chloro-2-oxo-4-(trifluoromethyl)-1,4-dihydro-2H-3,1-benzoxazin-4-yl]methyl}-4-(methanesulfonyl)benzamide The title compound was obtained by a method according to Example 27 using [6-chloro-2-oxo-4-(trifluoromethyl)-1,4-dihydro-2H-3,1-benzoxazin-4-yl]methylamine hydrochloride and 4-(methanesulfonyl)benzoic acid as raw materials.
$^1$H-NMR (400 MHz, DMSO-$d_6$) δ: 3.22 (3H, s), 3.89 (1H, dd, J=14.6, 4.0 Hz), 4.60 (1H, dd, J=14.6, 7.8 Hz), 6.91 (1H, d, J=8.8 Hz), 7.45 (1H, dd, J=8.8, 2.4 Hz), 7.48 (1H, s), 7.86

(2H, dd, J=6.8, 2.0 Hz), 7.96 (2H, dd, J=6.8, 2.0 Hz), 9.06 (1H, dd, J=7.6, 4.0 Hz), 10.87 (1H, s)

Example 47

N-{[6-chloro-2-oxo-4-(trifluoromethyl)-1,4-dihydro-2H-3,1-benzoxazin-4-yl]methyl}-6-fluoronicotinamide The title compound was obtained by a method according to Example 27 using [6-chloro-2-oxo-4-(trifluoromethyl)-1,4-dihydro-2H-3,1-benzoxazin-4-yl]methylamine hydrochloride and 6-fluoronicotinic acid as raw materials.

$^1$H-NMR (400 MHz, DMSO-$d_6$) δ: 3.90 (1H, dd, J=14.6, 4.1 Hz), 4.58 (1H, dd, J=14.6, 7.6 Hz), 6.92 (1H, d, J=8.3 Hz), 7.25 (1H, dd, J=8.3, 2.2 Hz), 7.43-7.49 (2H, m), 8.20 (1H, td, J=8.2, 2.9 Hz), 8.48 (1H, d, J=2.9 Hz), 9.00 (1H, dd, J=7.6, 4.1 Hz), 10.88 (1H, s)

Example 48

N-{[6-chloro-2-oxo-4-(trifluoromethyl)-1,4-dihydro-2H-3,1-benzoxazin-4-yl]methyl}-6-methylnicotinamide The title compound was obtained by a method according to Example 27 using [6-chloro-2-oxo-4-(trifluoromethyl)-1,4-dihydro-2H-3,1-benzoxazin-4-yl]methylamine hydrochloride and 6-methylnicotinic acid as raw materials.

$^1$H-NMR (400 MHz, DMSO-$d_6$) δ: 2.46 (3H, s), 3.86 (1H, dd, J=14.6, 3.9 Hz), 4.58 (1H, dd, J=14.6, 7.8 Hz), 6.91 (1H, d, J=8.8 Hz), 7.29 (1H, d, J=8.8 Hz), 7.43-7.45 (2H, m), 7.89 (1H, dd, J=8.0, 2.2 Hz), 8.65 (1H, d, J=2.2 Hz), 8.90 (1H, dd, J=7.8, 3.9 Hz), 10.86 (1H, s)

Example 49

N-{[6-chloro-2-oxo-4-(trifluoromethyl)-1,4-dihydro-2H-3,1-benzoxazin-4-yl]methyl}-6-(trifluoromethyl)nicotinamide The title compound was obtained by a method according to Example 27 using [6-chloro-2-oxo-4-(trifluoromethyl)-1,4-dihydro-2H-3,1-benzoxazin-4-yl]methylamine hydrochloride and 6-(trifluoromethyl)nicotinic acid as raw materials.

$^1$H-NMR (400 MHz, DMSO-$d_6$) δ: 3.93 (1H, dd, J=14.6, 3.7 Hz), 4.59 (1H, dd, J=14.6, 7.3 Hz), 6.91 (1H, d, J=8.8 Hz), 7.45 (1H, dd, J=8.8, 2.2 Hz), 7.48 (1H, s), 7.99 (1H, d, J=8.3 Hz), 8.24 (1H, dd, J=8.3, 2.0 Hz), 8.89 (1H, d, J=2.0 Hz), 9.17-9.23 (1H, br m), 10.20 (1H, br s)

Example 50

N-{[6-chloro-2-oxo-4-(trifluoromethyl)-1,4-dihydro-2H-3,1-benzoxazin-4-yl]methyl}-1,5-dimethyl-1H-pyrazole-3-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1,5-dimethyl-1H-pyrazole-3-carboxylic acid as raw materials.

$^1$H-NMR (400 MHz, DMSO-$d_6$) δ: 2.21 (3H, s), 3.71 (3H, s), 3.95 (1H, dd, J=14.6, 5.4 Hz), 4.37 (1H, dd, J=14.6, 7.3 Hz), 6.39 (1H, d, J=1.0 Hz), 6.91 (1H, d, J=8.8 Hz), 7.45 (1H, dd, J=8.8, 2.4 Hz), 7.54 (1H, s), 8.02 (1H, dd, J=7.3, 5.4 Hz), 10.84 (1H, s)

Example 51

N-{[6-chloro-2-oxo-4-(trifluoromethyl)-1,4-dihydro-2H-3,1-benzoxazin-4-yl]methyl}isoxazole-4-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and isoxazole-4-carboxylic acid as raw materials.

$^1$H-NMR (400 MHz, DMSO-$d_6$) δ: 3.95 (1H, dd, J=14.6, 4.9 Hz), 4.48 (1H, dd, J=14.6, 7.3 Hz), 6.92 (1H, d, J=8.5 Hz), 7.08 (1H, d, J=2.0 Hz), 7.47 (1H, dd, J=8.5, 2.2 Hz), 7.50 (1H, br s), 8.70 (1H, d, J=2.0 Hz), 9.28-9.34 (1H, m), 10.88 (1H, s)

Example 52

N-{[6-chloro-2-oxo-4-(trifluoromethyl)-1,4-dihydro-2H-3,1-benzoxazin-4-yl]methyl}-2-methoxybenzamide The title compound was obtained by a method according to Example 27 using [6-chloro-2-oxo-4-(trifluoromethyl)-1,4-dihydro-2H-3,1-benzoxazin-4-yl]methylamine hydrochloride and 2-methoxybenzoic acid as raw materials.

$^1$H-NMR (400 MHz, DMSO-$d_6$) δ: 3.66 (3H, s), 4.04 (1H, dd, J=14.4, 5.6 Hz), 4.47 (1H, dd, J=14.4, 6.6 Hz), 6.92-7.00 (2H, m), 7.05 (1H, d, J=7.8 Hz), 7.40-7.45 (1H, m), 7.48-7.53 (2H, m), 7.62 (1H, s), 8.34 (1H, dd, J=6.6, 5.6 Hz), 10.89 (1H, s)

Example 53

N-{[6-chloro-2-oxo-4-(trifluoromethyl)-1,4-dihydro-2H-3,1-benzoxazin-4-yl]methyl}-4-isopropylbenzamide The title compound was obtained by a method according to Example 27 using [6-chloro-2-oxo-4-(trifluoromethyl)-1,4-dihydro-2H-3,1-benzoxazin-4-yl]methylamine hydrochloride and 4-isopropylbenzoic acid as raw materials.

$^1$H-NMR (400 MHz, DMSO-$d_6$) δ: 1.16 (6H, d, J=6.8 Hz), 2.84-2.93 (1H, m), 3.82 (1H, dd, J=14.6, 4.4 Hz), 4.58 (1H, dd, J=14.6, 7.8 Hz), 6.90 (1H, d, J=8.3 Hz), 7.26 (2H, d, J=8.3 Hz), 7.41-7.48 (2H, m), 7.58 (2H, d, J=8.3 Hz), 8.69 (1H, dd, J=7.8, 4.4 Hz), 10.84 (1H, s)

Example 54

N-{[6-chloro-2-oxo-4-(trifluoromethyl)-1,4-dihydro-2H-3,1-benzoxazin-4-yl]methyl}-6-oxo-1,6-dihydro-2-pyridinecarboxamide The title compound was obtained by a method according to Example 27 using [6-chloro-2-oxo-4-(trifluoromethyl)-1,4-dihydro-2H-3,1-benzoxazin-4-yl]methylamine hydrochloride and 6-oxo-1,6-dihydropyridine-2-carboxylic acid as raw materials.

$^1$H-NMR (400 MHz, DMSO-$d_6$) δ: 4.10 (1H, d, J=14.6 Hz), 4.49 (1H, d, J=14.6 Hz), 6.72-6.79 (1H, br m), 6.95 (1H, d, J=8.8 Hz), 7.49 (1H, dd, J=8.8, 2.2 Hz), 7.61 (1H, s), 7.66-7.75 (2H, br m)

Example 55

N-{[6-chloro-2-oxo-4-(trifluoromethyl)-1,4-dihydro-2H-3,1-benzoxazin-4-yl]methyl}-1-methyl-1H-pyrazole-3-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1-methyl-1H-pyrazole-3-carboxylic acid as raw materials.
$^1$H-NMR (400 MHz, DMSO-$d_6$) δ: 3.85 (3H, s), 3.98 (1H, d, J=14.6 Hz), 4.39 (1H, dd, J=14.6, 6.6 Hz), 6.61 (1H, d, J=2.0 Hz), 6.93 (1H, d, J=8.8 Hz), 7.47 (1H, dd, J=8.8, 2.2 Hz), 7.56 (1H, br s), 7.74 (1H, d, J=2.0 Hz), 8.15 (1H, t, J=6.6 Hz), 10.86 (1H, br s)

Example 56

N-{[6-chloro-2-oxo-4-(trifluoromethyl)-1,4-dihydro-2H-3,1-benzoxazin-4-yl]methyl}-1H-pyrazole-3-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1H-pyrazole-3-carboxylic acid as raw materials.
$^1$H-NMR (400 MHz, DMSO-$d_6$) δ: 3.98 (1H, d, J=14.6 Hz), 4.41 (1H, d, J=14.6 Hz), 6.65 (1H, br s), 6.92 (1H, d, J=8.8 Hz), 7.46 (1H, dd, J=8.8, 2.2 Hz), 7.58 (1H, br s), 7.76 (1H, br s)

Example 57

N-{[6-chloro-2-oxo-4-(trifluoromethyl)-1,4-dihydro-2H-3,1-benzoxazin-4-yl]methyl}-1H-pyrazole-4-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1H-pyrazole-4-carboxylic acid as raw materials.
$^1$H-NMR (400 MHz, DMSO-$d_6$) δ: 3.76 (1H, dd, J=14.6, 4.4 Hz), 4.59 (1H, dd, J=14.6, 8.0 Hz), 6.92 (1H, dd, J=8.3, 1.5 Hz), 7.42-7.46 (1H, m), 7.48 (1H, s), 7.84 (1H, br s), 8.17 (1H, br s), 8.35 (1H, dd, J=8.0, 4.4 Hz), 10.87 (1H, s)

Example 58

N-{[6-chloro-2-oxo-4-(trifluoromethyl)-1,4-dihydro-2H-3,1-benzoxazin-4-yl]methyl}pyridazine-3-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and pyridazine-3-carboxylic acid as raw materials.
$^1$H-NMR (400 MHz, DMSO-$d_6$) δ: 4.19 (1H, d, J=14.6 Hz), 4.44 (1H, d, J=14.6 Hz), 6.91 (1H, d, J=8.8 Hz), 7.46 (1H, dd, J=8.8, 2.4 Hz), 7.62 (1H, s), 7.90 (1H, dd, J=8.3, 5.1 Hz), 8.17 (1H, dd, J=8.3, 1.7 Hz), 8.32 (1H, br s), 9.40 (1H, dd, J=5.1, 1.7 Hz)

Example 59

N-{[6-chloro-2-oxo-4-(trifluoromethyl)-1,4-dihydro-2H-3,1-benzoxazin-4-yl]methyl}pyrimidine-2-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and pyrimidine-2-carboxylic acid as raw materials.
$^1$H-NMR (400 MHz, DMSO-$d_6$) δ: 4.12 (1H, d, J=14.1 Hz), 4.45 (1H, d, J=14.1 Hz), 6.92 (1H, d, J=8.8 Hz), 7.47 (1H, dd, J=8.8, 2.4 Hz), 7.63 (1H, s), 7.67 (1H, t, J=4.9 Hz), 8.93 (2H, d, J=4.9 Hz)

Example 60

N-{[6-chloro-2-oxo-4-(trifluoromethyl)-1,4-dihydro-2H-3,1-benzoxazin-4-yl]methyl}pyrimidine-4-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and pyrimidine-4-carboxylic acid as raw materials.
$^1$H-NMR (400 MHz, DMSO-$d_6$) δ: 4.16 (1H, d, J=14.6 Hz), 4.41 (1H, d, J=14.6 Hz), 6.92 (1H, d, J=8.8 Hz), 7.47 (1H, dd, J=8.8, 2.4 Hz), 7.62 (1H, s), 7.97 (1H, dd, J=5.4, 1.5 Hz), 9.05 (1H, d, J=5.4 Hz), 9.30 (1H, d, J=1.5 Hz)

Example 61

N-{[6-chloro-2-oxo-4-(trifluoromethyl)-1,4-dihydro-2H-3,1-benzoxazin-4-yl]methyl}pyrimidine-5-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and pyrimidine-5-carboxylic acid as raw materials.
$^1$H-NMR (400 MHz, DMSO-$d_6$) δ: 3.94 (1H, d, J=14.6 Hz), 4.58 (1H, d, J=14.6 Hz), 6.93 (1H, d, J=8.3 Hz), 7.44-7.52 (2H, m), 8.95 (2H, s), 9.29 (1H, br s), 9.29 (1H, s)

Example 62

N-{[6-chloro-2-oxo-4-(trifluoromethyl)-1,4-dihydro-2H-3,1-benzoxazin-4-yl]methyl}-1,3-oxazole-5-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1,3-oxazole-5-carboxylic acid as raw materials.
$^1$H-NMR (400 MHz, DMSO-$d_6$) δ: 3.90 (1H, d, J=14.1 Hz), 4.49 (1H, dd, J=14.1, 6.3 Hz), 6.91 (1H, d, J=8.8 Hz), 7.45 (1H, dd, J=8.8, 2.2 Hz), 7.50 (1H, s), 7.81 (1H, d, J=1.0 Hz), 8.53 (1H, s), 8.93-8.99 (1H, br m)

Example 63

N-{[6-chloro-2-oxo-4-(trifluoromethyl)-1,4-dihydro-2H-3,1-benzoxazin-4-yl]methyl}-1,3-oxazole-2-carboxamide The title compound was obtained by a method according to Example 27 using [6-chloro-2-oxo-4-(trifluoromethyl)-1,4- dihydro-2H-3,1-benzoxazin-4-yl]methylamine hydrochloride and 1,3-oxazole-2-carboxylic acid as raw materials.
¹H-NMR (400 MHz, DMSO-d₆) δ: 4.02 (1H, d, J=14.4 Hz), 4.38 (1H, dd, J=14.4, 5.6 Hz), 6.92 (1H, d, J=8.5 Hz), 7.43 (1H, br s), 7.47 (1H, dd, J=8.5, 2.2 Hz), 7.54 (1H, br s), 8.31 (1H, br s), 9.16 (1H, br s)

Example 64

N-{[6-chloro-2-oxo-4-(trifluoromethyl)-1,4-dihydro-2H-3,1-benzoxazin-4-yl]methyl}-1,3-oxazole-4-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1,3-oxazole-4-carboxylic acid as raw materials.
¹H-NMR (400 MHz, DMSO-d₆) δ: 4.00 (1H, dd, J=14.6, 3.4 Hz), 4.39 (1H, dd, J=14.6, 5.9 Hz), 6.92 (1H, d, J=8.8 Hz), 7.46 (1H, dd, J=8.8, 2.2 Hz), 7.56 (1H, s), 8.35-8.38 (1H, m), 8.48 (1H, s), 8.67 (1H, t, J=1.0 Hz)

Example 65

N-{[6-chloro-2-oxo-4-(trifluoromethyl)-1,4-dihydro-2H-3,1-benzoxazin-4-yl]methyl}isoxazole-5-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and isoxazole-5-carboxylic acid as raw materials.
¹H-NMR (400 MHz, DMSO-d₆) δ: 3.95 (1H, d, J=14.6 Hz), 4.48 (1H, d, J=14.6 Hz), 6.93 (1H, d, J=8.5 Hz), 7.09 (1H, d, J=2.0 Hz), 7.47 (1H, dd, J=8.5, 2.2 Hz), 7.51 (1H, br s), 8.71 (1H, d, J=2.0 Hz), 9.31 (1H, br s)

Example 66

N-{[6-chloro-2-oxo-4-(trifluoromethyl)-1,4-dihydro-2H-3,1-benzoxazin-4-yl]methyl}-2-methylpropionamide The title compound was obtained by a method according to Example 27 using [6-chloro-2-oxo-4-(trifluoromethyl)-1,4-dihydro-2H-3,1-benzoxazin-4-yl]methylamine hydrochloride and 2-methylpropionic acid as raw materials.
¹H-NMR (400 MHz, DMSO-d₆) δ: 0.64 (3H, d, J=6.8 Hz), 0.88 (3H, d, J=6.8 Hz), 2.24-2.32 (1H, m), 3.53 (1H, d, J=14.6 Hz), 4.44 (1H, dd, J=14.6, 6.3 Hz), 6.93 (1H, d, J=8.8 Hz), 7.27 (1H, br s), 7.46 (1H, dd, J=8.8, 2.2 Hz), 8.18-8.23 (1H, m)

Example 67

N-{[6-chloro-2-oxo-4-(trifluoromethyl)-1,4-dihydro-2H-3,1-benzoxazin-4-yl]methyl}cyclopropane carboxamide The title compound was obtained by a method according to Example 27 using [6-chloro-2-oxo-4-(trifluoromethyl)-1,4-dihydro-2H-3,1-benzoxazin-4-yl]methylamine hydrochloride and cyclopropane carboxylic acid as raw materials.
¹H-NMR (400 MHz, DMSO-d₆) δ: 0.46-0.72 (4H, m), 1.50-1.56 (1H, m), 3.66 (1H, d, J=14.6 Hz), 4.43 (1H, dd, J=14.6, 5.9 Hz), 6.95 (1H, d, J=8.8 Hz), 7.37 (1H, d, J=2.0 Hz), 7.49 (1H, dd, J=8.8, 2.0 Hz), 8.44-8.49 (1H, m)

Example 68

N-{[6-chloro-2-oxo-4-(trifluoromethyl)-1,4-dihydro-2H-3,1-benzoxazin-4-yl]methyl}-2,2-dimethylpropionamide The title compound was obtained by a method according to Example 27 using [6-chloro-2-oxo-4-(trifluoromethyl)-1,4-dihydro-2H-3,1-benzoxazin-4-yl]methylamine hydrochloride and 2,2-dimethylpropionic acid as raw materials.
¹H-NMR (400 MHz, DMSO-d₆) δ: 0.88 (9H, s), 3.52 (1H, d, J=14.6 Hz), 4.46 (1H, dd, J=14.6, 7.3 Hz), 6.91 (1H, d, J=8.8 Hz), 7.23 (1H, br s), 7.45 (1H, dd, J=8.8, 2.2 Hz), 7.83 (1H, m)

Example 69

N-{[6-chloro-2-oxo-4-(trifluoromethyl)-1,4-dihydro-2H-3,1-benzoxazin-4-yl]methyl}-2-ethylbutanamide The title compound was obtained by a method according to Example 27 using [6-chloro-2-oxo-4-(trifluoromethyl)-1,4-dihydro-2H-3,1-benzoxazin-4-yl]methylamine hydrochloride and 2-ethylbutanecarboxylic acid as raw materials.
¹H-NMR (400 MHz, DMSO-d₆) δ: 0.37 (3H, t, J=7.6 Hz), 0.71 (3H, t, J=7.6 Hz), 1.09-1.44 (4H, m), 1.89-1.99 (1H, m), 3.55 (1H, d, J=14.6 Hz), 4.52 (1H, dd, J=14.6, 6.3 Hz), 6.92 (1H, d, J=8.8 Hz), 7.36 (1H, br s), 7.45 (1H, dd, J=8.8, 2.2 Hz), 8.21-8.27 (1H, m)

Example 70

N-{[6-chloro-2-oxo-4-(trifluoromethyl)-1,4-dihydro-2H-3,1-benzoxazin-4-yl]methyl}-2-phenylacetamide The title compound was obtained by a method according to Example 99 using [6-chloro-2-oxo-4-(trifluoromethyl)-1,4-dihydro-2H-3,1-benzoxazin-4-yl]methylamine hydrochloride and phenylacetyl chloride as raw materials.
¹H-NMR (400 MHz, CD₃OD) δ: 3.38 (2H, m), 3.64 (1H, d, J=14.6 Hz), 4.57 (1H, d, J=14.6 Hz), 6.81 (1H, d, J=9.3 Hz), 6.95-6.97 (2H, m), 7.11-7.17 (3H, m), 7.28-7.36 (2H, m)

Example 71

N-{[6-chloro-2-oxo-4-(trifluoromethyl)-1,4-dihydro-2H-3,1-benzoxazin-4-yl]methyl}-2-(4-fluorophenyl)acetamide The title compound was obtained by a method according to Example 27 using [6-chloro-2-oxo-4-(trifluoromethyl)-1,4-dihydro-2H-3,1-benzoxazin-4-yl]methylamine hydrochloride and (4-fluorophenyl)acetic acid as raw materials.
¹H-NMR (400 MHz, CD₃ OD) δ: 3.22-3.42 (2H, m), 3.63 (1H, d, J=14.6 Hz), 4.57 (1H, d, J=14.6 Hz), 6.78-6.91 (3H, m), 6.98 (2H, dd, J=8.8, 5.4 Hz), 7.27-7.35 (2H, m)

Example 72

N-{[6-chloro-2-oxo-4-(trifluoromethyl)-1,4-dihydro-2H-3,1-benzoxazin-4-yl]methyl}isoxazole-3-carboxamide The title compound was obtained by a method according to Example 27 using [6-chloro-2-oxo-4-(trifluoromethyl)-1,4- dihydro-2H-3,1-benzoxazin-4-yl]methylamine hydrochloride and isoxazole-3-carboxylic acid as raw materials.

$^1$H-NMR (400 MHz, DMSO-$d_6$) δ: 3.99 (1H, d, J=14.6 Hz), 4.44 (1H, dd, J=14.6, 6.1 Hz), 6.84-6.86 (1H, m), 6.92 (1H, d, J=8.8 Hz), 7.47 (1H, dd, J=8.8, 2.4 Hz), 7.51 (1H, br s), 9.06 (1H, d, J=1.5 Hz), 9.08-9.14 (1H, m)

Example 73

N-{[6-chloro-2-oxo-4-(trifluoromethyl)-1,4-dihydro-2H-3,1-benzoxazin-4-yl]methyl}-1,3-thiazole-4-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1,3-thiazole-4-carboxylic acid as raw materials.

$^1$H-NMR (400 MHz, DMSO-$d_6$) δ: 4.08 (1H, d, J=14.4 Hz), 4.40 (1H, dd, J=14.4, 5.6 Hz), 6.91 (1H, d, J=8.8 Hz), 7.46 (1H, dd, J=8.8, 2.4 Hz), 7.60 (1H, s), 8.37 (1H, dd, J=2.0, 1.0 Hz), 8.40-8.47 (1H, br m), 9.14 (1H, d, J=2.0 Hz)

Example 74

N-{[6-chloro-2-oxo-4-(trifluoromethyl)-1,4-dihydro-2H-3,1-benzoxazin-4-yl]methyl}-5-ethylisoxazole-3-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 5-ethylisoxazole-3-carboxylic acid as raw materials.

$^1$H-NMR (400 MHz, DMSO-$d_6$) δ: 1.20 (3H, t, J=7.8 Hz), 2.77 (2H, q, J=7.8 Hz), 3.96 (1H, d, J=14.6 Hz), 4.42 (1H, dd, J=14.6, 5.6 Hz), 6.53 (1H, s), 6.92 (1H, d, J=8.5 Hz), 7.46 (1H, dd, J=8.5, 2.2 Hz), 7.50 (1H, br s), 8.98-9.03 (1H, m)

Example 75

N-{[6-chloro-2-oxo-4-(trifluoromethyl)-1,4-dihydro-2H-3,1-benzoxazin-4-yl]methyl}-2-methyl-1,3-thiazole-4-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 2-methyl-1,3-thiazole-4-carboxylic acid as raw materials.

$^1$H-NMR (400 MHz, DMSO-$d_6$) δ: 2.66 (3H, s), 4.06 (1H, d, J=14.4 Hz), 4.39 (1H, dd, J=14.4, 5.6 Hz), 6.92 (1H, d, J=8.8 Hz), 7.47 (1H, dd, J=8.8, 2.4 Hz), 7.59 (1H, s), 8.15 (1H, s), 8.30-8.35 (1H, m)

Example 76

N-{[6-chloro-2-oxo-4-(trifluoromethyl)-1,4-dihydro-2H-3,1-benzoxazin-4-yl]methyl}-1,3-thiazole-2-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1,3-thiazole-2-carboxylic acid as raw materials.

$^1$H-NMR (400 MHz, DMSO-$d_6$) δ: 4.09 (1H, dd, J=14.8, 3.5 Hz), 4.38 (1H, dd, J=14.8, 5.8 Hz), 6.93 (1H, d, J=8.8 Hz), 7.47 (1H, dd, J=8.8, 2.3 Hz), 7.57 (1H, br s), 7.98 (1H, d, J=3.1 Hz), 8.05 (1H, d, J=3.1 Hz), 8.96-9.01 (1H, m)

Example 77

N-{[6-chloro-2-oxo-4-(trifluoromethyl)-1,4-dihydro-2H-3,1-benzoxazin-4-yl]methyl}-1,3-thiazole-5-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1,3-thiazole-5-carboxylic acid as raw materials.

$^1$H-NMR (400 MHz, DMSO-$d_6$) δ: 3.89 (1H, d, J=14.6 Hz), 4.54 (1H, d, J=14.6 Hz), 6.93 (1H, d, J=8.6 Hz), 7.44-7.51 (2H, m), 8.42 (1H, s), 9.02-9.08 (1H, m), 9.21 (1H, s)

Example 78

N-{[6-chloro-2-oxo-4-(trifluoromethyl)-1,4-dihydro-2H-3,1-benzoxazin-4-yl]methyl}-1,2,5-thiadiazole-3-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1,2,5-thiadiazole-3-carboxylic acid as raw materials.

$^1$H-NMR (400 MHz, DMSO-$d_6$) δ: 4.06 (1H, d, J=15.5 Hz), 4.45 (1H, d, J=15.5 Hz), 6.92 (1H, d, J=8.6 Hz), 7.47 (1H, d, J=8.6 Hz), 7.58 (1H, s), 9.11 (1H, br s), 9.16 (1H, s)

Example 79

N-{[6-chloro-2-oxo-4-(trifluoromethyl)-1,4-dihydro-2H-3,1-benzoxazin-4-yl]methyl}-5-methyl-1,3,4-oxadiazole-2-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 5-methyl-1,3,4-oxadiazole-2-carboxylic acid as raw materials.

$^1$H-NMR (400 MHz, DMSO-$d_6$) δ: 2.55 (3H, s), 4.04 (1H, d, J=14.6 Hz), 4.41 (1H, d, J=14.6 Hz), 6.94 (1H, d, J=8.8 Hz), 7.49 (1H, dd, J=8.8, 2.2 Hz), 7.55 (1H, br s), 9.61 (1H, br s)

Example 80

N-{[6-chloro-2-oxo-4-(trifluoromethyl)-1,4-dihydro-2H-3,1-benzoxazin-4-yl]methyl}-1,2,5-oxadiazole-3-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 1,2,5-oxadiazole-3-carboxylic acid as raw materials.

$^1$H-NMR (400 MHz, DMSO-$d_6$) δ: 3.99 (1H, dd, J=14.6, 5.9 Hz), 4.31 (1H, dd, J=14.6, 6.8 Hz), 6.93 (1H, dd, J=8.8, 4.9 Hz), 7.47 (1H, dd, J=8.8, 2.4 Hz), 7.54 (1H, s), 8.35 (1H, br s), 10.85 (1H, s)

Example 81

N-{[6-chloro-2-oxo-4-(trifluoromethyl)-1,4-dihydro-2H-3,1-benzoxazin-4-yl]methyl}-4-methyl-1,2,5-oxadiazole-3-carboxamide The title compound was obtained by a method according to Example 27 using [6-chloro-2-oxo-4-(trifluoromethyl)-1,4- dihydro-2H-3,1-benzoxazin-4-yl]methylamine hydrochloride and 4-methyl-1,2,5-oxadiazole-3-carboxylic acid as raw materials.

$^1$H-NMR (400 MHz, DMSO-d$_6$) δ: 2.29 (3H, s), 3.99 (1H, dd, J=14.6, 4.9 Hz), 4.51 (1H, dd, J=14.6, 6.8 Hz), 6.94 (1H, d, J=8.8 Hz), 7.49 (1H, dd, J=8.8, 2.9 Hz), 7.52 (1H, s), 9.49-9.55 (1H, m), 10.89 (1H, s)

Example 82

N-{[6-chloro-2-oxo-4-(trifluoromethyl)-1,4-dihydro-2H-3,1-benzoxazin-4-yl]methyl}-5-cyclopropylisoxazole-3-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 5-cyclopropylisoxazole-3-carboxylic acid as raw materials.

$^1$H-NMR (400 MHz, DMSO-d$_6$) δ: 0.85-0.91 (2H, m), 1.03-1.08 (2H, m), 2.10-2.19 (1H, m), 3.94 (1H, dd, J=14.6, 4.9 Hz), 4.40 (1H, dd, J=14.6, 6.8 Hz), 6.44 (1H, s), 6.91 (1H, d, J=8.8 Hz), 7.46 (1H, dd, J=8.8, 2.4 Hz), 7.49 (1H, s), 8.95 (1H, dd, J=6.8, 4.9 Hz)

Example 83

N-{[6-chloro-2-oxo-4-(trifluoromethyl)-1,4-dihydro-2H-3,1-benzoxazin-4-yl]methyl}-5-phenylisoxazole-3-carboxamide The title compound was obtained by a method according to Example 27 using [6-chloro-2-oxo-4-(trifluoromethyl)-1,4-dihydro-2H-3,1-benzoxazin-4-yl]methylamine hydrochloride and 5-phenylisoxazole-3-carboxylic acid as raw materials.

$^1$H-NMR (400 MHz, DMSO-d$_6$) δ: 4.00 (1H, dd, J=14.6, 5.4 Hz), 4.46 (1H, dd, J=14.6, 7.3 Hz), 6.93 (1H, d, J=8.5 Hz), 7.33 (1H, s), 7.47 (1H, dd, J=8.5, 2.2 Hz), 7.50-7.55 (4H, m), 7.87-7.91 (2H, m), 9.13 (1H, dd, J=7.3, 5.4 Hz)

Example 84

3-[6-chloro-2-oxo-4-(trifluoromethyl)-1,4-dihydro-2H-3,1-benzoxazin-4-yl]-N-(4-fluorophenyl)propanamide 1) Synthesis of 6-chloro-4-(3-hydroxypropyl)-4-(trifluoromethyl)-1,4-dihydro-2H-3,1-benzoxazin-2-one According to Example 1, the objective compound was synthesized using a known compound (J. Org. Chem., 1998, 63, 8536) 1-(2-amino-5-chlorophenyl)-2,2,2-trifluoroethanone and 3-butenyl magnesium bromide as raw materials. This compound can also be synthesized by the method shown in Reference example 3.

$^1$H-NMR (400 MHz, DMSO-d$_6$) δ: 1.17-1.28 (2H, m), 1.38-1.50 (2H, m), 3.40-3.43 (2H, m), 6.97 (1H, d, J=8.8 Hz), 7.49 (1H, dd, J=8.8, 2.0 Hz), 7.56 (1H, d, J=2.0 Hz), 10.84 (1H, s)

2) Synthesis of 3-[6-chloro-2-oxo-4-(trifluoromethyl)-1,4-dihydro-2H-3,1-benzoxazin-4-yl]propanoic acid While stirring a solution of 6-chloro-4-(3-hydroxypropyl)-4-(trifluoromethyl)-1,4-dihydro-2H-3,1-benzoxazin-2-one (1.0 g, 3.23 mmol) in acetone (20 mL), Jones reagent (8 N chromic acid, H$_2$SO$_4$—H$_2$O solution, 2 mL) was added dropwise thereto at room temperature. Then water (20 mL) was added thereto and the solution was stirred at room temperature for 3 hours. Then, to the reaction solution, 2-propanol was added and the solution was stirred at room temperature for 5 minutes. After the reaction solution was diluted with ethyl acetate, a 8 N aqueous sodium hydroxide solution was added thereto, and the aqueous layer was separated. After the aqueous layer was acidified by adding 8 N hydrochloric acid thereto, the solution was diluted with ethyl acetate and the organic layer was separated. The organic layer was washed with water and saturated brine, and then dried over magnesium sulfate. After the drying agent was removed by filtration, the solvent was evaporated under reduced pressure, whereby the objective compound (726 mg, 70%) was obtained as a pale yellow solid.

$^1$H-NMR (400 MHz, DMSO-d$_6$) δ: 2.07-2.15 (1H, m), 2.22-2.40 (2H, m), 2.75-2.82 (1H, m), 6.97 (1H, d, J=8.8 Hz), 7.51 (1H, dd, J=8.8, 2.2 Hz), 7.64 (1H, s), 10.87 (1H, s)

3) Synthesis of 3-[6-chloro-2-oxo-4-(trifluoromethyl)-1,4-dihydro-2H-3,1-benzoxazin-4-yl]-N-(4-fluorophenyl)propanamide 3-[6-Chloro-2-oxo-4-(trifluoromethyl)-1,4-dihydro-2H-3,1-benzoxazin-4-yl]propanoic acid (50 mg, 0.15 mmol) and 4-fluoroaniline (21 mg, 0.18 mmol) were dissolved in DMF (1 mL), and then, pyridine (31 μL, 0.39 mmol) and 1-ethyl-3-(3-dimethylaminopropyl)carbodiimide hydrochloride (35 mg, 0.18 mmol) were sequentially added thereto. After the reaction solution was stirred overnight at room temperature, water was added thereto. Then, the resulting solution was diluted with ethyl acetate and the organic layer was separated. The organic layer was washed with saturated brine and then dried over magnesium sulfate. After the drying agent was removed by filtration, the solvent was evaporated under reduced pressure. The residue was purified by thin-layer silica gel column chromatography (ethyl acetate/hexane=1/1), whereby the objective compound (33.1 mg, 51%) was obtained as a white solid.

$^1$H-NMR (400 MHz, DMSO-d$_6$) δ: 2.19-2.53 (3H, m), 2.75-2.87 (1H, m), 6.96 (1H, d, J=8.3 Hz), 7.08-7.12 (2H, m), 7.45-7.55 (3H, m), 7.61-7.65 (1H, m), 9.94 (1H, s), 10.87 (1H, s)

Example 85

2-[6-chloro-2-oxo-4-(trifluoromethyl)-1,4-dihydro-2H-3,1-benzoxazin-4-yl]-N-(4-fluorophenyl)acetamide The title compound was obtained by a method according to Example 84 using 1-(2-amino-5-chlorophenyl)-2,2,2-trifluoroethanone, allyl magnesium bromide and 4-fluoroaniline as raw materials.

$^1$H-NMR (400 MHz, DMSO-d$_6$) δ: 3.25 (1H, d, J=16.1 Hz), 3.85 (1H, d, J=16.1 Hz), 6.92 (1H, d, J=8.8 Hz), 7.10 (2H, t, J=8.8 Hz), 7.42-7.48 (3H, m), 7.67 (1H, br s), 10.25 (1H, br s), 10.78 (1H, br s)

Example 86

3-[6-chloro-2-oxo-4-(trifluoromethyl)-1,4-dihydro-2H-3,1-benzoxazin-4-yl]-N-pyridin-4-ylpropanamide The title compound was obtained by a method according to Example 84 using 1-(2-amino-5-chlorophenyl)-2,2,2-trifluoroethanone, 3-butenyl magnesium bromide and 4-aminopyridine as raw materials.

¹H-NMR (400 MHz, DMSO-d₆) δ: 2.27-2.38 (1H, m), 2.41-2.55 (2H, m), 2.80-2.87 (1H, m), 6.97 (1H, d, J=8.8 Hz), 7.45-7.52 (3H, m), 7.64 (1H, d, J=2.0 Hz), 8.39 (2H, dd, J=4.9, 1.5 Hz), 10.28 (1H, s)

Example 87

3-[6-chloro-2-oxo-4-(trifluoromethyl)-1,4-dihydro-2H-3,1-benzoxazin-4-yl]-N-pyridin-3-ylpropanamide The title compound was obtained by a method according to Example 84 using 1-(2-amino-5-chlorophenyl)-2,2,2-trifluoroethanone, 3-butenyl magnesium bromide and 3-aminopyridine as raw materials.

¹H-NMR (400 MHz, DMSO-d₆) δ: 2.37-2.26 (1H, m), 2.54-2.39 (2H, m), 2.89-2.79 (1H, m), 6.97 (1H, d, J=8.8 Hz), 7.32 (1H, dd, J=8.3, 4.9 Hz), 7.48 (1H, dd, J=8.8, 2.4 Hz), 7.64 (1H, d, J=2.4 Hz), 7.94-7.99 (1H, m), 8.23 (1H, dd, J=4.9, 1.5 Hz), 8.64 (1H, d, J=2.0 Hz), 10.12 (1H, s)

Example 88

3-[6-chloro-2-oxo-4-(trifluoromethyl)-1,4-dihydro-2H-3,1-benzoxazin-4-yl]-N-(pyridin-2-yl)propanamide The title compound was obtained by a method according to Example 84 using 1-(2-amino-5-chlorophenyl)-2,2,2-trifluoroethanone, 3-butenyl magnesium bromide and 2-aminopyridine as raw materials.

¹H-NMR (400 MHz, DMSO-d₆) δ: 2.33-2.56 (3H, m), 2.75-2.92 (1H, m), 6.97 (1H, d, J=8.5 Hz), 7.05-7.09 (1H, m), 7.48 (1H, dd, J=8.5, 2.2 Hz), 7.62 (1H, d, J=2.2 Hz), 7.73-7.77 (1H, m), 8.04 (1H, d, J=8.8 Hz), 8.24-8.29 (1H, m), 10.43 (1H, s)

Example 89

3-[6-chloro-2-oxo-4-(trifluoromethyl)-1,4-dihydro-2H-3,1-benzoxazin-4-yl]-N-(2-methoxyphenyl)propanamide The title compound was obtained by a method according to Example 84 using 1-(2-amino-5-chlorophenyl)-2,2,2-trifluoroethanone, 3-butenyl magnesium bromide and 2-methoxyaniline as raw materials.

¹H-NMR (400 MHz, DMSO-d₆) δ: 2.31-2.57 (3H, m), 2.73-2.88 (1H, m), 6.85-6.90 (1H, m), 6.94-7.09 (3H, m), 7.49 (1H, dd, J=8.8, 2.4 Hz), 7.62 (1H, s), 7.86-7.93 (1H, m), 9.18 (1H, s)

Example 90

3-[6-chloro-2-oxo-4-(trifluoromethyl)-1,4-dihydro-2H-3,1-benzoxazin-4-yl]-N-isoxazol-3-ylpropanamide The title compound was obtained by a method according to Example 84 using 1-(2-amino-5-chlorophenyl)-2,2,2-trifluoroethanone, 3-butenyl magnesium bromide and 3-aminoisoxazole as raw materials.

¹H-NMR (400 MHz, DMSO-d₆) δ: 2.33-2.54 (3H, m), 2.78-2.88 (1H, m), 6.88 (1H, d, J=2.0 Hz), 6.97 (1H, d, J=8.8 Hz), 7.49 (1H, dd, J=8.8, 2.4 Hz), 7.61 (1H, d, J=2.4 Hz), 8.76 (1H, d, J=2.0 Hz), 10.97 (1H, s)

Example 91

3-[6-chloro-2-oxo-4-(trifluoromethyl)-1,4-dihydro-2H-3,1-benzoxazin-4-yl]-N-(6-methoxypyridin-3-yl)propanamide The title compound was obtained by a method according to Example 84 using 1-(2-amino-5-chlorophenyl)-2,2,2-trifluoroethanone, 3-butenyl magnesium bromide and 3-amino-6-methoxypyridine as raw materials.

¹H-NMR (400 MHz, DMSO-d₆) δ: 2.19-2.53 (3H, m), 2.77-2.88 (1H, m), 3.80 (3H, s), 6.77 (1H, d, J=8.8 Hz), 6.97 (1H, d, J=8.5 Hz), 7.49 (1H, dd, J=8.5, 2.2 Hz), 7.64 (1H, d, J=2.2 Hz), 7.79-7.83 (1H, m), 8.27 (1H, t, J=2.2 Hz), 9.92 (1H, s)

Example 92

3-[6-chloro-2-oxo-4-(trifluoromethyl)-1,4-dihydro-2H-3,1-b enzoxazin-4-yl]-N-(6-fluoropyridin-3-yl)propanamide The title compound was obtained by a method according to Example 84 using 1-(2-amino-5-chlorophenyl)-2,2,2-trifluoroethanone, 3-butenyl magnesium bromide and 3-amino-6-fluoropyridine as raw materials.

¹H-NMR (400 MHz, DMSO-d₆): 2.26-2.36 (1H, m), 2.38-2.55 (2H, m), 2.80-2.88 (1H, m), 6.97 (1H, d, J=8.8 Hz), 7.14 (1H, dd, J=8.8, 3.4 Hz), 7.48 (1H, dd, J=8.8, 2.2 Hz), 7.63 (1H, d, J=2.2 Hz), 8.04-8.10 (1H, m), 8.32 (1H, s), 10.21 (1H, s)

Example 93

3-[6-chloro-2-oxo-4-(trifluoromethyl)-1,4-dihydro-2H-3,1-b enzoxazin-4-yl]-N-(6-methylpyridin-3-yl)propanamide The title compound was obtained by a method according to Example 84 using 1-(2-amino-5-chlorophenyl)-2,2,2-trifluoroethanone, 3-butenyl magnesium bromide and 3-amino-6-methylpyridine as raw materials.

¹H-NMR (400 MHz, DMSO-d₆) δ: 2.24-2.34 (1H, m), 2.35-2.48 (5H, m), 2.78-2.89 (1H, m), 6.97 (1H, d, J=8.8 Hz), 7.17 (1H, d, J=8.3 Hz), 7.49 (1H, dd, J=8.8, 2.4 Hz), 7.64 (1H, d, J=2.4 Hz), 7.82-7.86 (1H, m), 8.51 (1H, d, J=2.0 Hz), 10.01 (1H, s)

Example 94

3-[6-chloro-2-oxo-4-(trifluoromethyl)-1,4-dihydro-2H-3,1-benzoxazin-4-yl]-N-(3-methoxyphenyl)propanamide The title compound was obtained by a method according to Example 84 using 1-(2-amino-5-chlorophenyl)-2,2,2-trifluoroethanone, 3-butenyl magnesium bromide and 3-methoxyaniline as raw materials.

¹H-NMR (400 MHz, DMSO-d₆) δ: 2.22-2.30 (1H, m), 2.33-2.53 (2H, m), 2.78-2.86 (1H, m), 3.70 (3H, s), 6.58-6.63 (1H, m), 6.97 (1H, d, J=8.8 Hz), 7.00-7.05 (1H, m), 7.17 (1H, t, J=8.0 Hz), 7.24-7.25 (1H, m), 7.49 (1H, dd, J=8.8, 2.4 Hz), 7.65 (1H, d, J=2.4 Hz), 9.89 (1H, s)

Example 95

3-[6-chloro-2-oxo-4-(trifluoromethyl)-1,4-dihydro-2H-3,1-benzoxazin-4-yl]-N-(3-fluorophenyl)propanamide The title compound was obtained by a method according to Example 84 using 1-(2-amino-5-chlorophenyl)-2,2,2-trifluoroethanone, 3-butenyl magnesium bromide and 3-fluoroaniline as raw materials.

$^1$H-NMR (400 MHz, DMSO-$d_6$) δ: 2.24-2.34 (1H, m), 2.37-2.53 (2H, m), 2.78-2.88 (1H, m), 6.82-6.87 (1H, m), 6.97 (1H, d, J=8.8 Hz), 7.17-7.21 (1H, m), 7.28-7.33 (1H, m), 7.48 (1H, dd, J=8.8, 2.2 Hz), 7.53 (1H, m), 7.64 (1H, d, J=2.2 Hz), 10.11 (1H, s)

Example 96

3-[6-chloro-2-oxo-4-(trifluoromethyl)-1,4-dihydro-2H-3,1-benzoxazin-4-yl]-N-(2-fluorophenyl)propanamide The title compound was obtained by a method according to Example 84 using 1-(2-amino-5-chlorophenyl)-2,2,2-trifluoroethanone, 3-butenyl magnesium bromide and 2-fluoroaniline as raw materials.

$^1$H-NMR (400 MHz, DMSO-$d_6$) δ: 2.36-2.56 (3H, m), 2.78-2.89 (1H, m), 6.98 (1H, d, J=8.8 Hz), 7.10-7.16 (2H, m), 7.17-7.25 (1H, m), 7.49 (1H, dd, J=8.8, 2.4 Hz), 7.63 (1H, s), 7.83-7.92 (1H, m), 9.72 (1H, s)

Example 97

3-[6-chloro-2-oxo-4-(trifluoromethyl)-1,4-dihydro-2H-3,1-benzoxazin-4-yl]-N-[4-(methanesulfonyl)phenyl]propanamide The title compound was obtained by a method according to Example 84 using 1-(2-amino-5-chlorophenyl)-2,2,2-trifluoroethanone, 3-butenyl magnesium bromide and 4-(methanesulfonyl)aniline as raw materials.

$^1$H-NMR (400 MHz, DMSO-$d_6$) δ: 2.28-2.36 (1H, m), 2.39-2.55 (2H, m), 2.80-2.90 (1H, m), 3.17 (3H, s), 6.97 (1H, d, J=8.8 Hz), 7.48 (1H, dd, J=8.8, 2.4 Hz), 7.56-7.59 (2H, m), 7.63 (1H, d, 2.4 Hz), 7.76-7.79 (1H, m), 8.17 (1H, br s), 10.30 (1H, s)

Example 98

3-[6-chloro-2-oxo-4-(trifluoromethyl)-1,4-dihydro-2H-3,1-benzoxazin-4-yl]-N-(5-methyl-1H-pyrazol-3-yl)propanamide The title compound was obtained by a method according to Example 84 using 1-(2-amino-5-chlorophenyl)-2,2,2-trifluoroethanone, 3-butenyl magnesium bromide and 3-amino-5-methyl-1H-pyrazole as raw materials.

$^1$H-NMR (400 MHz, DMSO-$d_6$) δ: 2.16 (3H, s), 2.20-2.46 (3H, m), 2.73-2.84 (1H, m), 6.23 (1H, s), 6.97 (1H, d, J=8.8 Hz), 7.49 (1H, dd, J=8.8, 2.4 Hz), 7.62 (1H, s), 10.20 (1H, br s)

Example 99

N-{[6-chloro-2-oxo-4-(trifluoromethyl)-1,4-dihydro-2H-3,1-benzoxazin-4-yl]methyl}-4-fluorobenzenesulfonamide While stirring a solution of [6-chloro-2-oxo-4-(trifluoromethyl)-1,4-dihydro-2H-3,1-benzoxazin-4-yl]methylamine hydrochloride (60 mg, 0.19 mmol) in THF (1 mL) at room temperature, triethylamine (66 μL, 0.47 mmol) and 4-fluorobenzenesulfonyl chloride (44 mg, 0.23 mmol) were sequentially added thereto. After the reaction solution was stirred overnight at room temperature, water was added thereto. Then, the resulting solution was diluted with ethyl acetate and the organic layer was separated. The organic layer was washed with saturated brine and then dried over magnesium sulfate. After the drying agent was removed by filtration, the solvent was evaporated under reduced pressure. The residue was purified by thin-layer silica gel column chromatography (ethyl acetate/hexane=1/1), whereby the objective compound (58 mg, 70%) was obtained as a white solid.

$^1$H-NMR (400 MHz, DMSO-$d_6$) δ: 3.49 (1H, d, J=14.1 Hz), 3.98-4.09 (1H, m), 6.91 (1H, d, J=8.8 Hz), 7.38 (2H, m), 7.45-7.51 (2H, m), 7.77-7.81 (2H, m), 8.30 (1H, br s)

Example 100

N-{2-[6-chloro-2-oxo-4-(trifluoromethyl)-1,4-dihydro-2H-3,1-benzoxazin-4-yl]ethyl}-4-fluorobenzenesulfonamide The title compound was obtained by a method according to Example 1 and Example 99 using 1-(2-amino-5-chlorophenyl)-2,2,2-trifluoroethanone, allyl magnesium bromide and 4-fluorobenzenesulfonyl chloride as raw materials.

$^1$H-NMR (400 MHz, DMSO-$d_6$) δ: 2.19-2.30 (1H, m), 2.59-2.70 (2H, m), 2.74-2.83 (1H, m), 6.93 (1H, d, J=9.3 Hz), 7.35-7.44 (2H, m), 7.50-7.46 (2H, m), 7.74-7.83 (3H, m), 10.83 (1H, s)

Example 101

N-{[6-chloro-2-oxo-4-(trifluoromethyl)-1,4-dihydro-2H-3,1-benzoxazin-4-yl]methyl}-4-methylbenzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 4-methylbenzenesulfonyl chloride as raw materials.

$^1$H-NMR (400 MHz, DMSO-$d_6$) δ: 2.37 (3H, s), 3.40 (1H, dd, J=14.4, 5.9 Hz), 3.96 (1H, dd, J=14.4, 7.3 Hz), 6.90 (1H, d, J=8.8 Hz), 7.34 (2H, d, J=8.1 Hz), 7.44 (1H, d, J=2.4 Hz), 7.47 (1H, dd, J=8.8, 2.4 Hz), 7.63 (2H, d, J=8.1 Hz), 8.13 (1H, dd, J=7.3, 5.9 Hz), 10.79 (1H, s)

Example 102

N-{[6-chloro-2-oxo-4-(trifluoromethyl)-1,4-dihydro-2H-3,1-benzoxazin-4-yl]methyl}-4-methoxybenzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 4-methoxybenzenesulfonyl chloride as raw materials.

¹H-NMR (400 MHz, DMSO-d₆) δ: 3.38 (1H, dd, J=14.0, 5.8 Hz), 3.83 (3H, s), 3.94 (1H, dd, J=14.0, 7.6 Hz), 6.91 (1H, d, J=8.4 Hz), 7.05 (2H, d, J=9.1 Hz), 7.43 (1H, d, J=2.3 Hz), 7.47 (1H, dd, J=8.4, 2.3 Hz), 7.68 (2H, d, J=9.1 Hz), 8.05 (1H, dd, J=7.6, 5.8 Hz), 10.80 (1H, s)

Example 103

N-{[6-chloro-2-oxo-4-(trifluoromethyl)-1,4-dihydro-2H-3,1-benzoxazin-4-yl]methyl}-4-cyanobenzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 4-cyanobenzenesulfonyl chloride as raw materials.

¹H-NMR (400 MHz, DMSO-d₆) δ: 3.59 (1H, dd, J=14.6, 6.3 Hz), 4.14 (1H, dd, J=14.6, 6.3 Hz), 6.91-6.83 (1H, m), 7.43-7.48 (2H, m), 7.84 (2H, d, J=8.6 Hz), 8.00 (2H, d, J=8.6 Hz), 8.58 (1H, t, J=6.3 Hz), 10.75 (1H, s)

Example 104

N-{[6-chloro-2-oxo-4-(trifluoromethyl)-1,4-dihydro-2H-3,1-benzoxazin-4-yl]methyl}naphthalene-2-sulfonamide The title compound was obtained by a method according to Example 99 using [6-chloro-2-oxo-4-(trifluoromethyl)-1,4-dihydro-2H-3,1-benzoxazin-4-yl]methylamine hydrochloride and naphthalene-2-sulfonyl chloride as raw materials.

¹H-NMR (400 MHz, DMSO-d₆) δ: 3.84 (1H, dd, J=14.3, 6.1 Hz), 4.39 (1H, dd, J=14.3, 7.2 Hz), 7.22-7.14 (1H, m), 7.72-7.83 (2H, m), 7.96-8.12 (3H, m), 8.33-8.47 (3H, m), 8.66 (1H, dd, J=7.2, 6.1 Hz), 8.71-8.75 (1H, m), 11.09 (1H, s)

Example 105

4-chloro-N-{[6-chloro-2-oxo-4-(trifluoromethyl)-1,4-dihydro-2H-3,1-benzoxazin-4-yl]methyl}benzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 4-chlorobenzenesulfonyl chloride as raw materials.

¹H-NMR (400 MHz, DMSO-d₆) δ: 3.50 (1H, dd, J=14.3, 5.9 Hz), 4.05 (1H, dd, J=14.3, 5.9 Hz), 6.90 (1H, d, J=8.8 Hz), 7.43-7.50 (2H, m), 7.60 (2H, d, J=8.8 Hz), 7.73 (2H, d, J=8.8 Hz), 8.34 (1H, t, J=5.9 Hz), 10.80 (1H, s)

Example 106

N-{[6-chloro-2-oxo-4-(trifluoromethyl)-1,4-dihydro-2H-3,1-benzoxazin-4-yl]methyl}pyridine-3-sulfonamide The title compound was obtained by a method according to Example 99 using [6-chloro-2-oxo-4-(trifluoromethyl)-1,4-dihydro-2H-3,1-benzoxazin-4-yl]methylamine hydrochloride and pyridine-3-sulfonyl chloride as raw materials.

¹H-NMR (400 MHz, DMSO-d₆) δ: 3.57 (1H, d, J=14.6 Hz), 4.12 (1H, d, J=14.6 Hz), 6.91 (1H, d, J=8.8 Hz), 7.48 (1H, dd, J=8.8, 2.2 Hz), 7.51 (1H, s), 7.58 (1H, dd, J=8.8, 4.9 Hz), 8.11 (1H, d, J=8.8 Hz), 8.78 (1H, d, J=4.9 Hz), 8.88 (1H, d, J=2.2 Hz), 10.81 (1H, br s)

Example 107

N-{[6-chloro-2-oxo-4-(trifluoromethyl)-1,4-dihydro-2H-3,1-benzoxazin-4-yl]methyl}pyridine-2-sulfonamide The title compound was obtained by a method according to Example 99 using [6-chloro-2-oxo-4-(trifluoromethyl)-1,4-dihydro-2H-3,1-benzoxazin-4-yl]methylamine hydrochloride and pyridine-2-sulfonyl chloride as raw materials.

¹H-NMR (400 MHz, DMSO-d₆) δ: 3.76 (1H, d, J=14.6 Hz), 4.18 (1H, d, J=14.6 Hz), 6.90 (1H, d, J=8.8 Hz), 7.44-7.49 (2H, m), 7.63 (1H, m), 7.84 (1H, d, J=7.8 Hz), 8.04 (1H, t, J=7.8 Hz), 8.66 (1H, d, J=3.9 Hz)

Example 108

N-{[6-chloro-2-oxo-4-(trifluoromethyl)-1,4-dihydro-2H-3,1-benzoxazin-4-yl]methyl}-1-methyl-1H-imidazole-4-sulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 1-methyl-1H-imidazole-4-sulfonyl chloride as raw materials.

¹H-NMR (400 MHz, DMSO-d₆) δ: 3.57 (1H, d, J=14.1 Hz), 3.69 (3H, s), 3.96 (1H, d, J=14.1 Hz), 6.93 (1H, d, J=8.5 Hz), 7.37 (1H, s), 7.48 (1H, dd, J=8.5, 2.2 Hz), 7.70 (1H, br s), 7.75 (1H, d, J=1.0 Hz)

Example 109

N-{[6-chloro-2-oxo-4-(trifluoromethyl)-1,4-dihydro-2H-3,1-benzoxazin-4-yl]methyl}-3-fluorobenzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 3-fluorobenzenesulfonyl chloride as raw materials.

¹H-NMR (400 MHz, DMSO-d₆) δ: 3.53 (1H, d, J=14.1 Hz), 4.08 (1H, d, J=14.1 Hz), 6.90 (1H, d, J=8.8 Hz), 7.43-7.53 (4H, m), 7.54-7.63 (2H, m), 10.74-10.83 (1H, br m)

Example 110

N-{[6-chloro-2-oxo-4-(trifluoromethyl)-1,4-dihydro-2H-3,1-benzoxazin-4-yl]methyl}-2-fluorobenzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 2-fluorobenzenesulfonyl chloride as raw materials.

¹H-NMR (400 MHz, DMSO-d₆) δ: 3.69 (1H, d, J=14.1 Hz), 4.08-4.19 (1H, br m), 6.85 (1H, d, J=8.8 Hz), 7.27-7.35 (2H, m), 7.42-7.47 (2H, m), 7.60-7.72 (2H, m), 10.71 (1H, br s)

Example 111

N-{[6-chloro-2-oxo-4-(trifluoromethyl)-1,4-dihydro-2H-3,1-benzoxazin-4-yl]methyl}-3,4-difluorobenzenesulfonamide The title compound was obtained by a method according to Example 99 using [6-chloro-2-oxo-4-(trifluoromethyl)-1,4- dihydro-2H-3,1-benzoxazin-4-yl]methylamine hydrochloride and 3,4-difluorobenzenesulfonyl chloride as raw materials.

$^1$H-NMR (400 MHz, DMSO-$d_6$) δ: 3.56 (1H, d, J=14.6 Hz), 4.04-4.14 (1H, br m), 6.90 (1H, d, J=8.8 Hz), 7.46-7.48 (2H, m), 7.57-7.61 (2H, m), 7.67-7.75 (1H, m), 10.79 (1H, br s)

Example 112

N-{[6-chloro-2-oxo-4-(trifluoromethyl)-1,4-dihydro-2H-3,1-benzoxazin-4-yl]methyl}-3,5-difluorobenzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 3,5-difluorobenzenesulfonyl chloride as raw materials.

$^1$H-NMR (400 MHz, DMSO-$d_6$) δ: 3.62 (1H, d, J=14.6 Hz), 4.14 (1H, d, J=14.6 Hz), 6.89 (1H, d, J=8.8 Hz), 7.33-7.40 (2H, m), 7.43-7.61 (3H, m), 10.80 (1H, br s)

Example 113

N-{[6-chloro-2-oxo-4-(trifluoromethyl)-1,4-dihydro-2H-3,1-benzoxazin-4-yl]methyl}benzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and benzenesulfonyl chloride as raw materials.

$^1$H-NMR (400 MHz, DMSO-$d_6$) δ: 3.44 (1H, d, J=14.6 Hz), 4.00 (1H, d, J=14.6 Hz), 6.90 (1H, d, J=9.3 Hz), 7.45-7.49 (2H, m), 7.51-7.56 (2H, m), 7.58-7.64 (1H, m), 7.78-7.79 (2H, m)

Example 114

N-{[6-chloro-2-oxo-4-(trifluoromethyl)-1,4-dihydro-2H-3,1-benzoxazin-4-yl]methyl}-3-methylbenzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 3-methylbenzenesulfonyl chloride as raw materials.

$^1$H-NMR (400 MHz, DMSO-$d_6$) δ: 2.35 (3H, s), 3.46 (1H, d, J=14.1 Hz), 4.00 (1H, d, J=14.1 Hz), 6.88 (1H, d, J=9.3 Hz), 7.38-7.42 (2H, m), 7.43-7.48 (2H, m), 7.49-7.53 (2H, m)

Example 115

N-{[6-chloro-2-oxo-4-(trifluoromethyl)-1,4-dihydro-2H-3,1-benzoxazin-4-yl]methyl}-3-cyanobenzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 3-cyanobenzenesulfonyl chloride as raw materials.

$^1$H-NMR (400 MHz, DMSO-$d_6$) δ: 3.60 (1H, d, J=14.1 Hz), 4.13 (1H, d, J=14.1 Hz), 6.87 (1H, d, J=8.3 Hz), 7.42-7.50 (2H, m), 7.72 (1H, t, J=7.8 Hz), 7.97 (1H, d, J=7.8 Hz), 8.02-8.11 (2H, m), 8.50 (1H, br s), 10.76 (1H, s)

Example 116

N-{[6-chloro-2-oxo-4-(trifluoromethyl)-1,4-dihydro-2H-3,1-benzoxazin-4-yl]methyl}-3-methoxybenzenesulfonamide The title compound was obtained by a method according to Example 99 using [6-chloro-2-oxo-4-(trifluoromethyl)-1,4-dihydro-2H-3,1-benzoxazin-4-yl]methylamine hydrochloride and 3-methoxybenzenesulfonyl chloride as raw materials.

$^1$H-NMR (400 MHz, DMSO-$d_6$) δ: 3.45 (1H, d, J=14.1 Hz), 3.78 (3H, s), 4.01 (1H, d, J=14.1 Hz), 6.88 (1H, d, J=9.3 Hz), 7.15 (1H, dd, J=7.8, 2.0 Hz), 7.23 (1H, t, J=2.0 Hz), 7.29 (1H, d, J=7.8 Hz), 7.40-7.49 (3H, m), 8.26 (1H, br s), 10.76 (1H, br s)

Example 117

N-{2-[6-chloro-2-oxo-4-(trifluoromethyl)-1,4-dihydro-2H-3,1-benzoxazin-4-yl]ethyl}benzenesulfonamide The title compound was obtained by a method according to Example 99 using 1-(2-amino-5-chlorophenyl)-2,2,2-trifluoroethanone, allyl magnesium bromide and benzenesulfonyl chloride as raw materials.

$^1$H-NMR (400 MHz, DMSO-$d_6$) δ: 2.21-2.28 (1H, m), 2.58-2.68 (2H, m), 2.73-2.84 (1H, m), 6.92 (1H, d, J=8.3 Hz), 7.44-7.50 (2H, m), 7.53-7.59 (2H, m), 7.60-7.65 (1H, m), 7.70-7.80 (3H, m)

Example 118

N-{3-[6-chloro-2-oxo-4-(trifluoromethyl)-1,4-dihydro-2H-3,1-benzoxazin-4-yl]propyl}benzenesulfonamide The title compound was obtained by a method according to Example 99 using 1-(2-amino-5-chlorophenyl)-2,2,2-trifluoroethanone, 3-butenyl magnesium bromide and benzenesulfonyl chloride as raw materials.

$^1$H-NMR (400 MHz, DMSO-$d_6$) δ: 1.07-1.20 (1H, m), 1.28-1.40 (1H, m), 1.93-2.03 (1H, m), 2.38-2.47 (1H, m), 2.75-2.85 (2H, m), 6.93 (1H, d, J=8.8 Hz), 7.47 (1H, dd, J=8.8, 2.2 Hz), 7.51-7.65 (5H, m), 7.70-7.76 (2H, m)

Example 119

N-{3-[6-chloro-2-oxo-4-(trifluoromethyl)-1,4-dihydro-2H-3,1-benzoxazin-4-yl]propyl}pyridine-2-sulfonamide The title compound was obtained by a method according to Example 99 using 1-(2-amino-5-chlorophenyl)-2,2,2-trifluoroethanone, 3-butenyl magnesium bromide and pyridine-2-sulfonyl chloride as raw materials.

$^1$H-NMR (400 MHz, DMSO-$d_6$) δ: 1.11-1.23 (1H, m), 1.30-1.43 (1H, m), 1.95-2.03 (1H, m), 2.39-2.47 (1H, m), 2.93-3.02 (2H, m), 6.94 (1H, d, J=8.8 Hz), 7.47 (1H, dd, J=8.8, 2.4 Hz), 7.52 (1H, s), 7.60-7.64 (1H, m), 7.88 (2H, d, J=7.8 Hz), 8.04 (1H, td, J=7.8, 2.0 Hz), 8.64-8.67 (1H, m)

Synthesis of N-{3-[(4R*)-6-chloro-2-oxo-4-(trifluoromethyl)-1,4-dihydro-2H-3,1-benzoxazin-4-yl]propyl}pyridine-2-sulfonamide N-{3-[6-chloro-2-oxo-4-(trifluoromethyl)-1,4-dihydro-2H-3,1-benzoxazin-4-yl]propyl}pyridine-2-sulfonamide was subjected to optical resolution by HPLC (Chiralpack AD-H, n-hexane:2-propanol=3:2), and a fraction eluted at a later time was concentrated, whereby the objective compound was obtained.

Example 120

N-{2-[6-chloro-2-oxo-4-(trifluoromethyl)-1,4-dihydro-2H-3,1-benzoxazin-4-yl]ethyl}pyridine-2-sulfonamide The title compound was obtained by a method according to Example 99 using 1-(2-amino-5-chlorophenyl)-2,2,2-trifluoroethanone, allyl magnesium bromide and pyridine-2-sulfonyl chloride as raw materials.

$^1$H-NMR (400 MHz, DMSO-$d_6$) δ: 2.24-2.32 (1H, m), 2.61-2.71 (1H, m), 2.82-2.92 (1H, m), 2.95-3.07 (1H, m), 6.93 (1H, d, J=8.8 Hz), 7.46-7.50 (2H, m), 7.63-7.66 (1H, m), 7.88 (1H, d, J=7.8 Hz), 7.95 (1H, br s), 8.05 (1H, td, J=7.8, 2.0 Hz), 8.68-8.70 (1H, m)

N-{2-[(4R*)-6-chloro-2-oxo-4-(trifluoromethyl)-1,4-dihydro-2H-3,1-benzoxazin-4-yl]ethyl}pyridine-2-sulfonamide N-{2-[6-chloro-2-oxo-4-(trifluoromethyl)-1,4-dihydro-2H-3,1-benzoxazin-4-yl]ethyl}pyridine-2-sulfonamide was subjected to optical resolution by HPLC (Chiralpack AD-H, hexane:2-propanol=3:1), and a fraction eluted at a later time was concentrated, whereby the objective compound was obtained.

Example 121

2-[6-chloro-2-oxo-4-(trifluoromethyl)-1,4-dihydro-2H-3,1-benzoxazin-4-yl]-N-pyridin-2-ylethanesulfonamide 1) Synthesis of 6-chloro-4-(2-hydroxyethyl)-4-(trifluoromethyl)-1,4-dihydro-2H-3,1-benzoxazin-2-one According to Example 1, the objective compound was synthesized using 1-(2-amino-5-chlorophenyl)-2,2,2-trifluoroethanone and allyl magnesium bromide as raw materials.

$^1$H-NMR (400 MHz, DMSO-$d_6$) δ: 2.23 (1H, ddd, J=14.1, 8.3, 5.9 Hz), 2.68 (1H, ddd, J=14.1, 8.3, 5.9 Hz), 3.36-3.43 (1H, m), 3.43-3.51 (1H, m), 4.65 (1H, t, J=5.4 Hz), 6.95 (1H, d, J=8.8 Hz), 7.48 (1H, dd, J=8.8, 2.4 Hz), 7.60 (1H, d, J=2.4 Hz), 10.80 (1H, s)

2) Synthesis of S-(2-[6-chloro-2-oxo-4-(trifluoromethyl)-1,4-dihydro-2H-3,1-benzoxazin-4-yl]ethyl)ethanethioate To a solution of 6-chloro-4-(2-hydroxyethyl)-4-(trifluoromethyl)-1,4-dihydro-2H-3,1-benzoxazin-2-one (500 mg, 1.69 mmol) in ethyl acetate (10 mL), triethylamine (236 μL, 1.69 mmol) and methanesulfonyl chloride (132 μL, 1.69 mmol) were added at room temperature, and the mixture was stirred for 3 hours. Then, a saturated aqueous sodium hydrogen carbonate solution was added thereto, the resulting mixture was subjected to extraction with ethyl acetate. The organic layer was washed with saline and dried over sodium sulfate. After concentration, the resulting residue was used for the subsequent reaction as such. To a DMF solution containing the obtained mesylated compound and cesium carbonate (606 mg, 1.86 mmol), thioacetic acid (144 μL, 2.03 mmol) was added at room temperature, and the resulting mixture was heated overnight at 80° C. The reaction was stopped by adding water thereto, and extracted with ethyl acetate, and the extracted organic layer was washed with saline and dried over sodium sulfate. After concentration, the resulting residue was purified by silica gel column chromatography (ethyl acetate/hexane=2/1), whereby the objective compound (230 mg, 39%) was obtained as a brown solid.

$^1$H-NMR (400 MHz, DMSO-$d_6$) δ: 2.21-2.30 (1H, m), 2.27 (3H, s), 2.60-2.70 (1H, m), 2.86-2.70 (2H, m), 6.95 (1H, d, J=8.6 Hz), 7.49 (1H, dd, J=8.6, 2.3 Hz), 7.62 (1H, d, J=2.3 Hz), 10.86 (1H, s)

3) Synthesis of 2-[6-chloro-2-oxo-4-(trifluoromethyl)-1,4-dihydro-2H-3,1-benzoxazin-4-yl]-N-pyridin-2-ylethanesulfonamide To a solution of S-(2-[6-chloro-2-oxo-4-(trifluoromethyl)-1,4-dihydro-2H-3,1-benzoxazin-4-yl]ethyl)ethanethioate (100 mg, 0.283 mmol) in acetic acid (2 mL), a 35% hydrogen peroxide solution (245 μL, 2.80 mmol) was added, and the mixture was heated for 1 hour at 70° C. Then, 10% Pd/C (100 mg) was added thereto, and the mixture was stirred for 1 hour to inactivate excess hydrogen peroxide, followed by Celite filtration. Then, the filtrate was concentrated, whereby 102 mg of the objective compound was obtained. Subsequently, to obtained sulfonic acid, thionyl chloride (2 mL) was added, and the mixture was heated under reflux for 8 hours. After completion of the reaction, the reaction mixture was concentrated under reduced pressure, and the resulting sulfonyl chloride was used for the subsequent reaction as such. To a THF solution containing excess 2-aminopyridine and triethylamine, a THF-chloroform mixed solution containing sulfonyl chloride was added dropwise, and the mixture was stirred overnight at room temperature. After completion of the reaction, water was added to the mixture. Then, the mixture was extracted with ethyl acetate and the organic layer was washed with saline and dried over sodium sulfate and then concentrated. The resulting residue was purified by reverse-phase HPLC, whereby the objective compound (6.6 mg, 9%) was obtained as a brown solid.

$^1$H-NMR (400 MHz, DMSO-$d_6$) δ: 2.44-2.57 (3H, m), 2.84-2.96 (1H, m), 6.91-7.09 (3H, m), 6.95 (1H, d, J=8.7 Hz), 7.44 (1H, d, J=2.2 Hz), 7.48 (1H, dd, J=8.7, 2.2 Hz), 7.71-7.77 (1H, m), 8.00-8.16 (1H, m), 10.88 (1H, s)

Example 122

2-[6-chloro-2-oxo-4-(trifluoromethyl)-1,4-dihydro-2H-3,1-benzoxazin-4-yl]-N-(4-fluorophenyl)ethanesulfonamide The title compound was obtained by a method according to Example 121 using 1-(2-amino-5-chlorophenyl)-2,2,2-trifluoroethanone, allyl magnesium bromide and 4-fluoroaniline as raw materials.

$^1$H-NMR (400 MHz, DMSO-$d_6$) δ: 2.42-2.57 (1H, m), 2.78-2.95 (2H, m), 3.08-3.20 (1H, m), 6.92 (1H, d, J=8.4 Hz), 7.11-7.27 (4H, m), 7.43 (1H, d, J=2.2 Hz), 7.47 (1H, dd, J=8.4, 2.2 Hz), 9.92 (1H, s), 10.86 (1H, s)

Example 123

Synthesis of N-{[6-chloro-2-oxo-4-(trifluoromethyl)-1,4-dihydro-2H-3,1-benzoxazin-4-yl]methyl}-N'-(4-fluorophenyl)urea To a stirred solution of [6-chloro-2-oxo-4-(trifluoromethyl)-1,4-dihydro-2H-3,1-benzoxazin-4-yl]methylamine hydrochloride (60 mg, 0.20 mmol) in THF (1 mL), triethylamine (66 μL, 0.47 mmol) and 4-fluorophenyl isocyanate (32 mg, 0.24 mmol) were sequentially added at room temperature. The reaction solution was stirred overnight at room temperature and then concentrated. The residue was purified by thin-layer silica gel column chromatography (ethyl acetate/hexane=1/1), whereby the objective compound (24 mg, 28%) was obtained as a white solid.

$^1$H-NMR (400 MHz, DMSO-d$_6$) δ: 3.88 (1H, dd, J=14.6, 5.9 Hz), 4.26 (1H, dd, J=14.6, 6.8 Hz), 6.44 (1H, t, J=6.3 Hz), 6.96 (1H, d, J=8.8 Hz), 7.04 (2H, t, J=8.8 Hz), 7.27-7.35 (2H, m), 7.49 (1H, dd, J=8.3, 2.4 Hz), 7.59 (1H, d, J=2.0 Hz), 8.47 (1H, s), 10.92 (1H, s)

N-{[(4S*)-6-chloro-2-oxo-4-(trifluoromethyl)-1,4-dihydro-2H-3,1-benzoxazin-4-yl]methyl}-N'-(4-fluorophenyl)urea N-{[6-chloro-2-oxo-4-(trifluoromethyl)-1,4-dihydro-2H-3,1-benzoxazin-4-yl]methyl}-N'-(4-fluorophenyl)urea was subjected to optical resolution by HPLC (Chiralpack AD-H, n-hexane:2-propanol=3:1), and a fraction eluted at a later time was concentrated, whereby the objective compound was obtained.

Example 124

N-{[6-chloro-2-oxo-4-(trifluoromethyl)-1,4-dihydro-2H-3,1-benzoxazin-4-yl]methyl}-N'-pyridin-4-ylurea The title compound was obtained by a method according to Example 123 using [6-chloro-2-oxo-4-(trifluoromethyl)-1,4-dihydro-2H-3,1-benzoxazin-4-yl]methylamine hydrochloride and pyridine-3-isocyanate as raw materials.

$^1$H-NMR (400 MHz, DMSO-d$_6$) δ: 3.91 (1H, dd, J=14.6, 4.4 Hz), 4.28 (1H, dd, J=14.6, 4.4 Hz), 6.62 (1H, t, J=6.1 Hz), 6.96 (1H, d, J=8.8 Hz), 7.24 (1H, dd, J=8.3, 4.9 Hz), 7.49 (1H, dd, J=8.8, 2.4 Hz), 7.60 (1H, br s), 7.77-7.84 (1H, m), 8.11 (1H, dd, J=4.9, 2.4 Hz), 8.44 (1H, d, J=2.4 Hz), 8.63 (1H, s), 10.93 (1H, br s)

Example 125

4-fluoro-N-{[2-oxo-6-(1H-pyrazol-5-yl)-4-(trifluoromethyl)-1,4-dihydro-2H-3,1-benzoxazin-4-yl]methyl}benzamide 1) Synthesis of 1-(5-bromo-2-fluorophenyl)-2,2,2-trifluoroethanone To a stirring solution of diisopropylamine (56.4 g, 0.55 mol) in THF (500 mL) at −40° C., n-butyl lithium (200 mL, 2.66 M hexane solution) was added dropwise. The mixture was stirred at −40° C. for 1 hour and then cooled to −78° C. Then, a solution of 4-fluorobromobenzene (87.5 g, 0.50 mol) in THF (100 mL) was slowly added dropwise thereto such that the inner temperature of the reaction solution did not exceed −70° C. After the reaction solution was stirred at −78° C. for 1 hour, a solution of ethyl trifluoroacetate (65.4 mL, 0.55 mol) in THF (100 mL) was added thereto at the same temperature. After the temperature of the reaction solution was raised to 0° C. over 1 hour under stirring, a saturated aqueous ammonium chloride solution was added thereto, and the solution was diluted with ethyl acetate. The organic layer was separated and washed with saturated brine and then dried over magnesium sulfate. After the drying agent was removed by filtration, the solvent was evaporated under reduced pressure. The residue was purified by silica gel column chromatography (ethyl acetate/hexane=1/4), and the resulting yellow oily substance was purified again by distillation under reduced pressure (1 mmHg, 53° C.), whereby the objective compound (83.8 g, 61.8%) was obtained as a yellow oily substance.

$^1$H-NMR (400 MHz, CDCl$_3$) δ: 7.15 (1H, dd, J=10.2, 8.8 Hz), 7.78 (1H, ddd, J=8.8, 4.4, 2.4 Hz), 7.99 (1H, dd, J=6.3, 2.4 Hz)

2) Synthesis of 1-{5-bromo-2-[(4-methoxybenzyl)amino]phenyl}-2,2,2-trifluoroethanone 1-(5-Bromo-2-fluorophenyl)-2,2,2-trifluoroethanone (76.2 g, 0.281 mol), potassium carbonate (46.6 g, 0.337 mol) and 4-methoxybenzylamine (73.4 mL, 0.56 mmol) were suspended in toluene (300 mL). The reaction solution was heated and stirred under reflux overnight and then cooled to 0° C. Thereafter, water (300 mL) and citric acid monohydrate (118 g, 0.56 mol) were sequentially added to the reaction solution at 0° C. After the reaction solution was stirred at 0° C. for 30 minutes, the resulting solid was collected by filtration. The solid was suspended in a mixed solvent of hexane (500 mL) and ethyl acetate (10 mL), and the suspension was stirred at room temperature for 2 hours. The solid was collected by filtration and washed with hexane and then dried, whereby the objective compound (75.6 g, 69.3%) was obtained as an orange solid. The remaining mother liquid was concentrated, and the residue was washed with hexane and a small amount of ethyl acetate, and further, the objective compound (15.9 g, 14.5%) was obtained as a dark brown solid.

$^1$H-NMR (400 MHz, CDCl$_3$) δ: 3.81 (3H, s), 4.43 (2H, d, J=5.4 Hz), 6.69 (1H, d, J=9.3 Hz), 6.89 (2H, d, J=8.8 Hz), 7.24 (2H, d, J=8.8 Hz), 7.46 (1H, dd, J=9.3, 2.0 Hz), 7.87 (1H, dd, J=4.4, 2.0 Hz), 9.06 (1H, s)

3) Synthesis of 6-bromo-1-(4-methoxybenzyl)-4-(trifluoromethyl)-4-vinyl-1,4-dihydro-2H-3,1-benzoxazin-2-one To a stirred solution of 1-{5-bromo-2-[(4-methoxybenzyl)amino]phenyl}-2,2,2-trifluoroethanone (75.5 g, 0.195 mol) in THF (500 mL), vinyl magnesium bromide (1.0 M THF solution, 389 mL) was added dropwise at 0° C. over 1 hour. After the reaction solution was stirred at 0° C. for 3 hours, a saturated aqueous ammonium chloride solution (100 mL) was added thereto, and the solution was further stirred at room temperature for 10 minutes. The reaction solution was diluted with ethyl acetate and the organic layer was separated. The organic layer was washed with water and saturated brine and then dried over magnesium sulfate. After the drying agent was removed by filtration, the solvent was evaporated under reduced pressure. The residue was dissolved in triethylamine (81.2 mL, 0.59 mol) and toluene (500 mL), and while stirring the resulting solution, triphosgene (57.9 g, 0.195 mol) was gradually added thereto at 0° C. After the reaction solution was stirred at 0° C. for 30 minutes, a saturated aqueous sodium hydrogen carbonate solution (100 mL) was added thereto, and the solution was further stirred at 0° C. for 10 minutes. The reaction solution was diluted with ethyl acetate and the organic layer was separated. The organic layer was washed with water and saturated brine and then dried over magnesium sulfate. After the drying agent was removed by filtration, the solvent was evaporated under reduced pressure. The residue was suspended in hexane (50 mL) and the suspension was stirred overnight at room temperature. The resulting solid was collected by filtration and washed with hexane and then dried, whereby the objective compound (71.6 g, 83%) was obtained as a pale yellow solid.

$^1$H-NMR (400 MHz, CDCl$_3$) δ: 3.78 (3H, s), 5.10 (2H, s), 5.69 (1H, d, J=11.2 Hz), 5.72 (1H, d, J=17.1 Hz), 6.21 (1H, dd, J=17.1, 11.2 Hz), 6.80 (1H, d, J=8.8 Hz), 6.86 (2H, d, J=8.8 Hz), 7.17 (2H, d, J=8.8 Hz), 7.40 (1H, dd, J=8.8, 2.0 Hz), 7.45 (1H, s)

4) Synthesis of 6-bromo-4-(hydroxymethyl)-1-(4-methoxybenzyl)-4-(trifluoromethyl)-1,4-dihydro-2H-3,1-benzoxazin-2-one 6-Bromo-1-(4-methoxybenzyl)-4-(trifluoromethyl)-4-vinyl-1,4-dihydro-2H-3,1-benzoxazin-2-one (71.5 g, 0.161 mol) was dissolved in dichloromethane (200 mL) and methanol (200 mL), and the solution was cooled to 0° C. and stirred in an ozone atmosphere for 2 hours. After the ozone atmosphere was replaced by a nitrogen atmospher, sodium borohydride (12.2 g, 0.323 mol) was slowly added thereto at 0° C. After the reaction solution was stirred at 0° C. for 10 minutes, excess acetone was added thereto. After the solvent was evaporated under reduced pressure, the resulting residue was diluted with ethyl acetate, and 1 N hydrochloric acid was added until the pH of the aqueous layer reached about 6. The organic layer was separated and washed with water and saturated brine and then dried over magnesium sulfate. After the drying agent was removed by filtration, the solvent was evaporated under reduced pressure. The resulting residue was crystallized from water and ethanol, whereby the objective compound (62.4 g, 87%) was obtained as a white solid.

$^1$H-NMR (400 MHz, DMSO-d$_6$) δ: 3.71 (3H, s), 3.95 (1H, d, J=12.2 Hz), 4.33 (1H, d, J=12.2 Hz), 5.07 (1H, d, J=16.6 Hz), 5.14 (1H, d, J=16.6 Hz), 5.81 (1H, br s), 6.90 (2H, d, J=8.8 Hz), 7.06 (1H, d, J=8.8 Hz), 7.20 (2H, d, J=8.8 Hz), 7.60 (1H, dd, J=8.8, 2.0 Hz), 7.74 (1H, d, J=2.0 Hz)

5) Synthesis of 4-(azidomethyl)-6-bromo-1-(4-methoxybenzyl)-4-(trifluoromethyl)-1,4-dihydro-2H-3,1-benzoxazin-2-one 6-Bromo-4-(hydroxymethyl)-1-(4-methoxybenzyl)-4-(trifluoromethyl)-1,4-dihydro-2H-3,1-benzoxazin-2-one (61.3 g, 0.137 mol) was dissolved in chloroform (400 mL) and 2,6-dimethylpyridine (48.0 mL, 0.412 mol), and while stirring the solution at 0° C., trifluoromethanesulfonic anhydride (46.4 mL, 0.275 mol) was added dropwise thereto. After the reaction solution was stirred for 1 hour under ice-cooling, a saturated aqueous sodium hydrogen carbonate solution was added thereto. Then, the solution was diluted with ethyl acetate and the organic layer was separated. The organic layer was washed sequentially with a saturated aqueous ammonium chloride solution and saturated brine and then dried over magnesium sulfate. After the drying agent was removed by filtration, the solvent was evaporated under reduced pressure. The resulting residue was dissolved in DMF (270 mL), and sodium azide (26.7 g, 0.411 mol) was added thereto. After the reaction solution was stirred at 80° C. for 3 hours, the temperature of the solution was brought to room temperature and water was added thereto. The solution was diluted with ethyl acetate and the organic layer was separated. The organic layer was washed sequentially with an aqueous citric acid solution, water and saturated brine and then dried over magnesium sulfate. After the drying agent was removed by filtration, the solvent was evaporated under reduced pressure. The residue was purified by silica gel column chromatography (ethyl acetate/hexane=2/3) and further the resulting yellow solid was washed with hexane, whereby the objective compound (46 g, 71%) was obtained as a white solid.

$^1$H-NMR (400 MHz, CDCl$_3$) δ: 3.77 (3H, s), 3.90 (1H, d, J=13.7 Hz), 4.09 (1H, d, J=13.7 Hz), 5.07 (1H, d, J=16.1 Hz), 5.17 (1H, d, J=16.1 Hz), 6.84 (1H, d, J=8.8 Hz), 6.86 (2H, d, J=8.8 Hz), 7.19 (2H, d, J=8.8 Hz), 7.33 (1H, s), 7.44 (1H, dd, J=8.8, 2.4 Hz)

6) Synthesis of 4-(aminomethyl)-6-bromo-1-(4-methoxybenzyl)-4-(trifluoromethyl)-1,4-dihydro-2H-3,1-benzoxazin-2-one To a mixed solution of THF (130 mL) and water (65 mL) containing 4-(azidomethyl)-6-bromo-1-(4-methoxybenzyl)-4-(trifluoromethyl)-1,4-dihydro-2H-3,1-benzoxazin-2-one (46 g, 98.0 mmol), trimethyl phosphite (23.1 mL, 195 mmol) was added at room temperature, and the reaction solution was stirred overnight at 60° C. After the reaction solution was left to cool, water was added thereto, and the resulting solution was diluted with ethyl acetate and the organic layer was separated. The organic layer was washed with saturated brine and then dried over magnesium sulfate. After the drying agent was removed by filtration, the solvent was evaporated under reduced pressure. To the residue, a 4 N hydrochloric acid-dioxane solution (200 mL) was added, and the mixture was stirred at room temperature for 24 hours. After the solvent was removed under reduced pressure, the residue was diluted with ethyl acetate, which was washed sequentially with a 2 N aqueous sodium hydroxide solution and saturated brine and the organic layer was dried over magnesium sulfate, whereby the objective compound (30.9 g, 71%) was obtained as a white solid.

$^1$H-NMR (400 MHz, DMSO-d$_6$) δ: 3.21 (1H, d, J=14.1 Hz), 3.61 (1H, d, J=14.1 Hz), 3.71 (3H, s), 5.05 (1H, d, J=16.6 Hz), 5.14 (1H, d, J=16.6 Hz), 6.89 (2H, d, J=8.8 Hz), 7.04 (1H, d, J=8.8 Hz), 7.22 (2H, d, J=8.8 Hz), 7.59 (1H, dd, J=8.8, 2.4 Hz), 7.69 (1H, d, J=2.4 Hz)

Synthesis of (4S*)-4-(aminomethyl)-6-bromo-1-(4-methoxybenzyl)-4-(trifluoromethyl)-1,4-dihydro-2H-3,1-benzoxazin-2-one 4-(Aminomethyl)-6-bromo-1-(4-methoxybenzyl)-4-(trifluoromethyl)-1,4-dihydro-2H-3,1-benzoxazin-2-one was subjected to optical resolution by HPLC (Chiralpack AD, n-hexane:2-propanol=4:1), and a fraction eluted at an early time was concentrated, whereby the objective compound was obtained.

7) Synthesis of N-{[6-bromo-1-(4-methoxybenzyl)-2-oxo-4-(trifluoromethyl)-1,4-dihydro-2H-3,1-benzoxazin-4-yl]methyl}-4-fluorobenzamide While stirring a solution of DMF (50 mL) containing 4-(aminomethyl)-6-bromo-1-(4-methoxybenzyl)-4-(trifluoromethyl)-1,4-dihydro-2H-3,1-benzoxazin-2-one (13.67 g, 30.7 mmol), 4-fluorobenzoic acid (4.73 g, 33.8 mmol), hydroxybenzotriazole monohydrate (4.7 g, 30.7 mmol) and triethylamine (4.69 mL, 33.8 mmol) at 0° C., 1-ethyl-3-(3-dimethylaminopropyl)carbodiimide hydrochloride (6.47 g, 33.8 mmol) was added little by little thereto. After the reaction solution was stirred overnight at room temperature, water was slowly added thereto. After a solid began to precipitate, further excess water was added thereto, and the mixture was stirred at room temperature for 2 hours. The solid was collected by filtration and washed with water and then dried under reduced pressure, whereby the objective compound (15.6 g, 90%) was obtained as a white solid.

$^1$H-NMR (400 MHz, DMSO-$d_6$) δ: 3.69 (3H, s), 3.91 (1H, dd, J=14.6, 4.4 Hz), 4.63 (1H, dd, J=14.6, 7.8 Hz), 5.05 (1H, d, J=16.6 Hz), 5.13 (1H, d, J=16.6 Hz), 6.83 (2H, d, J=8.8 Hz), 7.02 (1H, d, J=8.8 Hz), 7.17 (2H, d, J=8.8 Hz), 7.26 (2H, t, J=8.8 Hz), 7.56 (1H, dd, J=8.8, 2.4 Hz), 7.63 (1H, s), 7.75 (2H, dd, J=8.8, 5.4 Hz), 8.87 (1H, dd, J=7.8, 4.4 Hz)

8) Synthesis of N-{[6-bromo-2-oxo-4-(trifluoromethyl)-1,4-dihydro-2H-3,1-benzoxazin-4-yl]methyl}-4-fluorobenzamide While stirring a solution of N-{[6-bromo-1-(4-methoxybenzyl)-2-oxo-4-(trifluoromethyl)-1,4-dihydro-2H-3,1-benzoxazin-4-yl]methyl}-4-fluorobenzamide (13.0 g, 22.9 mmol) in acetonitrile (50 mL), an aqueous solution (25 mL) of cerium ammonium nitrate (37.7 g, 68.7 mmol) was added dropwise thereto at room temperature. The reaction solution was stirred at room temperature for 4 hours. Sodium pyrosulfite was added to the reaction solution, and the solution was stirred for 30 minutes and then diluted with ethyl acetate, and the organic layer was separated. The organic layer was washed sequentially with water and saturated brine and then dried over magnesium sulfate. After the drying agent was removed by filtration, the solvent was evaporated under reduced pressure. The resulting residue was crystallized from ethyl acetate-heptane, whereby the objective compound (6.7 g of primary crystal, 2.5 g of secondary crystal, 9.2 g in total, 90%) was obtained as a white solid.

$^1$H-NMR (400 MHz, DMSO-$d_6$) δ: 3.85 (1H, d, J=14.6 Hz), 4.58 (1H, d, J=14.6 Hz), 6.86 (1H, d, J=8.8 Hz), 7.26 (2H, t, J=8.8 Hz), 7.54-7.58 (2H, m), 7.75 (2H, dd, J=8.8, 5.4 Hz)

9) Synthesis of 4-fluoro-N-{[2-oxo-6-(1H-pyrazol-5-yl)-4-(trifluoromethyl)-1,4-dihydro-2H-3,1-benzoxazin-4-yl]methyl}benzamide N-{[6-Bromo-2-oxo-4-(trifluoromethyl)-1,4-dihydro-2H-3,1-benzoxazin-4-yl]methyl}-4-fluorobenzamide (4.0 g, 8.94 mmol), [1-(tetrahydro-2H-pyran-2-yl)-1H-pyrazol-5-yl]boronic acid (2.63 g, 13.42 mmol), a palladium chloride-1,1-bis(diphenylphosphino)ferrocene complex (654 mg, 0.894 mmol) and potassium phosphate trihydrate (4.76 g, 17.88 mmol) were suspended in DMF (27 mL) and water (2.7 mL), and the mixed solution was stirred at 120° C. for 15 minutes under microwave irradiation. After the reaction solution was left to cool, water (10 mL) and concentrated hydrochloric acid (5 mL) were sequentially added thereto, and the solution was stirred at room temperature for 2 hours. The solution was diluted with ethyl acetate and the organic layer was separated. The organic layer was washed with water and saturated brine and then dried over magnesium sulfate. After the drying agent was removed by filtration, the solvent was evaporated under reduced pressure. The resulting residue was purified by silica gel column chromatography (ethyl acetate/hexane=1/1). The resulting foamy solid was recrystallized from ethyl acetate-heptane, whereby the objective compound (2.70 g, 69.5%) was obtained as a white solid.

$^1$H-NMR (400 MHz, DMSO-$d_6$) δ: 3.90 (1H, dd, J=14.6, 3.9 Hz), 4.66 (1H, dd, J=14.6, 7.3 Hz), 6.65 (1H, d, J=2.0 Hz), 6.95 (1H, d, J=8.8 Hz), 7.21 (2H, t, J=8.8 Hz), 7.70-7.80 (5H, m), 8.82 (1H, dd, J=7.3, 3.9 Hz), 12.92 (1H, br s)

(4S*)-4-fluoro-N-{[2-oxo-6-(1H-pyrazol-5-yl)-4-(trifluoromethyl)-1,4-dihydro-2H-3,1-benzoxazin-4-yl]methyl}benzamide The title compound was obtained by a method according to Example 125 using (4S*)-4-(aminomethyl)-6-bromo-1-(4-methoxybenzyl)-4-(trifluoromethyl)-1,4-dihydro-2H-3,1-benzoxazin-2-one, 4-fluorobenzoic acid and [1-(tetrahydro-2H-pyran-2-yl)-1H-pyrazol-5-yl]boronic acid as raw materials.

Example 126

N-{[6-bromo-2-oxo-4-(trifluoromethyl)-1,4-dihydro-2H-3,1-benzoxazin-4-yl]methyl}acetamide The title compound was obtained by a method according to Example 99 using 4-(aminomethyl)-6-bromo-1-(4-methoxybenzyl)-4-(trifluoromethyl)-1,4-dihydro-2H-3,1-benzoxazin-2-one and acetyl chloride as raw materials.

$^1$H-NMR (400 MHz, DMSO-$d_6$) δ: 1.73 (3H, s), 3.66 (1H, dd, J=14.6, 4.5 Hz), 4.34 (1H, dd, J=14.6, 7.0 Hz), 6.88 (1H, d, J=8.8 Hz), 7.51 (1H, br s), 7.60 (1H, dd, J=8.8, 2.4 Hz), 8.22 (1H, dd, J=7.0, 4.5 Hz)

Example 127

4-fluoro-N-{[2-oxo-6-phenyl-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and phenylboronic acid as raw materials.

$^1$H-NMR (400 MHz, DMSO-$d_6$) δ: 3.81 (1H, d, J=14.6 Hz), 4.85 (1H, dd, J=14.6, 6.8 Hz), 6.99 (1H, d, J=8.8 Hz), 7.22 (2H, t, J=8.8 Hz), 7.35 (1H, t, J=7.6 Hz), 7.46 (2H, t, J=7.6 Hz), 7.64-7.68 (4H, m), 7.75 (2H, dd, J=8.8, 5.4 Hz), 8.89-8.90 (1H, m)

Example 128

3-[4-{[(4-fluorobenzoyl)amino]methyl}-2-oxo-4-(trifluoromethyl)-1,4-dihydro-2H-3,1-benzoxazin-6-yl]benzoic acid The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 3-(dihydroxyboryl)benzoic acid as raw materials.

$^1$H-NMR (400 MHz, DMSO-$d_6$) δ: 3.84 (1H, dd, J=14.6, 3.4 Hz), 4.85 (1H, dd, J=14.6, 8.3 Hz), 7.01 (1H, d, J=8.8 Hz), 7.21 (2H, t, J=8.8 Hz), 7.59 (1H, t, J=7.8 Hz), 7.69-7.72 (2H, m), 7.80 (2H, dd, J=8.8, 5.4 Hz), 7.90 (2H, dd, J=17.1, 7.8 Hz), 8.18 (1H, s), 8.90 (1H, dd, J=8.3, 3.4 Hz), 10.86 (1H, s)

Example 129

N-{[7-bromo-2-oxo-4-(trifluoromethyl)-1,4-dihydro-2H-3,1-benzoxazin-4-yl]methyl}-4-fluorobenzamide The title compound was obtained by a method according to Example 125 using a known compound 1-(4-bromo-2-fluorophenyl)-2,2,2-trifluoroethanone (Tetrahedron Lett., 2003, 44, 7147) and 4-fluorobenzoic acid as raw materials.

$^1$H-NMR (400 MHz, DMSO-d$_6$) δ: 3.82 (1H, dd, J=14.1, 3.9 Hz), 4.56 (1H, dd, J=14.1, 7.8 Hz), 7.06 (1H, d, J=2.0 Hz), 7.23-7.25 (3H, m), 7.32 (1H, d, J=8.8 Hz), 7.74 (2H, dd, J=8.8, 5.4 Hz), 8.77 (1H, dd, J=7.8, 3.9 Hz)

Example 130

4-fluoro-N-{[6-(2-methylphenyl)-2-oxo-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and (2-methylphenyl)boronic acid as raw materials.

$^1$H-NMR (400 MHz, DMSO-d$_6$) δ: 2.07 (3H, s), 3.78 (1H, dd, J=14.6, 3.0 Hz), 4.71 (1H, dd, J=14.6, 7.8 Hz), 6.97 (1H, d, J=8.3 Hz), 7.11 (1H, d, J=7.3 Hz), 7.21-7.27 (6H, m), 7.33 (1H, dd, J=8.3, 2.0 Hz), 7.73 (2H, dd, J=8.8, 5.4 Hz), 8.84 (1H, dd, J=7.8, 3.0 Hz)

Example 131

4-fluoro-N-{[6-isoxazol-4-yl-2-oxo-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 4-(4,4,5,5-tetramethyl-1,3,2-dioxaborolan-2-yl)isoxazole as raw materials.

$^1$H-NMR (400 MHz, DMSO-d$_6$) δ: 3.95 (1H, d, J=14.5 Hz), 4.59 (1H, d, J=14.5 Hz), 6.92 (1H, d, J=8.2 Hz), 7.19 (2H, t, J=8.9 Hz), 7.64-7.71 (3H, m), 7.74 (1H, br s), 9.04 (1H, br s), 9.32 (1H, br s)

Example 132

4-fluoro-N-{[2-oxo-6-(1H-pyrazol-4-yl)-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 4-(4,4,5,5-tetramethyl-1,3,2-dioxaborolan-2-yl)-1H-pyrazole as raw materials.

$^1$H-NMR (400 MHz, DMSO-d$_6$) δ: 3.87 (1H, dd, J=14.1, 3.9 Hz), 4.72 (1H, dd, J=14.1, 8.3 Hz), 6.89 (1H, dd, J=8.3, 1.5 Hz), 7.22 (2H, t, J=8.8 Hz), 7.57 (1H, dd, J=8.3, 1.5 Hz), 7.61 (1H, br s), 7.72 (2H, dd, J=8.8, 5.4 Hz), 7.96 (2H, br s), 8.83 (1H, dd, J=8.3, 3.9 Hz), 10.68 (1H, s)

Synthesis of (4S*)-4-fluoro-N-{[2-oxo-6-(1H-pyrazol-4-yl)-4-(trifluoromethyl)-1,4-dihydro-2H-3,1-benzoxazin-4-yl]methyl}benzamide The title compound was obtained by a method according to Example 125 using (4S*)-4-(aminomethyl)-6-bromo-1-(4-methoxybenzyl)-4-(trifluoromethyl)-1,4-dihydro-2H-3,1-benzoxazin-2-one, 4-fluorobenzoic acid and 4-(4,4,5,5-tetramethyl-1,3,2-dioxaborolan-2-yl)-1H-pyrazole as raw materials.

Example 133

4-fluoro-N-{[6-(1-methyl-1H-pyrazol-4-yl)-2-oxo-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 1-methyl-4-(4,4,5,5-tetramethyl-1,3,2-dioxaborolan-2-yl)-1H-pyrazole as raw materials.

$^1$H-NMR (400 MHz, DMSO-d$_6$) δ: 3.85 (3H, s), 3.88 (1H, d, J=14.6 Hz), 4.70 (1H, dd, J=14.6, 7.0 Hz), 6.89 (1H, d, J=8.3 Hz), 7.22 (2H, t, J=8.8 Hz), 7.53 (1H, dd, J=8.3, 2.0 Hz), 7.57 (1H, br s), 7.73 (2H, dd, J=8.8, 5.4 Hz), 7.77 (1H, s), 8.03 (1H, s), 8.85-8.81 (1H, m), 10.70 (1H, br s)

Synthesis of (4S*)-4-fluoro-N-{[6-(1-methyl-1H-pyrazol-4-yl)-2-oxo-4-(trifluoromethyl)-1,4-dihydro-2H-3,1-benzoxazin-4-yl]methyl}benzamide The title compound was obtained by a method according to Example 125 using (4S*)-4-(aminomethyl)-6-bromo-1-(4-methoxybenzyl)-4-(trifluoromethyl)-1,4-dihydro-2H-3,1-benzoxazin-2-one, 4-fluorobenzoic acid and 1-methyl-4-(4,4,5,5-tetramethyl-1,3,2-dioxaborolan-2-yl)-1H-pyrazole as raw materials.

Example 134

3-[4-{[(4-fluorobenzoyl)amino]methyl}-2-oxo-4-(trifluoromethyl)-1,4-dihydro-2H-3,1-benzoxazin-4-yl]pyridinium trifluoroacetate The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 3-pyridinyl boronic acid as raw materials.

$^1$H-NMR (400 MHz, DMSO-d$_6$) δ: 3.87 (1H, dd, J=14.6, 3.9 Hz), 4.85 (1H, dd, J=14.6, 8.3 Hz), 7.05 (1H, dd, J=8.3, 1.5 Hz), 7.22 (2H, t, J=8.8 Hz), 7.72-7.77 (3H, m), 7.80 (1H, dd, J=8.3, 1.5 Hz), 7.83 (1H, s), 8.33 (1H, d, J=7.8 Hz), 8.68 (1H, dd, J=4.9, 1.5 Hz), 8.92 (1H, dd, J=8.3, 3.9 Hz), 8.99 (1H, d, J=2.0 Hz), 10.93 (1H, s)

Example 135

4-fluoro-N-{[2-oxo-6-(3-thienyl)-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 3-thienyl boronic acid as raw materials.

$^1$H-NMR (400 MHz, DMSO-d$_6$) δ: 3.84 (1H, d, J=14.6 Hz), 4.80 (1H, dd, J=14.6, 6.8 Hz), 6.94 (1H, d, J=8.8 Hz), 7.21 (2H, t, J=9.3 Hz), 7.51 (1H, dd, J=4.9, 1.5 Hz), 7.65 (1H, dd, J=4.9, 2.9 Hz), 7.68-7.71 (2H, m), 7.73 (2H, dd, J=8.8, 5.9 Hz), 7.77 (1H, dd, J=2.9, 1.5 Hz), 8.89-8.86 (1H, m)

Example 136

4-fluoro-N-{[6-(6-methoxypyridin-3-yl)-2-oxo-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-

1,4-dihydro-2H-3,1-benzoxazin-4-yl]methyl}-4-fluorobenzamide and (6-methoxypyridin-3-yl)boronic acid as raw materials.

¹H-NMR (400 MHz, DMSO-d₆) δ: 3.83 (1H, d, J=14.6 Hz), 3.89 (3H, s), 4.84 (1H, dd, J=14.6, 6.8 Hz), 6.93 (1H, d, J=8.8 Hz), 6.99 (1H, d, J=8.8 Hz), 7.22 (2H, t, J=8.8 Hz), 7.65-7.67 (2H, m), 7.73 (2H, dd, J=8.8, 5.4 Hz), 7.99 (1H, dd, J=8.8, 2.4 Hz), 8.46 (1H, d, J=2.4 Hz), 8.91-8.88 (1H, m), 10.79-10.83 (1H, br m)

Example 137

4-[4-{[(4-fluorobenzoyl)amino]methyl}-2-oxo-4-(trifluoromethyl)-1,4-dihydro-2H-3,1-benzoxazin-6-yl]benzoic acid The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 4-(dihydroxyboryl)benzoic acid as raw materials.

¹H-NMR (400 MHz, DMSO-d₆) δ: 3.85 (1H, dd, J=14.4, 3.9 Hz), 4.85 (1H, dd, J=14.4, 8.3 Hz), 7.02 (1H, dd, J=8.8, 1.0 Hz), 7.22 (2H, t, J=8.8 Hz), 7.74-7.80 (6H, m), 8.01 (2H, d, J=8.3 Hz), 8.91 (1H, dd, J=8.3, 3.9 Hz), 10.89 (1H, s)

Example 136

4-fluoro-N-{[6-methyl-2-oxo-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and trimethylboroxane as raw materials.

¹H-NMR (400 MHz, DMSO-d₆) δ: 2.21 (3H, s), 3.86 (1H, dd, J=14.6, 4.4 Hz), 4.54 (1H, dd, J=14.6, 7.8 Hz), 6.80 (1H, d, J=7.8 Hz), 7.17 (1H, d, J=8.3 Hz), 7.21 (1H, s), 7.24 (2H, t, J=8.8 Hz), 7.73 (2H, dd, J=8.8, 5.4 Hz), 8.75 (1H, dd, J=7.8, 4.4 Hz), 10.58 (1H, br s)

Example 139

4-fluoro-N-{[2-oxo-7-(1H-pyrazol-3-yl)-4-(trifluoromethyl)-1,4-dihydro-2H-3,1-benzoxazin-4-yl]methyl}benzamide The title compound was obtained by a method according to Example 125 using N-{[7-bromo-2-oxo-4-(trifluoromethyl)-1,4-dihydro-2H-3,1-benzoxazin-4-yl]methyl}-4-fluorobenzamide and [1-(tetrahydro-2H-pyran-2-yl)-1H-pyrazol-5-yl]boronic acid as raw materials.

¹H-NMR (400 MHz, DMSO-d₆) δ: 3.84 (1H, dd, J=14.6, 3.9 Hz), 4.63 (1H, dd, J=14.6, 7.8 Hz), 6.67 (1H, d, J=2.4 Hz), 7.22 (2H, t, J=8.8 Hz), 7.39 (2H, d, J=8.3 Hz), 7.46 (1H, dd, J=8.3, 1.5 Hz), 7.73-7.77 (3H, m), 8.80 (1H, dd, J=7.8, 3.9 Hz), 10.75 (1H, s)

Example 140

4-fluoro-N-{[2-oxo-7-(1H-pyrazol-4-yl)-4-(trifluoromethyl)-1,4-dihydro-2H-3,1-benzoxazin-4-yl]methyl}benzamide The title compound was obtained by a method according to Example 125 using N-{[7-bromo-2-oxo-4-(trifluoromethyl)-1,4-dihydro-2H-3,1-benzoxazin-4-yl]methyl}-4-fluorobenzamide and 4-(4,4,5,5-tetramethyl-1,3,2-dioxaborolan-2-yl)-1H-pyrazole as raw materials.

¹H-NMR (400 MHz, DMSO-d₆) δ: 3.82 (1H, dd, J=14.6, 3.9 Hz), 4.62 (1H, dd, J=14.6, 7.8 Hz), 7.04 (1H, d, J=1.5 Hz), 7.23 (2H, t, J=8.8 Hz), 7.30 (1H, dd, J=8.3, 1.5 Hz), 7.34 (1H, d, J=8.3 Hz), 7.76 (2H, dd, J=8.8, 5.4 Hz), 7.99 (2H, br s), 8.79 (1H, dd, J=7.8, 3.9 Hz), 10.68 (1H, s)

Example 141

4-fluoro-N-{[6-(1-methyl-1H-pyrazol-5-yl)-2-oxo-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and (1-methyl-1H-pyrazol-5-yl)boronic acid as raw materials.

¹H-NMR (400 MHz, DMSO-d₆) δ: 3.75 (3H, d, J=11.7 Hz), 3.82 (1H, dd, J=14.6, 3.9 Hz), 4.75 (1H, dd, J=14.6, 7.8 Hz), 6.37 (1H, d, J=2.0 Hz), 7.01 (1H, d, J=8.3 Hz), 7.24 (2H, t, J=8.8 Hz), 7.45 (1H, d, J=2.0 Hz), 7.51 (1H, br s), 7.54 (1H, dd, J=8.3, 2.0 Hz), 7.73 (2H, dd, J=8.8, 5.4 Hz), 8.86 (1H, dd, J=7.8, 3.9 Hz)

Example 142

4-fluoro-N-{[6-(3-methyl-1H-pyrazol-5-yl)-2-oxo-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and [3-methyl-1-(tetrahydro-2H-pyran-2-yl)-1H-pyrazol-5-yl]boronic acid as raw materials.

¹H-NMR (400 MHz, DMSO-d₆) δ: 2.23 (3H, s), 3.89 (1H, dd, J=14.6, 3.9 Hz), 4.63 (1H, dd, J=14.6, 7.8 Hz), 6.37 (1H, s), 6.91 (1H, d, J=8.8 Hz), 7.20 (2H, t, J=8.8 Hz), 7.68-7.74 (4H, m), 8.79 (1H, dd, J=7.8, 3.9 Hz), 10.73 (1H, s)

Example 143

4-fluoro-N-{[6-(4-methyl-1H-pyrazol-5-yl)-2-oxo-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and [4-methyl-1-(tetrahydro-2H-pyran-2-yl)-1H-pyrazol-5-yl]boronic acid as raw materials.

¹H-NMR (400 MHz, DMSO-d₆) δ: 2.13 (3H, s), 3.87-3.89 (1H, m), 4.56-4.58 (1H, m), 6.96 (1H, d, J=7.8 Hz), 7.21 (2H, t, J=8.8 Hz), 7.53-7.61 (2H, br m), 7.69 (2H, dd, J=8.8, 5.4 Hz), 8.78 (1H, dd, J=7.8, 3.9 Hz), 10.74 (1H, br s), 12.60 (1H, s)

Example 144

4-fluoro-N-{[2-oxo-6-(1H-pyrrol-2-yl)-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-

1,4-dihydro-2H-3,1-benzoxazin-4-yl]methyl}-4-fluorobenzamide and 1-(t-butoxycarbonyl)pyrrole-2-boronic acid as raw materials.
$^1$H-NMR (400 MHz, DMSO-d$_6$) δ: 3.98 (1H, dd, J=14.6, 4.9 Hz), 4.56 (1H, dd, J=14.6, 7.3 Hz), 6.08 (1H, dd, J=5.9, 2.4 Hz), 6.43-6.46 (1H, br m), 6.82 (1H, d, J=1.5 Hz), 6.86 (1H, d, J=8.3 Hz), 7.21 (2H, t, J=8.8 Hz), 7.58 (1H, dd, J=8.3, 2.0 Hz), 7.66 (1H, s), 7.73 (2H, dd, J=8.8, 5.9 Hz), 8.76 (1H, dd, J=7.3, 4.9 Hz), 10.65 (1H, s), 11.21 (1H, s)

Example 145

4-fluoro-N-{[2-oxo-6-(3-phenyl-1H-pyrazol-5-yl)-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and [3-phenyl-1-(tetrahydro-2H-pyran-2-yl)-1H-pyrazol-5-yl]boronic acid as raw materials.
$^1$H-NMR (400 MHz, DMSO-d$_6$) δ: 3.98 (1H, dd, J=14.6, 4.4 Hz), 4.62 (1H, dd, J=14.6, 7.3 Hz), 6.97 (1H, d, J=8.3 Hz), 7.10 (1H, s), 7.20 (2H, t, J=8.8 Hz), 7.34 (1H, t, J=7.3 Hz), 7.46 (2H, t, J=7.3 Hz), 7.72 (2H, dd, J=8.8, 5.4 Hz), 7.78-7.83 (3H, m), 7.87 (1H, s), 8.81 (1H, dd, J=7.3, 4.4 Hz), 10.80 (1H, s)

Example 146

4-fluoro-N-{[6-(2-furyl)-2-oxo-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 2-furylboronic acid as raw materials.
$^1$H-NMR (400 MHz, DMSO-d$_6$) δ: 3.89 (1H, dd, J=14.6, 3.9 Hz), 4.67 (1H, dd, J=14.6, 7.8 Hz), 6.59 (1H, dd, J=3.4, 1.5 Hz), 6.85 (1H, d, J=3.4 Hz), 6.95 (1H, d, J=8.3 Hz), 7.22 (2H, t, J=8.8 Hz), 7.68-7.74 (5H, m), 8.83 (1H, dd, J=7.8, 3.9 Hz), 10.83 (1H, s)

Example 147

4-fluoro-N-{[2-oxo-6-(2-thienyl)-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 2-thienylboronic acid as raw materials.
$^1$H-NMR (400 MHz, DMSO-d$_6$) δ: 3.83 (1H, dd, J=14.6, 3.9 Hz), 4.79 (1H, dd, J=14.6, 8.3 Hz), 6.95 (1H, d, J=8.3 Hz), 7.13 (1H, dd, J=4.9, 3.9 Hz), 7.22 (2H, t, J=8.8 Hz), 7.44 (1H, dd, J=3.9, 1.0 Hz), 7.53 (1H, dd, J=4.9, 1.0 Hz), 7.63 (1H, dd, J=8.3, 2.0 Hz), 7.66 (1H, br s), 7.74 (2H, dd, J=8.8, 5.4 Hz), 8.87 (1H, dd, J=8.3, 3.9 Hz), 10.84 (1H, s)

Example 148

4-fluoro-N-{[2-oxo-6-(1H-pyrazol-4-yl)-4-(trifluoromethyl)-1,4-dihydro-2H-3,1-benzoxazin-4-yl]methyl}benzenesulfonamide The title compound was obtained by a method according to Example 99 and Example 125 using 4-(aminomethyl)-6-bromo-1-(4-methoxybenzyl)-4-(trifluoromethyl)-1,4-dihydro-2H-3,1-benzoxazin-2-one, 4-(4,4,5,5-tetramethyl-1,3,2-dioxaborolan-2-yl)-1H-pyrazole and (4-fluorophenyl)sulfonyl chloride as raw materials.
$^1$H-NMR (400 MHz, DMSO-d$_6$) δ: 3.52 (1H, dd, J=14.1, 6.0 Hz), 4.09 (1H, dd, J=14.1, 7.0 Hz), 6.87 (1H, d, J=8.3 Hz), 7.39-7.29 (2H, m), 7.56 (1H, br s), 7.61 (1H, dd, J=8.3, 2.0 Hz), 7.84-7.76 (2H, m), 8.01 (2H, s), 8.28 (1H, dd, J=7.0, 6.0 Hz), 10.59 (1H, s)

Example 149

N-{[2-oxo-6-(1H-pyrazol-4-yl)-4-(trifluoromethyl)-1,4-dihydro-2H-3,1-benzoxazin-4-yl]methyl}pyridine-2-sulfonamide The title compound was obtained by a method according to Example 99 and Example 125 using 4-(aminomethyl)-6-bromo-1-(4-methoxybenzyl)-4-(trifluoromethyl)-1,4-dihydro-2H-3,1-benzoxazin-2-one, 4-(4,4,5,5-tetramethyl-1,3,2-dioxaborolan-2-yl)-1H-pyrazole and pyridine-2-sulfonyl chloride as raw materials.
$^1$H-NMR (400 MHz, DMSO-d$_6$) δ: 4.13 (1H, dd, J=14.3, 5.4 Hz), 4.58 (1H, dd, J=14.3, 7.5 Hz), 7.16-7.22 (1H, m), 7.86-7.98 (3H, m), 8.13-8.19 (1H, m), 8.29-8.38 (3H, m), 8.77 (1H, dd, J=7.5, 5.4 Hz), 8.99-8.95 (1H, m), 10.89 (1H, s)

Example 150

4-fluoro-N-{[2-oxo-6-(1H-pyrazol-3-yl)-4-(trifluoromethyl)-1,4-dihydro-2H-3,1-benzoxazin-4-yl]methyl}benzenesulfonamide The title compound was obtained by a method according to Example 99 and Example 125 using 4-(aminomethyl)-6-bromo-1-(4-methoxybenzyl)-4-(trifluoromethyl)-1,4-dihydro-2H-3,1-benzoxazin-2-one, [1-(tetrahydro-2H-pyran-2-yl)-1H-pyrazol-5-yl]boronic acid and 4-fluorobenzenesulfonyl chloride as raw materials.
$^1$H-NMR (400 MHz, DMSO-d$_6$) δ: 3.45-3.55 (1H, m), 3.99-4.06 (1H, m), 6.69 (1H, s), 6.92 (1H, d, J=8.8 Hz), 7.30-7.35 (2H, m), 7.69-7.89 (5H, m), 8.28-8.31 (1H, m), 10.69 (1H, s), 12.86 (1H, s)

4-fluoro-N-{[(4S*)-2-oxo-6-(1H-pyrazol-3-yl)-4-(trifluoromethyl)-1,4-dihydro-2H-3,1-benzoxazin-4-yl]methyl}benzenesulfonamide The title compound was obtained by a method according to Example 99 and Example 125 using (4S*)-4-(aminomethyl)-6-bromo-1-(4-methoxybenzyl)-4-(trifluoromethyl)-1,4-dihydro-2H-3,1-benzoxazin-2-one, [1-(tetrahydro-2H-pyran-2-yl)-1H-pyrazol-5-yl]boronic acid and 4-fluorobenzenesulfonyl chloride as raw materials.

Example 151

N-{[2-oxo-6-(1H-pyrazol-3-yl)-4-(trifluoromethyl)-1,4-dihydro-2H-3,1-benzoxazin-4-yl]methyl}pyridine-2-sulfonamide The title compound was obtained by a method according to Example 99 and Example 125 using 4-(aminomethyl)-6-bromo-1-(4-methoxybenzyl)-4-(trifluoromethyl)-1,4-dihydro-2H-3,1-benzoxazin-2-one, [1-(tetrahydro-2H-pyran-2-yl)-1H-pyrazol-5-yl]boronic acid and pyridine-2-sulfonyl chloride as raw materials.

$^1$H-NMR (400 MHz, DMSO-d$_6$) δ: 3.81 (1H, d, J=14.4 Hz), 4.19 (1H, dd, J=14.4, 6.6 Hz), 6.68 (1H, s), 6.92 (1H, d, J=8.3 Hz), 7.61 (1H, dd, J=7.8, 4.6 Hz), 7.68-7.89 (4H, m), 8.00 (1H, td, J=7.8, 1.5 Hz), 8.46 (1H, s), 8.65 (1H, s), 10.67 (1H, s), 12.86 (1H, s)

N-{[(4S*)-2-oxo-6-(1H-pyrazol-3-yl)-4-(trifluoromethyl)-1,4-dihydro-2H-3,1-benzoxazin-4-yl]methyl}pyridine-2-sulfonamide The title compound was obtained by a method according to Example 99 and Example 125 using (4S*)-4-(aminomethyl)-6-bromo-1-(4-methoxybenzyl)-4-(trifluoromethyl)-1,4-dihydro-2H-3,1-benzoxazin-2-one, [1-(tetrahydro-2H-pyran-2-yl)-1H-pyrazol-5-yl]boronic acid and pyridine-2-sulfonyl chloride as raw materials.

Example 152

4-fluoro-N-{[2-oxo-6-(pyridin-4-yl)-4-(trifluoromethyl)-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and 4-pyridinyl boronic acid as raw materials.
$^1$H-NMR (400 MHz, DMSO-d$_6$) δ: 3.85 (1H, dd, J=14.6, 3.4 Hz), 4.86 (1H, dd, J=14.6, 7.8 Hz), 7.03 (1H, d, J=8.8 Hz), 7.22 (2H, t, J=8.8 Hz), 7.69 (2H, d, J=6.3 Hz), 7.74 (2H, dd, J=8.8, 5.4 Hz), 7.82-7.84 (2H, m), 8.64 (2H, d, J=6.3 Hz), 8.91 (1H, dd, J=7.8, 3.4 Hz), 10.94 (1H, s)

Example 153

4-fluoro-N-{[2-oxo-4-(trifluoromethyl)6-[3-(trifluoromethyl)-1H-pyrazol-5-yl]-1,4-dihydro-2H-3,1-benzoxazin-4-yl]methyl}benzamide The title compound was obtained by a method according to Example 125 using N-{[6-bromo-2-oxo-4-(trifluoromethyl)-1,4-dihydro-2H-3,1-benzoxazin-4-yl]methyl}-4-fluorobenzamide and [3-trifluoromethyl-1-(tetrahydro-2H-pyran-2-yl)-1H-pyrazol-5-yl]boronic acid as raw materials.
$^1$H-NMR (400 MHz, DMSO-d$_6$) δ: 4.04 (1H, dd, J=14.6, 4.9 Hz), 4.57 (1H, dd, J=14.6, 7.3 Hz), 7.00 (1H, d, J=8.8 Hz), 7.15 (1H, s), 7.23 (2H, t, J=8.8 Hz), 7.72 (2H, dd, J=8.8, 5.4 Hz), 7.83 (1H, dd, J=8.8, 2.0 Hz), 7.94 (1H, s), 8.80 (1H, dd, J=7.3, 4.9 Hz), 10.93 (1H, s), 14.08 (1H, s)

Example 154

4-fluoro-N-{[2-oxo-6-(2-oxopyrrolidin-1-yl)-4-(trifluoromethyl)-1,4-dihydro-2H-3,1-benzoxazin-4-yl]methyl}benzamide 1) Synthesis of 4-fluoro-N-{[1-(4-methoxybenzyl)-2-oxo-6-(2-oxopyrrolidin-1-yl)-4-(trifluoromethyl)-1,4-dihydro-2H-3,1-benzoxazin-4-yl]methyl}benzamide A mixed solution of N-{[6-bromo-1-(4-methoxybenzyl)-2-oxo-4-(trifluoromethyl)-1,4-dihydro-2H-3,1-benzoxazin-4-yl]methyl}-4-fluorobenzamide (100 mg, 0.176 mmol), tris(dibenzylideneacetone)dipalladium (8.0 mg, 0.008 mmol), xantphos (15.2 mg, 0.024 mmol), cesium carbonate (57.4 mg, 0.176 mmol) and 2-pyrrolidinone (26.8 μL, 0.352 mmol) in dioxane (0.5 mL) was stirred at 120° C. for 30 minutes under microwave irradiation. After the reaction solution was left to cool, the solution was diluted with ethyl acetate and the organic layer was separated. The organic layer was washed with water and saturated brine and then dried over magnesium sulfate. After the drying agent was removed by filtration, the solvent was evaporated under reduced pressure. The residue was purified by silica gel column chromatography (ethyl acetate/hexane=1/1), whereby the objective compound (69 mg, 69%) was obtained as a yellow oily substance.
$^1$H-NMR (400 MHz, CDCl$_3$) δ: 2.09-2.20 (2H, m), 2.55-2.59 (2H, m), 3.76 (3H, s), 3.78-3.96 (3H, m), 4.93 (1H, dd, J=14.6, 8.8 Hz), 5.00 (1H, d, J=16.1 Hz), 5.14 (1H, d, J=16.1 Hz), 6.80 (2H, d, J=8.8 Hz), 6.89 (1H, d, J=9.3 Hz), 7.02 (2H, t, J=8.8 Hz), 7.16 (2H, d, J=8.8 Hz), 7.35 (1H, d, J=2.0 Hz), 7.66 (2H, dd, J=8.8, 4.9 Hz), 8.01 (1H, s), 8.05 (1H, dd, J=9.3, 2.4 Hz)

2) Synthesis of 4-fluoro-N-{[2-oxo-6-(2-oxopyrrolidin-1-yl)-4-(trifluoromethyl)-1,4-dihydro-2H-3,1-benzoxazin-4-yl]methyl}benzamide 4-Fluoro-N-{[1-(4-methoxybenzyl)-2-oxo-6-(2-oxopyrrolidin-1-yl)-4-(trifluoromethyl)-1,4-dihydro-2H-3,1-benzoxazin-4-yl]methyl}benzamide (30 mg, 0.0525 mmol), aluminum trichloride (70 mg, 0.525 mmol) were mixed in anisole (0.5 mL), and the mixture was stirred at room temperature. After all the ingredients were dissolved, the temperature of the solution was raised to 100° C. and the solution was stirred for 4 hours. The temperature of the solution was brought to room temperature and the solution was diluted with ethyl acetate and then water was added thereto. Then, the organic layer was separated and washed with saturated brine and then dried over magnesium sulfate. After the drying agent was removed by filtration, the solvent was evaporated under reduced pressure. The residue was purified by silica gel column chromatography (ethyl acetate/hexane=1/0), and a crude product was crystallized from ethyl acetate-diisopropyl ether, whereby the objective compound (10.1 mg, 43%) was obtained as a pale yellow solid.
$^1$H-NMR (400 MHz, DMSO-d$_6$) δ: 1.99-2.07 (2H, m), 2.43-2.48 (2H, m), 3.69-3.81 (2H, m), 3.85 (1H, dd, J=14.6, 4.4 Hz), 4.56 (1H, dd, J=14.6, 7.8 Hz), 6.89 (1H, d, J=8.8 Hz), 7.23 (2H, t, J=8.8 Hz), 7.50 (1H, d, J=2.0 Hz), 7.74 (2H, dd, J=8.8, 5.9 Hz), 7.79 (1H, dd, J=8.8, 2.4 Hz), 8.78 (1H, dd, J=7.8, 4.4 Hz), 10.67 (1H, s)

Synthesis of (4S*)-4-fluoro-N-{[2-oxo-6-(2-oxopyrrolidin-1-yl)-4-(trifluoromethyl)-1,4-dihydro-2H-3,1-benzoxazin-4-yl]methyl}benzamide The title compound was obtained in the same manner as described above using (4S*)-4-(aminomethyl)-6-bromo-1-(4-methoxybenzyl)-4-(trifluoromethyl)-1,4-dihydro-2H-3,1-benzoxazin-2-one, 4-fluorobenzoic acid and 2-pyrrolidinone as raw materials.

Example 155

4-fluoro-N-{[2-oxo-6-(2-oxoazetidin-1-yl)-4-(trifluoromethyl)-1,4-dihydro-2H-3,1-benzoxazin-4-yl]methyl}benzamide The title compound was obtained by a method according to Example 154 using 4-fluoro-N-{[1-(4-methoxybenzyl)-2- oxo-6-(2-oxopyrrolidin-1-yl)-4-(trifluoromethyl)-1,4-dihydro-2H-3,1-benzoxazin-4-yl]methyl}benzamide and 2-azetidinone as raw materials.

$^{1}$H-NMR (400 MHz, DMSO-d$_{6}$) δ: 3.04-3.06 (2H, m), 3.53-3.62 (2H, m), 3.86 (1H, dd, J=14.6, 4.4 Hz), 4.52 (1H, dd, J=14.6, 7.8 Hz), 6.89 (1H, d, J=8.8 Hz), 7.21-7.27 (3H, m), 7.47 (1H, dd, J=8.8, 2.0 Hz), 7.74 (2H, dd, J=8.8, 5.9 Hz), 8.78 (1H, br s)

Example 156

4-fluoro-N-{[2-oxo-6-(propionylamino)-4-(trifluoromethyl)-1,4-dihydro-2H-3,1-benzoxazin-4-yl]methyl}benzamide The title compound was obtained by a method according to Example 154 using 4-fluoro-N-{[1-(4-methoxybenzyl)-2-oxo-6-(2-oxopyrrolidin-1-yl)-4-(trifluoromethyl)-1,4-dihydro-2H-3,1-benzoxazin-4-yl]methyl}benzamide and propionamide as raw materials.

$^{1}$H-NMR (400 MHz, DMSO-d$_{6}$) δ: 1.04 (3H, t, J=7.3 Hz), 2.27 (2H, q, J=7.3 Hz), 3.93 (1H, dd, J=14.1, 4.9 Hz), 4.31 (1H, dd, J=14.1, 7.3 Hz), 6.82 (1H, d, J=8.8 Hz), 7.23 (2H, t, J=8.8 Hz), 7.61-7.65 (2H, m), 7.73 (2H, dd, J=8.8, 5.9 Hz), 8.74 (1H, dd, J=7.3, 4.9 Hz), 9.90 (1H, s), 10.58 (1H, s)

Example 157

4-fluoro-N-{[2-oxo-6-(1H-1,2,4-triazol-5-yl)-4-(trifluoromethyl)-1,4-dihydro-2H-3,1-benzoxazin-4-yl]methyl}benzamide To a stirring and cooling solution of 1-[(benzyloxy)methyl]-1H-1,2,4-triazole (41.7 mg, 0.22 mmol) in THF (0.3 mL) at −78° C., n-butyl lithium (92 μL, 2.4 M hexane solution) was added dropwise thereto. After the reaction solution was stirred at the same temperature for 10 minutes, a solution of zinc bromide (59.5 mg, 0.26 mmol) in THF (0.3 mL) was added thereto at −78° C. The solution was stirred at −78° C. for 20 minutes, and then the temperature of the solution was gradually raised to room temperature. To the reaction solution, tetrakis(triphenylphosphine)palladium (10 mg, 0.009 mmol), N-{[6-bromo-1-(4-methoxybenzyl)-2-oxo-4-(trifluoromethyl)-1,4-dihydro-2H-3,1-benzoxazin-4-yl]methyl}-4-fluorobenzamide (50 mg, 0.088 mmol) and DMF (0.5 mL) were added, and the solution was stirred overnight at 100° C. The temperature of the solution was brought to room temperature and the solution was diluted with ethyl acetate and water was added thereto. Then, the organic layer was separated. The organic layer was washed sequentially with an aqueous citric acid solution and saturated brine and then dried over magnesium sulfate. After the drying agent was removed by filtration, the solvent was evaporated under reduced pressure. The residue was purified by silica gel column chromatography (ethyl acetate/hexane=2/1), and 36.6 mg of a pale yellow liquid was obtained as a crude product.

The obtained crude product (35 mg) was subjected to deprotection under the same condition as in Example 154, whereby the objective compound (5.2 mg, 23%) was obtained as a pale white solid.

$^{1}$H-NMR (400 MHz, DMSO-d$_{6}$) δ: 3.95 (1H, dd, J=14.4, 4.4 Hz), 4.52 (1H, dd, J=14.4, 7.3 Hz), 7.00 (1H, d, J=8.3 Hz), 7.20 (2H, t, J=8.8 Hz), 7.69 (2H, dd, J=8.8, 5.4 Hz), 7.99 (1H, dd, J=8.3, 2.0 Hz), 8.05 (1H, br s), 8.42 (1H, br s), 8.79 (1H, dd, J=7.3, 4.4 Hz)

Example 158

4-fluoro-N-{[6-(1H-imidazol-2-yl)-2-oxo-4-(trifluoromethyl)-1,4-dihydro-2H-3,1-benzoxazin-4-yl]methyl}benzamide The title compound was obtained by a method according to Example 154 using N-{[6-bromo-1-(4-methoxybenzyl)-2-oxo-4-(trifluoromethyl)-1,4-dihydro-2H-3,1-benzoxazin-4-yl]methyl}-4-fluorobenzamide and imidazole as raw materials.

$^{1}$H-NMR (400 MHz, DMSO-d$_{6}$) δ: 4.08 (1H, dd, J=14.1, 4.9 Hz), 4.42 (1H, dd, J=14.1, 6.3 Hz), 6.96 (2H, d, J=8.8 Hz), 7.21 (3H, t, J=8.8 Hz), 7.23 (1H, br s), 7.71 (2H, dd, J=8.8, 5.4 Hz), 7.92 (1H, dd, J=8.8, 1.5 Hz), 8.02 (1H, br s), 8.74-8.77 (1H, br m), 10.81 (1H, br s), 12.50 (1H, s)

Example 159

4-{[(4-fluorobenzoyl)amino]methyl}-N-methyl-2-oxo-4-(trifluoromethyl)-1,4-dihydro-2H-3,1-benzoxazine-6-carboxamide 1) Synthesis of N-{[6-cyano-1-(4-methoxybenzyl)-2-oxo-4-(trifluoromethyl)-1,4-dihydro-2H-3,1-benzoxazin-4-yl]methyl}-4-fluorobenzamide A solution of N-{[6-bromo-1-(4-methoxybenzyl)-2-oxo-4-(trifluoromethyl)-1,4-dihydro-2H-3,1-benzoxazin-4-yl]methyl}-4-fluorobenzamide (1.0 g, 1.76 mmol), zinc cyanide (414 mg, 3.53 mmol) and tetrakis(triphenyl phosphine)palladium (102 mg, 0.088 mmol) in DMF (4.5 mL) was stirred at 100° C. for 3 hours. The temperature of the solution was brought to room temperature and the solution was diluted with ethyl acetate, which was washed sequentially with an aqueous citric acid solution and saturated brine and then dried over magnesium sulfate. After the drying agent was removed by filtration, the solvent was evaporated under reduced pressure. The residue was purified by silica gel column chromatography (ethyl acetate/hexane=1/1), whereby the objective compound (873 mg, 96%) was obtained as a white solid.

$^{1}$H-NMR (400 MHz, DMSO-d$_{6}$) δ: 3.70 (3H, s), 4.04 (1H, dd, J=14.6, 4.4 Hz), 4.62 (1H, dd, J=14.6, 6.8 Hz), 5.12 (1H, d, J=16.1 Hz), 5.19 (1H, d, J=16.1 Hz), 6.83 (2H, d, J=8.8 Hz), 7.18 (2H, d, J=8.8 Hz), 7.30-7.25 (3H, m), 7.75 (2H, dd, J=8.8, 5.4 Hz), 7.89 (1H, dd, J=8.8, 2.0 Hz), 8.03 (1H, s), 8.84 (1H, dd, J=6.8, 4.4 Hz)

2) Synthesis of 4-{[(4-fluorobenzoyl)amino]methyl}-2-oxo-4-(trifluoromethyl)-1,4-dihydro-2H-3,1-benzoxazine-6-carboxylic acid N-{[6-cyano-1-(4-methoxybenzyl)-2-oxo-4-(trifluoromethyl)-1,4-dihydro-2H-3,1-benzoxazin-4-yl]methyl}-4-fluorobenzamide was dissolved in 25% hydrogen bromide-acetic acid (5 mL) and water (1 mL), and the solution was stirred overnight at 100° C. The temperature of the solution was brought to room temperature, and water was added thereto under stirring. After the solution was stirred at room temperature for 30 minutes, the resulting brown solid was dried under reduced pressure, whereby the objective compound (317 mg, 55%) was obtained as a brown solid.

$^{1}$H-NMR (400 MHz, DMSO-d$_{6}$) δ: 3.88 (1H, dd, J=14.6, 4.4 Hz), 4.57 (1H, dd, J=14.6, 7.3 Hz), 6.98 (1H, d, J=8.3 Hz), 7.22 (2H, t, J=8.8 Hz), 7.68 (2H, dd, J=8.8, 5.4 Hz), 7.92 (1H, dd, J=8.3, 2.0 Hz), 7.94 (1H, br s), 8.78 (1H, dd, J=7.3, 4.4 Hz), 11.07 (1H, s)

3) Synthesis of 4-{[(4-fluorobenzoyl)amino]methyl}-N-methyl-2-oxo-4-(trifluoromethyl)-1,4-dihydro-2H-3,1-benzoxazine-6-carboxamide 4-{[(4-Fluorobenzoyl)amino]methyl}-2-oxo-4-(trifluoromethyl)-1,4-dihydro-2H-3,1-benzoxazine-6-carboxylic acid (30 mg, 0.073 mmol) and CDI (23.6 mg, 0.15 mmol) were dissolved in THF (230 μL) and DMF (90 μL), and the solution was stirred at room temperature for 30 minutes and thereafter, methylamine (182 μL, 0.36 mmol) was added thereto. The reaction solution was stirred at room temperature for 30 minutes and then diluted with ethyl acetate, which was washed sequentially with water and saturated brine and then dried over magnesium sulfate. After the drying agent was removed by filtration, the solvent was evaporated under reduced pressure. The resulting residue was purified by silica gel column chromatography, whereby the objective compound (10.2 mg, 33%) was obtained as a white solid.
$^1$H-NMR (400 MHz, DMSO-$d_6$) δ: 2.76 (3H, d, J=4.9 Hz), 4.04 (1H, dd, J=14.4, 5.4 Hz), 4.43 (1H, dd, J=14.4, 6.8 Hz), 6.94 (1H, d, J=8.8 Hz), 7.23 (2H, t, J=8.8 Hz), 7.71 (2H, dd, J=8.8, 5.9 Hz), 7.84 (1H, dd, J=8.8, 2.0 Hz), 7.94 (1H, br s), 8.35 (1H, q, J=4.9 Hz), 8.73 (1H, dd, J=6.8, 5.4 Hz), 10.94 (1H, br s)

Example 160

4-fluoro-N-{[2-oxo-6-(pyrrolidin-1-ylcarbonyl)-4-(trifluoromethyl)-1,4-dihydro-2H-3,1-benzoxazin-4-yl]methyl}benzamide The title compound was obtained by a method according to Example 159 using 4-{[(4-fluorobenzoyl)amino]methyl}-2-oxo-4-(trifluoromethyl)-1,4-dihydro-2H-3,1-benzoxazine-6-carboxylic acid and pyrrolidine as raw materials.
$^1$H-NMR (400 MHz, DMSO-$d_6$) δ: 1.57-1.70 (2H, m), 1.77-1.84 (2H, m), 3.12-3.17 (2H, br m), 3.36-3.39 (2H, br m), 3.82 (1H, dd, J=14.6, 3.4 Hz), 4.63 (1H, dd, J=14.6, 7.8 Hz), 6.93 (1H, d, J=8.3 Hz), 7.23 (2H, t, J=8.8 Hz), 7.44 (1H, s), 7.49 (1H, dd, J=8.3, 2.0 Hz), 7.73 (2H, dd, J=8.8, 5.4 Hz), 8.79 (1H, dd, J=7.8, 3.4 Hz), 10.89 (1H, s)

Example 161

N-cyclopentyl-4-{[(4-fluorobenzoyl)amino]methyl}-2-oxo-4-(trifluoromethyl)-1,4-dihydro-2H-3,1-benzoxazine-6-carboxamide The title compound was obtained by a method according to Example 159 using 4-{[(4-fluorobenzoyl)amino]methyl}-2-oxo-4-(trifluoromethyl)-1,4-dihydro-2H-3,1-benzoxazine-6-carboxylic acid and cyclopentylamine as raw materials.
$^1$H-NMR (400 MHz, DMSO-$d_6$) δ: 1.45-1.58 (4H, br m), 1.66-1.72 (2H, br m), 1.84-1.92 (2H, br m), 4.00 (1H, dd, J=14.6, 4.9 Hz), 4.19 (1H, dd, J=14.6, 7.3 Hz), 4.50 (1H, dd, J=14.6, 7.0 Hz), 6.92 (1H, d, J=8.8 Hz), 7.23 (2H, t, J=8.8 Hz), 7.71 (2H, dd, J=8.8, 5.4 Hz), 7.85 (1H, dd, J=8.8, 2.0 Hz), 7.90 (1H, s), 8.04 (1H, d, J=7.0 Hz), 8.79 (1H, dd, J=7.3, 4.9 Hz), 10.92 (1H, s)

Example 162

4-{[(4-fluorobenzoyl)amino]methyl}-N-(4-fluorophenyl)-2-oxo-4-(trifluoromethyl)-1,4-dihydro-2H-3,1-benzoxazine-6-carboxamide The title compound was obtained by a method according to Example 159 using 4-{[(4-fluorobenzoyl)amino]methyl}-2-oxo-4-(trifluoromethyl)-1,4-dihydro-2H-3,1-benzoxazine-6-carboxylic acid and 4-fluoroaniline as raw materials.
$^1$H-NMR (400 MHz, DMSO-$d_6$) δ: 4.02 (1H, dd, J=14.6, 5.4 Hz), 4.55 (1H, dd, J=14.6, 7.3 Hz), 7.00 (1H, d, J=8.3 Hz), 7.18-7.24 (4H, m), 7.70-7.75 (4H, m), 7.98 (1H, dd, J=8.8, 2.0 Hz), 8.06 (1H, s), 8.80 (1H, dd, J=7.3, 5.4 Hz), 10.13 (1H, s), 11.02 (1H, s)

Example 163

N-(2,3-dihydro-1H-inden-2-yl)-4-{[(4-fluorobenzoyl)amino]methyl}-2-oxo-4-(trifluoromethyl)-1,4-dihydro-2H-3,1-benzoxazine-6-carboxamide The title compound was obtained by a method according to Example 159 using 4-{[(4-fluorobenzoyl)amino]methyl}-2-oxo-4-(trifluoromethyl)-1,4-dihydro-2H-3,1-benzoxazine-6-carboxylic acid and indan-2-amine as raw materials.
$^1$H-NMR (400 MHz, DMSO-$d_6$) δ: 2.94 (2H, ddd, J=16.1, 12.2, 6.3 Hz), 3.25 (2H, ddd, J=16.1, 7.9, 5.0 Hz), 4.00 (1H, dd, J=14.6, 4.9 Hz), 4.48 (1H, dd, J=14.6, 6.8 Hz), 4.64-4.72 (1H, m), 6.92 (1H, d, J=8.3 Hz), 7.14-7.25 (6H, m), 7.68 (2H, dd, J=8.8, 5.4 Hz), 7.87 (1H, dd, J=8.3, 2.0 Hz), 7.94 (1H, s), 8.45 (1H, d, J=7.3 Hz), 8.77 (1H, dd, J=6.8, 4.9 Hz), 10.94 (1H, s)

Example 164

N-(2,2-difluoroethyl)-4-{[(4-fluorobenzoyl)amino]methyl}-2-oxo-4-(trifluoromethyl)-1,4-dihydro-2H-3,1-benzoxazine-6-carboxamide The title compound was obtained by a method according to Example 159 using 4-{[(4-fluorobenzoyl)amino]methyl}-2-oxo-4-(trifluoromethyl)-1,4-dihydro-2H-3,1-benzoxazine-6-carboxylic acid and 2,2-difluoroethylamine as raw materials.
$^1$H-NMR (400 MHz, DMSO-$d_6$) δ: 3.62-3.71 (2H, m), 4.06 (1H, dd, J=14.6, 4.9 Hz), 4.43 (1H, dd, J=14.6, 6.8 Hz), 6.10 (1H, tt, J=56.1, 4.0 Hz), 6.96 (1H, d, J=8.8 Hz), 7.23 (2H, t, J=8.8 Hz), 7.72 (2H, dd, J=8.8, 5.4 Hz), 7.90 (1H, dd, J=8.8, 2.0 Hz), 7.99 (1H, s), 8.73-8.78 (2H, m), 10.99 (1H, s)

Example 165

4-{[(4-fluorobenzoyl)amino]methyl}-2-oxo-N-(2,2,2-trifluoroethyl)-4-(trifluoromethyl)-1,4-dihydro-2H-3,1-benzoxazine-6-carboxamide The title compound was obtained by a method according to Example 159 using 4-{[(4-fluorobenzoyl)amino]methyl}-2-oxo-4-(trifluoromethyl)-1,4-dihydro-2H-3,1-benzoxazine-6-carboxylic acid and 2,2,2-trifluoroethylamine as raw materials.
$^1$H-NMR (400 MHz, DMSO-$d_6$) δ: 4.02-4.16 (3H, m), 4.45 (1H, dd, J=14.1, 6.8 Hz), 6.97 (1H, d, J=8.3 Hz), 7.22 (2H, t, J=8.8 Hz), 7.72 (2H, dd, J=8.8, 5.4 Hz), 7.92 (1H, dd, J=8.3, 2.0 Hz), 8.01 (1H, s), 8.75 (1H, dd, J=6.8, 4.9 Hz), 8.99 (1H, t, J=6.1 Hz), 11.01 (1H, s)

Example 166

4-{[(4-fluorobenzoyl)amino]methyl}-2-oxo-N-((3R)-tetrahydrofuran-3-yl)-4-(trifluoromethyl)-1,4-dihydro-2H-3,1-benzoxazine-6-carboxamide The title compound was obtained by a method according to Example 159 using 4-{[(4-fluorobenzoyl)amino]methyl}-2- oxo-4-(trifluoromethyl)-1,4-dihydro-2H-3,1-benzoxazine-6-carboxylic acid and (3R)-tetrahydrofuran p-toluene sulfonate as raw materials.

$^1$H-NMR (400 MHz, DMSO-d$_6$) δ: 1.83-1.93 (1H, m), 2.10-2.20 (1H, m), 3.54-3.61 (1H, m), 3.67-3.73 (1H, m), 3.81-3.89 (2H, m), 4.02 (1H, dd, J=14.4, 4.9 Hz), 4.41-4.45 (1H, br m), 4.48 (1H, dd, J=14.4, 6.8 Hz), 6.93 (1H, d, J=8.3 Hz), 7.23 (2H, t, J=8.8 Hz), 7.70-7.74 (2H, m), 7.87 (1H, dd, J=8.3, 1.5 Hz), 7.94 (1H, s), 8.35 (1H, d, J=6.3 Hz), 8.77 (1H, dd, J=6.8, 4.9 Hz), 10.95 (1H, s)

Example 167

N-bicyclo[2.2.1]heptan-2-yl-4-{[(4-fluorobenzoyl)amino]methyl}-2-oxo-4-(trifluoromethyl)-1,4-dihydro-2H-3,1-benzoxazine-6-carboxamide The title compound was obtained by a method according to Example 159 using 4-{[(4-fluorobenzoyl)amino]methyl}-2-oxo-4-(trifluoromethyl)-1,4-dihydro-2H-3,1-benzoxazine-6-carboxylic acid and bicyclo[2.2.1]heptan-2-amine as raw materials.

$^1$H-NMR (400 MHz, DMSO-d$_6$) δ: 1.07-1.16 (1H, m), 1.23-1.64 (6H, m), 1.87-1.94 (1H, m), 2.16-2.19 (1H, br m), 2.37-2.41 (1H, br m), 3.93 (1H, td, J=14.1, 4.4 Hz), 4.02-4.09 (1H, br m), 4.57 (1H, td, J=14.9, 7.6 Hz), 6.93 (1H, dd, J=8.3, 2.4 Hz), 7.22 (2H, td, J=8.8, 3.4 Hz), 7.68-7.73 (2H, m), 7.83-7.91 (3H, m), 8.81-8.85 (1H, m), 10.93 (1H, s)

Example 168

N-{[6-cyano-2-oxo-4-(trifluoromethyl)-1,4-dihydro-2H-3,1-benzoxazin-4-yl]methyl}-4-fluorobenzamide The title compound was obtained by deprotecting N-{[6-cyano-1-(4-methoxybenzyl)-2-oxo-4-(trifluoromethyl)-1,4-dihydro-2H-3,1-benzoxazin-4-yl]methyl}-4-fluorobenzamide synthesized in Example 159 by a method according to Example 125.

$^1$H-NMR (400 MHz, DMSO-d$_6$) δ: 3.95 (1H, dd, J=14.6, 3.4 Hz), 4.57 (1H, dd, J=14.6, 6.8 Hz), 7.03 (1H, d, J=8.8 Hz), 7.26 (2H, t, J=8.8 Hz), 7.73 (2H, dd, J=8.8, 5.4 Hz), 7.85 (1H, dd, J=8.8, 1.5 Hz), 7.95 (1H, s), 8.77-8.80 (1H, m)

Example 169

4-fluoro-N-{[2-oxo-6-(5-oxo-4,5-dihydro-1,2,4-oxadiazol-3-yl)-4-(trifluoromethyl)-1,4-dihydro-2H-3,1-benzoxazin-4-yl]methyl}benzamide To a solution of N-{[6-cyano-2-oxo-4-(trifluoromethyl)-1,4-dihydro-2H-3,1-benzoxazin-4-yl]methyl}-4-fluorobenzamide (50 mg, 0.127 mmol) synthesized in Example 159 in ethanol (0.5 mL), hydroxylamine (50% aqueous solution, 40 μL) was added, and the solution was stirred overnight at room temperature. The solution was diluted with ethyl acetate, which was washed sequentially with water and saturated brine and then dried over magnesium sulfate. The residue was dissolved in dioxane (1 mL), and under stirring the solution at room temperature, CDI (41 mg, 0.25 mmol) was added thereto. After the reaction solution was stirred at 90° C. for 3 hours, the temperature of the solution was brought to room temperature. Then, the solution was diluted with ethyl acetate, which was washed sequentially with water, 1 N hydrochloric acid and saturated brine and then dried over magnesium sulfate. After the drying agent was removed by filtration, the residue was crystallized with ethanol and water, whereby the objective compound (18 mg, 31%) was obtained as a white solid.

$^1$H-NMR (400 MHz, DMSO-d$_6$) δ: 4.02 (1H, dd, J=14.6, 4.9 Hz), 4.44 (1H, dd, J=14.6, 6.8 Hz), 7.05 (1H, d, J=8.5 Hz), 7.23 (2H, t, J=8.8 Hz), 7.71 (2H, dd, J=8.8, 5.4 Hz), 7.82 (1H, dd, J=8.5, 2.0 Hz), 7.90 (1H, br s), 8.77 (1H, dd, J=6.8, 4.9 Hz), 11.12 (1H, s)

Example 170

4-fluoro-N-{[2-oxo-6-(1H-tetrazol-5-yl)-4-(trifluoromethyl)-1,4-dihydro-2H-3,1-benzoxazin-4-yl]methyl}benzamide N-{[6-cyano-2-oxo-4-(trifluoromethyl)-1,4-dihydro-2H-3,1-benzoxazin-4-yl]methyl}-4-fluorobenzamide (30 mg, 0.076 mmol) synthesized in Example 159, sodium azide (24.8 mg, 0.38 mmol) and ammonium chloride (20.4 mg, 0.38 mmol) were dissolved in DMF (0.5 mL), and the solution was stirred for 12 hours under heating at 110° C. Water was added to the solution and the solution was extracted twice with ethyl acetate-ethanol, and the resulting organic layer was dried over magnesium sulfate. After the drying agent was removed by filtration, the solvent was evaporated under reduced pressure. The residue was purified by reverse-phase HPLC, whereby the objective compound (3.4 mg, 10%) was obtained as a white solid.

$^1$H-NMR (400 MHz, DMSO-d$_6$) δ: 3.99-4.05 (1H, m), 4.52 (1H, dd, J=14.1, 7.3 Hz), 7.09 (1H, d, J=8.5 Hz), 7.20 (2H, t, J=8.8 Hz), 7.68 (2H, dd, J=8.8, 5.4 Hz), 8.04 (1H, dd, J=8.5, 1.5 Hz), 8.12 (1H, br s), 8.81 (1H, dd, J=7.3, 4.9 Hz), 11.08 (1H, s)

Example 171

4-fluoro-N-{[2-oxo-6-(1H-1,2,4-triazol-1-yl)-4-(trifluoromethyl)-1,4-dihydro-2H-3,1-benzoxazin-4-yl]methyl}benzamide 1) Synthesis of N-{[6-iodo-1-(4-methoxybenzyl)-2-oxo-4-(trifluoromethyl)-1,4-dihydro-2H-3,1-benzoxazin-4-yl]methyl}-4-fluorobenzamide To a solution of N-{[6-bromo-1-(4-methoxybenzyl)-2-oxo-4-(trifluoromethyl)-1,4-dihydro-2H-3,1-benzoxazin-4-yl]methyl}-4-fluorobenzamide (1.18 g, 2.08 mmol), copper iodide (I) (79 mg, 0.416 mmol) and sodium iodide (624 mg, 4.16 mmol) in dioxane (4.2 mL), N,N'-dimethylethylene diamine (89 μL, 0.832 mmol) was added at room temperature. The reaction solution was stirred for 5 hours under heating at 110° C. The temperature of the solution was brought to room temperature, and the solution was diluted with ethyl acetate, which was washed sequentially with a saturated aqueous ammonium chloride solution and saturated brine and then dried over magnesium sulfate. After the drying agent was removed by filtration, the solvent was evaporated under reduced pressure. The resulting solid was washed with hexane and ethyl acetate, whereby the objective compound (995 mg, 78%) was obtained as a white solid.

$^1$H-NMR (400 MHz, DMSO-d$_6$) δ: 3.68 (3H, s), 3.87 (1H, dd, J=14.6, 3.9 Hz), 4.61 (1H, dd, J=14.6, 7.8 Hz), 5.02 (1H, d, J=16.6 Hz), 5.10 (1H, d, J=16.6 Hz), 6.83 (2H, d, J=8.8 Hz), 6.87 (1H, d, J=8.8 Hz), 7.17 (2H, d, J=8.8 Hz), 7.25 (2H, t, J=8.8 Hz), 7.68 (1H, dd, J=8.8, 2.0 Hz), 7.72-7.77 (3H, m), 8.85 (1H, dd, J=7.8, 3.9 Hz)

2) Synthesis of 4-fluoro-N-{[2-oxo-6-(1H-1,2,4-triazol-1-yl)-4-(trifluoromethyl)-1,4-dihydro-2H-3,1-benzoxazin-4-yl]methyl}benzamide A solution of N-{[6-iodo-1-(4-methoxybenzyl)-2-oxo-4-(trifluoromethyl)-1,4-dihydro-2H-3,1-benzoxazin-4-yl]methyl}-4-fluorobenzamide (50 mg, 0.081 mmol), 1,2,4-triazole (16.9 mg, 0.244 mmol), potassium phosphate (25.9 mg, 0.122 mmol), N,N'-dimethylethylenediamine (6.9 μL, 0.065 mmol) and copper iodide (I) (3.1 mg, 0.016 mmol) in DMF (0.4 mL) was stirred for 1 hour under heating at 110° C. The temperature of the solution was brought to room temperature, and the solution was diluted with ethyl acetate, which was washed sequentially with a saturated aqueous ammonium chloride solution and saturated brine and then dried over magnesium sulfate. After the drying agent was removed by filtration, the solvent was evaporated under reduced pressure. The residue was subjected to the same condition as in Example 154 to effect deprotection of the 4-methoxybenzyl group, whereby the objective compound (8.0 mg, 23%) was obtained as a pale white solid.

$^1$H-NMR (400 MHz, DMSO-$d_6$) δ: 3.99 (1H, dd, J=14.6, 4.4 Hz), 4.59 (1H, dd, J=14.6, 6.8 Hz), 7.05 (1H, d, J=8.8 Hz), 7.21 (2H, t, J=8.8 Hz), 7.70 (2H, dd, J=8.8, 5.4 Hz), 7.85 (1H, dd, J=8.8, 2.4 Hz), 7.95 (1H, s), 8.23 (1H, s), 8.81 (1H, dd, J=6.8, 4.4 Hz), 9.18 (1H, s), 10.94 (1H, s)

Example 172

N-{[6-(benzoylamino)-2-oxo-4-(trifluoromethyl)-1,4-dihydro-2H-3,1-benzoxazin-4-yl]methyl}-4-fluorobenzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and benzamide as raw materials.

$^1$H-NMR (400 MHz, DMSO-$d_6$) δ: 4.00 (1H, dd, J=14.6, 4.9 Hz), 4.33 (1H, dd, J=14.6, 6.8 Hz), 6.89 (1H, d, J=8.3 Hz), 7.23 (2H, t, J=8.8 Hz), 7.50-7.54 (2H, m), 7.56-7.60 (1H, m), 7.75 (2H, dd, J=8.8, 5.4 Hz), 7.83 (1H, dd, J=8.8, 2.4 Hz), 7.86 (1H, s), 7.92-7.94 (2H, m), 8.76 (1H, dd, J=6.8, 4.9 Hz), 10.30 (1H, s), 10.65 (1H, s)

Example 173

4-fluoro-N-{[2-oxo-6-(2-oxo-1,3-oxazolidin-3-yl)-4-(trifluoromethyl)-1,4-dihydro-2H-3,1-benzoxazin-4-yl]methyl}benzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and 1,3-oxazolidin-2-one as raw materials.

$^1$H-NMR (400 MHz, DMSO-$d_6$) δ: 3.85 (1H, dd, J=14.6, 4.4 Hz), 3.95 (1H, q, J=8.3 Hz), 4.05 (1H, q, J=8.3 Hz), 4.42 (2H, t, J=8.3 Hz), 4.57 (1H, dd, J=14.6, 7.8 Hz), 6.92 (1H, d, J=8.8 Hz), 7.22 (2H, t, J=8.8 Hz), 7.45 (1H, d, J=2.4 Hz), 7.68 (1H, dd, J=8.8, 2.4 Hz), 7.74 (2H, dd, J=8.8, 5.9 Hz), 8.79 (1H, dd, J=7.8, 4.4 Hz), 10.68 (1H, s)

4-fluoro-N-{[(4S*)-2-oxo-6-(2-oxo-1,3-oxazolidin-3-yl)-4-(trifluoromethyl)-1,4-dihydro-2H-3,1-benzoxazin-4-yl]methyl}benzamide 4-Fluoro-N-{[2-oxo-6-(2-oxo-1,3-oxazolidin-3-yl)-4-(trifluoromethyl)-1,4-dihydro-2H-3,1-benzoxazin-4-yl]methyl}benzamide was subjected to optical resolution by HPLC (Chiralpack AD-H, n-hexane:ethanol=3:1), and a fraction eluted at a later time was concentrated, whereby the objective compound was obtained.

Example 174

4-fluoro-N-{[6-(3-methyl-2-oxazolidin-1-yl)-2-oxo-4-(trifluoromethyl)-1,4-dihydro-2H-3,1-benzoxazin-4-yl]methyl}benzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and 1-methylimidazolidin-2-one as raw materials.

$^1$H-NMR (400 MHz, DMSO-$d_6$) δ: 2.73 (3H, s), 3.41 (2H, t, J=8.3 Hz), 3.71 (2H, dt, J=12.7, 8.3 Hz), 3.84 (1H, dd, J=14.4, 4.1 Hz), 4.53 (1H, dd, J=14.6, 7.8 Hz), 6.85 (1H, d, J=8.8 Hz), 7.22 (2H, t, J=8.8 Hz), 7.40 (1H, s), 7.70-7.75 (3H, m), 8.77 (1H, dd, J=7.8, 4.1 Hz), 10.56 (1H, s)

Example 175

4-fluoro-N-{[2-oxo-6-(2-oxopyridin-1(2H)-yl)-4-(trifluoromethyl)-1,4-dihydro-2H-3,1-benzoxazin-4-yl]methyl}benzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and 2-hydroxypyridine as raw materials.

$^1$H-NMR (400 MHz, DMSO-$d_6$) δ: 3.86 (1H, dd, J=14.6, 4.4 Hz), 4.59 (1H, dd, J=14.6, 7.8 Hz), 6.34 (1H, td, J=6.8, 1.5 Hz), 6.47 (1H, dd, J=9.8, 1.5 Hz), 6.97 (1H, d, J=9.3 Hz), 7.24 (2H, t, J=8.8 Hz), 7.45-7.52 (4H, m), 7.74 (2H, dd, J=8.8, 5.4 Hz), 8.82 (1H, dd, J=7.8, 4.4 Hz), 10.90 (1H, s)

Example 176

4-fluoro-N-{[2-oxo-6-(1H-pyrazol-1-yl)-4-(trifluoromethyl)-1,4-dihydro-2H-3,1-benzoxazin-4-yl]methyl}benzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and pyrazole as raw materials.

$^1$H-NMR (400 MHz, DMSO-$d_6$) δ: 3.94 (1H, dd, J=14.4, 4.9 Hz), 4.63 (1H, dd, J=14.4, 7.3 Hz), 6.55 (1H, t, J=2.4 Hz), 7.00 (1H, d, J=8.8 Hz), 7.21 (2H, t, J=8.8 Hz), 7.69-7.73 (3H, m), 7.82-7.86 (2H, m), 8.39 (1H, d, J=2.4 Hz), 8.83 (1H, dd, J=7.3, 4.9 Hz), 10.84 (1H, s)

4-fluoro-N-{[(4S*)-2-oxo-6-(1H-pyrazol-1-yl)-4-(trifluoromethyl)-1,4-dihydro-2H-3,1-benzoxazin-4-yl]methyl}benzamide 4-Fluoro-N-{[2-oxo-6-(1H-pyrazol-1-yl)-4-(trifluoromethyl)-1,4-dihydro-2H-3,1-benzoxazin-4-yl]methyl}benzamide was subjected to optical resolution by HPLC (Chiralpack AD-H, n-hexane:ethanol=4:1), and a fraction eluted at a later time was concentrated, whereby the objective compound was obtained.

Example 177

4-fluoro-N-{[6-(4-methyl-1H-pyrazol-1-yl)-2-oxo-4-(trifluoromethyl)-1,4-dihydro-2H-3,1-benzoxazin-4-yl]methyl}benzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and 4-methylpyrazole as raw materials.
$^1$H-NMR (400 MHz, DMSO-$d_6$) δ: 2.09 (3H, d, J=6.3 Hz), 3.96 (1H, dd, J=14.6, 4.4 Hz), 4.62 (1H, dd, J=14.6, 6.8 Hz), 6.99 (1H, d, J=8.8 Hz), 7.23 (2H, t, J=8.8 Hz), 7.54 (1H, s), 7.72 (2H, dd, J=8.8, 5.4 Hz), 7.78-7.80 (2H, m), 8.18 (1H, s), 8.84 (1H, dd, J=6.8, 4.4 Hz), 10.83 (1H, s)

Example 178

4-fluoro-N-{[6-(3-methyl-1H-pyrazol-1-yl)-2-oxo-4-(trifluoromethyl)-1,4-dihydro-2H-3,1-benzoxazin-4-yl]methyl}benzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and 3-methylpyrazole as raw materials.
$^1$H-NMR (400 MHz, DMSO-$d_6$) δ: 2.26 (3H, s), 3.99 (1H, dd, J=14.6, 4.9 Hz), 4.62 (1H, dd, J=14.6, 7.3 Hz), 6.34 (1H, d, J=2.4 Hz), 6.98 (1H, d, J=8.8 Hz), 7.23 (2H, t, J=8.8 Hz), 7.73 (2H, dd, J=8.8, 5.4 Hz), 7.78-7.81 (2H, m), 8.26 (1H, d, J=2.4 Hz), 8.85 (1H, dd, J=7.3, 4.9 Hz), 10.82 (1H, s)

Example 179

N-{[6-(3-amino-1H-pyrazol-1-yl)-2-oxo-4-(trifluoromethyl)-1,4-dihydro-2H-3,1-benzoxazin-4-yl]methyl}-4-fluorobenzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and 3-aminopyrazole as raw materials.
$^1$H-NMR (400 MHz, DMSO-$d_6$) δ: 3.96 (1H, dd, J=14.6, 4.4 Hz), 4.56 (1H, dd, J=14.6, 7.3 Hz), 5.94 (1H, d, J=2.4 Hz), 6.95 (1H, d, J=8.3 Hz), 7.23 (2H, t, J=8.8 Hz), 7.67-7.75 (4H, m), 8.15 (1H, d, J=2.4 Hz), 8.85 (1H, dd, J=7.3, 4.4 Hz), 10.78 (1H, s)

Example 180

4-fluoro-N-{[2-oxo-4-(trifluoromethyl)-6-[3-(trifluoromethyl)-1H-pyrazol-1-yl]-1,4-dihydro-2H-3,1-benzoxazin-4-yl]methyl}benzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and 3-(trifluoromethyl) pyrazole as raw materials.
$^1$H-NMR (400 MHz, DMSO-$d_6$) δ: 3.99 (1H, dd, J=14.6, 4.4 Hz), 4.65 (1H, dd, J=14.6, 7.3 Hz), 7.06 (1H, d, J=8.8 Hz), 7.08 (1H, d, J=2.4 Hz), 7.23 (2H, t, J=8.8 Hz), 7.73 (2H, dd, J=8.8, 5.4 Hz), 7.89 (1H, dd, J=8.8, 2.4 Hz), 7.94 (1H, br s), 8.63 (1H, br s), 8.86 (1H, dd, J=7.3, 4.4 Hz), 10.97 (1H, s)

Example 181

4-fluoro-N-{[6-[(3S)-3-hydroxy-2-oxopyrrolidin-1-yl]-2-oxo-4-(trifluoromethyl)-1,4-dihydro-2H-3,1-benzoxazin-4-yl]methyl}benzamide The title compound was obtained by a method according to Example 171 using N-{[6-iodo-1-(4-methoxybenzyl)-2-oxo-4-(trifluoromethyl)-1,4-dihydro-2H-3,1-benzoxazin-4-yl]methyl}-4-fluorobenzamide and (3S)-3-hydroxypyrrolidin-2-one as raw materials.
$^1$H-NMR (400 MHz, DMSO-$d_6$) δ: 1.76-1.87 (1H, m), 2.35-2.44 (1H, m), 3.57-3.75 (1H, m), 3.86 (1H, td, J=14.1, 3.9 Hz), 4.25-4.31 (1H, m), 4.58 (1H, ddd, J=23.4, 14.1, 7.8 Hz), 5.76 (1H, br s), 6.92 (1H, d, J=8.8 Hz), 7.24 (2H, t, J=8.8 Hz), 7.46 (1H, s), 7.73-7.77 (3H, m), 8.78-8.83 (1H, m), 10.71 (1H, d, J=3.4 Hz)

Example 182

4-fluoro-N-{[2-oxo-6-(1H-pyrazol-5-yl)-4-(trifluoromethyl)-1,2,3,4-tetrahydroquinazolin-4-yl]methyl}benzamide 1) Synthesis of 6-bromo-4-hydroxy-1-(4-methoxybenzyl)-4-trifluoromethyl-3,4-dihydroquinazolin-2(1H)-one 1-{5-Bromo-2-[(4-methoxybenzyl)amino]phenyl}-2,2,2-trifluoroethanone (5.0 g, 12.9 mmol) was dissolved in a mixed solvent of acetic acid (20 mL) and water (2 mL), and under stirring the solution with heating at 60° C., sodium cyanate (85%, 2.96 g, 38.7 mmol) was added thereto. The reaction solution was stirred overnight under heating at 60° C., and then, the solution was cooled to room temperature and water (100 mL) was added thereto. After the solution was stirred at room temperature for 1 hour, the resulting solid was collected by filtration and washed with water. After the solid was dried, it was crystallized from ethyl acetate-hexane, whereby the objective compound (4.53 g, 81%) was obtained as a pale green solid.
$^1$H-NMR (400 MHz, CDCl$_3$) δ: 3.77 (3H, s), 4.92 (1H, d, J=17.1 Hz), 5.19 (1H, d, J=17.1 Hz), 6.00 (1H, s), 6.76 (1H, d, J=8.8 Hz), 6.84 (2H, d, J=8.8 Hz), 7.12 (2H, d, J=8.8 Hz), 7.42 (1H, dd, J=8.8, 2.4 Hz), 7.77 (1H, d, J=2.4 Hz)

2) Synthesis of 6-bromo-1-(4-methoxybenzyl)-4-(nitromethyl)-4-(trifluoromethyl)-3,4-dihydroquinazolin-2(1H)-one A mixture of 6-bromo-4-hydroxy-1-(4-methoxybenzyl)-4-trifluoromethyl-3,4-dihydroquinazolin-2(1H)-one (3.0 g, 6.96 mmol) and p-toluenesulfonic acid monohydrate (13.2 mg, 0.07 mmol) was stirred in xylene (30 mL) for 3 hours under heating at 150° C. After the solution was cooled to room temperature, nitromethane (1.88 mL, 35 mmol) and N,N-diisopropylethylamine (1.33 mL, 7.7 mmol) were added thereto, and the reaction solution was stirred for 1 hour under heating at 100° C. The reaction solution was cooled to 0° C., and hexane (20 mL) was gradually added thereto under stirring, and the resulting mixture was stirred at 0° C. for 2 hours. The resulting solid was collected by filtration and washed with hexane, whereby the objective compound (3.29 g, 99%) was obtained as a white solid.

$^1$H-NMR (400 MHz, CDCl$_3$) δ: 3.77 (3H, s), 4.90 (1H, d, J=13.2 Hz), 5.06 (1H, d, J=13.2 Hz), 5.10 (2H, br s), 6.77 (1H, d, J=8.8 Hz), 6.86 (2H, d, J=8.8 Hz), 7.06 (1H, s), 7.13 (2H, d, J=8.8 Hz), 7.39 (1H, dd, J=8.8, 2.0 Hz), 7.43 (1H, br s)

3) Synthesis of 4-(aminomethyl)-6-bromo-1-(4-methoxybenzyl)-4-(trifluoromethyl)-3,4-dihydroquinazolin-2(1H)-one 6-Bromo-1-(4-methoxybenzyl)-4-(nitromethyl)-4-(trifluoromethyl)-3,4-dihydroquinazolin-2(1H)-one (1.0 g, 2.1 mmol), iron (294 mg, 5.3 mmol) and ammonium chloride (562 mg, 10.5 mmol) were stirred in methanol (5 mL) and water (5 mL) and the resulting solution was heated overnight under reflux. After the reaction solution was cooled to room temperature, methanol (10 mL) was added thereto, and the mixture was stirred at room temperature for 1 hour. After the resulting solid was removed by filtration, the mother liquid was concentrated, and the residue was washed sequentially with water and saturated brine and then dried over magnesium sulfate. After the drying agent was removed by filtration, the solvent was evaporated under reduced pressure, whereby the objective compound (958 mg, quant.) was obtained as a colorless foamy solid.

$^1$H-NMR (400 MHz, DMSO-d$_6$) δ: 3.11 (1H, d, J=13.7 Hz), 3.42 (1H, d, J=13.7 Hz), 3.70 (3H, s), 4.90 (1H, d, J=16.1 Hz), 5.16 (1H, d, J=16.1 Hz), 6.85 (1H, d, J=8.8 Hz), 6.86 (2H, d, J=8.8 Hz), 7.16 (2H, d, J=8.8 Hz), 7.45 (1H, dd, J=8.8, 2.4 Hz), 7.57 (1H, s), 8.06 (1H, br s)

4) Synthesis of N-{[6-bromo-1-(4-methoxybenzyl)-2-oxo-4-(trifluoromethyl)-1,2,3,4-tetrahydroquinazolin-4-yl]methyl}-4-fluorobenzamide To a stirring solution of DMF (5 mL) containing 4-(aminomethyl)-6-bromo-1-(4-methoxybenzyl)-4-(trifluoromethyl)-3,4-dihydroquinazolin-2(1H)-one (710 mg, 1.60 mmol), 4-fluorobenzoic acid (246 mg, 1.76 mmol), hydroxybenzotriazole monohydrate (245 mg, 1.60 mmol) and triethylamine (0.22 mL, 1.6 mmol) at 0° C., 1-ethyl-3-(3-dimethylaminopropyl)carbodiimide hydrochloride (368 mg, 1.9 mmol) was added little by little thereto. After the reaction solution was stirred overnight at room temperature, water was slowly added thereto under stirring. After a solid began to precipitate, further excess water was added thereto, and the mixture was stirred at room temperature for 2 hours. The solid was collected by filtration and washed with water and then dried under reduced pressure, whereby the objective compound (815 mg, 90%) was obtained as a white solid.

$^1$H-NMR (400 MHz, DMSO-d$_6$) δ: 3.70 (3H, s), 3.87 (1H, dd, J=14.1, 3.9 Hz), 4.43 (1H, dd, J=14.1, 6.8 Hz), 4.92 (1H, d, J=16.6 Hz), 5.16 (1H, d, J=16.6 Hz), 6.83 (2H, d, J=8.8 Hz), 6.84 (1H, d, J=8.8 Hz), 7.14 (2H, d, J=8.8 Hz), 7.27 (2H, t, J=9.3 Hz), 7.44 (1H, dd, J=8.8, 2.4 Hz), 7.56 (1H, br s), 7.76 (1H, d, J=8.8 Hz), 7.77 (1H, d, J=8.8 Hz), 8.13 (1H, s), 8.64 (1H, dd, J=6.8, 3.9 Hz)

5) Synthesis of N-{[6-bromo-2-oxo-4-(trifluoromethyl)-1,2,3,4-tetrahydroquinazolin-4-yl]methyl}-4-fluorobenzamide To a stirring solution of N-{[6-bromo-1-(4-methoxybenzyl)-2-oxo-4-(trifluoromethyl)-1,2,3,4-tetrahydroquinazolin-4-yl]methyl}-4-fluorobenzamide (260 mg, 0.46 mmol) in acetonitrile (6 mL), an aqueous solution (1 mL) of cerium ammonium nitrate (755 mg, 1.38 mmol) was added dropwise at room temperature. The reaction solution was stirred at room temperature for 4 hours. Sodium pyrosulfite was added to the reaction solution, and the solution was stirred for 30 minutes, and then diluted with ethyl acetate and the organic layer was separated. The organic layer was washed sequentially with water and saturated brine and then dried over magnesium sulfate. After the drying agent was removed by filtration, the solvent was evaporated under reduced pressure. The residue was purified by silica gel column chromatography (ethyl acetate/hexane=2/1), whereby the objective compound (150 mg, 73%) was obtained as a white solid.

$^1$H-NMR (400 MHz, CD$_3$OD) δ: 3.88 (1H, d, J=14.4 Hz), 4.43 (1H, d, J=14.4 Hz), 6.80 (1H, d, J=8.7 Hz), 7.08-7.15 (2H, m), 7.44 (1H, dd, J=8.7, 2.1 Hz), 7.61 (1H, br s), 7.65-7.71 (2H, m)

6) Synthesis of 4-fluoro-N-{[2-oxo-6-(1H-pyrazol-5-yl)-4-(trifluoromethyl)-1,2,3,4-tetrahydroquinazolin-4-yl]methyl}benzamide N-{[6-bromo-2-oxo-4-(trifluoromethyl)-1,2,3,4-tetrahydroquinazolin-4-yl]methyl}-4-fluorobenzamide (50 mg, 0.112 mmol), 1H-pyrazol-5-boronic acid (29 mg, 0.23 mmol), a palladium chloride-1,1-bis(diphenylphosphino)ferrocene complex (18.3 mg, 0.022 mmol) and potassium phosphate trihydrate (60 mg, 0.23 mmol) were suspended in DMF (0.5 mL) and water (0.05 mL), and the mixed solution was stirred at 120° C. for 30 minutes under microwave irradiation. After the reaction solution was left to cool, the solution was diluted with ethyl acetate and the organic layer was separated. The organic layer was washed with water and saturated brine and then dried over magnesium sulfate. After the drying agent was removed by filtration, the solvent was evaporated under reduced pressure. The residue was purified by reverse-phase HPLC, whereby the objective compound (10 mg, 21%) was obtained as a pale yellow solid.

$^1$H-NMR (400 MHz, DMSO-d$_6$) δ: 3.97 (1H, d, J=13.7 Hz), 4.36 (1H, dd, J=13.7, 6.3 Hz), 6.60 (1H, d, J=2.4 Hz), 6.88 (1H, d, J=8.3 Hz), 7.22 (2H, t, J=8.8 Hz), 7.76-7.62 (6H, m), 8.58-8.60 (1H, br m), 9.71 (1H, s)

4-fluoro-N-{[(4S*)-2-oxo-6-(1H-pyrazol-5-yl)-4-(trifluoromethyl)-1,2,3,4-tetrahydroquinazolin-4-yl]methyl}benzamide 4-Fluoro-N-{[2-oxo-6-(1H-pyrazol-5-yl)-4-(trifluoromethyl)-1,2,3,4-tetrahydroquinazolin-4-yl]methyl}benzamide was subjected to optical resolution by HPLC (Chiralpack AD-H, n-hexane:2-propanol=3:1), and a fraction eluted at a later time was concentrated, whereby the objective compound was obtained.

Example 183

N-{[6-chloro-2-oxo-4-(trifluoromethyl)-1,2,3,4-tetrahydroquinazolin-4-yl]methyl}benzamide The title compound was obtained by a method according to Example 182 using 1-(2-amino-5-chlorophenyl)-2,2,2-trifluoroethanone and benzoic acid as raw materials.

$^1$H-NMR (400 MHz, DMSO-d$_6$) δ: 3.82 (1H, dd, J=14.1, 4.4 Hz), 4.35 (1H, dd, J=14.1, 7.3 Hz), 6.85 (1H, d, J=8.8 Hz), 7.33 (1H, dd, J=8.8, 2.4 Hz), 7.39-7.42 (4H, m), 7.47-7.51 (1H, m), 7.64-7.66 (3H, m), 8.55 (1H, dd, J=7.3, 4.4 Hz), 9.78 (1H, s)

Example 184

2-chloro-N-{[6-chloro-2-oxo-4-(trifluoromethyl)-1,2,3,4-tetrahydroquinazolin-4-yl]methyl}benzamide The title compound was obtained by a method according to Example 182 using 1-(2-amino-5-chlorophenyl)-2,2,2-trifluoroethanone and 2-chlorobenzoic acid as raw materials.

$^1$H-NMR (400 MHz, DMSO-d$_6$) δ: 3.62 (1H, dd, J=14.1, 2.4 Hz), 4.45 (1H, dd, J=14.1, 8.3 Hz), 6.85 (1H, d, J=8.3 Hz), 7.05 (1H, dd, J=6.8, 1.5 Hz), 7.27-7.35 (3H, m), 7.35-7.39 (2H, m), 7.77 (1H, s), 8.81 (1H, dd, J=8.3, 2.4 Hz), 9.75 (1H, s)

Example 185

3-chloro-N-{[6-chloro-2-oxo-4-(trifluoromethyl)-1,2,3,4-tetrahydroquinazolin-4-yl]methyl}benzamide The title compound was obtained by a method according to Example 182 using 1-(2-amino-5-chlorophenyl)-2,2,2-trifluoroethanone and 3-chlorobenzoic acid as raw materials.

$^1$H-NMR (400 MHz, DMSO-d$_6$) δ: 3.83 (1H, dd, J=14.1, 4.4 Hz), 4.34 (1H, dd, J=14.1, 7.3 Hz), 6.85 (1H, d, J=8.8 Hz), 7.34 (1H, dd, J=8.5, 2.2 Hz), 7.36 (1H, br s), 7.45 (1H, t, J=7.8 Hz), 7.56-7.58 (1H, m), 7.60-7.63 (1H, m), 7.67 (1H, t, J=1.7 Hz), 7.70 (1H, d, J=2.0 Hz), 8.69 (1H, dd, J=7.3, 4.4 Hz), 9.79 (1H, s)

Example 186

4-chloro-N-{[6-chloro-2-oxo-4-(trifluoromethyl)-1,2,3,4-tetrahydroquinazolin-4-yl]methyl}benzamide The title compound was obtained by a method according to Example 182 using 1-(2-amino-5-chlorophenyl)-2,2,2-trifluoroethanone and 4-chlorobenzoic acid as raw materials.

$^1$H-NMR (400 MHz, DMSO-d$_6$) δ: 3.82 (1H, dd, J=14.1, 3.9 Hz), 4.34 (1H, dd, J=14.1, 6.8 Hz), 6.85 (1H, d, J=8.8 Hz), 7.33 (1H, dd, J=8.8, 2.2 Hz), 7.37 (1H, br s), 7.49 (2H, d, J=8.3 Hz), 7.68 (2H, d, J=8.3 Hz), 7.68 (1H, br s), 8.64 (1H, br s), 9.78 (1H, s)

Example 187

N-{[6-chloro-2-oxo-4-(trifluoromethyl)-1,2,3,4-tetrahydroquinazolin-4-yl]methyl}4-fluorobenzamide The title compound was obtained by a method according to Example 182 using 1-(2-amino-5-chlorophenyl)-2,2,2-trifluoroethanone and 4-fluorobenzoic acid as raw materials.

$^1$H-NMR (400 MHz, DMSO-d$_6$) δ: 3.84 (1H, d, J=14.6 Hz), 4.34 (1H, d, J=14.6 Hz), 6.86 (1H, d, J=8.8 Hz), 7.26 (2H, t, J=8.8 Hz), 7.34 (1H, dd, J=8.8, 2.0 Hz), 7.39 (1H, s), 7.69 (1H, br s), 7.75 (2H, dd, J=8.8, 5.4 Hz), 8.58-8.62 (1H, m), 9.79 (1H, s).

$^1$H-NMR (DMSO-D$_6$) δ: 9.79 (1H, s), 8.62-8.58 (1H,

N-{[(4S*)-6-chloro-2-oxo-4-(trifluoromethyl)-1,2,3,4-tetrahydroquinazolin-4-yl]methyl}4-fluorobenzamide N-{[6-chloro-2-oxo-4-(trifluoromethyl)-1,2,3,4-tetrahydroquinazolin-4-yl]methyl}4-fluorobenzamide was subjected to optical resolution by HPLC (Chiralpack AD-H, n-hexane: 2-propanol=3:1), and a fraction eluted at a later time was concentrated, whereby the objective compound was obtained.

Example 188

4-fluoro-N-{[2-oxo-4-(trifluoromethyl)-1,2,3,4-tetrahydroquinazolin-4-yl]methyl}benzamide The title compound was obtained by a method according to Example 182 using 1-(2-aminophenyl)-2,2,2-trifluoroethanone and 4-fluorobenzoic acid as raw materials.

$^1$H-NMR (400 MHz, DMSO-d$_6$) δ: 3.91 (1H, d, J=14.1 Hz), 4.29 (1H, d, J=14.1 Hz), 6.86 (1H, d, J=8.3 Hz), 6.93 (1H, t, J=7.8 Hz), 7.23-7.28 (3H, m), 7.33 (1H, d, J=7.8 Hz), 7.58 (1H, br s), 7.75 (2H, dd, J=8.8, 5.4 Hz), 8.49-8.52 (1H, br m), 9.64 (1H, br s)

Example 189

N-{[6-chloro-2-oxo-4-(trifluoromethyl)-1,2,3,4-tetrahydroquinazolin-4-yl]methyl}4-fluorobenzenesulfonamide The title compound was obtained by a method according to Example 99 and Example 182 using 1-(2-amino-5-chlorophenyl)-2,2,2-trifluoroethanone and (4-fluorophenyl)sulfonyl chloride as raw materials.

$^1$H-NMR (400 MHz, DMSO-d$_6$) δ: 3.35 (1H, d, J=13.2 Hz), 3.72 (1H, d, J=13.2 Hz), 6.86 (1H, d, J=8.3 Hz), 7.19 (1H, br s), 7.34-7.43 (3H, m), 7.66 (1H, br s), 7.85 (2H, dd, J=8.8, 5.4 Hz), 8.02 (1H, br s), 9.77 (1H, br s)

Example 190

4-fluoro-N-{[2-oxo-6-(1H-pyrazol-4-yl)-4-(trifluoromethyl)-1,2,3,4-tetrahydroquinazolin-4-yl]methyl}benzamide The title compound was obtained by a method according to Example 182 using 1-(2-amino-5-chlorophenyl)-2,2,2-trifluoroethanone and 4-(4,4,5,5-tetramethyl-1,3,2-dioxaborolan-2-yl)-1H-pyrazole as raw materials.

$^1$H-NMR (400 MHz, DMSO-d$_6$) δ: 3.86 (1H, dd, J=13.9, 3.9 Hz), 4.48 (1H, dd, J=13.9, 7.8 Hz), 6.82 (1H, d, J=8.3 Hz), 7.21 (2H, t, J=8.8 Hz), 7.46 (1H, dd, J=8.3, 2.0 Hz), 7.53 (2H, d, J=2.4 Hz), 7.72 (2H, dd, J=8.8, 5.4 Hz), 7.80 (1H, br s), 8.02 (1H, br s), 8.57 (1H, dd, J=7.8, 3.9 Hz), 9.60 (1H, s), 12.86 (1H, s)

Example 191

N-{[6-bromo-3-methyl-2-oxo-4-(trifluoromethyl)-1,2,3,4-tetrahydroquinazolin-4-yl]methyl}4-fluorobenzamide 1) 6-bromo-1-(4-methoxybenzyl)-3-methyl-4-(nitromethyl)-4-(trifluoromethyl)-3,4-dihydroquinazolin-2(1H)-one 6-Bromo-1-(4-methoxybenzyl)-4-(nitromethyl)-4-(trifluoromethyl)-3,4-dihydroquinazolin-2(1H)-one (192.1 mg, 0.405 mmol) was dissolved in DMF (2.0 mL), and sodium hydride (40.5 mg, 1.013 mmol) and methyl iodide (76 μL, 215 mmol) were sequentially added to the reaction solution at room temperature. The reaction solution was stirred overnight at 50° C. and then cooled to room temperature. Ethyl acetate and water were added thereto and the solution was stirred at room temperature for 10 minutes. The organic layer was separated and washed with saturated brine and then dried over magnesium sulfate. After the drying agent was removed by filtration, the solvent was evaporated under reduced pressure. The residue was purified by thin-layer chromatography (ethyl acetate/hexane), whereby the objective 6-bromo-1-(4-methoxybenzyl)-3-methyl-4-(nitromethyl)-4-(trifluoromethyl)-3,4-dihydroquinazolin-2(1H)-one (44.3 mg, 22.4%) was obtained as a white solid.

$^1$H-NMR (400 MHz, CDCl$_3$) δ: 3.36 (3H, s), 3.77 (3H, s), 5.12 (2H, s), 5.28 (1H, d, J=14.6 Hz), 5.39 (1H, d, J=14.6 Hz), 6.73 (1H, d, J=9.0 Hz), 6.85 (2H, d, J=8.8 Hz), 7.11 (2H, d, J=8.8 Hz), 7.37 (1H, dd, J=9.0, 2.1 Hz), 7.45 (1H, br s)

2) 4-(aminomethyl)-6-bromo-1-(4-methoxybenzyl)-3-methyl-4-(trifluoromethyl)-3,4-dihydroquinazolin-2(1H)-one 6-Bromo-1-(4-methoxybenzyl)-3-methyl-4-(nitromethyl)-4-(trifluoromethyl)-3,4-dihydroquinazolin-2(1H)-one (217.3 mg, 0.445 mmol) was dissolved in THF (0.9 mL), methanol (0.9 mL) and water (0.5 mL), and iron (497 mg, 8.9 mmol) and ammonium chloride (476 mg, 8.9 mmol) were sequentially added to the reaction solution at room temperature. The reaction solution was stirred at 90° C. for 2.5 hours and then cooled to room temperature and insoluble substances were removed by Celite filtration. After the solvent was evaporated under reduced pressure, to the residue, chloroform and saturated sodium hydrogen carbonate were added, and the mixture was stirred at room temperature. The organic layer was separated and washed with saturated brine and then dried over magnesium sulfate. After the drying agent was removed by filtration, the solvent was evaporated under reduced pressure. The residue was purified by silica gel column chromatography (chloroform/methanol=1/4), whereby the objective 4-(aminomethyl)-6-bromo-1-(4-methoxybenzyl)-3-methyl-4-(trifluoromethyl)-3,4-dihydroquinazolin-2(1H)-one (148.3 mg, 72.7%) was obtained as a white solid.

3) Synthesis of N-{[6-bromo-1-(4-methoxybenzyl)-3-methyl-2-oxo-4-(trifluoromethyl)-1,2,3,4-tetrahydroquinazolin-4-yl]methyl}4-fluorobenzamide 4-(Aminomethyl)-6-bromo-1-(4-methoxybenzyl)-3-methyl-4-(trifluoromethyl)-3,4-dihydroquinazolin-2(1H)-one (36.8 mg, 0.080 mmol) was dissolved in DMF (1.0 mL), and 4-fluorobenzoic acid (28.1 mg, 0.201 mmol), 1-(3-dimethylaminopropyl)-3-ethylcarbodiimide hydrochloride (46.2 mg, 0.241 mmol), 1-hydroxybenzotriazole monohydride (36.9 mg, 0.241 mmol) and pyridine (0.032 mL, 0.402 mmol) were sequentially added to the reaction solution at room temperature. After the reaction solution was stirred overnight at room temperature, chloroform and water were added thereto and the mixture was stirred at room temperature. The organic layer was separated and washed with saturated brine and then dried over magnesium sulfate. After the drying agent was removed by filtration, the solvent was evaporated under reduced pressure. The residue was purified by thin-layer chromatography (chloroform/methanol=1/10), whereby the objective N-{[6-bromo-1-(4-methoxybenzyl)-3-methyl-2-oxo-4-(trifluoromethyl)-1,2,3,4-tetrahydroquinazolin-4-yl]methyl}4-fluorobenzamide (33.9 mg, 73%) was obtained as a white solid.

$^1$H-NMR (400 MHz, CDCl$_3$) δ: 3.28 (3H, d, J=1.0 Hz), 3.77 (3H, s), 4.35 (1H, dd, J=15.1, 4.9 Hz), 4.57 (1H, dd, J=15.1, 5.9 Hz), 4.99 (1H, d, J=16.6 Hz), 5.24 (1H, d, J=16.6 Hz), 5.77 (1H, br s), 6.84-6.78 (3H, m), 7.06-7.10 (2H, m), 7.14 (2H, d, J=8.8 Hz), 7.39 (1H, dd, J=8.8, 2.0 Hz), 7.52 (1H, s), 7.56-7.61 (2H, m)

4) Synthesis of N-{[6-bromo-3-methyl-2-oxo-4-(trifluoromethyl)-1,2,3,4-tetrahydroquinazolin-4-yl]methyl}4-fluorobenzamide N-{[6-bromo-1-(4-methoxybenzyl)-3-methyl-2-oxo-4-(trifluoromethyl)-1,2,3,4-tetrahydroquinazolin-4-yl]methyl}4-fluorobenzamide (9.6 mg, 0.017 mmol) was dissolved in acetonitrile (1.0 mL) and water (0.25 mL), and cerium ammonium nitrate (27.2 mg, 0.050 mmol) was added to the reaction solution under ice-cooling. After the reaction solution was stirred at room temperature for 4 hours, chloroform and water were added thereto and the solution was stirred at room temperature. The organic layer was separated and washed with saturated brine and then dried over magnesium sulfate. After the drying agent was removed by filtration, the solvent was evaporated under reduced pressure. The residue was purified by thin-layer chromatography (chloroform/methanol=1/4), whereby the objective N-{[6-bromo-3-methyl-2-oxo-4-(trifluoromethyl)-1,2,3,4-tetrahydroquinazolin-4-yl]methyl}4-fluorobenzamide (4.0 mg, 53%) was obtained as a white solid.

$^1$H-NMR (400 MHz, CD$_3$OD) δ: 3.88 (1H, d, J=14.4 Hz), 4.43 (1H, d, J=14.4 Hz), 6.80 (1H, d, J=8.5 Hz), 7.08-7.15 (2H, m), 7.44 (1H, dd, J=8.5, 2.1 Hz), 7.61 (1H, br s), 7.65-7.71 (2H, m)

Reference Example 1

[1-(tetrahydro-2H-pyran-2-yl)-1H-pyrazol-5-yl]boronic acid 1-(tetrahydropyran-2-yl)-1H-pyrazole A mixture of pyrazole (14.3 g, 0.21 mmol), 3,4-dihydro-2H-pyrane (29 mL, 0.32 mmol) and trifluoroacetic acid (0.1 mL, 0.0013 mmol) was heated under reflux for 5 hours. After the mixture was cooled to room temperature, sodium hydride (60%, 0.2 g, 0.008 mmol) was added thereto, and the mixture was stirred for 10 minutes. The reaction mixture was subjected to distillation under reduced pressure (60-65° C., 0.5-1 mmHg), whereby 1-(tetrahydropyran-2-yl)-1H-pyrazole (30.8 g, 96%) was obtained. To a stirred solution of the obtained 1-(tetrahydropyran-2-yl)-1H-pyrazole (30 g, 197 mmol) in THF (197 mL), n-butyl lithium (2.6 M hexane solution, 79 mL) was added at −78° C., and the reaction solution was stirred at −78° C. for 30 minutes. To the reaction solution, triisopropyl borate (50.0 mL, 217 mmol) was added at −78° C., and the solution was stirred for 1 hour. To the reaction solution, 2 N hydrochloric acid (200 mL) was added, and the solution was stirred at room temperature for 30 minutes. The solution was extracted three times with chloroform-ethanol. The extracted organic layer was washed sequentially with water and saturated brine and then dried over magnesium sulfate. After the drying agent was removed by filtration, the solvent was evaporated under reduced pressure. The residue was crystallized from ethyl acetate-hexane, whereby the objective compound (16.0 g, 41.4%) was obtained as a colorless solid.

$^1$H-NMR (400 MHz, DMSO-d$_6$) δ: 1.46-1.52 (2H, m), 1.54-1.66 (1H, m), 1.80 (1H, dq, J=13.2, 2.9 Hz), 1.92-1.98 (1H, m), 2.21-2.31 (1H, m), 3.49-3.55 (1H, m), 3.85-3.90 (1H, m), 5.92 (1H, dd, J=10.2, 2.4 Hz), 6.72 (1H, d, J=1.5 Hz), 7.50 (1H, d, J=1.5 Hz)

Reference Example 2

4-allyl-6-chloro-4-(trifluoromethyl)-1,4-dihydro-2H-3,1-benzoxazin-2-one

The title compound was obtained by a method according to Example 1 using 1-(2-amino-5-chlorophenyl)-2,2,2-trifluoroethanone and allyl magnesium bromide as raw materials.

$^1$H-NMR (400 MHz, CDCl$_3$) δ: 2.99 (2H, m), 5.17-5.31 (2H, m), 5.53-5.64 (1H, m), 6.85 (1H, d, J=8.8 Hz), 7.23 (1H, br s), 7.33 (1H, dd, J=8.8, 2.2 Hz), 9.31 (1H, s)

Reference Example 3

6-chloro-4-(3-hydroxypropyl)-4-(trifluoromethyl)-1,4-dihydro-2H-3,1-benzoxazin-2-one 4-Allyl-6-chloro-4-(trifluoromethyl)-1,4-dihydro-2H-3,1-benzoxazin-2-one (2.55 g, 8.74 mmol) obtained in Reference example 2 was dissolved in THF (30 mL), and while stirring the reaction solution, 9-BBN (0.5 M-THF, 52 mL) was added dropwise thereto at room temperature. The reaction solution was stirred overnight at room temperature, followed by ice-cooling, and a 2 N aqueous sodium hydroxide solution and a 30% aqueous hydrogen peroxide solution were added dropwise thereto under ice-cooling. The reaction solution was stirred at room temperature for 30 minutes. After a saturated aqueous sodium thiosulfate solution was added to the reaction solution, a 10% aqueous citric acid solution was added thereto to neutralize the reaction solution and the pH thereof was adjusted to 4. The reaction solution was diluted with ethyl acetate to effect extraction. The organic layer was separated and washed with water and saturated brine and then dried over sodium sulfate. After the drying agent was removed by filtration, the solvent was evaporated under reduced pressure. The resulting residue was purified by silica gel column chromatography (ethyl acetate/hexane=1/1), whereby 6-chloro-4-(3-hydroxypropyl)-4-(trifluoromethyl)-1,4-dihydro-2H-3,1-benzoxazin-2-one (2.56 mg, 94.5%) was obtained as a colorless solid.

$^1$H-NMR (400 MHz, DMSO-d$_6$) δ: 1.17-1.28 (2H, m), 1.38-1.50 (2H, m), 3.40-3.43 (2H, m), 6.97 (1H, d, J=8.8 Hz), 7.49 (1H, dd, J=8.8, 2.0 Hz), 7.56 (1H, d, J=2.0 Hz), 10.84 (1H, s).

Reference Example 4

4-(2-aminoethyl)-6-chloro-4-(trifluoromethyl)-1,4-dihydro-2H-3,1-benzoxazin-2-one The title compound was obtained by a method according to Example 27 using 1-(2-amino-5-chlorophenyl)-2,2,2-trifluoroethanone and allyl magnesium bromide as raw materials.

$^1$H-NMR (400 MHz, DMSO-d$_6$) δ: 2.09-2.17 (1H, m), 2.30-2.39 (1H, m), 2.51-2.57 (2H, m), 6.94 (1H, d, J=8.8 Hz), 7.47 (1H, dd, J=8.8, 2.4 Hz), 7.57 (1H, br s)

Reference Example 5

4-(2-aminopropyl)-6-chloro-4-(trifluoromethyl)-1,4-dihydro-2H-3,1-benzoxazin-2-one The title compound was obtained by a method according to Example 27 using 1-(2-amino-5-chlorophenyl)-2,2,2-trifluoroethanone and allyl magnesium bromide as raw materials.

$^1$H-NMR (400 MHz, DMSO-d$_6$) δ: 1.05-1.20 (1H, m), 1.27-1.41 (1H, m), 1.99-2.09 (1H, m), 2.42-2.56 (3H, m), 6.95 (1H, d, J=8.8 Hz), 7.47 (1H, dd, J=8.8, 2.4 Hz), 7.57 (1H, br s)

Reference Example 6

[3-phenyl-1-(tetrahydro-2H-pyran-2-yl)-1H-pyrazol-5-yl]boronic acid

The title compound was obtained by a method according to Reference example 1 using 3-phenylpyrazole as a raw material.

$^1$H-NMR (DMSO-d$_6$) δ: 8.47 (1H, br s), 7.76 (2H, d, J=7.8 Hz), 7.40 (2H, t, J=7.8 Hz), 7.29 (1H, t, J=7.8 Hz), 7.10 (1H, s), 5.94 (1H, dd, J=9.8, 2.4 Hz), 3.91 (1H, d, J=11.2 Hz), 3.58-3.52 (1H, m), 2.40-2.30 (1H, m), 2.02-1.98 (1H, m), 1.90-1.85 (1H, m), 1.68-1.50 (3H, m), 1.31-1.19 (1H, m)

INDUSTRIAL APPLICABILITY

The compounds according to the invention have an excellent LCE inhibitory effect and are useful as a treatment agent for various diseases related to LCE such as cardiovascular diseases, nervous system diseases, metabolic diseases, reproductive system diseases and gastrointestinal system diseases.

The invention claimed is:
1. A compound represented by the formula (I) or a pharmaceutically acceptable salt thereof:

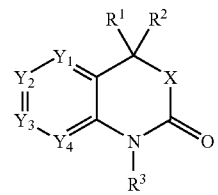

wherein R$^1$ represents optionally halogenated C$_{1-6}$ alkyl or optionally halogenated C$_{3-8}$ cycloalkyl;
R$^2$ represents a substituent selected from a group consisting of the following groups:

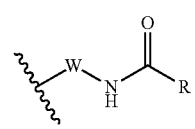
(II-1)

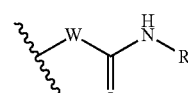
(II-2)

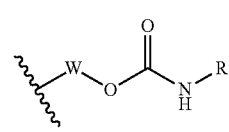
(II-3)

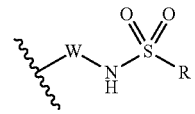
(II-4)

-continued

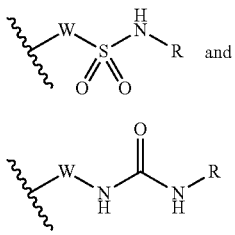

(II-5)

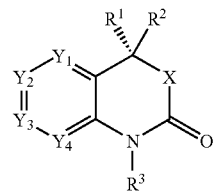

(II-6)

wherein W represents $C_{1-6}$ alkylene, $C_{2-6}$ alkenylene, $C_{2-6}$ alkynylene or $C_{3-6}$ cycloalkylene, wherein the alkylene, alkenylene, alkynylene or cycloalkylene may be substituted by optionally halogenated $C_{1-3}$ alkyl, optionally halogenated $C_{1-3}$ alkyloxy, hydroxyl or halogen;

R represents $C_{1-6}$ alkyl, $C_{3-8}$ cycloalkyl, aryl or heteroaryl, wherein the $C_{1-6}$ alkyl, $C_{3-8}$ cycloalkyl, aryl or heteroaryl may be substituted by halogen, optionally halogenated $C_{1-6}$ alkyl, optionally halogenated $C_{1-6}$ alkyloxy, $C_{1-6}$ alkylsulfonyl, cyano, phenyl, $C_{1-6}$ alkylthio, hydroxyl, amino, $C_{1-6}$ alkylamino, di-$C_{1-6}$ alkylamino, hydroxy-$C_{1-6}$ alkyl, amino-$C_{1-6}$ alkyl, $C_{1-6}$ alkylamino-$C_{1-6}$ alkyl, di-$C_{1-6}$ alkylaminoalkyl, $C_{1-6}$ alkoxy-$C_{1-6}$ alkyl, $C_{1-6}$ alkylcarbonyl, $C_{1-6}$ alkylcarbonylamino, $C_{1-6}$ alkylcarbamoyl, $C_{3-8}$ cycloalkylcarbamoyl, $C_{1-6}$ alkylsulfonylamino or $C_{1-6}$ alkylaminosulfonyl;

$R^3$ represents a hydrogen atom, $C_{1-6}$ alkyl, aryl or heteroaryl;

X represents —O—, —C($R^{4a}$)($R^{4b}$)— or —N$R^5$—;

$R^{4a}$, $R^{4b}$ and $R^5$ each independently represent hydrogen, $C_{1-6}$ alkyl, $C_{3-8}$ cycloalkyl, aryl or heteroaryl, wherein the $C_{1-6}$ alkyl, $C_{3-8}$ cycloalkyl, aryl or heteroaryl may be substituted by halogen, optionally halogenated $C_{1-6}$ alkyl, optionally halogenated $C_{1-6}$ alkyloxy, $C_{1-6}$ alkylsulfonyl, cyano, aryl or heteroaryl;

$Y_1$ represents —C$R^6$— or —N—;

$Y_2$ represents —C$R^7$— or —N—;

$Y_3$ represents —C$R^8$— or —N—;

$Y_4$ represents —C$R^9$— or —N—;

$R^6$, $R^7$, $R^8$ and $R^9$ each independently represent a hydrogen atom, halogen, cyano, $C_{1-6}$ alkyl, $C_{3-8}$ cycloalkyl, $C_{1-6}$ alkoxy, hydroxyl, hydroxy-$C_{1-6}$ alkyl, amino, $C_{1-6}$ alkylamino, di-$C_{1-6}$ alkylamino, amino-$C_{1-6}$ alkyl, $C_{1-6}$ alkylamino-$C_{1-6}$ alkyl, di-$C_{1-6}$ alkylamino-($C_{1-6}$)alkyl, $C_{1-6}$ alkoxy-$C_{1-6}$ alkyl, heterocyclyl, aryl, heteroaryl, $C_{1-6}$ alkylsulfonyl, $C_{1-6}$ alkylsulfinyl, $C_{1-6}$ alkylthio, arylsulfonyl, heteroarylsulfonyl, arylsulfinyl, heteroarylsulfinyl, arylthio, heteroarylthio, $C_{1-6}$ alkylcarbonyl, arylcarbonyl, heteroarylcarbonyl, $C_{1-6}$ alkylcarbonylamino, arylcarbonylamino, heteroarylcarbonylamino, $C_{1-6}$ alkylcarbamoyl, $C_{3-8}$ cycloalkylcarbamoyl, heterocyclylcarbamoyl, arylcarbamoyl, heteroarylcarbamoyl, $C_{1-6}$ alkylsulfonylamino, arylsulfonylamino, heteroarylsulfonylamino, $C_{1-6}$ alkylsulfamoyl, arylsulfamoyl or heteroarylsulfamoyl, wherein the alkyl, cycloalkyl, heterocyclyl, aryl or heteroaryl may be substituted by a group selected from the group consisting of halogen, optionally halogenated $C_{1-6}$ alkyl, optionally halogenated $C_{1-6}$ alkyloxy, $C_{1-6}$ alkylsulfonyl, carboxyl and cyano.

2. A compound of claim 1, represented by the formula (I-1) or a pharmaceutically acceptable salt thereof:

(I-1)

wherein $R^1$ represents optionally halogenated $C_{1-6}$ alkyl or optionally halogenated $C_{3-8}$ cycloalkyl;

$R^2$ represents a substituent selected from a group consisting of the following groups:

(II-1)

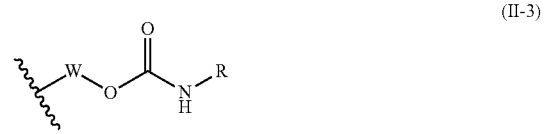

(II-2)

(II-3)

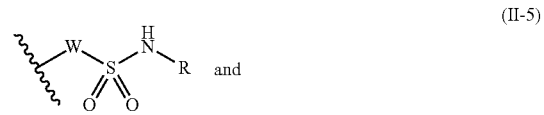

(II-4)

(II-5)

and (II-6)

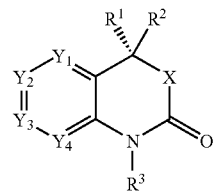

wherein W represents $C_{1-6}$ alkylene, $C_{2-6}$ alkenylene, $C_{2-6}$ alkynylene or $C_{3-6}$ cycloalkylene, wherein the alkylene, alkenylene, alkynylene or cycloalkylene may be substituted by optionally halogenated $C_{1-3}$ alkyl, optionally halogenated $C_{1-3}$ alkyloxy, hydroxyl or halogen;

R represents $C_{1-6}$ alkyl, $C_{3-8}$ cycloalkyl, aryl or heteroaryl, wherein the $C_{1-6}$ alkyl, $C_{3-8}$ cycloalkyl, aryl or heteroaryl may be substituted by halogen, optionally halogenated $C_{1-6}$ alkyl, optionally halogenated $C_{1-6}$ alkyloxy, $C_{1-6}$ alkylsulfonyl, cyano, phenyl, $C_{1-6}$ alkylthio, hydroxyl, amino, $C_{1-6}$ alkylamino, di-$C_{1-6}$ alkylamino, hydroxy-$C_{1-6}$ alkyl, amino-$C_{1-6}$ alkyl, $C_{1-6}$ alkylamino-$C_{1-6}$ alkyl, di-$C_{1-6}$ alkylaminoalkyl, $C_{1-6}$ alkoxy-$C_{1-6}$ alkyl, $C_{1-6}$ alkylcarbonyl, $C_{1-6}$ alkylcarbonylamino, $C_{1-6}$ alkylcarbamoyl, $C_{3-8}$ cycloalkylcarbamoyl, $C_{1-6}$ alkylsulfonylamino or $C_{1-6}$ alkylaminosulfonyl;

R³ represents a hydrogen atom, $C_{1-6}$ alkyl, aryl or heteroaryl;

X represents —O—, —C(R$^{4a}$)(R$^{4b}$)— or —NR⁵—;

R$^{4a}$, R$^{4b}$ and R⁵ each independently represent hydrogen, $C_{1-6}$ alkyl, $C_{3-8}$ cycloalkyl, aryl or heteroaryl, wherein the $C_{1-6}$ alkyl, $C_{3-8}$ cycloalkyl, aryl or heteroaryl may be substituted by halogen, optionally halogenated $C_{1-6}$ alkyl, optionally halogenated $C_{1-6}$ alkyloxy, $C_{1-6}$ alkylsulfonyl, cyano, aryl or heteroaryl;

Y₁ represents —CR⁶— or —N—;
Y₂ represents —CR⁷— or —N—;
Y₃ represents —CR⁸— or —N—;
Y₄ represents —CR⁹— or —N—;

R⁶, R⁷, R⁸ and R⁹ each independently represent a hydrogen atom, halogen, cyano, $C_{1-6}$ alkyl, $C_{3-8}$ cycloalkyl, $C_{1-6}$ alkoxy, hydroxyl, hydroxy-$C_{1-6}$ alkyl, amino, $C_{1-6}$ alkylamino, di-$C_{1-6}$ alkylamino, amino-$C_{1-6}$ alkyl, $C_{1-6}$ alkylamino-$C_{1-6}$ alkyl, di-$C_{1-6}$ alkylamino-($C_{1-6}$)alkyl, $C_{1-6}$ alkoxy-$C_{1-6}$ alkyl, heterocyclyl, aryl, heteroaryl, $C_{1-6}$ alkylsulfonyl, $C_{1-6}$ alkylsulfinyl, $C_{1-6}$ alkylthio, arylsulfonyl, heteroarylsulfonyl, arylsulfinyl, heteroarylsulfinyl, arylthio, heteroarylthio, $C_{1-6}$ alkylcarbonyl, arylcarbonyl, heteroarylcarbonyl, $C_{1-6}$ alkylcarbonylamino, arylcarbonylamino, heteroarylcarbonylamino, $C_{1-6}$ alkylcarbamoyl, $C_{3-8}$ cycloalkylcarbamoyl, heterocyclylcarbamoyl, arylcarbamoyl, heteroarylcarbamoyl, $C_{1-6}$ alkylsulfonylamino, arylsulfonylamino, heteroarylsulfonylamino, $C_{1-6}$ alkylsulfamoyl, arylsulfamoyl or heteroarylsulfamoyl, wherein the alkyl, cycloalkyl, heterocyclyl, aryl or heteroaryl may be substituted by a group selected from the group consisting of halogen, optionally halogenated $C_{1-6}$ alkyl, optionally halogenated $C_{1-6}$ alkyloxy, $C_{1-6}$ alkylsulfonyl, carboxyl and cyano.

3. The compound or a pharmaceutically acceptable salt thereof according to claim 1, wherein R¹ is trifluoromethyl.

4. The compound or a pharmaceutically acceptable salt thereof according to claim 1, wherein R² is a substituent represented by the formula (II-1), (II-4) or (II-6).

5. The compound or a pharmaceutically acceptable salt thereof according to claim 1, wherein R in R² is phenyl or heteroaryl, which may be substituted by a substituent selected from the group consisting of halogen, cyano, optionally halogenated $C_{1-6}$ alkyl, optionally halogenated $C_{1-6}$ alkyloxy, $C_{1-6}$ alkylsulfonyl, $C_{1-6}$ alkylthio, hydroxyl, amino, $C_{1-6}$ alkylamino, di-$C_{1-6}$ alkylamino, hydroxy-$C_{1-6}$ alkyl, amino-$C_{1-6}$ alkyl, $C_{1-6}$ alkylamino-$C_{1-6}$ alkyl, di-$C_{1-6}$ alkylamino-$C_{1-6}$ alkyl, $C_{1-6}$ alkoxy-$C_{1-6}$ alkyl, $C_{1-6}$ alkylcarbonyl, $C_{1-6}$ alkylcarbonylamino, $C_{1-6}$ alkylcarbamoyl, $C_{3-8}$ cycloalkylcarbamoyl, $C_{1-6}$ alkylsulfonylamino and $C_{1-6}$ alkylsulfamoyl.

6. The compound or a pharmaceutically acceptable salt thereof according to claim 1, wherein R³ is a hydrogen atom.

7. The compound or a pharmaceutically acceptable salt thereof according to claim 1, wherein in the case where Y₁, Y₂, Y₃ and Y₄ are —CR⁶—, —CR⁷—, —CR⁸— and —CR⁹—, respectively, at least one of R⁶, R⁷, R⁸ and R⁹ is selected from the group consisting of halogen, cyano, $C_{1-6}$ alkyl, $C_{3-8}$ cycloalkyl, $C_{1-6}$ alkoxy, hydroxyl, hydroxy-$C_{1-6}$ alkyl, amino, $C_{1-6}$ alkylamino, di-$C_{1-6}$ alkylamino, amino-$C_{1-6}$ alkyl, $C_{1-6}$ alkylamino-$C_{1-6}$ alkyl, di-$C_{1-6}$ alkylaminoalkyl, $C_{1-6}$ alkoxy-$C_{1-6}$ alkyl, heterocyclyl, aryl, heteroaryl, $C_{1-6}$ alkylsulfonyl, $C_{1-6}$ alkylsulfinyl, $C_{1-6}$ alkylthio, arylsulfonyl, heteroarylsulfonyl, arylsulfinyl, heteroarylsulfinyl, arylthio, heteroarylthio, $C_{1-6}$ alkylcarbonyl, arylcarbonyl, heteroarylcarbonyl, $C_{1-6}$ alkylcarbonylamino, arylcarbonylamino, heteroarylcarbonylamino, $C_{1-6}$ alkylcarbamoyl, $C_{3-8}$ cycloalkylcarbamoyl, heterocyclylcarbamoyl, arylcarbamoyl, heteroarylcarbamoyl, $C_{1-6}$ alkylsulfonylamino, arylsulfonylamino, heteroarylsulfonylamino, $C_{1-6}$ alkylsulfamoyl, arylsulfamoyl and heteroarylsulfamoyl, wherein the aryl or heteroaryl may be substituted by a group selected from the substituent consisting of halogen, optionally halogenated $C_{1-6}$ alkyl, optionally halogenated $C_{1-6}$ alkyloxy, $C_{1-6}$ alkylsulfonyl, carboxyl and cyano, and the rest are each a hydrogen atom.

8. The compound or a pharmaceutically acceptable salt thereof according to claim 1, wherein X is —O— or —NR⁵—.

9. The compound or a pharmaceutically acceptable salt thereof according to claim 2, wherein R¹ is trifluoromethyl.

10. The compound or a pharmaceutically acceptable salt thereof according to claim 2, wherein R² is a substituent represented by the formula (II-1), (II-4) or (II-6).

11. The compound or a pharmaceutically acceptable salt thereof according to claim 2, wherein R in R² is phenyl or heteroaryl, which may be substituted by a substituent selected from the group consisting of halogen, cyano, optionally halogenated $C_{1-6}$ alkyl, optionally halogenated $C_{1-6}$ alkyloxy, $C_{1-6}$ alkylsulfonyl, $C_{1-6}$ alkylthio, hydroxyl, amino, $C_{1-6}$ alkylamino, di-$C_{1-6}$ alkylamino, hydroxy-$C_{1-6}$ alkyl, amino-$C_{1-6}$ alkyl, $C_{1-6}$ alkylamino-$C_{1-6}$ alkyl, di-$C_{1-6}$ alkylamino-$C_{1-6}$ alkyl, $C_{1-6}$ alkoxy-$C_{1-6}$ alkyl, $C_{1-6}$ alkylcarbonyl, $C_{1-6}$ alkylcarbonylamino, $C_{1-6}$ alkylcarbamoyl, $C_{3-8}$ cycloalkylcarbamoyl, $C_{1-6}$ alkylsulfonylamino and $C_{1-6}$ alkylsulfamoyl.

12. The compound or a pharmaceutically acceptable salt thereof according to claim 2, wherein R³ is a hydrogen atom.

13. The compound or a pharmaceutically acceptable salt thereof according to claim 2, wherein in the case where Y₁, Y₂, Y₃ and Y₄ are —CR⁶—, —CR⁷—, —CR⁸— and —CR⁹—, respectively, at least one of R⁶, R⁷, R⁸ and R⁹ is selected from the group consisting of halogen, cyano, $C_{1-6}$ alkyl, $C_{3-8}$ cycloalkyl, $C_{1-6}$ alkoxy, hydroxyl, hydroxy-$C_{1-6}$ alkyl, amino, $C_{1-6}$ alkylamino, di-$C_{1-6}$ alkylamino, amino-$C_{1-6}$ alkyl, $C_{1-6}$ alkylamino-$C_{1-6}$ alkyl, di-$C_{1-6}$ alkylaminoalkyl, $C_{1-6}$ alkoxy-$C_{1-6}$ alkyl, heterocyclyl, aryl, heteroaryl, $C_{1-6}$ alkylsulfonyl, $C_{1-6}$ alkylsulfinyl, $C_{1-6}$ alkylthio, arylsulfonyl, heteroarylsulfonyl, arylsulfinyl, heteroarylsulfinyl, arylthio, heteroarylthio, $C_{1-6}$ alkylcarbonyl, arylcarbonyl, heteroarylcarbonyl, $C_{1-6}$ alkylcarbonylamino, arylcarbonylamino, heteroarylcarbonylamino, $C_{1-6}$ alkylcarbamoyl, $C_{3-8}$ cycloalkylcarbamoyl, heterocyclylcarbamoyl, arylcarbamoyl, heteroarylcarbamoyl, $C_{1-6}$ alkylsulfonylamino, arylsulfonylamino, heteroarylsulfonylamino, $C_{1-6}$ alkylsulfamoyl, arylsulfamoyl and heteroarylsulfamoyl, wherein the aryl or heteroaryl may be substituted by a group selected from the substituent consisting of halogen, optionally halogenated $C_{1-6}$ alkyl, optionally halogenated $C_{1-6}$ alkyloxy, $C_{1-6}$ alkylsulfonyl, carboxyl and cyano, and the rest are each a hydrogen atom.

14. The compound or a pharmaceutically acceptable salt thereof according to claim 2, wherein X is —O— or —NR⁵—.

15. An inhibitor of a long-chain fatty acyl elongase (LCE) comprising the compound or a pharmaceutically acceptable salt thereof according to claim 1 as an active ingredient.

16. A pharmaceutical composition comprising the compound or a pharmaceutically acceptable salt thereof according to claim 1 and a pharmaceutically acceptable additive.

17. A therapeutic treatment agent for metabolic syndrome, fatty liver, hyperlipidemia, dyslipidemia, non-alcoholic fatty liver, obesity, diabetes or bulimia, comprising the compound or a pharmaceutically acceptable salt thereof according to claim 1 as an active ingredient.

* * * * *